(12) United States Patent
Enomura

(10) Patent No.: US 8,592,498 B2
(45) Date of Patent: Nov. 26, 2013

(54) METHOD FOR PRODUCING ORGANIC COMPOUND AND ORGANIC COMPOUND OBTAINED BY THE METHOD

(75) Inventor: Masakazu Enomura, Izumi (JP)

(73) Assignee: M. Technique Co., Ltd., Osaka (JP)

( * ) Notice: Subject to any disclaimer, the term of this patent is extended or adjusted under 35 U.S.C. 154(b) by 586 days.

(21) Appl. No.: 12/739,136

(22) PCT Filed: Sep. 11, 2008

(86) PCT No.: PCT/JP2008/066397
§ 371 (c)(1),
(2), (4) Date: Aug. 9, 2010

(87) PCT Pub. No.: WO2009/054202
PCT Pub. Date: Apr. 30, 2009

(65) Prior Publication Data
US 2011/0178199 A1    Jul. 21, 2011

(30) Foreign Application Priority Data
Oct. 22, 2007 (JP) .................. 2007-274510

(51) Int. Cl.
| C07C 2/70 | (2006.01) |
| C07C 6/04 | (2006.01) |
| C07C 67/46 | (2006.01) |
| C07C 231/10 | (2006.01) |
| C07D 209/12 | (2006.01) |
| C07D 209/88 | (2006.01) |
| C07D 211/32 | (2006.01) |
| C07D 213/48 | (2006.01) |
| C07D 213/61 | (2006.01) |

(52) U.S. Cl.
USPC .......... 522/3; 526/88; 544/367; 548/242; 548/341.1; 549/272; 549/466; 558/315; 585/350; 585/422

(58) Field of Classification Search
None
See application file for complete search history.

(56) References Cited

U.S. PATENT DOCUMENTS

| 3,902,857 A | 9/1975 | Vander Mey et al. |
| 4,549,998 A | 10/1985 | Porter et al. |
| 7,534,404 B2 * | 5/2009 | Holl ............... 422/209 |
| 2005/0053532 A1 | 3/2005 | Holl |
| 2005/0158220 A1 | 7/2005 | Ramshaw et al. |

FOREIGN PATENT DOCUMENTS

| JP | 57-042308 A | 3/1982 |
| JP | 58-104623 A | 6/1983 |
| JP | 4-214736 A | 8/1992 |
| JP | 2004-049957 A | 2/2004 |
| JP | 2004-174297 A | 6/2004 |
| JP | 2005-60281 A | 3/2005 |
| JP | 2006-341232 A | 12/2006 |
| JP | 2007-50340 A | 3/2007 |
| JP | 2007-503993 A | 3/2007 |
| WO | 2006/008510 A1 | 1/2006 |

OTHER PUBLICATIONS

Brechtelsbauer, C. et al. "Evaluation of a Spinning Disc Reactor for Continuous Processing", Organic Process Research and Development, 2001, vol. 5, No. 1, p. 65-68.

Oxley, P. et al. "Evaluation of Spinning Disk Reactor Technology for the Manufacture of Pharmaceuticals", Industrial & Engineering Chemistry Research, 2000, vol. 39, p. 2175-2182.

* cited by examiner

*Primary Examiner* — Kamal Saeed
(74) *Attorney, Agent, or Firm* — Birch, Stewart, Kolasch & Birch, LLP

(57) ABSTRACT

Disclosed herein are a reaction method and a production method of an organic compound which are capable of achieving high reaction selectivity according to the purpose and a high production rate of a target substance. The methods include at least two fluids, wherein at least one kind of the fluids is a fluid containing at least one organic compound and at least one kind of the fluids other than the above fluid is a fluid containing at least one reactant in the form of a liquid or solution, and the respective fluids join together in a thin film fluid foamed between processing surfaces arranged to be opposite to each other so as to be able to approach to and separate from each other, at least one of which rotates relative to the other, whereby an organic reaction is performed in the thin film fluid.

11 Claims, 29 Drawing Sheets

FIG. 2A
FIG. 2B
FIG. 2C
FIG. 2D
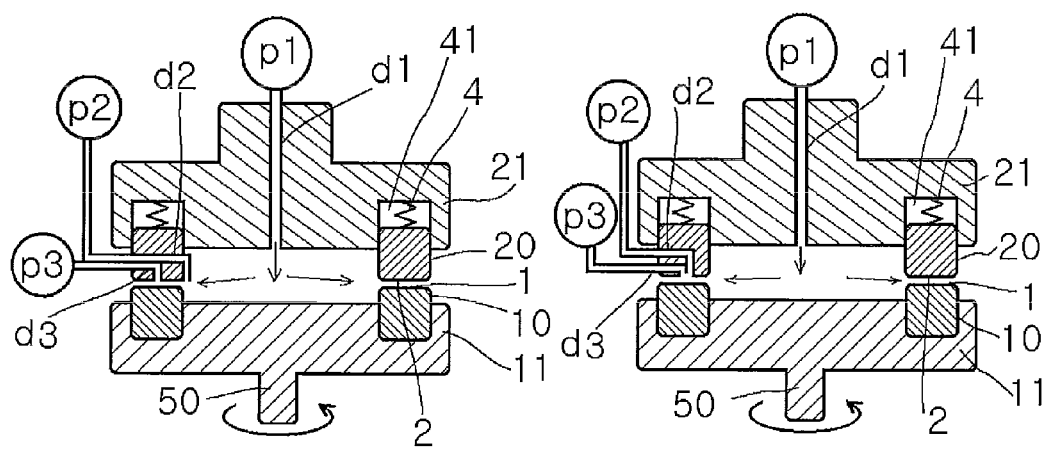
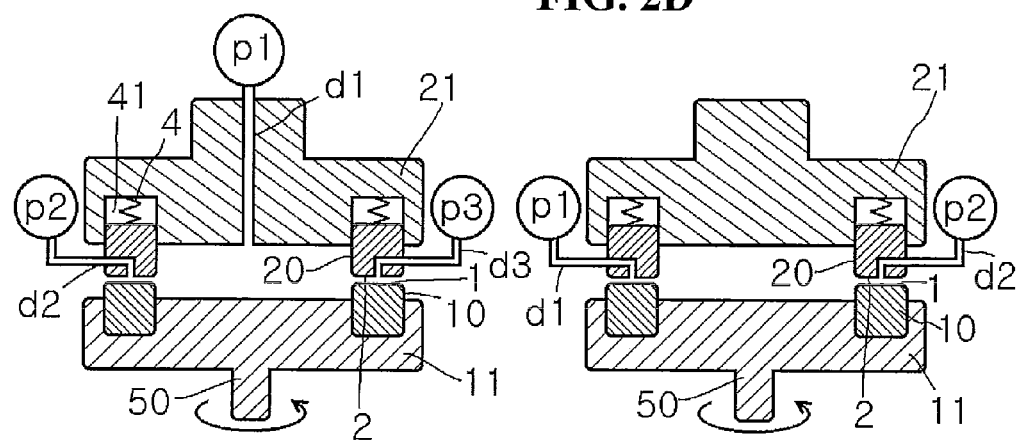

FIG. 19A
FIG. 19B
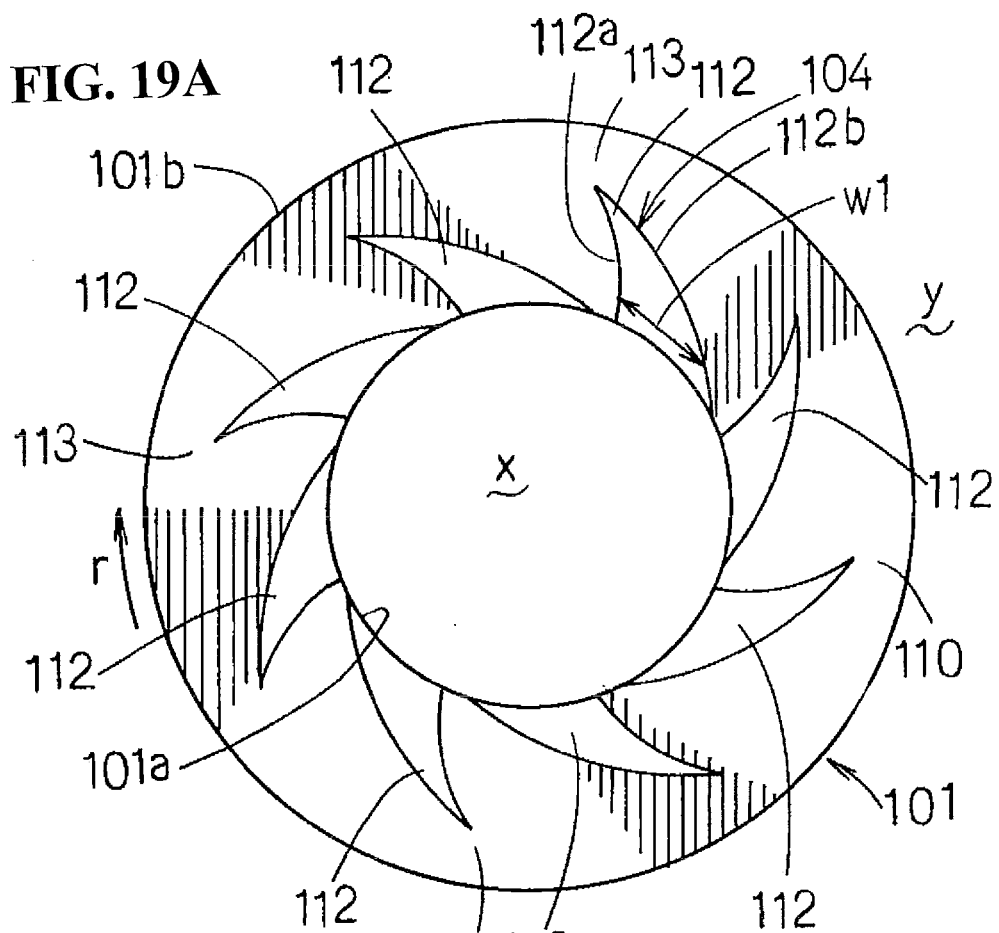
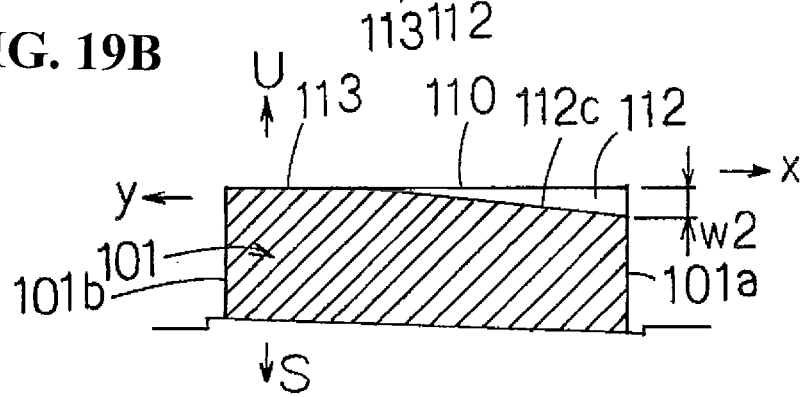

METHOD FOR PRODUCING ORGANIC COMPOUND AND ORGANIC COMPOUND OBTAINED BY THE METHOD

TECHNICAL FIELD

The present invention relates to a reaction method of an organic compound in a thin film fluid formed between processing surfaces arranged to be opposite to each other so as to be able to approach to and separate from each other, at least one of which rotates relative to the other. More specifically, the present invention relates to a reaction method and a production method of an organic compound which use a continuous reactor and which are effective and useful in the fields of chemistry, biochemistry, agriculture, medication, and pharmaceutical industry, particularly for chemical reaction and chemical synthesis using organic compounds.

BACKGROUND ART

Patent Document 1: JP-A-H04-214736
Patent Document 2: JP-A-2005-60281
Patent Document 3: JP-A-2007-50340

In general, a reactor for use in obtaining a new substance by the chemical reaction between two or more reactants or the same reactants is broadly divided into a batch type reactor and a flow (continuous) type reactor. In the case of a batch type reactor, a solvent, a substrate, and a reactant are placed in a reactor typified by a flask used in a laboratory, and are then stirred by, for example, a stirrer to perform a reaction. On the other hand, in the case of a flow type reactor such as an apparatus disclosed in Patent Document 1, a substrate solution is stirred and mixed and then flowed, and a reactant is added to the flowed substrate solution under stirring to perform a reaction. Both the batch type reactor and the flow type reactor are practically used in industry, and their reaction fields, of course, have a capacity. The capacity of such a reactor has an influence on nonuniformity in its reaction field. For example, in a case where a reactant is added to a uniform substrate solution to perform a chemical reaction, a certain period of time is required to make the concentration of the reactant uniform. The same can be said for temperature as a reaction condition. More specifically, in a case where a reactor is externally or internally heated or cooled, a certain period of time is required to heat or cool the entire reactor to a certain temperature. Further, it can be considered that it is very difficult to make the temperature of the entire reaction field in the reactor completely uniform. Further, in a case where a reactant is added in order to a solvent and a substrate placed in a batch type reactor, reaction conditions at the end of adding the reactant are already different from those at the start of adding the reactant. Nonuniformity of reaction conditions in a reaction field caused by the above-described factors has an influence on a finally-obtained reaction product. That is, reaction conditions vary even in the same reactor, and therefore a target reaction cannot be performed ideally. For example, a main reaction and a side reaction cannot be completely selectively performed and this results in the generation of a by-product, and in the case of polymerization reaction, it is difficult to obtain a reaction product having a uniform molecular weight distribution. Further, when adhesion to the inner wall of a reactor is taken into consideration, the yield of a reaction product is naturally lowered. In order to solve such problems related to a reaction field, a dynamic stirring device such as a stirrer or a turbine or a static stirring device such as a jet mixer is usually provided in a reactor. In this case, the speed of mixing a subject reaction mixture fluid is increased by such a stirring device for the purpose of achieving uniformity in a reaction field at a speed comparable to a reaction speed. However, nonuniformity in the reaction field again becomes a problem as the viscosity of the reaction mixture fluid increases. Even when the viscosity of the reaction mixture fluid is increased, stirring is continued for the purpose of instantaneously achieving uniformity in the reaction field so that power required for stirring naturally keeps steadily increasing. Further, there is also a problem that when the reaction fluid is heated in a short period of time, excessive heat energy is required due to a large temperature gradient.

The above-described problems are likely to become particularly serious in chemical reactions using organic compounds as starting materials, typified by Friedel-Crafts reaction, nitration reaction, addition reaction, elimination reaction, transfer reaction, polycondensation, coupling reaction, acylation, carbonylation, aldehyde synthesis, peptide synthesis, aldol reaction, and indole reaction, that is, in reactions, such as organic reactions, where a side reaction proceeds under reaction conditions very similar to those of a main reaction, or in reactions that need to form a reaction intermediate, or in reactions performed to obtain an intermediate. These reactions are required to make reaction conditions such as a concentration gradient and a temperature gradient uniform throughout a reaction field.

Further, the above-described organic reactions involve safety issues and dangers in spite of the fact that they are frequently used in chemical industry. In most cases, relatively large amounts of highly toxic chemical substances are used, which poses significant risks to humans and the environment, and solvents are environmental pollutants from various viewpoints, which creates particular problems. Further, in a case where, for example, carbon disulfide is used as a starting material, its low vapor pressure and flash point indicate that there is an additional risk that an explosible air/carbon disulfide mixture will be produced. Further, in the case of Friedel-Crafts acylation, there is a risk posed by its highly exothermic reaction, and in the case of nitration, there is also a serious risk of explosion in addition to a risk posed by its exothermic reaction. These risks come to the fore along with scale-up for real production.

In order to solve the above problems, a micromixer or a microreactor is proposed in, for example, Patent Documents 2 and 3, and it is advantageous in that a target substance can be synthesized in a very small amount, temperature control can be highly efficiently performed, interface reaction can be highly efficiently performed, and mixing is efficiently performed. However, when the general microreactor is used, there are many advantages in the micro-device and system, but as the micro-flow path diameter is decreased, pressure loss is inversely proportional to the biquadrate of the flow path; that is, an extremely high feeding pressure becomes necessary thus making a pump for actually feeding a fluid hardly available. In addition, there are many problems; for example, a phenomena of clogging of a flow path with a product occurs when the reaction is accompanied by separation, a micro-flow path is clogged with bubbles generated by a reaction, a microscopic space is not effective or applicable to every reaction although the speed of molecular diffusion is fundamentally expected for the reaction. Actually, the reaction should be attempted by trial and error in order to select good results. In the case of a microreactor disclosed in Patent Document 2, the problem of production of a deposit in the microreactor is solved by ultrasonic treatment. However, there is a strong possibility that irregular turbulent flow and cavitation generated in a microchannel by ultrasound do not always successfully act on a target reaction. Scaling up has been coped with a method of increasing the number of microreactors, that is numbering up, but the number of microreactors which can be stuck is limited to several dozen, thus inherently aiming exclusively at products of high value, and the increase in the number of devices leads to an increase the absolute number of failure causes, and when the problem of clogging actually occurs, it can be very difficult to detect a problem site such as failure site.

In view of the above problems, it is an object of the present invention to provide a reaction method of an organic compound and a production method of an organic compound which comprise performing a reaction of an organic compound in a forced thin film fluid formed between processing surfaces arranged to be opposite to each other so as to be able to approach to and separate from each other, at least one of which rotates relative to the other. This makes it possible to achieve high reaction selectivity according to the purpose and a high production rate of a target substance because the temperature of the thin film fluid is highly uniform and high uniformity in a reactor is achieved by stirring. Further, it is also possible to control the molecular weight distribution of a reaction product and a selective reaction irrespective of whether a target organic reaction is a reaction which produces a deposit or a reaction which produces no deposit because clogging of a reaction product does not occur due to self-dischargeability and high pressure is not required. Further, it is also possible to secure reaction uniformity irrespective of whether the viscosity of a fluid is low or high because a reaction is performed in a forced thin film fluid and therefore the viscosity of a fluid has a low impact on reaction uniformity, and to achieve a high productivity, and to achieve scale-up production while minimizing risks specific to organic reactions because a reaction is performed in a thin film fluid.

DISCLOSURE OF INVENTION

The invention in the present application provides a method for producing an organic compound, wherein:
- at least two fluids to be treated, comprising at least one kind of fluid and at least one kind of other fluid, are used,
- the method comprises:
- at least two processing members of a first processing member and a second processing member, the second processing member being capable of relatively approaching to and separating from the first processing member, and a rotation drive mechanism for rotating the first processing member and the second processing member relative to each other,
- wherein each of the processing members is provided with at least two processing surfaces of a first processing surface and a second processing surface disposed in a position they are faced with each other,
- each of the processing surfaces constitutes a part of a flow path through which the fluid to be processed under pressure is passed, and
- the fluid to be processed is passed between the first and second processing surfaces being capable of approaching and separating from each other and rotating relative to each other, whereby the fluid to be processed forms a thin film fluid while passing between both the processing surfaces, thereby reacting in the thin film fluid a component contained in one kind of the fluid with a component contained in one kind of the other fluid.

The reaction can be an organic reaction.

Further, the invention can be executed as the method characterized in that:

- a supply pressure of the fluid to be processed generates a force to move in the direction of separating at least two processing surfaces,
- the force thereby generated is balanced with a force to move in the direction of approaching at least two processing surfaces thereby keeping a minute space in the distance between the first and second processing surfaces, and
- the fluid to be processed is passed in the minute space kept between both the processing surfaces thereby forming the thin film fluid of the fluid to be processed.

Further, the invention can be executed as the method characterized in that:
- a fluid pressure imparting mechanism for imparting predetermined pressure to a fluid to be processed is provided,
- of the first and second processing members, at least the second processing member is provided with a pressure-receiving surface,
- at least a part of the pressure-receiving surface is comprised of the second processing surface,
- the pressure-receiving surface receives a pressure that imparts to the fluid to be processed by the fluid pressure imparting mechanism thereby generating a force to move in the direction of separating the second processing surface from the first processing surface, and
- the fluid to be processed under the imparted pressure is passed between the first and second processing surfaces, whereby the fluid to be processed forms a thin film fluid.

Further, the invention can be executed as the method characterized in that:
- one kind of the fluid is passed between the processing surfaces,
- an another introduction path independent of the flow path of the one kind of fluid is provided,
- at least one opening leading to the introduction path is arranged in at least either the first processing surface or the second processing surface,
- one kind of the other fluid is introduced between both the processing surfaces through the introduction path, and
- one kind of the fluid and one kind of the other fluid are mixed in the thin film fluid thereby performing the reaction.

At that time, the invention can be executed as the method characterized in that:
- a grooved depression causing the micro-pump effect by a relative rotation of the first and second processing surfaces is formed in at least any one of the processing surfaces of the first and second members,
- the grooved depression introduces one kind of the fluid to the space between the first and second processing surfaces,
- the opening is arranged in the downstream side of the grooved depression, and
- one kind of the other fluid is introduced to the space between both the processing surfaces from the opening.

Further, the invention can be executed as the method characterized in that:
- in at least any one of the first and second processing surfaces a grooved depression extending from its upstream to downstream is formed,
- the grooved depression introduces one kind of the fluid to the space between the first and second surfaces,
- the opening is arranged in the downstream side of the grooved depression, and
- one kind of the other fluid is introduced to the space between both the processing surfaces from the opening.

Further, the invention can be executed as the method characterized in that:
the opening is arranged in the downstream side of the position at which the direction of the flow of one kind of the fluid introduced from the grooved depression to the space between both the processing surfaces is converted into the direction of a spiral flow formed between both the processing surfaces.

Further, the invention can be executed as the method characterized in that:
the opening is arranged in a distance of 0.5 mm or more from the most downstream end of the grooved depression in the downstream side.

The method can be advantageously executed by performing the reaction under the condition of the laminar flow in the thin film fluid, wherein the thin film fluid is a laminar flow thin film fluid. Further, it is possible to heat (warm) at least either one of the processing surfaces, irradiate a ultraviolet (UV) beam between both the processing surfaces, and apply a ultrasonic energy between both the processing surfaces. Further, deaeration of a gas generated during the reaction and a gas contained in the fluid to be processed or removal of a solvent in the fluid can be done by performing the reaction in a vessel capable of securing a reduced pressure or a vacuum state and making a secondary side, to which at least a fluid after the treatment is discharged from the space between the first and second processing surfaces, a reduced pressure or a vacuum state.

Combination of one kind of the fluid, one kind of the other fluid, and the reaction can be exemplified by the following first to twenty-seventh combinations:

a first combination comprising:
a fluid containing at least one organic compound,
a fluid containing at least one reacting agent, and
the reaction in which an organic reaction is performed between the organic compound and the reacting agent, a second combination comprising:
a fluid containing one or two selected from three members composed of an acylating agent, a strong acid, and an organic compound,
a fluid containing at least one not selected in the above three members thereby resulting in containing all the three members in the fluid to be processed, and
the reaction in which a Friedel-Craft acylation reaction is performed, a third combination comprising:
a fluid containing at least one nitration reagent,
a fluid containing at least one organic compound, and
the reaction in which a nitration reaction is performed, a fourth combination comprising:
a fluid containing at least one brominating reagent,
a fluid containing at least one organic compound, and
the reaction in which a bromination reaction is performed, a fifth combination comprising:
a fluid containing at least one oxidant,
a fluid containing at least one organic carbonyl compound, and
the reaction in which a Baeyer-Villiger oxidation reaction is performed, a sixth combination comprising:
a fluid containing at least one metathesis catalyst,
a fluid containing at least one unsaturated organic compound, and
the reaction in which a metathesis reaction is performed, a seventh combination comprising:
a fluid containing at least one hydride and/or its derivative,
a fluid containing at least one organic compound, and
the reaction in which a reduction reaction is performed, a eighth combination comprising:
a fluid containing at least one dehydrating agent,
a fluid containing at least one organic compound, and
the reaction in which a dehydration reaction is performed, a ninth combination comprising:
a fluid containing at least one transfer reagent,
a fluid containing at least one organic oxime, and
the reaction in which a Beckmann rearrangement of the organic oxime is performed, a tenth combination comprising:
a fluid containing at least one oximation reagent,
a fluid containing at least one organic carbonyl compound and/or CH-acid compound, and
the reaction in which an oximation reaction of the organic carbonyl compound and/or CH-acid compound is performed, an eleventh combination comprising:
a fluid containing at least one dipolarophile,
a fluid containing at least one organic compound, and
the reaction in which a 1,3-dipolar cycloaddition of the organic compound is performed, a twelfth combination comprising:
a fluid containing at least one oxidant,
a fluid containing at least one tertiary amine and/or at least one nitrogen-containing aromatic heterocyclic compound, and
the reaction in which the tertiary amine and/or the nitrogen-containing aromatic heterocyclic compound is oxidized to an amine oxide, a thirteenth combination comprising:
a fluid containing at least one oxidant,
a fluid containing at least one olefin, and
the reaction in which the olefin is epoxidized, a fourteenth combination comprising:
a fluid containing at least one formylating agent,
a fluid containing at least one organic compound, and
the reaction in which a formylation reaction is performed, a fifteenth combination comprising:
a fluid containing at least one catalyst,
a fluid containing at least one aryl hydrazone, and
the reaction in which a reaction to obtain an indole compound is performed, a sixteenth combination comprising:
a fluid containing at least one alkylidene group transfer reagent,
a fluid containing at least one organic compound, and
the reaction in which the alkylidene group is transferred to the organic compound, a seventeenth combination comprising:
a fluid containing at least one or two selected from three members composed of a catalyst, an organic compound containing at least one vinyl hydrogen atom or acetylenic hydrogen atom, and an organic compound containing at least one eliminating group,
a fluid containing at least one not selected in the above three members thereby resulting in containing all the three members in the fluid to be processed, and
the reaction in which a coupling reaction is performed, a eighteenth combination comprising:
a fluid containing at least one or two selected from three members composed of at least one organic compound selected from an alcohol, a thiol, and an amine, a catalyst, and diketene,
a fluid containing at least one not selected in the above three members thereby resulting in containing all the three members in the fluid to be processed, and the reaction in which an acetoacetylation reaction is performed, a nineteenth combination comprising:
- a fluid containing at least one or two selected from three members composed of any nitrile represented by $R_1$—CN and $R_2$—CN (wherein $R_1$ and $R_2$ each are an unsubstituted or substituted isocyclic or heterocyclic aromatic group), a mixture of the nitriles, and a succinate diester,
- a fluid containing at least one not selected in the above three members thereby resulting in containing all the three members in the fluid to be processed, and
- the reaction in which the nitrile and the succinate diester are reacted or along with the reaction a salt generated by the reaction is hydrolyzed, a twentieth combination comprising:
- a fluid containing at least one alkaline metal,
- a fluid containing at least one alcohol, and
- the reaction in which the alkaline metal and the alcohol are reacted, a twenty-first combination comprising:
- a fluid containing at least one aldehydes and/or ketones,
- a fluid containing at least one catalyst in liquid or quasi-liquid state, and
- the reaction in which an aldol reaction is performed, a twenty-second combination comprising:
- a fluid containing at least one compound selected from a lithium aromatic and/or lithium aliphatic compound or a magnesium aromatic and/or magnesium aliphatic compound,
- a fluid containing at least one boron compound, and
- the reaction in which a boration reaction is performed, a twenty-third combination comprising:
- a fluid containing at least one organic compound containing a unsaturated bond,
- a fluid containing at least one ozone, and
- the reaction in which an oxidation reaction is performed, a twenty-fourth combination comprising:
- a fluid containing at least one acid,
- a fluid containing at least one vinyl compound or vinylidene compound, and
- the reaction in which a dimerization reaction is performed, a twenty-fifth combination comprising:
- a fluid containing at least one monomer capable of undergoing a cationic polymerization reaction,
- a fluid containing at least one cation, and
- the reaction in which a cationic polymerization reaction is performed, a twenty-sixth combination comprising:
- a fluid containing at least one metalation reagent (lithium, magnesium),
- a fluid containing at least one halogen compound, and
- the reaction in which a halogen-metal exchange reaction is performed, and a twenty-seventh combination comprising:
- a fluid containing at least one alkyl esters,
- a fluid containing at least one metal hydride-based reducing agent, and
- the reaction in which a reduction reaction is performed.

An aspect of the invention in the present application is a method for producing an organic compound, wherein at least two fluids are used, wherein at least one of the fluids contains at least one nitrating reagent and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to perform a nitration reaction in the thin film fluid.

An aspect of the invention in the present application is a method for producing an organic compound, wherein at least two fluids are used, wherein at least one of the fluids contains at least one brominating reagent and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to perform a bromination reaction in the thin film fluid.

An aspect of the invention in the present application is a method for producing an organic compound, wherein at least two fluids are used, wherein at least one of the fluids contains at least one oxidant and at least one of the fluids other than the above fluid contains at least one organic carbonyl compound, and the respective fluids join together in a thin film fluid formed between processing surfaces arranged to be opposite to each other so as to be able to approach to and separate from each other, at least one of which rotates relative to the other, to perform a Baeyer-Villiger oxidation reaction in the thin film fluid.

An aspect of the invention in the present application is a method for producing an organic compound, wherein at least two fluids are used, wherein at least one of the fluids contains at least one metathesis catalyst and at least one of the fluids other than the above fluid contains at least one unsaturated organic compound, and the respective fluids join together in a thin film fluid formed between processing surfaces arranged to be opposite to each other so as to be able to approach to and separate from each other, at least one of which rotates relative to the other, to perform a metathesis reaction in the thin film fluid.

An aspect of the invention in the present application is a method for producing an organic compound, wherein at least two fluids are used, wherein at least one of the fluids contains at least one hydride and/or at least one derivative thereof and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to perform a reduction reaction in the thin film fluid.

It is to be noted that the phrase "contains at least one hydride and/or at least one derivative thereof" includes three cases, that is, a case where only at least one hydride is contained, a case where only at least one hydride derivative is contained, and a case where both at least one hydride and at least one hydride derivative are contained.

An aspect of the invention in the present application is a method for producing an organic compound, wherein at least two fluids are used, wherein at least one of the fluids contains at least one dehydrating agent and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to perform a dehydration reaction in the thin film fluid.

An aspect of the invention in the present application is a method for producing an organic compound, wherein at least two fluids are used, wherein at least one of the fluids contains at least one transfer reagent and at least one of the fluids other than the above fluid contains at least one organic oxime, and the respective fluids join together in a thin film fluid formed between processing surfaces arranged to be opposite to each other so as to be able to approach to and separate from each other, at least one of which rotates relative to the other, to perform Beckmann rearrangement of the organic oxime in the thin film fluid.

An aspect of the invention in the present application is a method for producing an organic compound, wherein at least two fluids are used, wherein at least one of the fluids contains at least one oximation reagent and at least one of the fluids other than the above fluid contains at least one organic carbonyl compound and/or at least one CH-acid compound, and the respective fluids join together in a thin film fluid formed between processing surfaces arranged to be opposite to each other so as to be able to approach to and separate from each other, at least one of which rotates relative to the other, to perform oximation of the organic carbonyl compound and/or CH-acid compound in the thin film fluid.

It is to be noted that the phrase "contains at least one organic carbonyl compound and/or at least one CH-acid compound" includes three cases, that is, a case where only at least one organic carbonyl compound is contained, a case where only at least one CH-acid compound is contained, and a case where both at least one organic carbonyl compound and at least one CH-acid compound are contained.

An aspect of the invention in the present application is a method for producing an organic compound, wherein at least two fluids are used, wherein at least one of the fluids contains at least one dipolarophile and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to perform 1,3-dipolar cycloaddition of the organic compound in the thin film fluid.

An aspect of the invention in the present application is a method for producing an organic compound, wherein at least two fluids are used, wherein at least one of the fluids contains at least one oxidant and at least one of the fluids other than the above fluid contains at least one tertiary amine and/or at least one nitrogen-containing aromatic heterocyclic compound, and the respective fluids join together in a thin film fluid formed between processing surfaces arranged to be opposite to each other so as to be able to approach to and separate from each other, at least one of which rotates relative to the other, to oxidize the tertiary amine and/or nitrogen-containing aromatic heterocyclic compound to an amine oxide in the thin film fluid.

It is to be noted that the phrase "contains at least one tertiary amine and/or at least one nitrogen-containing aromatic heterocyclic compound" includes three cases, that is, a case where only at least one tertiary amine is contained, a case where only at least one nitrogen-containing aromatic heterocyclic compound is contained, and a case where both at least one tertiary amine and the at least one nitrogen-containing aromatic heterocyclic compound are contained.

An aspect of the invention in the present application is a method for producing an organic compound, wherein at least two fluids are used, wherein at least one of the fluids contains at least one oxidant and at least one of the fluids other than the above fluid contains at least one olefin, and the respective fluids join together in a thin film fluid formed between processing surfaces arranged to be opposite to each other so as to be able to approach to and separate from each other, at least one of which rotates relative to the other, to epoxidize the olefin in the thin film fluid.

An aspect of the invention in the present application is a method for producing an organic compound, wherein at least two fluids are used, wherein at least one of the fluids contains at least one formylating agent and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to formylate the organic compound in the thin film fluid.

An aspect of the invention in the present application is a method for producing an organic compound, wherein at least two fluids are used, wherein at least one of the fluids contains at least one catalyst and at least one of the fluids other than the above fluid contains at least one aryl hydrazone, and the respective fluids join together in a thin film fluid formed between processing surfaces arranged to be opposite to each other so as to be able to approach to and separate from each other, at least one of which rotates relative to the other, to obtain an indole compound in the thin film fluid.

An aspect of the invention in the present application is a method for producing an organic compound, wherein at least two fluids are used, wherein at least one of the fluids contains at least one alkylidene group transfer reagent and at least one of the fluids other than the above fluid contains at least one organic compound, and the respective fluids join together in a thin film fluid formed between processing surfaces arranged to be opposite to each other so as to be able to approach to and separate from each other, at least one of which rotates relative to the other, to transfer an alkylidene group to the organic compound in the thin film fluid.

An aspect of the invention in the present application is a method for producing an organic compound, wherein at least two fluids are used, wherein at least one of the fluids contains one or two selected from three choices, that is, a catalyst, an organic compound containing at least one of a vinylic hydrogen atom and an acetylenic hydrogen atom, and an organic compound containing at least one elimination group and at least one of the fluids other than the above fluid contains at least one of the one or two choices not yet selected, and the respective fluids join together in a thin film fluid formed between processing surfaces arranged to be opposite to each other so as to be able to approach to and separate from each other, at least one of which rotates relative to the other, to perform a coupling reaction in the thin film fluid, the at least two fluids containing all the three choices as a whole.

It is to be noted that the fluid containing one or two selected from three choices, that is, a catalyst, an organic compound containing at least one of a vinylic hydrogen atom and an acetylenic hydrogen atom, and an organic compound containing at least one elimination group may contain one or two of the choices not selected to such an extent that the reaction performed in a space between the processing surfaces is not affected.

An aspect of the invention in the present application is a method for producing an organic compound, wherein at least two fluids are used, wherein at least one of the fluids contains one or two selected from three choices, that is, at least one organic compound selected from an alcohol, a thiol, and an amine, a catalyst, and diketene and at least one of the fluids other than the above fluid contains at least one of the one or two choices not yet selected, and the respective fluids join together in a thin film fluid formed between processing surfaces arranged to be opposite to each other so as to be able to approach to and separate from each other, at least one of which rotates relative to the other, to perform an acetoacetylation reaction in the thin film fluid, the at least two fluids containing all the three choices as a whole.

It is to be noted that the fluid containing one or two selected from three choices, that is, at least one organic compound selected from an alcohol, a thiol, and an amine, a catalyst, and diketene may contain one or two of the choices not selected to such an extent that the reaction performed in a space between the processing surfaces is not affected.

An aspect of the invention in the present application is a method for producing an organic compound, wherein at least two fluids are used, wherein at least one of the fluids contains one or two selected from three choices, that is, a strong base, any one of a nitrile represented by the following general formula: $R_1$—CN (wherein $R_1$ is an unsubstituted or substituted isocyclic or heterocyclic aromatic group) and a nitrile represented by the following general formula: $R_2$—CN (wherein $R_2$ is an unsubstituted or substituted isocyclic or heterocyclic aromatic group) or a mixture of these nitriles, and a succinic acid diester and at least one of the fluid other than the above fluid contains at least one of the one or two choices not yet selected, and the respective fluids join together in a thin film fluid formed between processing surfaces arranged to be opposite to each other so as to be able to approach to and separate from each other, at least one of which rotates relative to the other, to perform a reaction between the nitrile and the succinic acid diester or to perform the reaction and hydrolysis of a salt generated by the reaction in the thin film fluid, the at least two fluids containing all the three choices as a whole.

An aspect of the invention in the present application is a method for producing an organic compound, wherein at least two fluids are used, wherein at least one of the fluids contains at least one alkali metal and at least one of the fluids other than the above fluid contains at least one alcohol, and the respective fluids join together in a thin film fluid formed between processing surfaces arranged to be opposite to each other so as to be able to approach to and separate from each other, at least one of which rotates relative to the other, to perform a reaction between the alkali metal and the alcohol in the thin film fluid.

An aspect of the invention in the present application is a method for producing an organic compound, wherein at least two fluids are used, wherein at least one of the fluids contains at least one aldehyde and/or at least one ketone and at least one of the fluids other than the above fluid contains at least one catalyst, and the respective fluids join together in a thin film fluid formed between processing surfaces arranged to be opposite to each other so as to be able to approach to and separate from each other, at least one of which rotates relative to the other, to perform an aldol reaction in the thin film fluid.

It is to be noted that the phrase "contains at least one aldehyde and/or at least one ketone" includes three cases, that is, a case where only at least one aldehyde is contained, a case where only at least one ketone is contained, and a case where both at least one aldehyde and at least one ketone are contained.

An aspect of the invention in the present application is a method for producing an organic compound, wherein at least two fluids are used, wherein at least one of the fluids contains at least one lithium aromatic and/or at least one lithiated aliphatic or at least one magnesium aromatic and/or at least one magnesium aliphatic and at least one of the fluids other than the above fluid contains at least one boron compound, and the respective fluids join together in a thin film fluid formed between processing surfaces arranged to be opposite to each other so as to be able to approach to and separate from each other, at least one of which rotates relative to the other, to perform a boration reaction in the thin film fluid.

It is to be noted that the phrase "contains at least one lithium aromatic and/or at least one lithiated aliphatic" includes three cases, that is, a case where only at least one lithium aromatic is contained, a case where only at least one lithiated aliphatic is contained, and a case where both at least one lithium aromatic and at least one lithiated aliphatic are contained. The same applies to the phrase "contains at least one magnesium aromatic and/or at least one magnesium aliphatic."

An aspect of the invention in the present application is a method for producing an organic compound, wherein at least two fluids are used, wherein at least one of the fluids contains at least one organic compound having an unsaturated bond and at least one of the fluids other than the above fluid contains at least one ozone, and the respective fluids join together in a thin film fluid formed between processing surfaces arranged to be opposite to each other so as to be able to approach to and separate from each other, at least one of which rotates relative to the other, to perform an oxidation reaction in the thin film fluid.

An aspect of the invention in the present application is a method for producing an organic compound, wherein at least two fluids are used, wherein at least one of the fluids contains at least one acid and at least one of the fluids other than the above fluid contains at least one vinyl compound or at least one vinylidene compound, and the respective fluids join together in a thin film fluid formed between processing surfaces arranged to be opposite to each other so as to be able to approach to and separate from each other, at least one of which rotates relative to the other, to perform a dimerization reaction in the thin film fluid.

An aspect of the invention in the present application is a method for producing an organic compound, wherein at least two fluids are used, wherein at least one of the fluids contains at least one cationic polymerizable monomer and at least one of the fluids other than the above fluid contains at least one cation, and the respective fluids join together in a thin film fluid formed between processing surfaces arranged to be opposite to each other so as to be able to approach to and separate from each other, at least one of which rotates relative to the other, to perform a dimerization reaction in the thin film fluid.

An aspect of the invention in the present application is a method for producing an organic compound, wherein at least two fluids are used, wherein at least one of the fluids contains at least one metalation reagent (lithium, magnesium) and at least one of the fluids other than the above fluid contains at least one halide, and the respective fluids join together in a thin film fluid formed between processing surfaces arranged to be opposite to each other so as to be able to approach to and separate from each other, at least one of which rotates relative to the other, to perform a halogen-metal exchange reaction in the thin film fluid.

An aspect of the invention in the present application is a method for producing an organic compound, wherein at least two fluids are used, wherein at least one of the fluids contains at least one alkyl ester and at least one of the fluids other than the above fluid contains at least one metal hydride-based reducing agent, and the respective fluids join together in a thin film fluid formed between processing surfaces arranged to be opposite to each other so as to be able to approach to and separate from each other, at least one of which rotates relative to the other, to perform a reduction reaction in the thin film fluid.

An aspect of the invention in the present application is the method for producing an organic compound, wherein the reaction includes a fluid pressure imparting mechanism that imparts predetermined pressure to a fluid to be processed, at least two processing members of a first processing member and a second processing member capable of relatively approaching to and separating from the first processing member, and a rotation drive mechanism that rotates the first processing member and the second processing member relative to each other, wherein each of the processing members is provided with at least two processing surfaces of a first processing surface and a second processing surface disposed in a position they are faced with each other; each of the processing surfaces constitutes part of a sealed flow path through which the fluid under the predetermined pressure is passed; two or more fluids to be processed, at least one of which contains a reactant, are uniformly mixed and positively reacted between the processing surfaces; of the first and second processing members, at least the second processing member is provided with a pressure-receiving surface, and at least part of the pressure-receiving surface is comprised of the second processing surface, the pressure-receiving surface receives pressure applied to the fluid by the fluid pressure imparting mechanism thereby generating a force to move in the direction of separating the second processing surface from the first processing surface; and the fluid under the predetermined pressure is passed between the first and second processing surfaces being capable of approaching to and separating from each other and rotating relative to each other, whereby the processed fluid forms a fluid film of predetermined thickness while passing between both the processing surfaces, and the reaction further includes another introduction path independent of the flow path through which the fluid to be processed under the predetermined pressure is passed, and at least one opening leading to the separate introduction path and being arranged in at least either the first processing surface or the second processing surface, wherein at least one processed fluid sent from the separate introduction path is introduced into between the processing surfaces, whereby the reactant contained in at least any one of the aforementioned processed fluids, and a fluid other than said processed fluid enable a state of desired reaction by mixing under uniform stirring in the fluid film.

An aspect of the invention in the present application is the method for producing an organic compound, wherein, during the reaction, heat (warmth) is added between the processing surfaces; ultraviolet ray (UV) is irradiated between the processing surfaces; or ultrasonic energy is supplied between the processing surfaces.

An aspect of the invention in the present application is the method for producing an organic compound, wherein the reaction is conducted in a reactor capable of securing a depressurized or vacuum state, and at least a secondary side at which the fluid after processing is discharged is depressurized or vacuumized to remove a gas generated during the reaction, to remove a gas contained in the fluid, or to remove the solvent of the fluid.

An aspect of the invention in the present application is an organic compound obtained by the method.

As described above, the present invention provides a reaction method of an organic compound and a production method of an organic compound which comprise performing a reaction of an organic compound in a forced thin film fluid formed between processing surfaces arranged to be opposite to each other so as to be able to approach to and separate from each other, at least one of which rotates relative to the other, and further provides an organic compound obtained by the production method. According to the production method of an organic compound of the present invention, it is possible to control reaction selectivity at a higher level as compared to a conventional reaction method, thereby achieving a high yield of a reaction product. Further, it is also possible to complete processing in a continuous manner in a short period of time, thereby enabling an organic compound to be supplied at a lower price. Further, with respect to the reaction temperature, it is also possible to perform a reaction at a temperature closer to room temperature as compared to a conventional method because the reaction is performed in a thin film fluid. Depending on a necessary amount of production, the present invention can grow in size by using general scale-up concept. Further, it is also possible to secure reaction uniformity irrespective of whether the viscosity of a fluid is low or high because a reaction is performed in a forced thin film fluid and therefore the viscosity of a fluid has a low impact on reaction uniformity, and to achieve a high productivity, and to achieve scale-up production while minimizing risks specific to organic reactions because a reaction is performed in a thin film fluid.

Further, the production method of an organic compound according to the present invention is advantageous in that higher energy efficiency is achieved as compared to a conventional method.

BRIEF DESCRIPTION OF DRAWINGS

FIG. 2(A) to FIG. 2(D) each show a schematic vertical sectional view showing the concept of still another embodiment of the apparatus shown in FIG. 1.

FIG. 19(A) is a plane view of a first processing member in the apparatus shown in FIG. 12(A), and FIG. 19(B) is a schematic vertical sectional view showing an important part thereof.

FIG. 29 is a diagram for explaining a pressure-receiving surface arranged in the processing member.

BEST MODE FOR CARRYING OUT THE INVENTION

Figure 1A:
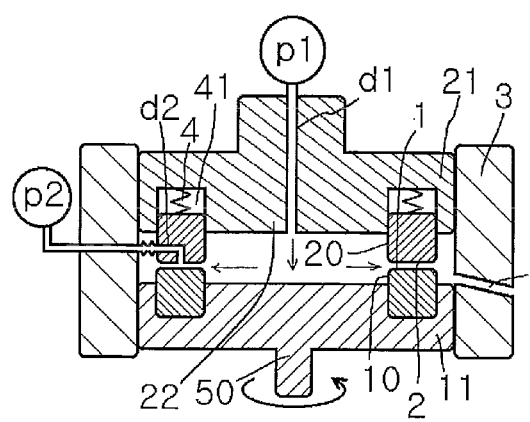
FIG. 1(A) is a schematic vertical sectional view showing the concept of the apparatus used for carrying out the present invention.

Hereinbelow, an organic reaction method according to the present invention will be described in detail.

When an organic reaction is performed in the present invention, a fluid to be used for the reaction is formed into a thin film fluid formed between processing surfaces arranged to be opposite to each other so as to be able to approach to and separate from each other, at least one of which rotates relative to the other. Various organic reactions are performed between an organic compound and a reactant using an organic compound as a starting material in the thin film fluid, such as Friedel-Crafts reaction, nitration reaction, addition reaction, elimination reaction, transfer reaction, polymerization reaction, condensation reaction, coupling reaction, acylation, carbonylation, aldehyde synthesis, peptide synthesis, aldol reaction, indole reaction, electrophilic substitution reaction, nucleophilic substitution reaction, Wittig reaction, Michael addition reaction, enamine synthesis, ester synthesis, enzyme reaction, diazo coupling reaction, oxidation reaction, reduction reaction, multistep reaction, selective addition reaction, Suzuki-Miyaura coupling reaction, Kumada-Corriu reaction, metathesis reaction, isomerization, radical polymerization reaction, anionic polymerization reaction, cationic polymerization reaction, metallic catalytic polymerization reaction, consecutive reaction, macromolecule synthesis, acetylene coupling reaction, episulfide synthesis, episulfide synthesis, Bamberger rearrangement, Chapman rearrangement, Claisen condensation, quinoline synthesis, Paal-Knorr furan synthesis, Paal-Knorr pyrrole synthesis, Passerini reaction, Paterno-Buchi reaction, carbonyl-ene reaction (Prins reaction), Jacobsen rearrangement, Koenigs-Knorr glycosidation reaction, Leuckart-Wallach reaction, Horner-Wadsworth-Emmons reaction, Gassman reaction, Noyori asymmetric hydrogenation reaction, Perkin reaction, Petasis reaction, Tishchenko reaction, Tishchenko reaction, Ullmann coupling, Nazarov cyclization, Tiffeneau-Demjanov rearrangement, template synthesis, oxidation with selenium dioxide, Reimer-Tiemann reaction, Grob fragmentation, haloform reaction, Malaprade glycol oxidation cleavage, Hofmann elimination, thiocarbonylation by Lawesson's reagent, Lossen rearrangement, cyclic ketone synthesis using FAMSO, Favorskii rearrangement, Feist-Benary furan synthesis, Gabriel amine synthesis, Glaser reaction, Grignard reaction, Cope elimination, Cope rearrangement, diimide reduction of alkynes, Eschenmoser aminomethylation reaction, [2+2] photocyclization, Appel reaction, aza-Wittig reaction, Bartoli indole synthesis, Carroll rearrangement, Chichibabin reaction, Clemmensen reduction, Combes quinoline synthesis, Tsuji-Trost reaction, TEMPO oxidation, dihydroxylation with osmium tetroxide, Fries rearrangement, Neber rearrangement, Barton-McCombie deoxygenation, Barton decarboxylation, Seyferth-Gilbert alkyne synthesis, Pinnick (Kraus) oxidation, Ito-Saegusa oxidation, Eschenmoser fragmentation, Eschenmoser-Claisen rearrangement, Doering-LaFlamme allene synthesis, Corey-Chaykovsky reaction, acyloin condensation, Wolff-Kishner reduction, IBX oxidation, Parikh-Doering oxidation, Reissert reaction, Jacobsen hydrolytic kinetic optical resolution, benzilic acid rearrangement, Hiyama cross coupling, Luche reduction, oxymercuration, Vilsmeier-Haak reaction, Wolff rearrangement, Kolbe-Schmitt reaction, Corey-Kim oxidation, Cannizzaro reaction, Henry reaction, transformation of alcohol into alkane, Arndt-Eistert synthesis, hydroformylation, Peterson olefination, decarbonylation, Curtius rearrangement, Wohl-Zieglar bromination, Pfitzner-Moffatt oxidation, McMurry coupling, Barton reaction, Balz-Schiemann reaction, Masamune-Bergman reaction, Dieckmann condensation, pinacol coupling, Williamson ether synthesis, iodolactonization, Harries ozonolysis, oxidation with active manganese dioxide, alkyne cyclotrimerization, Kumada-Tamao-Corriu cross coupling, sulfoxide and selenoxide syn-β elimination, Fischer indole synthesis, Oppenauer oxidation, Darzens condensation, Alder Ene reaction, Sarett-Collins oxidation, Nozaki-Hiyama-Kishi coupling reaction, Weinreb ketone synthesis, DAST fluorination, Corey-Winter olefin synthesis, Hosomi-Sakurai reaction, alcohol oxidation using PCC (PDC), Jones oxidation (Jones Oxidation), Keck allylation, cyanide addition using Nagata reagent, Negishi coupling, Ireland-Claisen rearrangement, Baeyer-Villiger oxidation, p-methoxybenzyl (PMB or MPM), dimethoxybenzyl (DMB) protection, deprotection, Wacker oxidation, Myers asymmetric alkylation, Yamaguchi macrolactonization, Mukaiyama-Corey macrolactonization, Bode peptide synthesis, Lindlar reduction, homogeneous hydrogenation, ortho metalation, Wagnar-Meerwein rearrangement, Wurtz reaction, ketone synthesis using 1,3-dithiane, Michael addition, Stork enamine synthesis of ketone, Pauson-Khand cyclopentene synthesis, and Tebbe reaction.

An apparatus of the same principle as described in JP-A 2004-49957 filed by the present applicant, for example, can be used in the method of uniform stirring and mixing in a thin film fluid formed between processing surfaces arranged to be opposite to each other so as to be able to approach to and separate from each other, at least one of which rotates relative to the other.

Hereinafter, the fluid processing apparatus suitable for carrying out this method is described.

As shown in FIG. 1(A), this apparatus includes opposing first and second processing members 10 and 20, at least one of which rotates to the other. The opposing surfaces of both the processing members 10 and 20 serve as processing surfaces 1 and 2 to process a fluid to be processed therebetween. The first processing member 10 includes a first processing surface 1, and the second processing member 20 includes a second processing surface 2.

Both the processing surfaces 1 and 2 are connected to a flow path of the fluid to constitute a part of the flow path of the fluid.

Specifically, this apparatus constitutes flow paths of at least two fluids to be processed and joins the flow paths together.

That is, this apparatus is connected to a flow path of a first fluid to form a part of the flow path of the first fluid and simultaneously forms a part of a flow path of a second fluid different from the first fluid. This apparatus joins both the flow paths together thereby mixing and when the mixing is accompanied by reaction, reacting both the fluids between the processing surfaces 1 and 2. In the embodiment shown in FIG. 1(A), each of the flow paths is hermetically closed and made liquid-tight (when the processed fluid is a liquid) or air-tight (when the processed fluid is a gas).

Specifically, this apparatus as shown in FIG. 1(A) includes the first processing member 10, the second processing member 20, a first holder 11 for holding the first processing member 10, a second holder 21 for holding the second processing member 20, a surface-approaching pressure imparting mechanism 4, a rotation drive member, a first introduction part d1, a second introduction part d2, a fluid pressure imparting mechanism p1, a second fluid supply part p2, and a case 3.

Illustration of the rotation drive member is omitted.

At least one of the first processing member 10 and the second processing member 20 is able to approach to and separate from each other, and the processing surfaces 1 and 2 are able to approach to and separate from each other.

In this embodiment, the second processing member 20 approaches to and separates from the first processing member 10. On the contrary, the first processing member 10 may approach to and separate from the second processing member 20, or both the processing members 10 and 20 may approach to and separate from each other.

The second processing member 20 is disposed over the first processing member 10, and the lower surface of the second processing member 20 serves as the second processing surface 2, and the upper surface of the first processing member 10 serves as the first processing surface 1.

As shown in FIG. 1(A), the first processing member 10 and the second processing member 20 in this embodiment are circular bodies, that is, rings. Hereinafter, the first processing member 10 is referred to as a first ring 10, and the second processing member 20 as a second ring 20.

Both the rings 10 and 20 in this embodiment are metallic members having, at one end, a mirror-polished surface, respectively, and their mirror-polished surfaces are referred to as the first processing surface 1 and the second processing surface 2, respectively. That is, the upper surface of the first ring 10 is mirror-polished as the first processing surface 1, and the lower surface of the second ring is mirror-polished as the second processing surface 2.

At least one of the holders can rotate relative to the other holder by the rotation drive member. In FIG. 1(A), numerical 50 indicates a rotary shaft of the rotation drive member. The rotation drive member may use an electric motor. By the rotation drive member, the processing surface of one ring can rotate relative to the processing surface of the other ring.

In this embodiment, the first holder 11 receives drive power on the rotary shaft 50 from the rotation drive member and rotates relative to the second holder 21, whereby the first ring 10 integrated with the first holder 11 rotates relative to the second ring 20. Inside the first ring 10, the rotary shaft 50 is disposed in the first holder 11 so as to be concentric, in a plane, with the center of the circular first ring 10.

The first ring 10 rotates centering on the shaft center of the ring 10. The shaft center (not shown) is a virtual line referring to the central line of the ring 10.

In this embodiment, as described above, the first holder 11 holds the first ring 10 such that the first processing surface 1 of the first ring 10 is directed upward, and the second holder 21 holds the second ring 20 such that the second processing surface 2 of the second ring 20 is directed downward.

Specifically, the first and second holders 11 and 21 include a ring-accepting concave part, respectively. In this embodiment, the first ring 10 is fitted in the ring-accepting part of the first holder 11, and the first ring 10 is fixed in the ring-accepting part so as not to rise from, and set in, the ring-accepting part of the first holder 11.

That is, the first processing surface 1 is exposed from the first holder 11 and faces the second holder 21.

Examples of the material for the first ring 10 include metal, ceramics, sintered metal, abrasion-resistant steel, metal subjected to hardening treatment, and rigid materials subjected to lining, coating or plating. Particularly, the first processing member 10 is preferably formed of a lightweight material for rotation. A material for the second ring 20 may be the same as that for the first ring 10.

On the other hand, the ring-accepting part 41 arranged in the second holder 21 accepts the processing member 2 of the second ring 20 such that the processing member can rise and set.

The ring-accepting part 41 of the second holder 21 is a concave portion for mainly accepting that side of the second ring 20 opposite to the processing surface 2, and this concave portion is a groove which has been formed into a circle when viewed in a plane.

The ring-accepting part 41 is formed larger in size than the second ring 20 and accepts the second ring 20 with sufficient clearance between itself and the second ring 20.

By this clearance, the second ring 20 in the ring-accepting part 41 can be displaced not only in the axial direction of the circular ring-accepting part 41 but also in a direction perpendicular to the axial direction. In other words, the second ring 20 can, by this clearance, be displaced relative to the ring-accepting part 41 to make the central line of the ring 20 unparallel to the axial direction of the ring-accepting part 41.

Hereinafter, that portion of the second holder 21 which is surrounded by the second ring 20 is referred to as a central portion 22.

In other words, the second ring 20 is displaceably accepted within the ring-accepting part 41 not only in the thrust direction of the ring-accepting part 41, that is, in the direction in which the ring 20 rises from and sets in the part 41, but also in the decentering direction of the ring 20 from the center of the ring-accepting part 41. Further, the second ring 20 is accepted in the ring-accepting part 41 such that the ring 20 can be displaced (i.e. run-out) to vary the width between itself upon rising or setting and the ring-accepting part 41, at each position in the circumferential direction of the ring 20.

The second ring 20, while maintaining the degree of its move in the above three directions, that is, the axial direction, decentering direction and run-out direction of the second ring 20 relative to the ring-accepting part 41, is held on the second holder 21 so as not to follow the rotation of the first ring 10. For this purpose, suitable unevenness (not shown) for regulating rotation in the circumferential direction of the ring-accepting part 41 may be arranged both in the ring-accepting part 41 and in the second ring 20. However, the unevenness should not deteriorate displacement in the degree of its move in the three directions.

The surface-approaching pressure imparting mechanism 4 supplies the processing members with a force exerted in the direction of approaching the first processing surface 1 and the second processing surface 2 each other. In this embodiment, the surface-approaching pressure imparting mechanism 4 is disposed in the second holder 21 and biases the second ring 20 toward the first ring 10.

The surface-approaching pressure imparting mechanism 4 uniformly biases each position in the circumferential direction of the second ring 20, that is, each position of the processing surface 2, toward the first ring 10. A specific structure of the surface-approaching pressure imparting mechanism 4 will be described later.

As shown in FIG. 1(A), the case 3 is arranged outside the outer circumferential surfaces of both the rings 10 and 20, and accepts a product formed between the processing surfaces 1 and 2 and discharged to the outside of both the rings 10 and 20. As shown in FIG. 1(A), the case 3 is a liquid-tight container for accepting the first holder 10 and the second holder 20. However, the second holder 20 may be that which as a part of the case, is integrally formed with the case 3.

As described above, the second holder 21 whether formed as a part of the case 3 or formed separately from the case 3 is not movable so as to influence the distance between both the rings 10 and 20, that is, the distance between the processing surfaces 1 and 2. In other words, the second holder 21 does not influence the distance between the processing surfaces 1 and 2.

The case 3 is provided with an outlet 32 for discharging a product to the outside of the case 3.

The first introduction part d1 supplies a first fluid to the space between the processing surfaces 1 and 2.

The fluid pressure imparting mechanism p1 is connected directly or indirectly to the first introduction part d1 to impart fluid pressure to the first processed fluid. A compressor or a pump can be used in the fluid pressure imparting mechanism p1.

In this embodiment, the first introduction part d1 is a fluid path arranged inside the central portion 22 of the second holder 21, and one end of the first introduction part d1 is open at the central position of a circle, when viewed in a plane, of the second ring 20 on the second holder 21. The other end of the first introduction part d1 is connected to the fluid pressure imparting mechanism p1 outside the second holder 20, that is, outside the case 3.

The second introduction part d2 supplies a second fluid to be mixed with the first fluid to the space between the processing surfaces 1 and 2. In this embodiment, the second introduction part is a fluid passage arranged inside the second ring 20, and one end of the second introduction part is open at the side of the second processing surface 2, and a second fluid-feeding part p2 is connected to the other end.

A compressor or a pump can be used in the second fluid-feeding part p2.

The first processed fluid pressurized with the fluid pressure imparting mechanism p1 is introduced from the first introduction part d1 to the space between the rings 10 and 20 and will pass through the space between the first processing surface 1 and the second processing surface 2 to the outside of the rings 10 and 20.

At this time, the second ring 20 receiving the supply pressure of the first fluid stands against the bias of the surface-approaching pressure imparting mechanism 4, thereby receding from the first ring 10 and making a minute space between the processing surfaces. The space between both the processing surfaces 1 and 2 by approach and separation of the surfaces 1 and 2 will be described in detail later.

A second fluid is supplied from the second introduction part d2 to the space between the processing surfaces 1 and 2, flows into the first fluid, and is subjected to a mixing (reaction) promoted by rotation of the processing surface. Then, a reaction product formed by the mixing (reaction) of both the fluids is discharged from the space between the processing surfaces 1 and 2 to the outside of the rings 10 and 20. The product discharged to the outside of the rings 10 and 20 is discharged finally through the outlet of the case to the outside of the case (self-discharge).

The mixing and reaction (when the mixing is accompanied by reaction) of the processed fluid are effected between the first processing surface 1 and the second processing surface 2 by rotation, relative to the second processing member 20, of the first processing member 10 with the drive member 5.

Between the first and second processing surfaces 1 and 2, a region downstream from an opening m2 of the second introduction part d2 serves as a processing chamber where the first and second processed fluids are mixed with each other. Specifically, as shown in FIG. 11(C) illustrating a bottom face of the second ring 20, a region H shown by oblique lines, outside the second opening m2 of the second introduction part in the radial direction r1 of the second ring 20, serves as the processing chamber. Accordingly, this processing chamber is located downstream from the openings m1 and m2 of the first introduction part d1 and the second introduction part d2 between the processing surfaces 1 and 2.

The first fluid introduced from the first opening m1 through a space inside the ring into the space between the processing surfaces 1 and 2, and the second fluid introduced from the second opening m2 into the space between the processing surfaces 1 and 2, are mixed with each other in the region H serving as the reaction chamber, and if the mixing is accompanied by reaction, both the processed fluids are reacted with each other. The fluid will, upon receiving supply pressure from the fluid pressure imparting mechanism p1, move through the minute space between the processing surfaces 1 and 2 to the outside of the rings, but because of rotation of the first ring 10, the fluid mixed in the reaction region H does not move linearly from the inside to the outside of the rings in the radial direction, but moves from the inside to the outside of the ring spirally around the rotary shaft of the ring when the processing surfaces are viewed in a plane. In the region H where the fluids are thus mixed (reacted), the fluids can move spirally from inside to outside to secure a zone necessary for sufficient mixing (reaction) in the minute space between the processing surfaces 1 and 2, thereby promoting their uniform reaction.

The product formed by the mixing (reaction) becomes a uniform reaction product in the minute space between the first processing surface 1 and the second processing surface 2 and appears as microparticles particularly in the case of crystallization or separation.

By the balance among at least the supply pressure applied by the fluid pressure imparting mechanism p1, the bias of the surface-approaching pressure imparting mechanism 4, and the centrifugal force resulting from rotation of the ring, the distance between the processing surfaces 1 and 2 can be balanced to attain a preferable minute space, and further the processed fluid receiving the supply pressure applied by the fluid pressure imparting mechanism p1 and the centrifugal force by rotation of the ring moves spirally in the minute space between the processing surfaces 1 and 2, so that their mixing (reaction) is promoted.

The mixing (reaction) is forcedly effected by the supply pressure applied by the fluid pressure imparting mechanism p1 and the rotation of the ring. That is, the mixing (reaction) occurs under forced uniform mixing between the processing surfaces 1 and 2 arranged opposite to each other so as to be able to approach to and separate from each other, at least one of which rotates relative to the other.

Accordingly, the crystallization and separation of the product formed by the reaction can be regulated by relatively easily controllable methods such as regulation of supply pressure applied by the fluid pressure imparting mechanism p1 and regulation of the rotation speed of the ring, that is, the number of rotations of the ring.

As described above, this fluid processing apparatus is excellent in that the space between the processing surfaces 1 and 2, which can exert influence on the size of a product, and the distance in which the processed fluid moves in the region H, which can exert influence on formation of a uniform product, can be regulated by the supply pressure and the centrifugal force.

The reaction processing gives not only deposit of the product but also liquids. When the product is fine mass such as microparticles, it may be a deposit in the fluid after processing or may be in a dispersion state in which a dispersed phase is present in a continuous phase.

The rotary shaft 50 is not limited to the vertically arranged one and may be arranged in the horizontal direction or arranged at a slant. This is because during processing, the reaction occurs in such a minute space between the processing surfaces 1 and 2 that the influence of gravity can be substantially eliminated.

In FIG. 1(A), the first introduction part d1 extends vertically and coincides with the shaft center of the second ring 20 in the second holder 21. However, the first introduction part d1 is not limited to the one having a center coinciding with the shaft center of the second ring 20 and may be arranged in other positions in the central portion 22 of the second holder 21 as long as the first fluid can be supplied into the space surrounded by the rings 10 and 20, and the first introduction part d1 may extend obliquely as well as vertically.

Figure 12A:
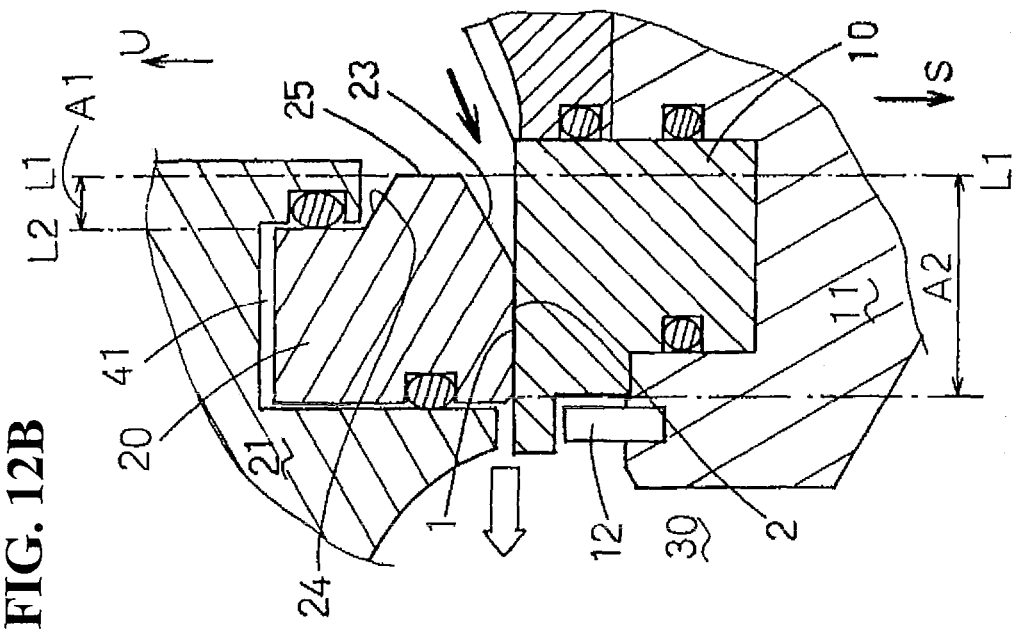
FIG. 12(A) is a schematic vertical sectional view showing an important part of another embodiment of a pressure-receiving surface in the apparatus shown in FIG. 1(A)

A more preferable embodiment of the apparatus is shown in FIG. 12(A). As shown in this figure, the second processing member 20 has the second processing surface 2 and a pressure-receiving surface 23 which is positioned inside, and situated next to, the second processing surface 2. Hereinafter, the pressure-receiving surface 23 is also referred to as a separation-regulating surface 23. As shown in the figure, the separation regulating surface 23 is an inclined surface.

As described above, the ring-accepting part 41 is formed in the bottom (i.e. a lower part) of the second holder 21, and the second processing member 20 is accepted in the ring-accepting part 41. The second processing member 20 is accepted by the second holder 21 so as not to be rotated with a baffle (not shown). The second processing surface 2 is exposed from the second holder 21.

In this embodiment, a material to be processed is introduced inside the first processing member 10 and the second processing member 20 between the processing surfaces 1 and 2, and the processed material is discharged to the outside of the first processing member 10 and the second processing member 20.

The surface-approaching pressure imparting mechanism 4 presses by pressure the second processing surface 2 against the first processing surface 1 to make them contacted with or close to each other, and generates a fluid film of predetermined thickness by the balance between the surface-approaching pressure and the force, e.g. fluid pressure, of separating the processing surfaces 1 and 2 from each other. In other words, the distance between the processing surfaces 1 and 2 is kept in a predetermined minute space by the balance between the forces.

Specifically, the surface-approaching pressure imparting mechanism 4 in this embodiment is comprised of the ring-accepting part 41, a spring-accepting part 42 arranged in the depth of the ring-accepting part 41, that is, in the deepest part of the ring-accepting part 41, a spring 43, and an air introduction part 44.

However, the surface-approaching pressure imparting mechanism 4 may be the one including at least one member selected from the ring-accepting part 41, the spring-accepting part 42, the spring 43, and the air introduction part 44.

The ring-accepting part 41 has the second processing member 20 fit into it with play to enable the second processing member 20 to be displaced vertically deeply or shallowly, that is, vertically in the ring-accepting part 41.

One end of the spring 43 is abutted against the depth of the spring-accepting part 42, and the other end of the spring 43 is abutted against the front (i.e., the upper part) of the second processing member 20 in the ring-accepting part 41. In FIG. 1, only one spring 43 is shown, but a plurality of springs 44 are preferably used to press various parts of the second processing member 20. This is because as the number of the springs 43 increases, pressing pressure can be given more uniformly to the second processing member 20. Accordingly, several to a few dozen springs 43 comprising a multi-spring type preferably attach to the second holder 21.

In this embodiment, air can be introduced through the air introduction part 44 into the ring-accepting part 41. By such introduction of air, air pressure together with pressure by the spring 43 can be given as pressing pressure from the space, as a pressurizing chamber, between the ring-accepting part 41 and the second processing member 20 to the second processing member 20. Accordingly, adjusting the pressure of air introduced through the air introduction part 44 can regulate the surface-approaching pressure of the second processing surface 2 toward the first processing surface 1 during operation. A mechanism of generating pressing pressure with another fluid pressure such as oil pressure can be utilized in place of the air introduction part 44 utilizing air pressure.

The surface-approaching pressure imparting mechanism 4 not only supplies and regulates a part of the pressing pressure, that is, the surface-approaching pressure, but also serves as a displacement regulating mechanism and a buffer mechanism.

Specifically, the surface-approaching pressure imparting mechanism 4 as a displacement regulating mechanism can maintain initial pressing pressure by regulating air pressure against the change in the axial direction caused by elongation or abrasion at the start of or in the operation. As described above, the surface-approaching pressure imparting mechanism 4 uses a floating mechanism of maintaining the second processing member 20 so as to be displaced, thereby also functioning as a buffer mechanism for micro-vibration or rotation alignment.

Now, the state of the thus constituted processing apparatus during use is described with reference to FIG. 1(A).

At the outset, a first processed fluid is pressurized with the fluid pressure imparting mechanism p1 and introduced through the first introduction part d1 into the internal space of the sealed case. On the other hand, the first processing member 10 is rotated with the rotation of the rotary shaft 50 by the rotation drive member. The first processing surface 1 and the second processing surface 2 are thereby rotated relatively with a minute space kept therebetween.

The first processed fluid is formed into a fluid film between the processing surfaces 1 and 2 with a minute space kept therebetween, and a second processed fluid which is introduced through the second introduction part d2 flows into the fluid film between the processing surfaces 1 and 2 to comprise a part of the fluid film. By this, the first and second processed fluids are mixed with each other to form a reaction product. When the mixing is accompanied by reaction, a uniform reaction of both of the fluids being reacted with each other is promoted to form a reaction product. When the reaction is accompanied by separation, relatively uniform and fine particles can be formed. Even when the reaction is not accompanied by separation, a uniform mixing (uniform reaction when the mixing is accompanied by reaction) can be realized. The separated product may be further finely pulverized by shearing between the first processing surface 1 and the second processing surface 2 with the rotation of the first processing surface 1. The first processing surface 1 and the second processing surface 2 are regulated to form a minute space of 1 µm to 1 mm, particularly 1 µm to 10 µm, thereby realizing a uniform mixing (uniform reaction when the mixing is accompanied by reaction) and enabling formation of superfine particles of several nm in diameter.

The product is discharged from the processing surfaces 1 and 2 through an outlet 33 of the case 3 to the outside of the case. The discharged product is atomized in a vacuum or depressurized atmosphere with a well-known decompression device and converted into liquid in the atmosphere to hit each other, then what trickled down in the liquid is able to be collected as degassed liquid.

In this embodiment, the processing apparatus is provided with a case, but may be carried out without a case. For example, a decompression tank for degassing, that is, a vacuum tank, is arranged, and the processing apparatus may be arranged in this tank. In this case, the outlet mentioned above is naturally not arranged in the processing apparatus.

As described above, the first processing surface 1 and the second processing surface 2 can be regulated to form a minute space in the order of µm which cannot be formed by arranging mechanical clearance. Now, this mechanism is described.

The first processing surface 1 and the second processing surface 2 are capable of approaching to and separating from each other, and simultaneously rotate relative to each other. In this example, the first processing surface 1 rotates, and the second processing surface 2 approaches to and separates from the first processing surface with a structure capable of moving in the axial direction (floating structure).

In this example, therefore, the position of the second processing surface 2 in the axial direction is arranged accurately in the order of µm by the balance between forces, that is, the balance between the surface-approaching pressure and the separating pressure, thereby establishing a minute space between the processing surfaces 1 and 2.

As shown in FIG. 12(A), the surface-approaching pressure includes the pressure by air pressure (positive pressure) from the air introduction part 44 by the surface-approaching pressure imparting mechanism 4, the pressing pressure with the spring 43, and the like.

Figure 13:
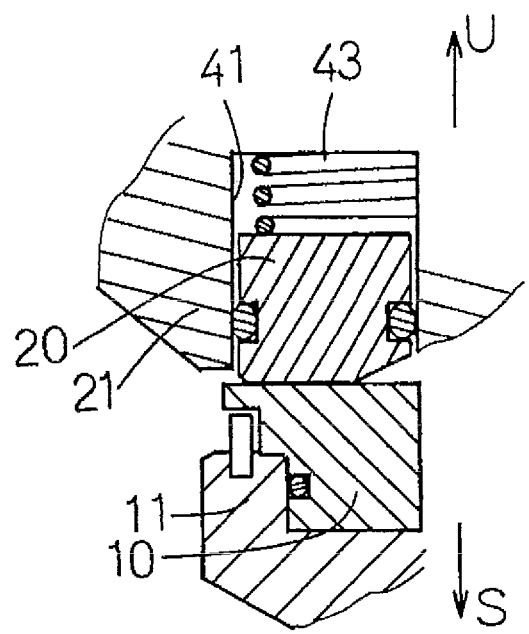
FIG. 13 is a schematic vertical sectional view showing an important part of another embodiment of a surface-approaching pressure imparting mechanism 4 in the apparatus shown in FIG. 12(A).
Figure 14:
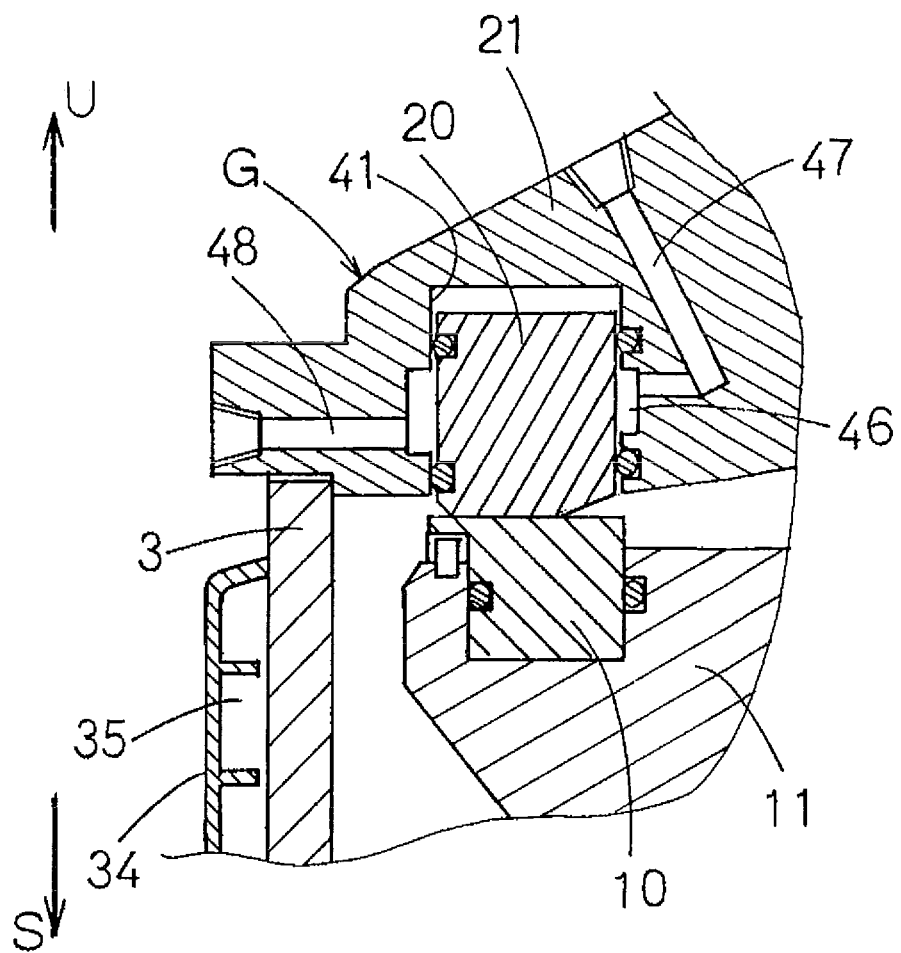
FIG. 14 is a schematic vertical sectional view showing an important part of another embodiment of the apparatus shown in FIG. 12(A), which is provided with a temperature regulating jacket.
Figure 15:
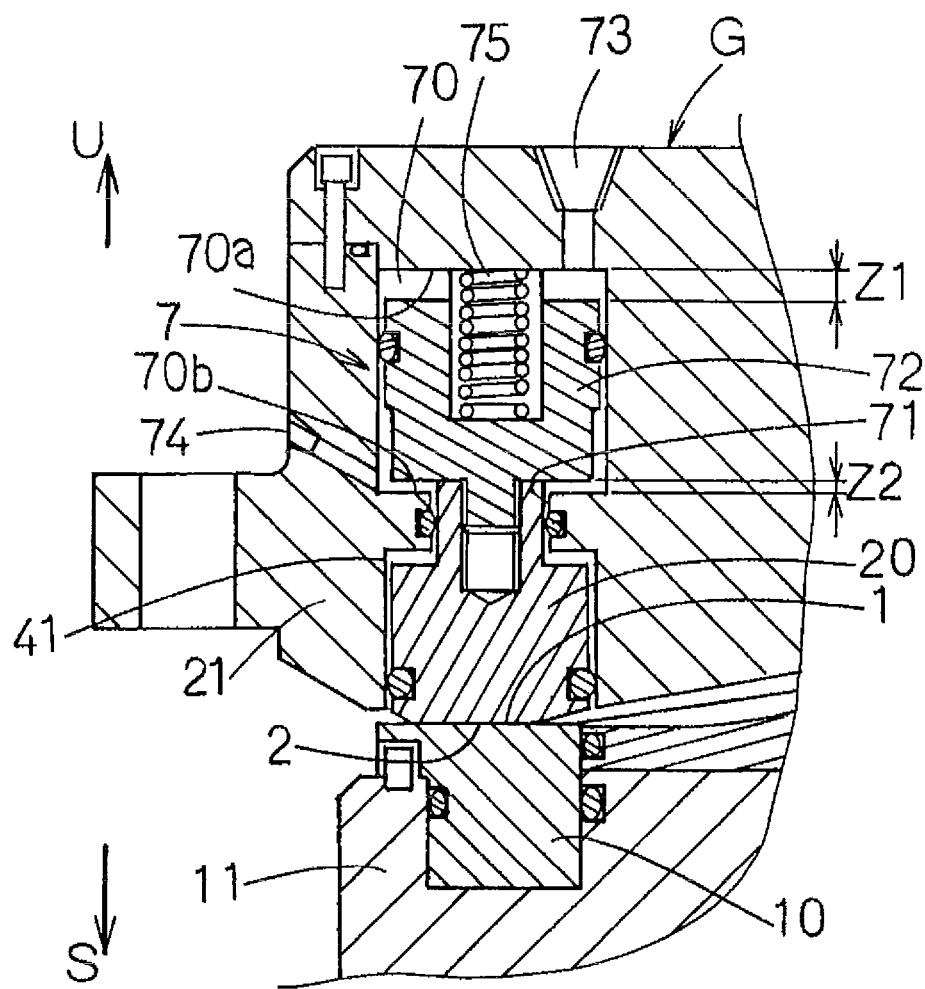
FIG. 15 is a schematic vertical sectional view showing an important part of still another embodiment of the surface-approaching pressure imparting mechanism 4 in the apparatus shown in FIG. 12(A).

The embodiments shown in FIG. 13 to FIG. 15 are shown by omitting the second introduction part d2 to simplify the drawings. In this respect, these drawings may be assumed to show sections at a position not provided with the second introduction part d2. In the figures, U and S show upward and downward directions respectively.

On the other hand, the separating force include the fluid pressure acting on the pressure-receiving surface at the separating side, that is, on the second processing surface 2 and the separation regulating surface 23, the centrifugal force resulting from rotation of the first processing member 1, and the negative pressure when negative pressure is applied to the air introduction part 44.

When the apparatus is washed, the negative pressure applied to the air introduction part 44 can be increased to significantly separate the processing surfaces 1 and 2 from each other, thereby facilitating washing.

By the balance among these forces, the second processing surface 2 while being remote by a predetermined minute space from the first processing surface 1 is stabilized, thereby realizing establishment with accuracy in the order of μm.

The separating force is described in more detail.

With respect to fluid pressure, the second processing member 20 in a closed flow path receives feeding pressure of a processed fluid, that is, fluid pressure, from the fluid pressure imparting mechanism p. In this case, the surfaces opposite to the first processing surface in the flow path, that is, the second processing surface 2 and the separation regulating surface 23, act as pressure-receiving surfaces at the separating side, and the fluid pressure is applied to the pressure-receiving surfaces to generate a separating force due to the fluid pressure.

With respect to centrifugal force, the first processing member 10 is rotated at high speed, centrifugal force is applied to the fluid, and a part of this centrifugal force acts as a separating force in the direction in which the processing surfaces 1 and 2 are separated from each other.

When negative pressure is applied from the air introduction part 44 to the second processing member 20, the negative pressure acts as a separating force.

In the foregoing description of the present invention, the force of separating the first and second processing surfaces 1 and 2 from each other has been described as a separating force, and the above-mentioned force is not excluded from the separating force.

By forming a balanced state of the separating force and the surface-approaching pressure applied by the surface-approaching pressure imparting mechanism 4 via the processed fluid between the processing surfaces 1 and 2 in the flow path of the closed processed fluid, a uniform mixing (uniform reaction when the mixing is accompanied by reaction) is realized between the processing surfaces 1 and 2, and simultaneously a fluid film suitable for crystallization and separation of microscopic products is formed as described above. In this manner, this apparatus can form a forced fluid film between the processing surfaces 1 and 2 via which a minute space not achievable with a conventional mechanical apparatus can be kept between the processing surfaces 1 and 2, and microparticles can be formed highly accurately as the reaction product.

In other words, the thickness of the fluid film between the processing surfaces 1 and 2 is regulated as desired by regulating the separating force and surface-approaching pressure, thereby realizing a necessary uniform mixing (uniform reaction when the mixing is accompanied by reaction) to form and process microscopic products. Accordingly, when the thickness of the fluid film is to be decreased, the surface-approaching pressure or separating force may be regulated such that the surface-approaching pressure is made relatively higher than the separating force. When the thickness of the fluid film is to be increased, the separating force or surface-approaching pressure may be regulated such that the separating force is made relatively higher than the surface-approaching pressure.

When the surface-approaching pressure is increased, air pressure, that is, positive pressure is applied from the air introduction part 44 by the surface-approaching pressure imparting mechanism 4, or the spring 43 is changed to the one having higher pressing pressure, or the number of the springs may be increased.

When the separating force is to be increased, the feeding pressure of the fluid pressure imparting mechanism p1 is increased, or the area of the second processing surface 2 or the separation regulating surface 23 is increased, or in addition, the rotation of the second processing member 20 is regulated to increase centrifugal force or reduce pressure from the air introduction part 44. Alternatively, negative pressure may be applied. The spring 43 shown is a pressing spring that generates pressing pressure in an extending direction, but may be a pulling spring that generates a force in a compressing direction to constitute a part or the whole of the surface-approaching pressure imparting mechanism 4.

When the separating force is to be decreased, the feeding pressure of the fluid pressure imparting mechanism p1 is reduced, or the area of the second processing surface 2 or the separation regulating surface 23 is reduced, or in addition, the rotation of the second processing member 20 is regulated to decrease centrifugal force or increase pressure from the air introduction part 44. Alternatively, negative pressure may be reduced.

Further, properties of a processed fluid, such as viscosity, can be added as a factor for increasing or decreasing the surface-approaching pressure and separating force, and regulation of such properties of a processed fluid can be performed as regulation of the above factor.

In the separating force, the fluid pressure exerted on the pressure-receiving surface at the separating side, that is, the second processing surface 2 and the separation regulating surface 23 is understood as a force constituting an opening force in mechanical seal.

In the mechanical seal, the second processing member 20 corresponds to a compression ring, and when fluid pressure is applied to the second processing member 2, the force of separating the second processing member 2 from the first processing member 1 is regarded as an opening force.

More specifically, when the pressure-receiving surfaces at a separating side, that is, the second processing surface 2 and the separation regulating surface 23 only are arranged in the second processing member 20 as shown in the first embodiment, all feeding pressure constitutes the opening force. When a pressure-receiving surface is also arranged at the backside of the second processing member 20, specifically in the case of FIG. 12(B) and FIG. 17 described later, the difference between the feeding pressure acting as a separating force and the feeding pressure acting as surface-approaching pressure is the opening force.

Now, other embodiments of the second processing member 20 are described with reference to FIG. 12(B).

Figure 12B:
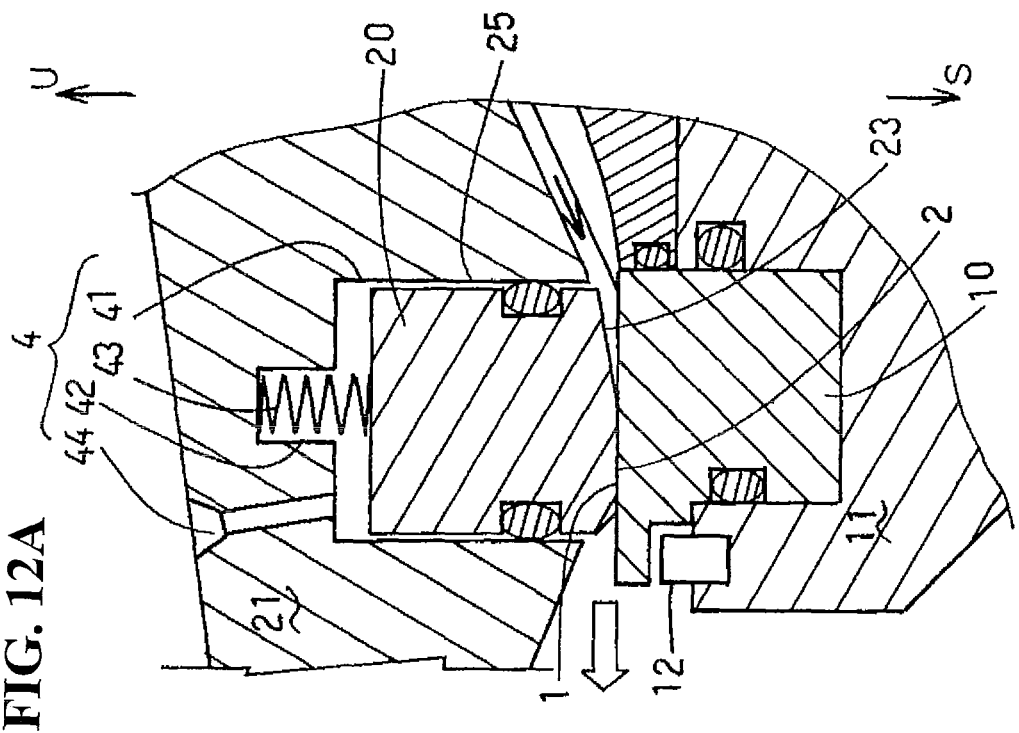
FIG. 12(B) is a schematic vertical sectional view showing an important part of still another embodiment of the apparatus.

As shown in FIG. 12(B), an approach regulating surface 24 facing upward, that is, at the other side of the second processing surface 2, is disposed at the inner periphery of the second processing member 20 exposed from the ring-accepting part 41.

That is, the surface-approaching pressure imparting mechanism 4 in this embodiment is comprised of a ring-accepting part 41, an air introduction part 44, and the approach regulating surface 24. However, the surface-approaching pressure imparting mechanism 4 may be one including at least one member selected from the ring-accepting part 41, the spring-accepting part 42, the spring 43, the air introduction part 44, and the approach regulating surface 24.

The approach regulating surface 24 receives predetermined pressure applied to a processed fluid to generate a force of approaching the second processing surface 2 to the first processing surface 1, thereby functioning in feeding surface-approaching pressure as a part of the surface-approaching pressure imparting mechanism 4. On the other hand, the second processing surface 2 and the separation regulating surface 23 receive predetermined pressure applied to a processed fluid to generate a force of separating the second processing surface 2 from the first processing surface 1, thereby functioning in feeding a part of the separating force.

The approach regulating surface 24, the second processing surface 2 and the separation regulating surface 23 are pressure-receiving surfaces receiving feeding pressure of the processed fluid, and depending on its direction, exhibits different actions, that is, generation of the surface-approaching pressure and generation of a separating force.

The ratio (area ratio A1/A2) of a projected area A1 of the approach regulating surface 24 projected on a virtual plane perpendicular to the direction of approaching and separating the processing surfaces, that is, in the direction of rising and setting of the second ring 20, to a total area A2 of the projected area of the second processing surface 2 and the separating side pressure-receiving surface 23 of the second processing member 20 projected on the virtual plane is called balance ratio K which is important for regulation of the opening force. Both the top of the approach regulating surface 24 and the top of the separating side pressure-receiving surface 23 are defined by the inner periphery 25 of the circular second regulating part 20, that is, by top line L1. Accordingly, the balance ratio K is regulated for deciding the place where base line L2 of the approach regulating surface 24 is to be placed.

That is, in this embodiment, when the feeding pressure of the processed fluid is utilized as an opening force, the total projected area of the second processing surface 2 and the separation regulating surface 23 is made larger than the projected area of the approach regulating surface 24, thereby generating an opening force in accordance with the area ratio.

The opening force can be regulated by the pressure of the processed fluid, that is, the fluid pressure, by changing the balance line, that is, by changing the area A1 of the approach regulating surface 24.

Sliding surface actual surface pressure P, that is, the fluid pressure out of the surface-approaching pressure, is calculated according to the following equation:

$$P = P1 \times (K-k) + Ps$$

wherein P1 represents the pressure of a processed fluid, that is, fluid pressure, K represents the balance ratio, k represents an opening force coefficient, and Ps represents a spring and back pressure.

By regulating this balance line to regulate the sliding surface actual surface pressure P, the space between the processing surfaces 1 and 2 is formed as a desired minute space, thereby forming a fluid film of a processed fluid to make the product minute and effecting uniform mixing (reaction) processing.

Usually, as the thickness of a fluid film between the processing surfaces 1 and 2 is decreased, the product can be made finer. On the other hand, as the thickness of the fluid film is increased, processing becomes rough and the throughput per unit time is increased. By regulating the sliding surface actual surface pressure P on the sliding surface, the space between the processing surfaces 1 and 2 can be regulated to realize the desired uniform mixing (uniform reaction when the mixing is accompanied by reaction) and to give the minute product. Hereinafter, the sliding surface actual surface pressure P is referred to as surface pressure P.

From this relation, it is concluded that when the product is to be made coarse, the balance ratio may be decreased, the surface pressure P may be decreased, the space may be increased and the thickness of the film may be increased. On the other hand, when the product is to be made finer, the balance ratio K may be increased, the surface pressure P may be increased, the space may be decreased and the thickness of the film may be decreased.

As a part of the surface-approaching pressure imparting mechanism 4, the approach regulating surface 24 is formed, and at the position of the balance line, the surface-approaching pressure may be regulated, that is, the space between the processing surfaces may be regulated.

As described above, the space is regulated in consideration of the pressing pressure of the spring 43 and the air pressure of the air introduction part 44. Regulation of the fluid pressure, that is, the feeding pressure of the processed fluid, and regulation of the rotation of the first processing member 10 for regulating centrifugal force, that is, the rotation of the first holder 11, are also important factors to regulate the space.

As described above, this apparatus is constituted such that for the second processing member 20 and the first processing member 10 that rotates relative to the second processing member 20, a predetermined fluid film is formed between the processing surfaces by pressure balance among the feeding pressure of the processed fluid, the rotation centrifugal force, and the surface-approaching pressure. At least one of the rings is formed in a floating structure by which alignment such as run-out is absorbed to eliminate the risk of abrasion and the like.

The embodiment shown in FIG. 1(A) also applies to the embodiment in FIG. 12(B) except that the regulating surface is arranged.

Figure 17:
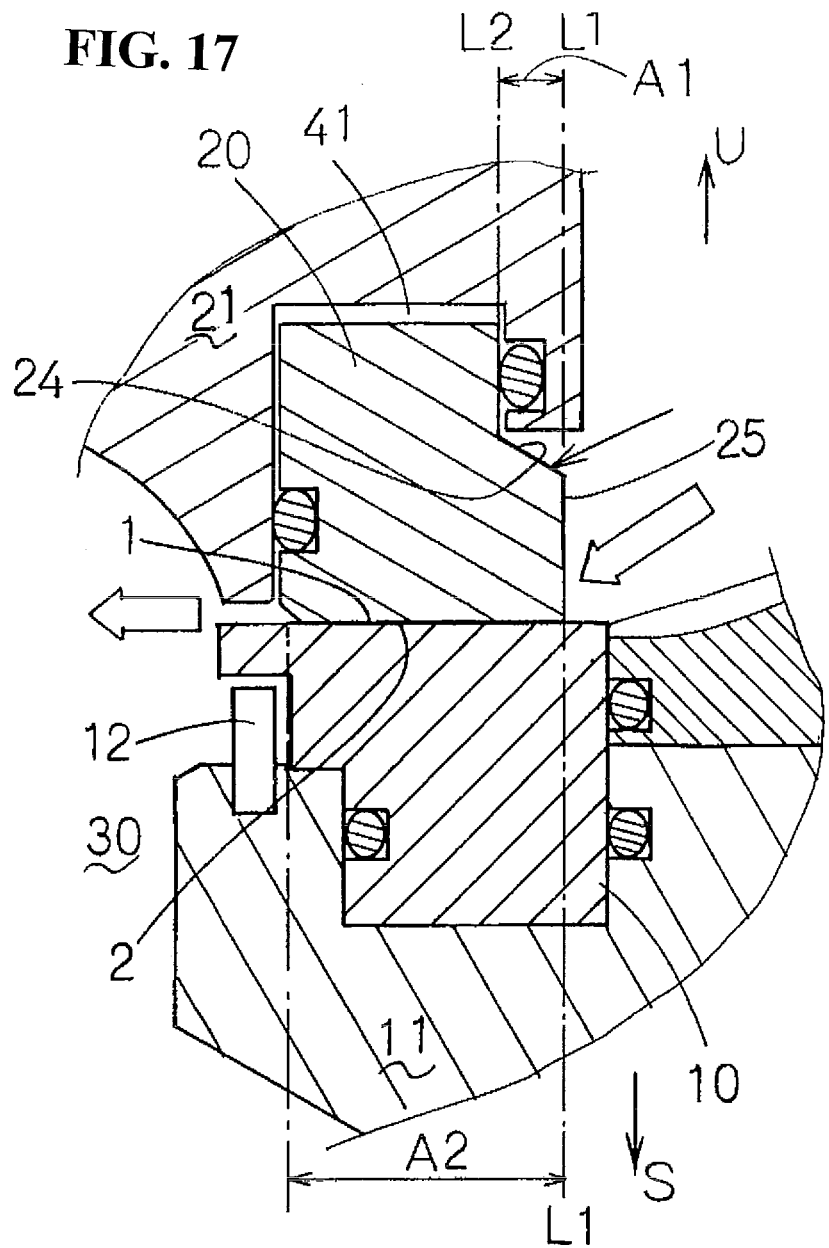
FIG. 17 is a schematic vertical sectional view showing an important part of still another embodiment of the apparatus shown in FIG. 12(A).

The embodiment shown in FIG. 12(B) can be carried out without arranging the pressure-receiving surface 23 on the separating side, as shown in FIG. 17.

When the approach regulating surface 24 is arranged as shown in the embodiment shown in FIG. 12(B) and FIG. 17, the area A1 of the approach regulating surface 24 is made larger than the area A2, whereby all of the predetermined pressure exerted on the processed fluid functions as surface-approaching pressure, without generating an opening force. This arrangement is also possible, and in this case, both the processing surfaces 1 and 2 can be balanced by increasing other separating force.

With the area ratio described above, the force acting in the direction of separating the second processing surface 2 from the first processing surface 1 is fixed as the resultant force exerted by the fluid.

In this embodiment, as described above, the number of the springs 43 is preferably larger in order to impart uniform stress on the sliding surface, that is, the processing surface. However, the spring 43 may be a single coil-type spring as shown in FIG. 13. As shown in the figure, this spring is a single coil spring having a center concentric with the circular second processing member 20.

The space between the second processing member 20 and the second holder 21 is sealed air-tightly with methods well known in the art.

As shown in FIG. 14, the second holder 21 is provided with a temperature regulation jacket 46 capable of regulating the temperature of the second processing member 20 by cooling or heating. Numerical 3 in FIG. 14 is the above-mentioned case, and the case 3 is also provided with a jacket 35 for the same purpose of temperature regulation.

The temperature regulation jacket 46 for the second holder 21 is a water-circulating space formed at a side of the ring-accepting part 41 and communicates with paths 47 and 48 leading to the outside of the second holder 21. One of the paths 47 and 48 introduces a cooling or heating medium into the temperature regulation jacket 46, and the other discharges the medium.

The temperature regulation jacket 35 for the case 3 is a path for passing heating water or cooling water, which is arranged between outer periphery of the case 3 and a covering part 34 for covering the outer periphery of the case 3.

In this embodiment, the second holder 21 and the case 3 are provided with the temperature regulation jacket, but the first holder 11 can also be provided with such a jacket.

As a part of the surface-approaching pressure imparting mechanism 4, a cylinder mechanism 7 shown in FIG. 15 may be arranged besides the members described above.

The cylinder mechanism 7 includes a cylinder space 70 arranged in the second holder 21, a communicating part 71 that communicates the cylinder space 70 with the ring-accepting part 41, a piston 72 that is accepted in the cylinder space 70 and connected via the communication part 71 to the second processing member 20, a first nozzle 73 that communicates to the upper part of the cylinder space 70, a second nozzle 74 in a lower part of the cylinder space 70, and a pressing body 75 such as spring between the upper part of the cylinder space 70 and the piston 72.

The piston 72 can slide vertically in the cylinder space 70, and the second processing member 20 can slide vertically with sliding of the piston 72, to change the gap between the first processing surface 1 and the second processing surface 2.

Although not shown in the figure, specifically, a pressure source such as a compressor is connected to the first nozzle 73, and air pressure, that is, positive pressure is applied from the first nozzle 73 to the upper part of the piston 72 in the cylinder space 70, thereby sliding the piston 72 downward, to allow the second processing member 20 to narrow the gap between the first and second processing surfaces 1 and 2. Although not shown in the figure, a pressure source such as a compressor is connected to the second nozzle 74, and air pressure, that is, positive pressure is applied from the second nozzle 74 to the lower part of the piston 72 in the cylinder space 70, thereby sliding the piston 72 upward, to allow the second processing member 20 to widen the gap between the first and second processing surfaces 1 and 2, that is, to enable it to move in the direction of opening the gap. In this manner, the surface-approaching pressure can be regulated by air pressure with the nozzles 73 and 74.

Even if there is a space between the upper part of the second processing member 20 in the ring-accepting part 41 and the uppermost part of the ring-accepting part 41, the piston 7 is arranged so as to abut against an uppermost part 70a of the cylinder space 70, whereby the uppermost part 70a of the cylinder space 70 defines the upper limit of the width of the gap between the processing surfaces 1 and 2. That is, the piston 7 and the uppermost part 70a of the cylinder space 70 function as a separation preventing part for preventing the separation of the processing surfaces 1 and 2 from each other, in other words, function in regulating the maximum opening of the gap between both the processing surfaces 1 and 2.

Even if the processing surfaces 1 and 2 do not abut on each other, the piston 7 is arranged so as to abut against a lowermost part 70b of the cylinder space 70, whereby the lowermost part 70b of the cylinder space 70 defines the lower limit of the width of the gap between the processing surfaces 1 and 2. That is, the piston 7 and the lowermost part 70b of the cylinder space 70 function as an approach preventing part for preventing the approaching of the processing surfaces 1 and 2 each other, in other words, function in regulating the minimum opening of the gap between both the processing surfaces 1 and 2.

In this manner, the maximum and minimum openings of the gap are regulated, while a distance z1 between the piston 7 and the uppermost part 70a of the cylinder space 70, in other words, a distance z2 between the piston 7 and the lowermost part 70b of the cylinder space 70, is regulated with air pressure by the nozzles 73 and 74.

The nozzles 73 and 74 may be connected to a different pressure source respectively, and further may be connected to a single pressure source alternatively or switched the connections to the sources.

The pressure source may be a source applying positive or negative pressure. When a negative pressure source such as a vacuum is connected to the nozzles 73 and 74, the action described above goes to the contrary.

In place of the other surface-approaching pressure imparting mechanism 4 or as a part of the surface-approaching pressure imparting mechanism 4, such cylinder mechanism 7 is provided to set the pressure of the pressure source connected to the nozzle 73 and 74, and the distances z1 and z2 according to the viscosity and properties of the fluid to be processed in a fashion to bring the thickness value of fluid film of the fluid to a desired level under a shear force to realize a uniform mixing (uniform reaction when the mixing is accompanied by reaction) for forming fine particles. Particularly, such cylinder mechanism 7 can be used to increase the reliability of cleaning and sterilization by forcing the sliding part open and close during cleaning and steam sterilization.

Figure 16A:
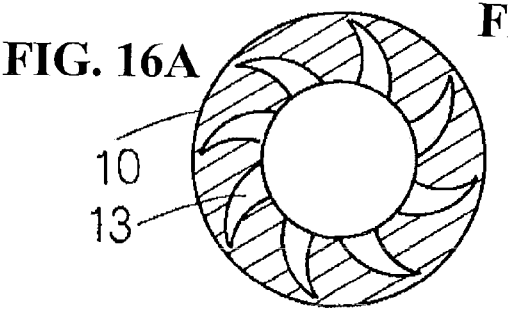
FIG. 16(A) is a schematic transverse sectional view showing an important part of still another embodiment of the apparatus shown in FIG. 12(A), FIG. 16(B), FIG. 16(C), and FIG. 16(E) to FIG. 16(G) are schematic transverse sectional views each showing an important part of still another embodiment of the apparatus.
Figure 16E:
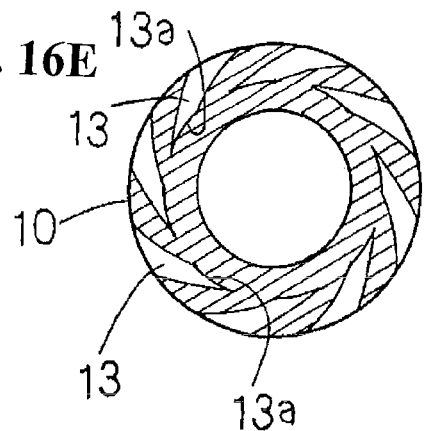
FIG. 16(D) is a partially cut schematic vertical sectional view showing an important part of still another embodiment of the apparatus.
Figure 16B:
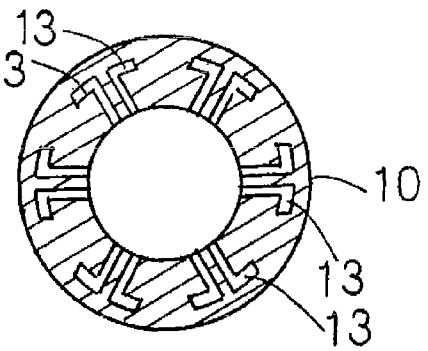
Figure 16F:
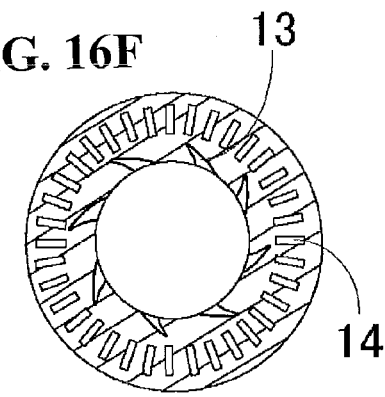
Figure 16C:
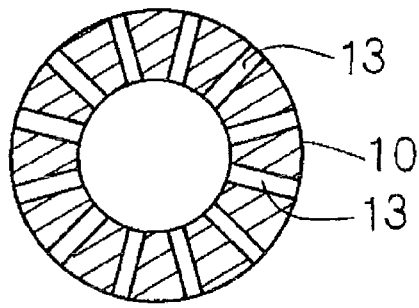

As shown in FIG. 16(A) to FIG. 16(C), the first processing surface 1 of the first processing member 10 may be provided with groove-like depressions 13 . . . 13 extending in the radial direction, that is, in the direction from the center to the outside of the first processing member 10. In this case, as shown in FIG. 16(A), the depressions 13 . . . 13 can be curved or spirally elongated on the first processing surface 1, and as shown in FIG. 16(B), the individual depression 13 may be bent at a right angle, or as shown in FIG. 16(C), the depressions 13 . . . 13 may extend straight radially.

Figure 16G:
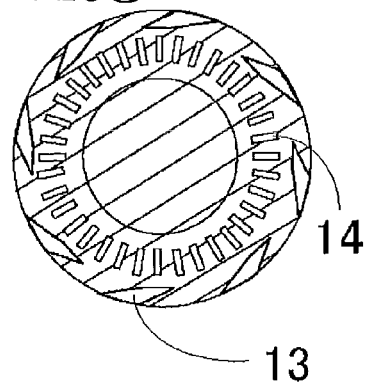
Figure 16D:
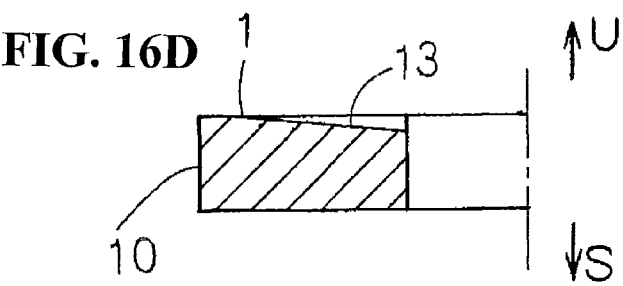

As shown in FIG. 16(D), the depressions 13 in FIG. 16(A) to FIG. 16(C) preferably deepen gradually in the direction toward the center of the first processing surface 1. The groove-like depressions 13 may continue in sequence or intermittence.

Formation of such depression 13 may correspond to the increase of delivery of the processed fluid or to the decrease of calorific value, while having effects of cavitation control and fluid bearing.

In the embodiments shown in FIG. 16, the depressions 13 are formed on the first processing surface 1, but may be formed on the second processing surface 2 or may be formed on both the first and second processing surfaces 1 and 2.

When the depressions 13 or tapered sections are not provided on the processing surface or are arranged unevenly on a part of the processing surface, the influence exerted by the surface roughness of the processing surfaces 1 and 2 on the processed fluid is greater than that by the above depressions 13. In this case, the surface roughness should be reduced, that is, the surface should be fine-textured, as the particle size of the processed fluid are to be decreased. Particularly, regarding the surface roughness of the processing surface, the mirror surface, that is, a surface subjected to mirror polishing is advantageous in realizing uniform mixing (uniform reaction when the mixing is accompanied by reaction) for the purpose of uniform mixing (reaction), and in realizing crystallization and separation of fine monodisperse products for the purpose of obtaining microparticles.

In the embodiments shown in FIG. 12 to FIG. 17, structures other than those particularly shown are the same as in the embodiments shown in FIG. 1(A) or FIG. 11(C).

In the embodiments described above, the case is closed. Alternatively, the first processing member 10 and the second processing member 20 may be closed inside but may be open outside. That is, the flow path is sealed until the processed fluid has passed through the space between the first processing surface 1 and the second processing surface 2, to allow the processed fluid to receive the feeding pressure, but after the passing, the flow path may be opened so that the processed fluid after processing does not receive feeding pressure.

The fluid pressure imparting mechanism p1 preferably uses a compressor as a pressure device described above, but if predetermined pressure can always be applied to the processed fluid, another means may be used. For example, the own weight of the processed fluid can be used to apply certain pressure constantly to the processed fluid.

In summary, the processing apparatus in each embodiment described above is characterized in that predetermined pressure is applied to a fluid to be processed, at least two processing surfaces, that is, a first processing surface 1 and a second processing surface 2 capable of approaching to and separating from each other are connected to a sealed flow path through which the processed fluid receiving the predetermined pressure flows, a surface-approaching pressure of approaching the processing surfaces 1 and 2 each other is applied to rotate the first processing surface 1 and the second processing surface 2 relative to each other, thereby allowing a fluid film used for seal in mechanical seal to be generated out of the processed fluid, and the fluid film is leaked out consciously (without using the fluid film as seal) from between the first processing surface 1 and the second processing surface 2, contrary to mechanical seal, whereby mixing (reaction) processing is realized between the processed fluid formed into a film between the surfaces 1 and 2, and the product is recovered.

By this epoch-making method, the space between the processing surfaces 1 and 2 can be regulated in the range of 1 μm to 1 mm, particularly 1 μm to 10 μm.

In the embodiment described above, a flow path for a sealed fluid is constituted in the apparatus, and the processed fluid is pressurized with the fluid pressure imparting mechanism p1 arranged at the side of the introduction part (for the first processing fluid) in the processing apparatus.

Alternatively, the flow path for the processed fluid may be opened without pressurization with the fluid pressure imparting mechanism p1.

One embodiment of the processing apparatus is shown in FIG. 18 to FIG. 20. The processing apparatus illustrated in this embodiment is an apparatus including a degassing mechanism, that is, a mechanism of removing a liquid from the formed processed product thereby finally securing objective solids (crystals) only.

Figure 18A:
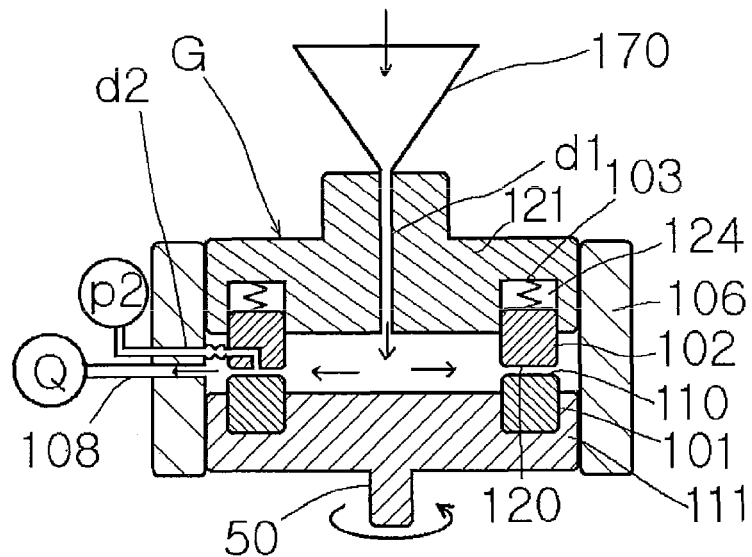
FIG. 18(A) is a schematic vertical sectional view showing the concept of still another embodiment of the apparatus used for carrying out the present invention.
Figure 18B:
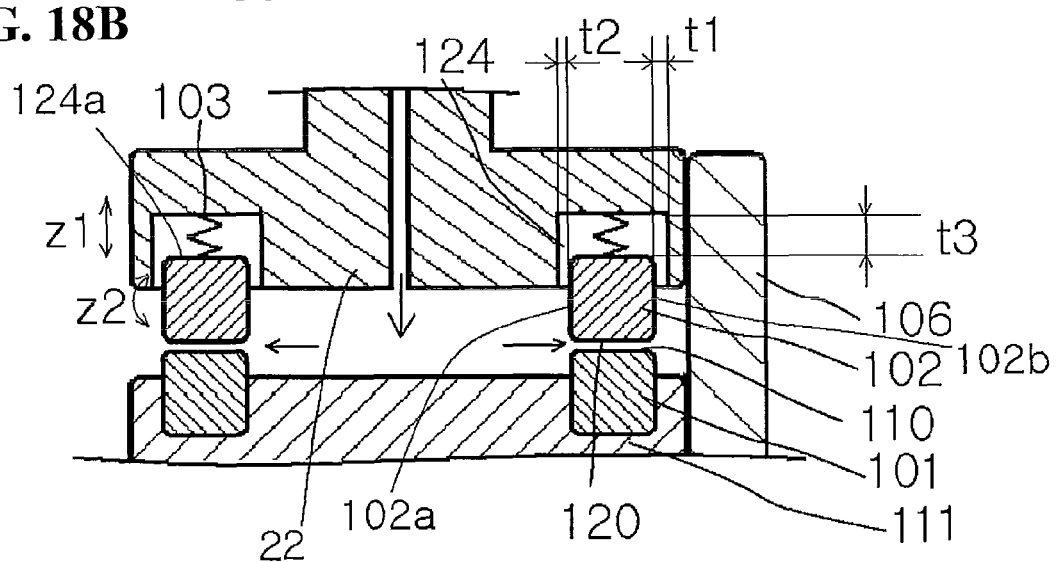
FIG. 18(B) is a partially cut explanatory view showing an important part of the apparatus.

FIG. 18(A) is a schematic vertical sectional view of the processing apparatus, and FIG. 18(B) is its partially cut enlarged sectional view. FIG. 19 is a plane view of the first processing member 1 arranged in the processing apparatus in FIG. 18. FIG. 20 is a partially cut schematic vertical sectional view showing an important part of the first and second processing members 1 and 2 in the processing apparatus.

As described above, the apparatus shown in FIG. 18 to FIG. 20 is the one into which a fluid as the object of processing, that is, a processed fluid, or a fluid carrying the object of processing, is to be introduced at atmospheric pressure.

In FIG. 18(B) and FIG. 20, the second introduction part d2 is omitted for simplicity of the drawing (these drawings can be regarded as showing a section at the position where the second introduction part d2 is not arranged).

As shown in FIG. 18(A), this fluid processing apparatus includes a mixing apparatus G and a decompression pump Q. This mixing apparatus G includes a first processing member 101 as a rotating member, a first holder 111 for holding the processing member 101, a second processing member 102 that is a member fixed to the case, a second holder 121 having the second processing member 102 fixed thereto, a bias mechanism 103, a dynamical pressure generating mechanism 104 (FIG. 19(A)), a drive part which rotates the first processing member 101 with the first holder 111, a housing 106, a first introduction part d1 which supplies (introduces) a first processed fluid, and a discharge part 108 that discharges the fluid to the decompression pump Q. The drive part is not shown.

The first processing member 101 and the second processing member 102 are cylindrical bodies that are hollow in the center. The processing members 101 and 102 are members wherein the bottoms of the processing members 101 and 102 in a cylindrical form are processing surfaces 110 and 120, respectively.

The processing surfaces 110 and 120 have a mirror-polished flat part. In this embodiment, the processing surface 120 of the second processing member 102 is a flat surface subjected as a whole to mirror polishing. The processing surface 110 of the first processing member 101 is a flat surface as a whole like the second processing member 102, but has a plurality of grooves 112 . . . 112 in the flat surface as shown in FIG. 19(A). The grooves 112 . . . 112 while centering on the first processing member 101 in a cylindrical form extend radially toward the outer periphery of the cylinder.

The processing surfaces 110 and 120 of the first and second processing members 101 and 102 are mirror-polished such that the surface roughness Ra comes to be in the range of 0.01 μm to 1.0 μm. By this mirror polishing, Ra is regulated preferably in the range of 0.03 μm to 0.3 μm.

The material for the processing members 101 and 102 is one which is rigid and capable of mirror polishing. The rigidity of the processing members 101 and 102 is preferably at least 1500 or more in terms of Vickers hardness. A material having a low linear expansion coefficient or high thermal conductance is preferably used. This is because when the difference in coefficient of expansion between a part which generates heat upon processing and other parts is high, distortion is generated and securement of suitable clearance is influenced.

As the material for the processing members 101 and 102, it is preferable to use particularly SIC, that is, silicon carbide, SIC having a Vickers hardness of 2000 to 2500, SIC having a Vickers hardness of 3000 to 4000 coated thereon with DLC (diamond-like carbon), WC, that is, tungsten carbide having a Vickers hardness of 1800, WC coated thereon with DLC, and boron ceramics represented by $ZrB_2$, BTC and $B_4C$ having a Vickers hardness of 4000 to 5000.

The housing 106 shown in FIG. 18, the bottom of which is not shown though, is a cylinder with a bottom, and the upper part thereof is covered with the second holder 121. The second holder 121 has the second processing member 102 fixed to the lower surface thereof, and the introduction part d1 is arranged in the upper part thereof. The introduction part d1 is provided with a hopper 170 for introducing a fluid or a processed material from the outside.

Although not shown in the figure, the drive part includes a power source such as a motor and a shaft 50 that rotates by receiving power from the power source.

As shown in FIG. 18(A), the shaft 50 is arranged in the housing 106 and extends vertically. Then, the first holder 111 is arranged on the top of the shaft 50. The first holder 111 is to hold the first processing member 101 and is arranged on the shaft 50 as described above, thereby allowing the processing surface 110 of the first processing member 101 to correspond to the processing surface 120 of the second processing member 102.

The first holder 111 is a cylindrical body, and the first processing member 101 is fixed on the center of the upper surface. The first processing member 101 is fixed so as to be integrated with the first holder 111, and does not change its position relative to the first holder 111.

On the other hand, a receiving depression 124 for receiving the second processing member 102 is formed on the center of the upper surface of the second holder 121.

The receiving depression 124 has a circular cross-section. The second processing member 102 is accepted in the cylindrical receiving depression 124 so as to be concentric with the receiving depression 124.

The structure of the receiving depression 124 is similar to that in the embodiment as shown in FIG. 1(A) (the first processing member 101 corresponds to the first ring 10, the first holder 111 to the first holder 11, the second processing member 102 to the second ring 20, and the second holder 121 to the second holder 21).

Then, the second holder 121 is provided with the bias mechanism 103. The bias mechanism 103 preferably uses an elastic body such as spring. The bias mechanism 103 corresponds to the surface-approaching pressure imparting mechanism 4 in FIG. 1(A) and has the same structure. That is, the bias mechanism 103 presses that side (bottom) of the second processing member 102 which is opposite to the processing surface 120 and biases each position of the second processing member 102 uniformly downward to the first processing member 101.

On the other hand, the inner diameter of the receiving depression 124 is made larger than the outer diameter of the second processing member 102, so that when arranged concentrically as described above, a gap t1 is set between outer periphery 102b of the second processing member 102 and inner periphery of the receiving depression 124, as shown in FIG. 18(B).

Similarly, a gap t2 is set between inner periphery 102a of the second processing member 102 and outer periphery of the central portion 22 of the receiving depression 124, as shown in FIG. 18(B).

The gaps t1 and t2 are those for absorbing vibration and eccentric behavior and are set to be in a size to secure operational dimensions or more and to enable sealing. For example, when the diameter of the first processing member 101 is 100 mm to 400 mm, the gaps t1 and t2 are preferably 0.05 mm to 0.3 mm, respectively.

The first holder 111 is fixed integrally with the shaft 50 and rotated with the shaft 50. The second processing member 102 is not rotated relative to the second holder 121 by a baffle (not shown). However, for securing 0.1 µm to 10 µm clearance necessary for processing, that is, the minute gap t between the processing surfaces 110 and 120 as shown in FIG. 20(B), a gap t3 is, as shown in FIG. 18(B), arranged between the bottom of the receiving depression 124, that is, the top part, and the surface facing a top part 124a of the second processing member 102, that is, the upper part. The gap t3 is established in consideration of the clearance and the vibration and elongation of the shaft 50.

As described above, by the provision of the gaps t1 to t3, the first processing member 101, as shown in FIG. 18(B), can move not only in the direction z1 of approaching to and separating from the second processing member 102, but also relative to the center and direction of the processing surface 110, that is, relative to the direction z2.

That is, in this embodiment, the bias mechanism 103 and the gaps t1 to t3 constitute a floating mechanism, and by this floating mechanism, the center and inclination of at least the second processing member 102 are made variable in the small range of several µm to several mm. The run-out and expansion of the rotary shaft and the surface vibration and vibration of the first processing member 101 are absorbed.

The groove 112 on the processing surface 110 of the first processing member 101 is described in more detail. The rear end of the groove 112 reaches the inner periphery 101a of the first processing member 101, and its top is elongated toward the outside y of the first processing member 101, that is, toward the outer periphery. As shown in FIG. 19(A), the sectional area of the groove 112 is gradually decreased in the direction from the center x of the circular first processing member 101 to the outside y of the first processing member 101, that is, toward the outer periphery.

The distance w1 of the left and right sides 112a and 112b of the groove 112 is decreased in the direction from the center x of the first processing member 101 to the outside y of the first processing member 101, that is, toward the outer periphery. As shown in FIG. 19(B), the depth w2 of the groove 112 is decreased in the direction from the center x of the first processing member 101 to the outside y of the first processing member 101, that is, toward the outer periphery. That is, the bottom 112c of the groove 112 is decreased in depth in the direction from the center x of the first processing member 101 to the outside y of the first processing member 101, that is, toward the outer periphery.

As described above, the groove 112 is gradually decreased both in width and depth toward the outside y, that is, toward the outer periphery, and its sectional area is gradually decreased toward the outside y. Then, the top of the groove 112, that is, the y side, is a dead end. That is, the top of the groove 112, that is, the y side does not reach the outer periphery 101b of the first processing member 101, and an outer flat surface 113 is interposed between the top of the groove 112 and the outer periphery 101b. The outer flat surface 113 is a part of the processing surface 110.

In the embodiment shown in FIG. 19, the left and right sides 112a and 112b and the bottom 112c of the groove 112 constitute a flow path limiting part. This flow path limiting part, the flat part around the groove 112 of the first processing member 101, and the flat part of the second processing member 102 constitute the dynamical pressure generating mechanism 104.

However, only one of the width and depth of the groove 112 may be constituted as described above to decrease the sectional area.

While the first processing member 101 rotates, the dynamical pressure generating mechanism 104 generates a force in the direction of separating the processing members 101 and 102 from each other to secure a desired minute space between the processing members 101 and 102 by a fluid passing through the space between the processing members 101 and 102. By generation of such dynamical pressure, a 0.1 µm to 10 µm minute space can be generated between the processing surfaces 110 and 120. A minute space like that can be regulated and selected depending on the object of processing, but is preferably 1 µm to 6 µm, more preferably 1 µm to 2 µm. This apparatus can realize a uniform mixing (uniform reaction when the mixing is accompanied by reaction) and form microparticles by the minute space, which are not achieved in the prior art.

The grooves 112 . . . 112 may extend straight from the center x to the outside y. In this embodiment, however, as shown in FIG. 19(A), the grooves 112 are curved to extend such that with respect to a rotation direction r of the first processing member 101, the center x of the groove 112 is positioned in front of the outside y of the groove 112.

In this manner, the grooves 112 . . . 112 are curved to extend so that the separation force by the dynamical pressure generating mechanism 104 can be effectively generated.

Then, the working of this apparatus is described.

As shown in FIG. 18(A), a first processed fluid R which has been introduced from a hopper 170 and has passed through the first introduction part d1, passes through the hollow part of the circular second processing member 102, and the fluid that has received the centrifugal force resulting from rotation of the first processing member 101 enters the space between the processing members 101 and 102, and uniform mixing (reaction) and, in any case, generation of microparticles are effected and processed between the processing surface 110 of the rotating first processing member 101 and the processing surface 120 of the second processing member 102, then exits from the processing members 101 and 102 and is then discharged from the discharge part 108 to the side of the decompression pump Q (hereinafter, the first processed fluid R is referred to simply as a fluid R, if necessary).

Figure 20A:
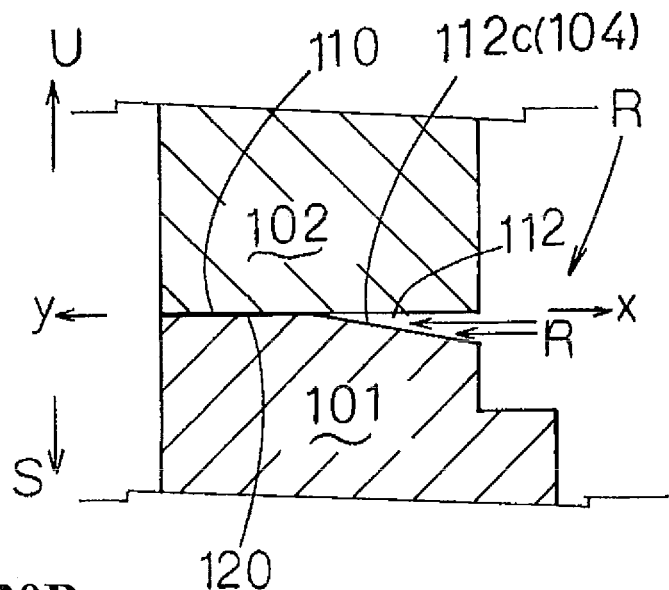
FIG. 20(A) is a vertical sectional view showing an important part of first and second processing members in the apparatus shown in FIG. 12(A)
Figure 20B:
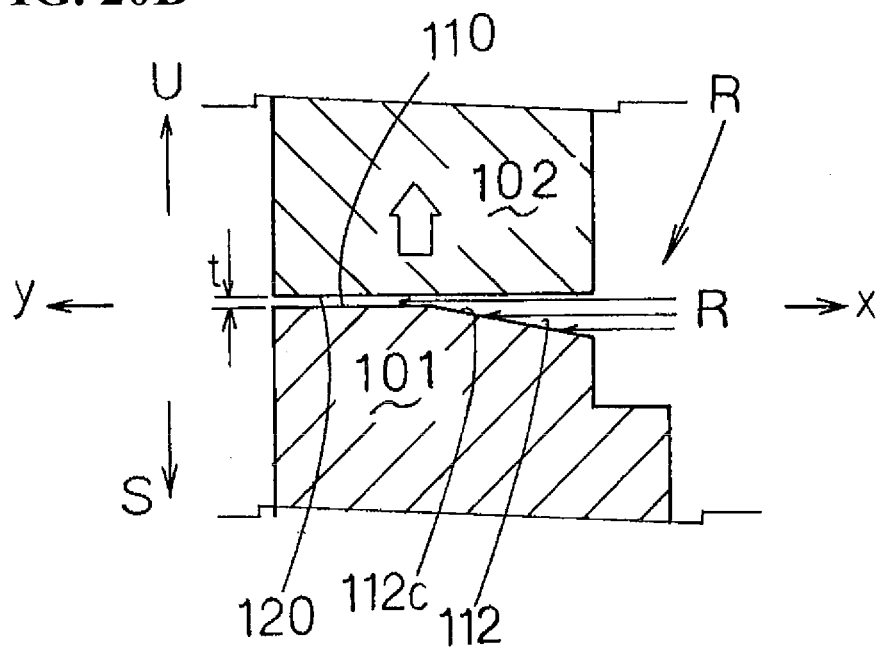
FIG. 20(B) is a vertical sectional view showing an important part of the first and second processing members with a minute gap.

In the foregoing description, the fluid R that has entered the hollow part of the circular second processing member 102 first enters the groove 112 of the rotating first processing member 101 as shown in FIG. 20(A). On the other hand, the processing surfaces 110 and 120 that are mirror-polished flat parts are kept airtight even by passing a gas such as air or nitrogen. Accordingly, even if the centrifugal force by rotation is received, the fluid R cannot enter through the groove 112 into the space between the processing surfaces 110 and 120 that are pushed against each other by the bias mechanism 103. However, the fluid R gradually runs against both the sides 112a and 112b and the bottom 112c of the groove 112 formed as a flow path limiting part to generate dynamical pressure acting in the direction of separating the processing surfaces 110 and 120 from each other. As shown in FIG. 20(B), the fluid R can thereby exude from the groove 112 to the flat surface, to secure a minute gap t, that is, clearance, between the processing surfaces 110 and 120. Then, a uniform mixing (reaction) and generation of microparticles are effected and processed between the mirror-polished flat surfaces. The groove 112 has been curved so that the centrifugal force is applied more accurately to the fluid to make generation of dynamical pressure more effectively.

In this manner, the fluid processing apparatus can secure a minute and uniform gap, that is, clearance, between the mirror surfaces, that is, the processing surfaces 110 and 120, by the balance between the dynamical pressure and the bias force by the bias mechanism 103. By the structure described above, the minute gap can be as superfine as 1 μm or less.

By utilizing the floating mechanism, the automatic regulation of alignment between the processing surfaces 110 and 120 becomes possible, and the clearance in each position between the processing surfaces 110 and 120 can be prevented from varying against physical deformation of each part by rotation or generated heat, and the minute gap in each position can be maintained.

In the embodiment described above, the floating mechanism is a mechanism arranged for the second holder 121 only. Alternatively, the floating mechanism can be arranged in the first holder 111 instead of, or together with, the second holder 121.

Other embodiments of the groove 112 are shown in FIG. 21 to FIG. 23.

Figure 21A:
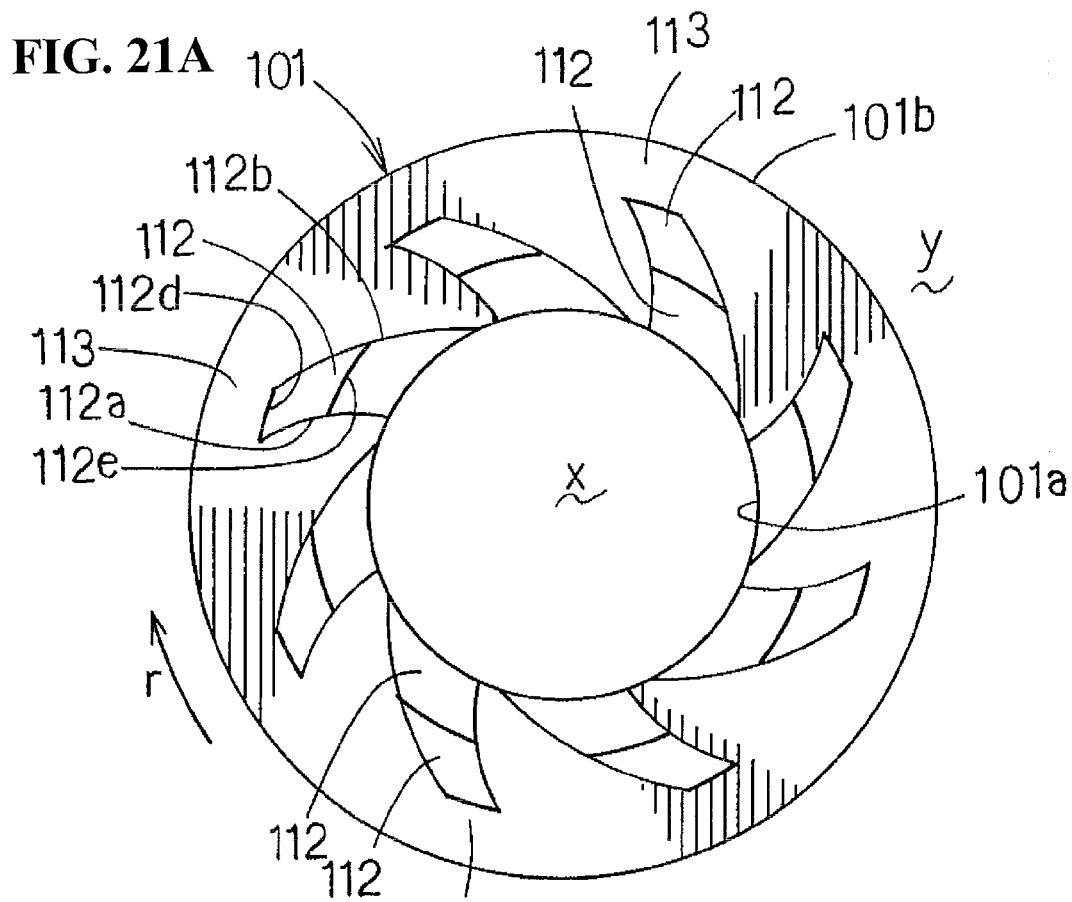
FIG. 21(A) is a plane view of another embodiment of the first processing member.
Figure 21B:
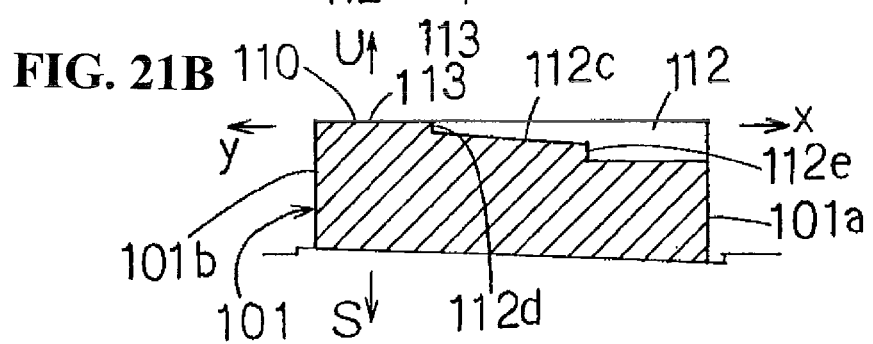
FIG. 21(B) is a vertical sectional view showing an important part thereof.

As shown in FIG. 21(A) and FIG. 21(B), the groove 112 can be provided at the top with a flat wall surface 112d as a part of the flow path limiting part. In the embodiment shown in FIG. 21, a step 112e is arranged between the first wall surface 112d and the inner periphery 101a in the bottom 112c, and the step 112e also constitutes a part of the flow path limiting part.

Figure 22A:
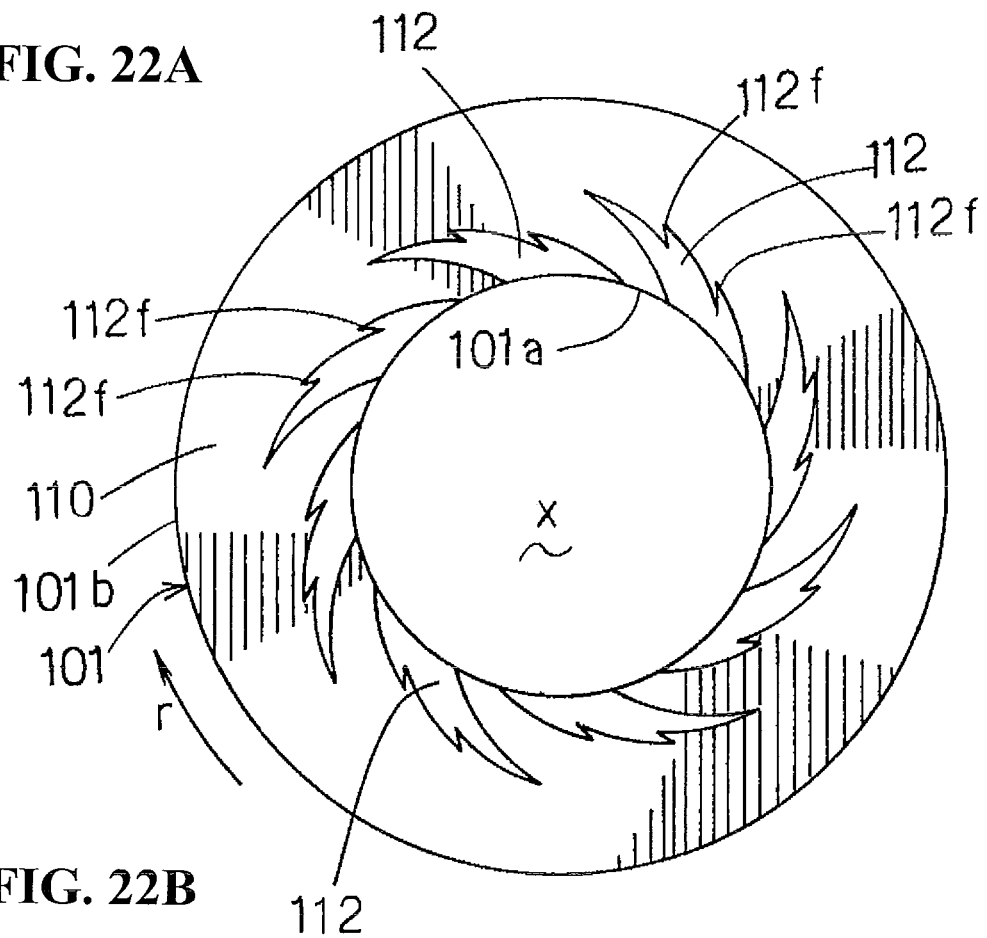
FIG. 22(A) is a plane view of still another embodiment of the first processing member.
Figure 22B:
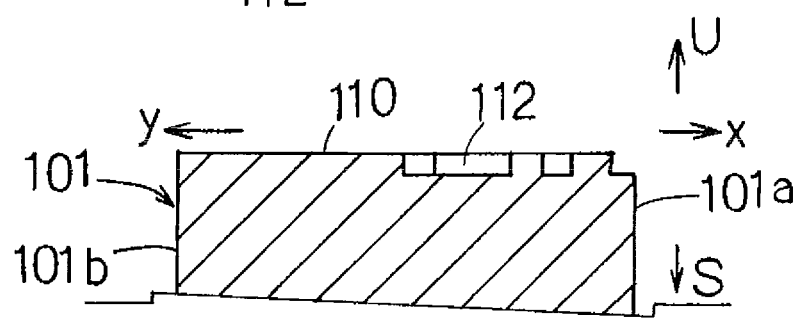
FIG. 22(B) is a schematic vertical sectional view showing an important part thereof.

As shown in FIG. 22(A) and FIG. 22(B), the groove 112 includes a plurality of branches 112f . . . 112f, and each branch 112f narrows its width thereby being provided with a flow path limiting part.

With respect to the embodiments in FIG. 21 and FIG. 22, structures other than those particularly shown are similar to those of embodiments as shown in FIG. 1(A), FIG. 11(C), and FIG. 18 to FIG. 20.

Figure 23A:
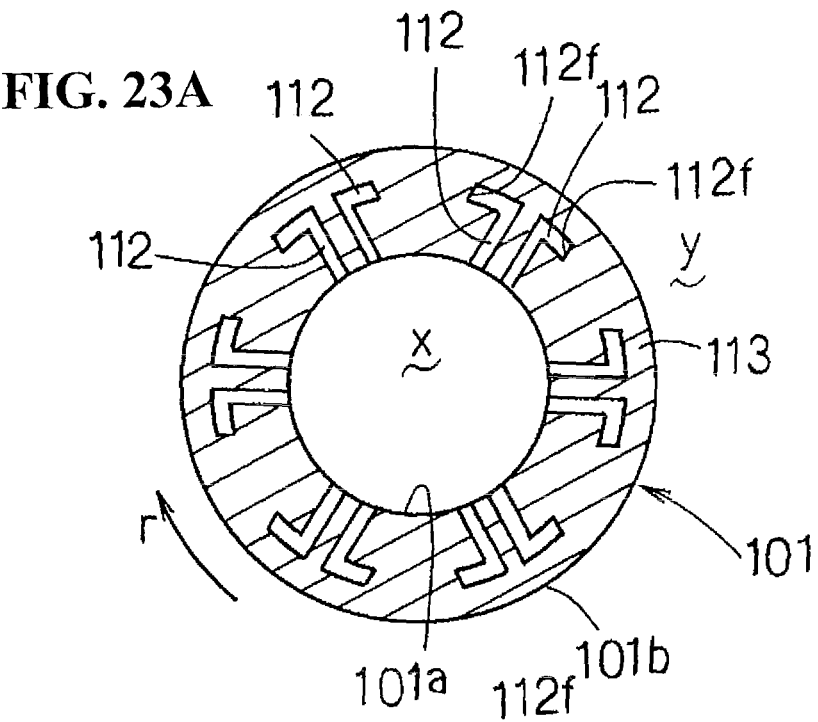
FIG. 23(A) is a plane view of still another embodiment of the first processing member.
Figure 23B:
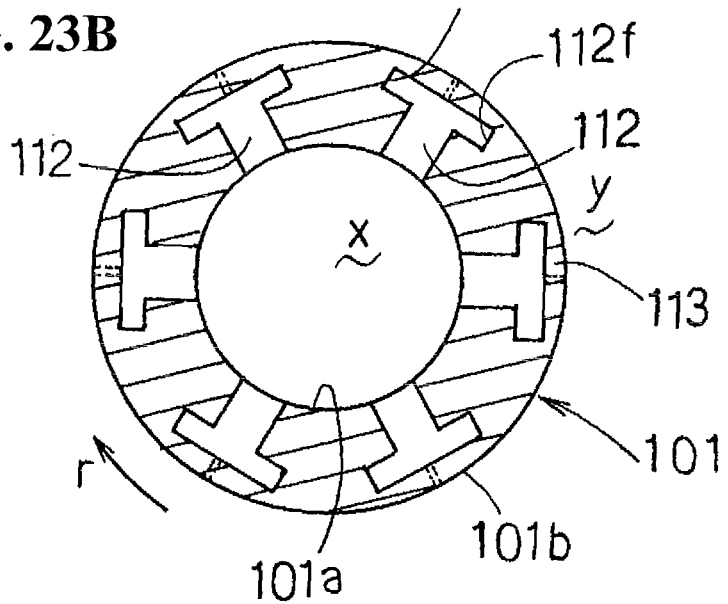
FIG. 23(B) is a plane view of still another embodiment of the first processing member.

In the embodiments described above, at least either the width or depth of the groove 112 is gradually decreased in size in the direction from inside to outside the first processing member 101, thereby constituting a flow path limiting part. Alternatively, as shown in FIG. 23(A) or FIG. 23(B), the groove 112 can be provided with a termination surface 112f without changing the width and depth of the groove 112, and the termination surface 112f of the groove 112 can serve as a flow path limiting part. As shown in the embodiments in FIG. 19, FIG. 21 and FIG. 22, the width and depth of the groove 112 can be changed as described above thereby slanting the bottom and both sides of the groove 112, so that the slanted surface serves as a pressure-receiving part toward the fluid to generate dynamical pressure. In the embodiment shown in FIG. 23(A) and FIG. 23(B), on the other hand, the termination surface of the groove 112 serves as a pressure-receiving part toward the fluid to generate dynamical pressure.

In the embodiment shown in FIG. 23(A) and FIG. 23(B), at least one of the width and depth of the groove 112 may also be gradually decreased in size.

The structure of the groove 112 is not limited to the one shown in FIG. 19 and FIG. 21 to FIG. 23 and can be provided with a flow path limiting part having other shapes.

For example, in the embodiments shown in FIG. 19 and FIG. 21 to FIG. 23, the groove 112 does not penetrate to the outer side of the first processing member 101. That is, there is an outer flat surface 113 between outer periphery of the first processing member 101 and the groove 112. However, the structure of the groove 112 is not limited to such embodiment, and the groove 112 may reach the outer periphery of the first processing member 101 as long as the dynamical pressure can be generated.

For example, in the case of the first processing member 101 shown in FIG. 23(B), as shown in the dotted line, a part having a smaller sectional area than other sites of the groove 112 can be formed on the outer flat surface 113.

The groove 112 may be formed so as to be gradually decreased in size in the direction from inside to outside as described above, and the part (terminal) of the groove 112 that had reached the outer periphery of the first processing member 101 may have the minimum sectional area (not shown). However, the groove 112 preferably does not penetrate to the outer periphery of the first processing member 101 as shown in FIG. 19 and FIG. 21 to FIG. 23, in order to effectively generate dynamical pressure.

Now, the embodiments shown in FIG. 18 to FIG. 23 are summarized.

This fluid processing apparatus is a processing apparatus wherein a rotating member having a flat processing surface and a fixed member having the same flat processing surface are opposite to each other so as to be concentric with each other, and while the rotating member is rotated, a raw material to be processed is fed through an opening of the fixed member and subjected to processing between the opposite flat processing surfaces of both members, wherein the rotating member is provided with a pressurizing mechanism by which pressure is generated to maintain clearance without mechanically regulating clearance and enables 1 μm to 6 μm microscopic clearance not attainable by mechanical regulation of clearance, thereby significantly improving an ability to uniformize the mixing (reaction) and in some cases, an ability to pulverize the formed particles.

That is, this fluid processing apparatus have a rotating member and a fixed member each having a flat processing surface in the outer periphery thereof and has a sealing mechanism in a plane on the flat processing surface, thereby providing a high speed rotation processing apparatus generating hydrostatic force, hydrodynamic force, or aerostatic-aerodynamic force. The force generates a minute space between the sealed surfaces, and contributes a fluid processing apparatus with a function of non-contact and mechanically safe and high-level uniformizing of mixing (reaction). One factor for forming this minute space is due to the rotation speed of the rotating member, and the other factor is due to a pressure difference between the introduction side and discharge side of a processed material (fluid). When a pressure imparting mechanism is arranged in the introduction side, when the pressure imparting mechanism is not arranged in the introduction side, that is, when the processed material (fluid) is introduced at atmospheric pressure, there is no pressure difference, and thus the sealed surfaces should be separated by only the rotation speed of the rotating member. This is known as hydrodynamic or aerodynamic force.

Figure 24A:
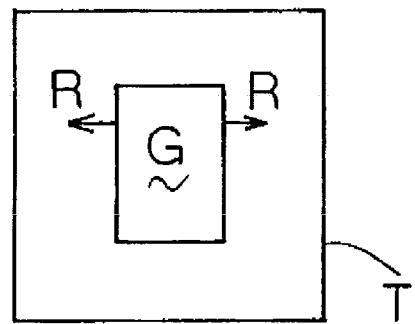
FIG. 24(A), FIG. 24(B), and FIG. 24(C) are diagrams showing embodiments other than those described above with respect to the method of separating a processed material after processing.

FIG. 18(A) shows the apparatus wherein a decompression pump Q is connected to the discharge part of the mixing apparatus G, but as described above, the mixing apparatus G may be arranged in a decompression tank T without arranging the housing 106 and the decomposition pump Q, as shown in FIG. 24(A).

In this case, the tank T is decompressed in a vacuum or in an almost vacuum, whereby the processed product formed in the mixing apparatus G is sprayed in a mist form in the tank T, and the processed material colliding with, and running down along, the inner wall of the tank T can be recovered, or a gas (vapor) separated from the processed material and filled in an upper part of the tank T, unlike the processed material running down along the wall, can be recovered to obtain the objective product after processing.

Figure 24B:
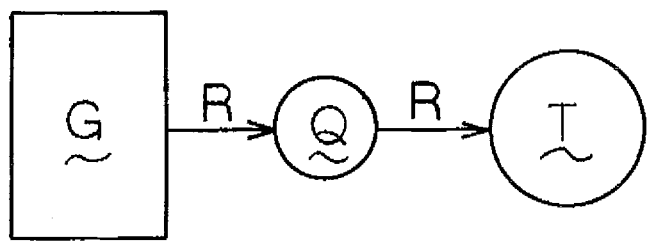

When the decompression pump Q is used, as shown in FIG. 24(B), an airtight tank T is connected via the decompression pump Q to the mixing apparatus G, whereby the processed material after processing can be formed into mist to separate and extract the objective product.

Figure 24C:
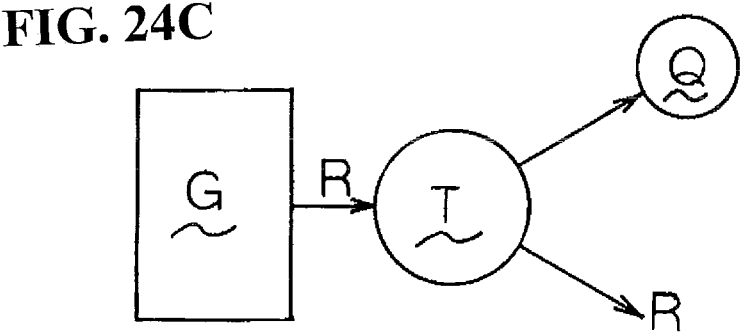

As shown in FIG. 24(C), the decompression pump Q is connected directly to the tank T, and the decompression pump Q and a discharge part for fluid R, different from the decompression pump Q, are connected to the tank T, whereby the objective product can be separated. In this case, a gasified portion is sucked by the decompression pump Q, while the fluid R (liquid portion) is discharged from the discharge part separately from the gasified portion.

In the embodiments described above, the first and second processed fluids are introduced via the second holders 21 and 121 and the second rings 20 and 102 respectively and mixed (reacted) with each other.

Now, other embodiments with respect to introduction of fluids to be processed into the apparatus are described.

Figure 1B:
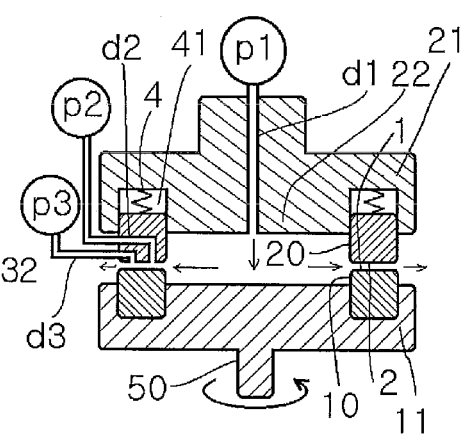
FIG. 1(B) is a schematic vertical sectional view showing the concept of another embodiment of the apparatus.

As shown in FIG. 1(B), the processing apparatus shown in FIG. 1(A) is provided with a third introduction part d3 to introduce a third fluid to be processed into the space between the processing surfaces 1 and 2, and the third fluid is mixed (reacted) with the first processed fluid as well as the second processed fluid.

By the third introduction part d3, the third fluid to be mixed with the first processed fluid is fed to the space between the processing surfaces 1 and 2. In this embodiment, the third introduction part d3 is a fluid flow path arranged in the second ring 20 and is open at one end to the second processing surface 2 and has a third fluid feed part p3 connected to the other end.

In the third fluid feed part p3, a compressor or another pump can be used.

The opening of the third introduction part d3 in the second processing surface 2 is positioned outside, and more far from, the rotation center of the first processing surface 1 than the opening of the second introduction part d2. That is, in the second processing surface 2, the opening of the third introduction part d3 is located downstream from the opening of the second introduction part d2. A gap is arranged between the opening of the third introduction part d3 and the opening of the second introduction part d2 in the radial direction of the second ring 20.

With respect to structures other than the third introduction part d3, the apparatus shown in FIG. 1(B) is similar to that in the embodiment as in FIG. 1(A). In FIG. 1(B) and further in FIG. 1(C), FIG. 1(D) and FIG. 2 to FIG. 11 described later, the case 3 is omitted to simplify the drawings. In FIG. 9(B), FIG. 9(C), FIG. 10, FIG. 11(A) and FIG. 11(B), a part of the case 3 is shown.

Figure 1C:
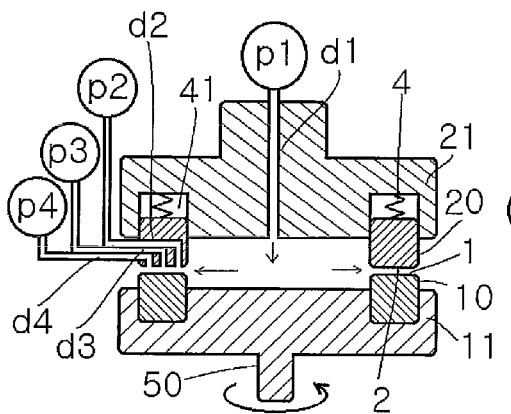
FIG. 1(C) is a schematic vertical sectional view showing the concept of still another embodiment of the apparatus.

As shown in FIG. 1(C), the processing apparatus shown in FIG. 1(B) is provided with a fourth introduction part d4 to introduce a fourth fluid to be processed into the space between the processing surfaces 1 and 2, and the fourth fluid is mixed (reacted) with the first processed fluid as well as the second and third processed fluids.

By the fourth introduction part d4, the fourth fluid to be mixed with the first processed fluid is fed to the space between the processing surfaces 1 and 2. In this embodiment, the fourth introduction part d4 is a fluid flow path arranged in the second ring 20, is open at one end to the second processing surface 2, and has a fourth fluid feed part p4 connected to the other end.

In the fourth fluid feed part p4, a compressor or another pump can be used.

The opening of the fourth introduction part d4 in the second processing surface 2 is positioned outside, and more far from, the rotation center of the first processing surface 1 than the opening of the third introduction part d3. That is, in the second processing surface 2, the opening of the fourth introduction part d4 is located downstream from the opening of the third introduction part d3.

With respect to structures other than the fourth introduction part d4, the apparatus shown in FIG. 1(C) is similar to that in the embodiment as in FIG. 1(B).

Five or more introduction parts further including a fifth introduction part, a sixth introduction part and the like can be arranged to mix (react) five or more fluids to be processed with one another.

Figure 1D:
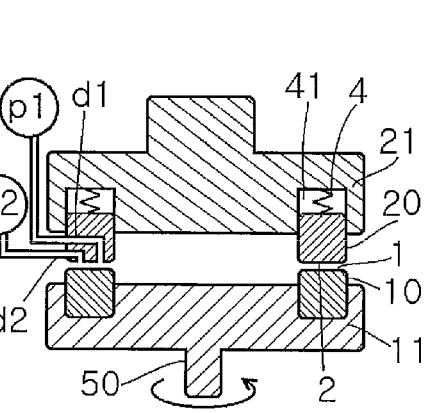
FIG. 1(D) is a schematic vertical sectional view showing the concept of still another embodiment of the apparatus.

As shown in FIG. 1(D), the first introduction part d1 arranged in the second holder 21 in the apparatus in FIG. 1(A) can, similarly in the second introduction part d2, be arranged in the second processing surface 2 in place of the second holder 21. In this case, the opening of the first introduction part d1 is located at the upstream side from the second introduction part d2, that is, it is positioned nearer to the rotation center than the second introduction part d2 in the second processing surface 2.

In the apparatus shown in FIG. 1(D), the opening of the second introduction part d2 and the opening of the third introduction part d3 both are arranged in the second processing surface 2 of the second ring 20. However, arrangement of the opening of the introduction part is not limited to such arrangement relative to the processing surface. Particularly as shown in FIG. 2(A), the opening of the second introduction part d2 can be arranged in a position adjacent to the second processing surface 2 in the inner periphery of the second ring 20. In the apparatus shown in FIG. 2(A), the opening of the third introduction part d3 is arranged in the second processing surface 2 similarly in the apparatus shown in FIG. 1(B), but the opening of the second introduction part d2 can be arranged inside the second processing surface 2 and adjacent to the second processing surface 2, whereby the second processed fluid can be immediately introduced onto the processing surfaces.

In this manner, the opening of the first introduction part d1 is arranged in the second holder 21, and the opening of the second introduction part d2 is arranged inside the second processing surface 2 and adjacent to the second processing surface 2 (in this case, arrangement of the third introduction part d3 is not essential), so that particularly in reaction of a plurality of processed fluids, the processed fluid introduced from the first introduction part d1 and the processed fluid introduced from the second introduction part d2 are introduced, without being reacted with each other, into the space between the processing surfaces 1 and 2, and then both the fluids can be reacted first between the processing surfaces 1 and 2. Accordingly, the structure described above is suitable for obtaining a particularly reactive processed fluid.

The term "adjacent" is not limited to the arrangement where the opening of the second introduction part d2 is contacted with the inner side of the second ring 20 as shown in FIG. 2(A). The distance between the second ring 20 and the opening of the second introduction part d2 may be such a degree that a plurality of processed fluids are not completely mixed (reacted) with one another prior to introduction into the space between the processing surfaces 1 and 2. For example, the opening of the second introduction part d2 may be arranged in a position near the second ring 20 of the second holder 21. Alternatively, the opening of the second introduction part d2 may be arranged on the side of the first ring 10 or the first holder 11.

In the apparatus shown in FIG. 1(B), a gap is arranged between the opening of the third introduction part d3 and the opening of the second introduction part d2 in the radial direction of the second ring 20, but as shown in FIG. 2(B), the second and third processed fluids can be introduced into the space between the processing surfaces 1 and 2, without providing such gap, thereby immediately joining both the fluids together. The apparatus shown in FIG. 2(B) can be selected depending on the object of processing.

In the apparatus shown in FIG. 1(D), a gap is also arranged between the opening of the first introduction part d1 and the opening of the second introduction part d2 in the radial direction of the second ring 20, but the first and second processed fluids can be introduced into the space between the processing surfaces 1 and 2, without providing such gap, thereby immediately joining both the fluids together (not shown). Such arrangement of the opening can be selected depending on the object of processing.

Figure 3A:
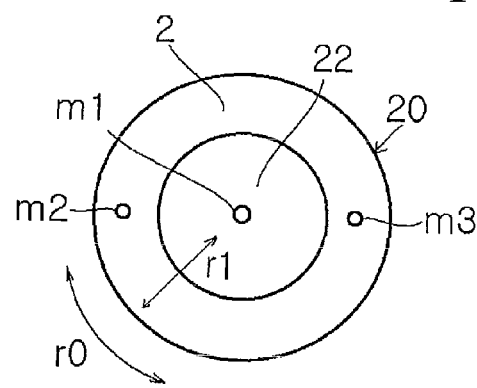
FIG. 3(A) is a schematic bottom view showing an important part of the apparatus shown in FIG. 2(C)

In the embodiment shown in FIG. 1(B) and FIG. 1(C), the opening of the third introduction part d3 is arranged in the second processing surface 2 downstream from the opening of the second introduction part d2, in other words, outside the opening of the second introduction part d2 in the radial direction of the second ring 20. Alternatively, as shown in FIG. 2(C) and FIG. 3(A), the opening of the third introduction part d3 and the opening of the second introduction part d2 can be arranged in the second processing surface 2 in positions different in a circumferential direction r0 of the second ring 20. In FIG. 3, numeral m1 is the opening (first opening) of the first introduction part d1, numeral m2 is the opening (second opening) of the second introduction part d2, numeral m3 is the opening (third opening) of the third introduction part d3, and numeral r1 is the radical direction of the ring.

When the first introduction part d1 is arranged in the second ring 20, as shown in FIG. 2(D), the opening of the first introduction part d1 and the opening of the second introduction part d2 can be arranged in the second processing surface 2 in positions different in the circumferential direction of the second ring 20.

Figure 3B:
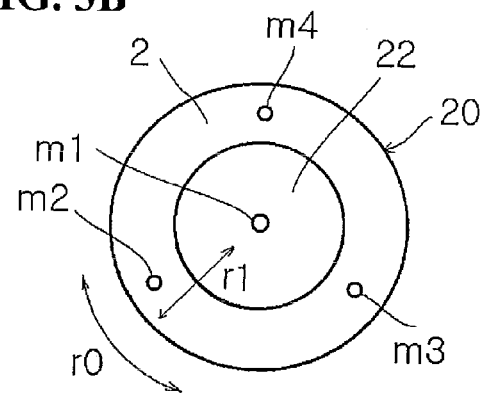
FIG. 3(B) is a schematic bottom view showing an important part of another embodiment of the apparatus.
Figure 3C:
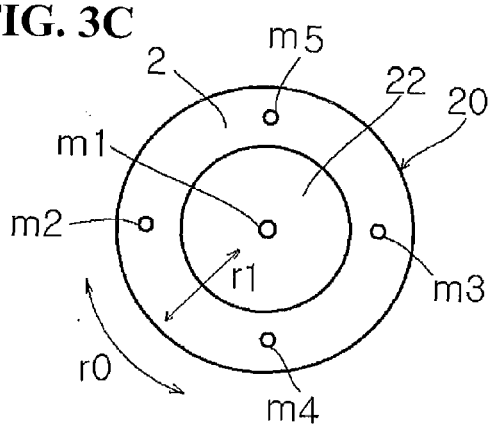
FIG. 3(C) is a schematic bottom view showing an important part of still another embodiment of the apparatus.

In the apparatus shown in FIG. 3(A), the openings of two introduction parts are arranged in the second processing surface 2 of the second ring 20 in positions different in the circumferential direction r0, but as shown in FIG. 3(B), the openings of three introduction parts can be arranged in positions different in the circumferential direction r0 of the ring, or as shown in FIG. 3(C), the openings of four introduction parts can be arranged in positions different in the circumferential direction r0 of the ring. In FIG. 3(B) and FIG. 3(C), numeral m4 is the opening of the fourth introduction part, and in FIG. 3(C), numeral m5 is the opening of the fifth introduction part. Five or more openings of introduction parts may be arranged in positions different in the circumferential direction r0 of the ring (not shown).

In the apparatuses shown in above, the second to fifth introduction parts can introduce different fluids, that is, the second, third, fourth and fifth fluids. On the other hand, the second to fifth openings m2 to m5 can introduce the same fluid, that is, the second fluid into the space between the processing surfaces. In this case, the second to fifth introduction parts are connected to the inside of the ring and can be connected to one fluid feed part, that is, the second fluid feed part p2 (not shown).

A plurality of openings of introduction parts arranged in positions different in the circumferential direction r0 of the ring can be combined with a plurality of openings of introduction parts arranged in positions different in the radial direction r1 of the ring.

Figure 3D:
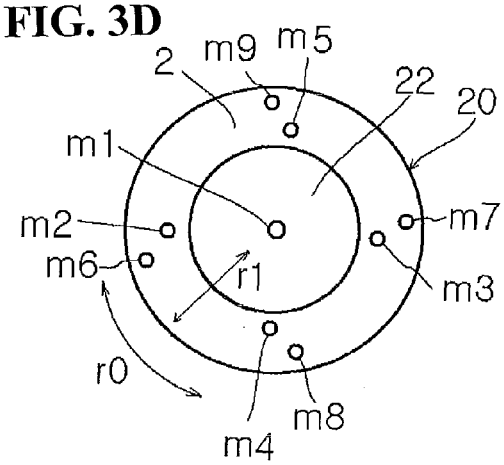
FIG. 3(D) is a schematic bottom view showing the concept of still another embodiment of the apparatus.

For example, as shown in FIG. 3(D), the openings m2 to m9 of eight introduction parts are arranged in the second processing surface 2, wherein four openings m2 to m5 of them are arranged in positions different in the circumferential direction r0 of the ring and identical in the radial direction r1 of the ring, and the other four openings m6 to m9 are arranged in positions different in the circumferential direction r0 of the ring and identical in the radial direction r1 of the ring. Then, the other openings m6 to m9 are arranged outside the radial direction r of the four openings m2 to m5. The outside openings and inside openings may be arranged in positions identical in the circumferential direction r0 of the ring, but in consideration of rotation of the ring, may be arranged in positions different in the circumferential direction r0 of the ring as shown in FIG. 3(D). In this case too, the openings are not limited to the arrangement and number shown in FIG. 3(D).

Figure 3E:
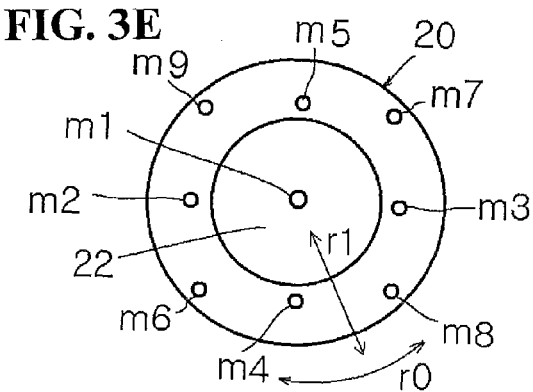
FIG. 3(E) is a schematic bottom view showing the concept of still another embodiment of the apparatus.

For example, as shown in FIG. 3(E), the outside opening in the radial direction can be arranged in the apex of a polygon, that is, in the apex of a rectangle in this case, and the inside opening in the radial direction can be positioned on one side of the rectangle. As a matter of course, other arrangements can also be used.

Figure 3F:
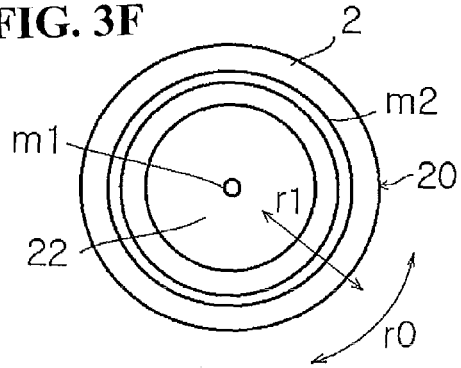
FIG. 3(F) is a schematic bottom view showing the concept of still another embodiment of the apparatus.

When the openings other than the first opening m1 feed the second processed fluid into the space between the processing surfaces, each of the openings may be arranged as continuous openings in the circumferential direction r0 as shown in FIG. 3(F), instead of being arranged discretely in the circumferential direction r0 of the processing surface.

Figure 4A:
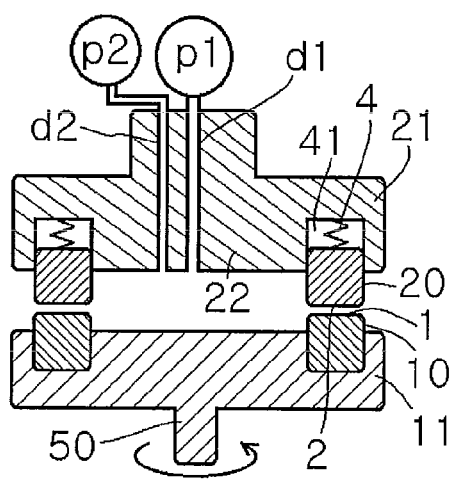
FIG. 4(A) to FIG. 4(D) each show a schematic vertical sectional view showing the concept of still another embodiment of the apparatus shown in FIG. 1.
Figure 4B:
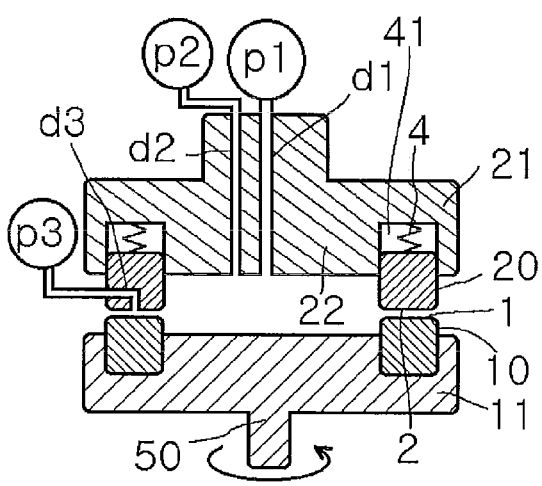
Figure 4C:
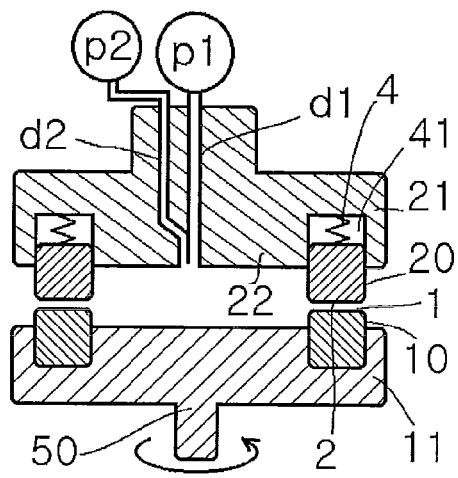
Figure 4D:
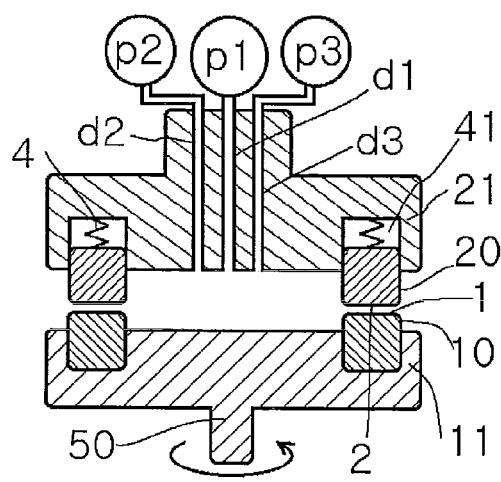

As shown in FIG. 4(A), depending on the object of processing, the second introduction part d2 arranged in the second ring 20 in the apparatus shown in FIG. 1(A) can be, similar to the first introduction part d1, arranged in the central portion 22 of the second holder 21. In this case, the opening of the second introduction part d2 is positioned with a gap outside the opening of the first introduction part d1 positioned in the center of the second ring 20. As shown in FIG. 4(B), in the apparatus shown in FIG. 4(A), the third introduction part d3 can be arranged in the second ring 20. As shown in FIG. 4(C), in the apparatus shown in FIG. 4(A), the second and third processed fluids can be introduced into the space inside the second ring 20 without arranging a gap between the opening of the first introduction part d1 and the opening of the second introduction part d2, so that both the fluids can immediately join together. As shown in FIG. 4(D), depending on the object of processing, in the apparatus shown in FIG. 4(A), the third introduction part d3 can be, similar to the second introduction part d2, arranged in the second holder 21. Four or more introduction parts may be arranged in the second holder 21 (not shown).

Figure 5A:
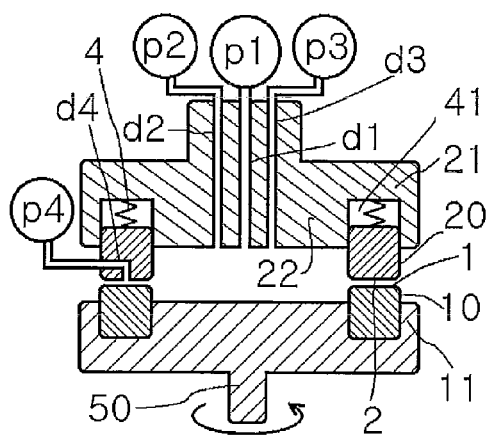
FIG. 5(A) to FIG. 5(D) each show a schematic vertical sectional view showing the concept of still another embodiment of the apparatus shown in FIG. 1.

As shown in FIG. 5(A), depending on the object of processing, in the apparatus shown in FIG. 4(D), the fourth introduction part d4 can be arranged in the second ring 20, so that the fourth processed fluid may be introduced into the space between the processing surfaces 1 and 2.

Figure 5B:
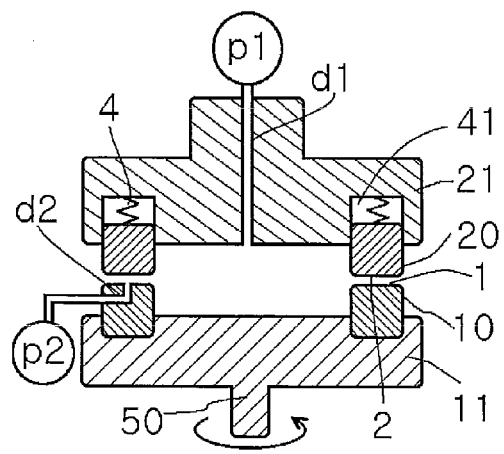

As shown in FIG. 5(B), in the apparatus shown in FIG. 1(A), the second introduction part d2 can be arranged in the first ring 10, and the opening of the second introduction part d2 can be arranged in the first processing surface 1.

Figure 5C:
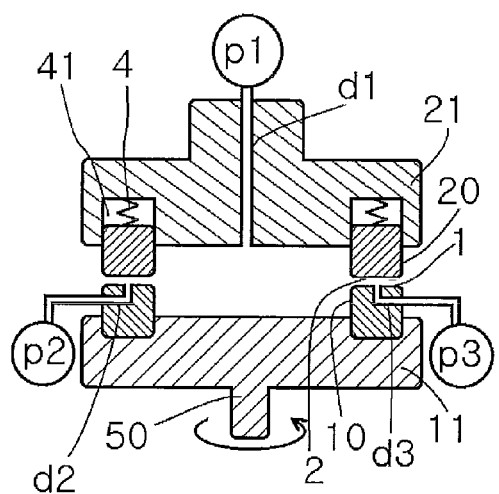

As shown in FIG. 5(C), in the apparatus shown in FIG. 5(B), the third introduction part d3 can be arranged in the first ring 10, and the opening of the third introduction part d3 and the opening of the second introduction part d2 can be arranged in the first processing surface 1 in positions different in the circumferential direction of the first ring 10.

Figure 5D:
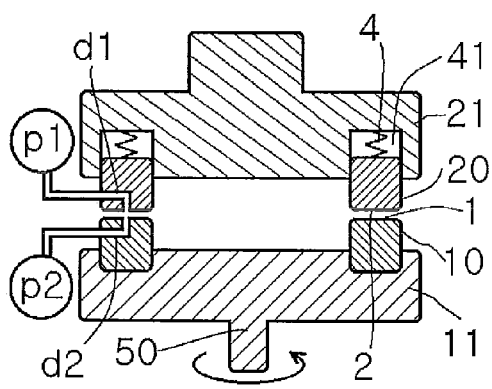

As shown in FIG. 5(D), in the apparatus shown in FIG. 5(B), the first introduction part d1 can be arranged in the second ring 20 instead of arranging the first introduction part d1 in the second holder 21, and the opening of the first introduction part d1 can be arranged in the second processing surface 2. In this case, the openings of the first and second introduction parts d1 and d2 are arranged in positions identical in the radial direction of the ring.

Figure 6A:
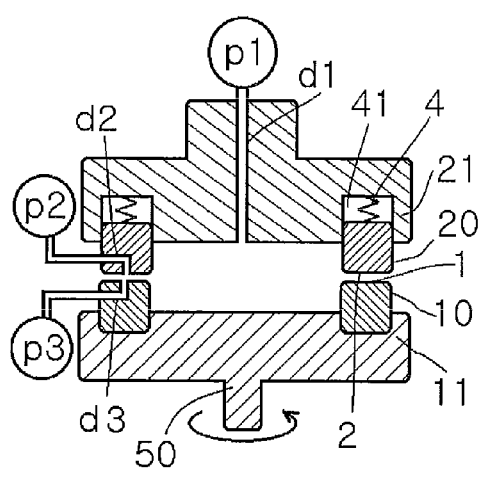
FIG. 6(A) to FIG. 6(D) each show a schematic vertical sectional view showing the concept of still another embodiment of the apparatus shown in FIG. 1.

As shown in FIG. 6(A), in the apparatus shown in FIG. 1(A), the third introduction part d3 can be arranged in the first ring 10, and the opening of the third introduction part d3 can be arranged in the first processing surface 1. In this case, both the openings of the second and third introduction parts d2 and d3 are arranged in positions identical in the radial direction of the ring. However, both the openings may be arranged in positions different in the radial direction of the ring.

Figure 6B:
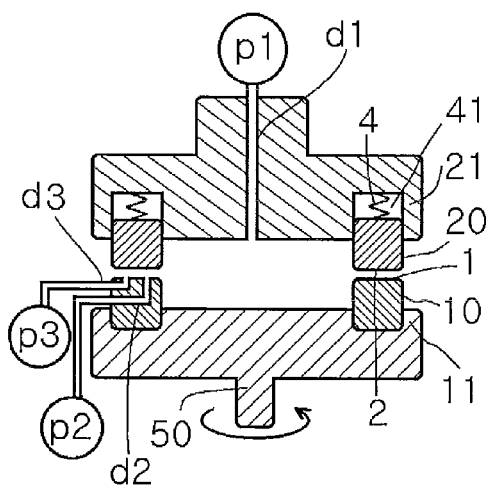

In the apparatus shown in FIG. 5(C), both the openings of the second and third introduction parts d2 and d3 are arranged in positions identical in the radial direction of the first ring 10 and simultaneously arranged in positions different in the circumferential direction (that is, rotation direction) of the first ring 10, however in this apparatus, as shown in FIG. 6(B), both the openings of the second and third introduction parts d2 and d3 can be arranged in positions identical in the circumferential direction of the first ring 10 and simultaneously arranged in positions different in the radical direction of the first ring 10. In this case, as shown in FIG. 6(B), a gap can be arranged between both the openings of the second and third introduction parts d2 and d3 in the radial direction of the first ring 10, or without arranging the gap, the second and third processed fluids may immediately join together (not shown).

Figure 6C:
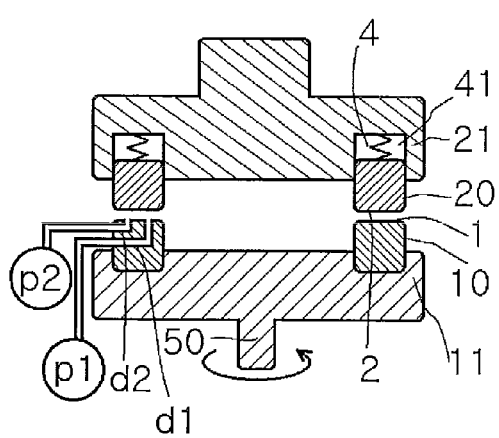

As shown in FIG. 6(C), the first introduction part d1 together with the second introduction part d2 can be arranged in the first ring 10 instead of arranging the first introduction part d1 in the second holder 21. In this case, in the first processing surface 1, the opening of the first introduction part d1 is arranged upstream (inside the radial direction of the first ring 11) from the opening of the second introduction part d2. A gap is arranged between the opening of the first introduction part d1 and the opening of the second introduction part d2 in the radial direction of the first ring 11. Alternatively, such gap may not be arranged (not shown).

Figure 6D:
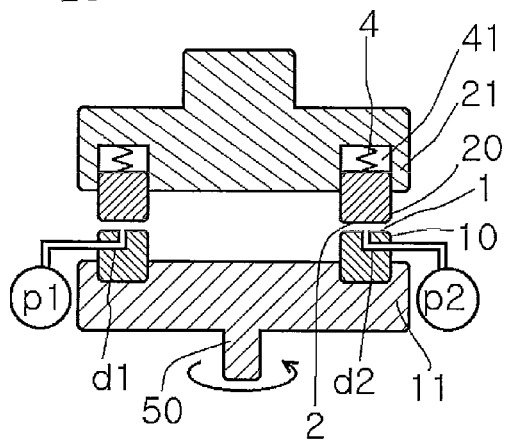

As shown in FIG. 6(D), both the openings of the first introduction part d1 and the second introduction part d2 can be arranged in positions different in the circumferential direction of the first ring 10 in the first processing surface 1 in the apparatus shown in FIG. 6(C).

In the embodiment shown in FIG. 6(C) and FIG. 6(D), three or more introduction parts may be arranged in the first ring 10, and in the second processing surface 2, so the respective openings may be arranged in positions different in the circumferential direction or in positions different in the radial direction of the ring (not shown). For example, the arrangement of openings in the second processing surface 2, shown in FIG. 3(B) to FIG. 3(F), can also be used in the first processing surface 1.

Figure 7A:
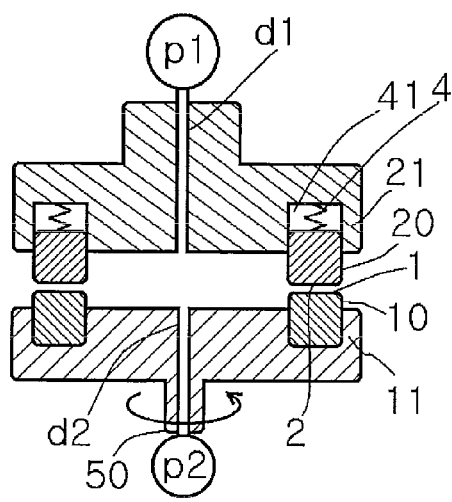
FIG. 7(A) to FIG. 7(D) each show a schematic vertical sectional view showing the concept of still another embodiment of the apparatus shown in FIG. 1.

As shown in FIG. 7(A), in the apparatus shown in FIG. 1(A), the second introduction part d2 can be arranged in the first holder 11 instead of arranging the part d2 in the second ring 20. In this case, the opening of the second introduction part d2 is arranged preferably in the center of the central shaft of rotation of the first ring 10, in the site surrounded with the first ring 10 on the upper surface of the first holder 11.

Figure 7B:
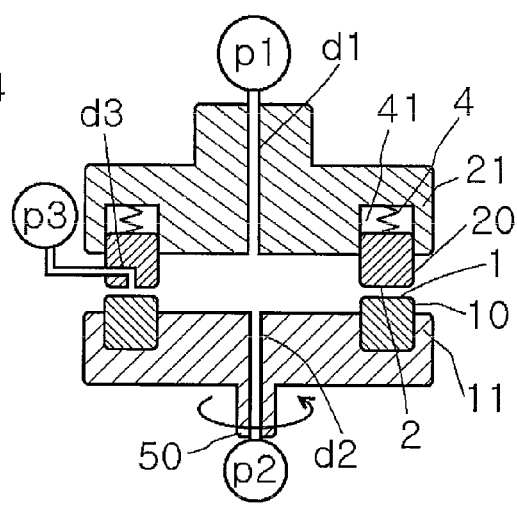

As shown in FIG. 7(B), in the embodiment shown in FIG. 7(A), the third introduction part d3 can be arranged in the second ring 20, and the opening of the third introduction part d3 can be arranged in the second processing surface 2.

Figure 7C:
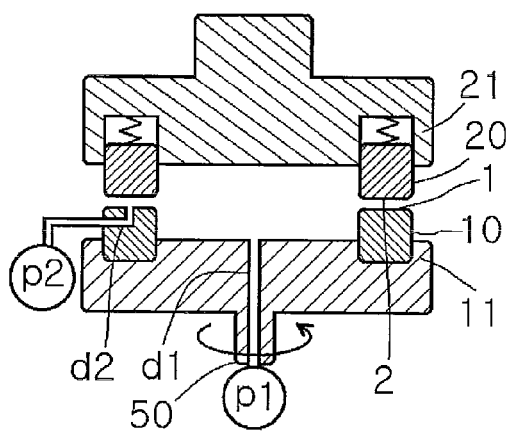

As shown in FIG. 7(C), the first introduction part d1 can be arranged in the first holder 11 instead of arranging the part d1 in the second holder 21. In this case, the opening of the first introduction part d1 is arranged preferably in the central shaft of rotation of the first ring 10, in the site surrounded with the first ring 10 on the upper surface of the first holder 11. In this case, as shown in the figure, the second introduction part d2 can be arranged in the first ring 10, and its opening can be arranged in the first processing surface 1. In this case, the second introduction part d2 can be arranged in the second ring 20, and its opening can be arranged in the second processing surface 2 (not shown).

Figure 7D:
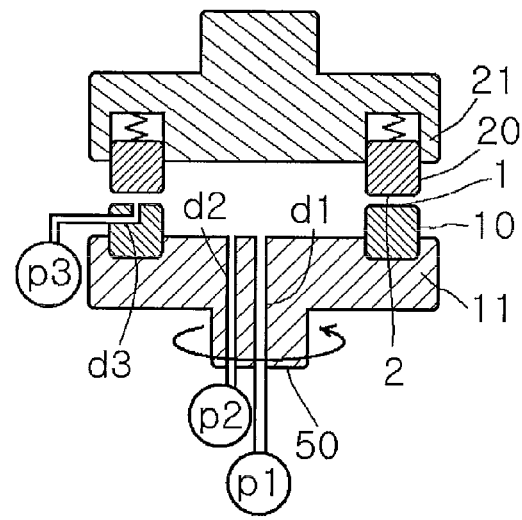

As shown in FIG. 7(D), the second introduction part d2 shown in FIG. 7(C) together with the first introduction part d1 can be arranged in the first holder 11. In this case, the opening of the second introduction part d2 is arranged in the site surrounded with the first ring 10 on the upper surface of the first holder 11. In this case, the second introduction part d2 arranged in the second ring 20 may serve as the third introduction part d3 in FIG. 7(C).

Figure 8A:
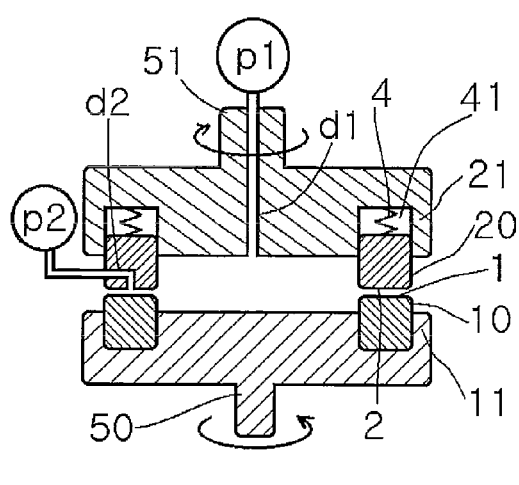
FIG. 8(A) to FIG. 8(D) each show a schematic vertical sectional view showing the concept of still another embodiment of the apparatus shown in FIG. 1.

In the embodiments shown in FIG. 1 to FIG. 7, the first holder 11 and the first ring 10 are rotated relative to the second holder 21 and the second ring 20, respectively. As shown in FIG. 8(A), in the apparatus shown in FIG. 1(A), the second holder 2 may be provided with a rotary shaft 51 rotating with the turning force from the rotation drive member, to rotate the second holder 21 in a direction opposite to the first holder 11. The rotation drive member in the rotary shaft 51 may be arranged separately from the one for rotating the rotary shaft 50 of the first holder 11 or may receive power from the drive part for rotating the rotary shaft 50 of the first holder 11 by a power transmission means such as a gear. In this case, the second holder 2 is formed separately from the case, and shall, like the first holder 11, be rotatably accepted in the case.

Figure 8B:
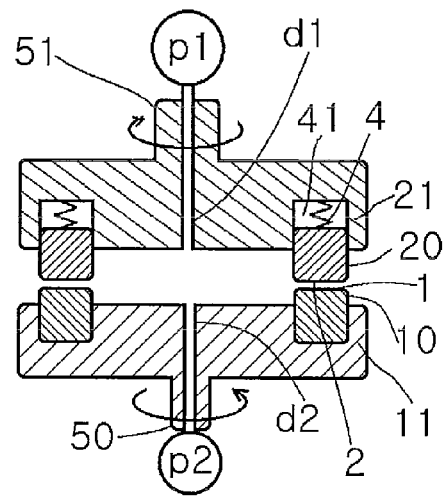

As shown in FIG. 8(B), in the apparatus shown in FIG. 8(A), the second introduction part d2 can be, similarly in the apparatus in FIG. 7(B), arranged in the first holder 11 in place of the second ring 20.

Figure 8C:
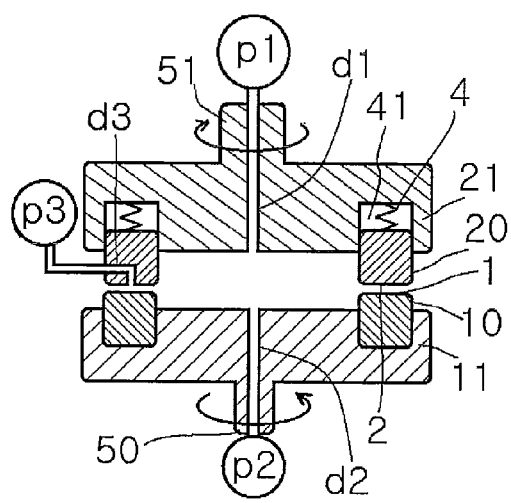

In the apparatus shown in FIG. 8(B), the second introduction part d2 can be arranged in the second holder 21 in place of the first holder 11 (not shown). In this case, the second introduction part d2 is the same as one in the apparatus in FIG. 4(A). As shown in FIG. 8(C), in the apparatus shown in FIG. 8(B), the third introduction part d3 can be arranged in the second ring 20, and the opening of the third introduction part d3 can be arranged in the second processing surface 2.

Figure 8D:
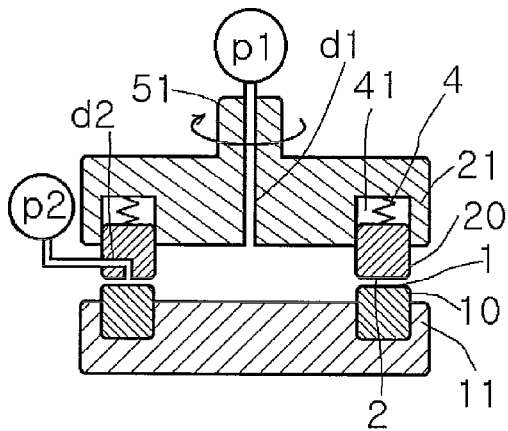

As shown in FIG. 8(D), the second holder 21 only can be rotated without rotating the first holder 11. Even in the apparatuses shown in FIG. 1(B) to FIG. 7, the second holder 21 together with the first holder 11, or the second holder 21 alone, can be rotated (not shown).

Figure 9A:
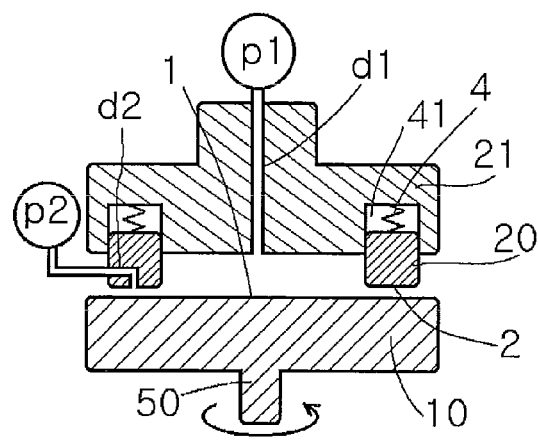
FIG. 9(A) to FIG. 9(C) each show a schematic vertical sectional view showing the concept of still another embodiment of the apparatus shown in FIG. 1.

As shown in FIG. 9(A), the second processing member 20 is a ring, while the first processing member 10 is not a ring and can be a rotating member provided directly with a rotary shaft 50 like that of the first holder 11 in other embodiments. In this case, the upper surface of the first processing member 10 serves as the first processing surface 1, and the processing surface is an evenly flat surface which is not circular (that is, hollow-free). In the apparatus shown in FIG. 9(A), similarly in the apparatus in FIG. 1(A), the second introduction part d2 is arranged in the second ring 20, and its opening is arranged in the second processing surface 2.

Figure 9B:
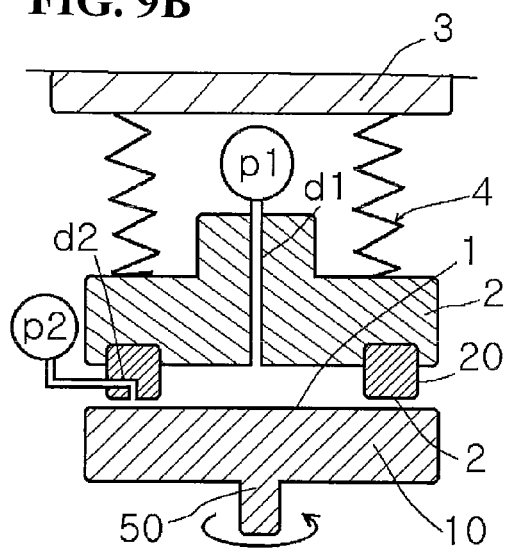
Figure 9C:
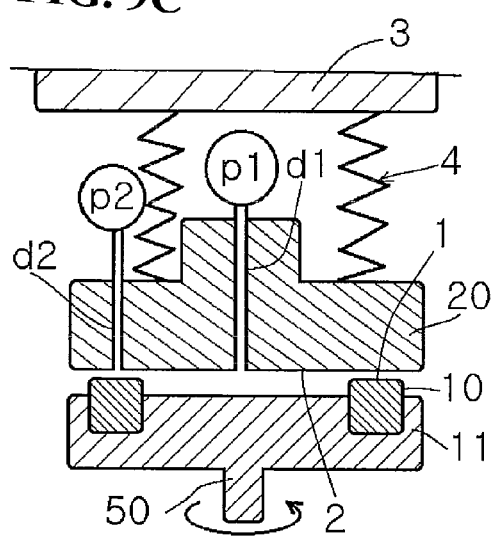
Figure 10A:
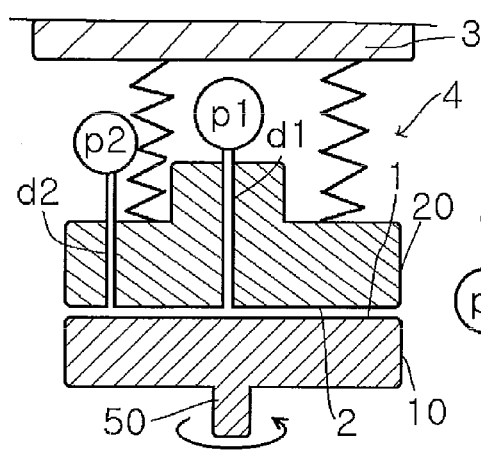
FIG. 10(A) to FIG. 10(D) each show a schematic vertical sectional view showing the concept of still another embodiment of the apparatus shown in FIG. 1.

As shown in FIG. 9(B), in the apparatus shown in FIG. 9(A), the second holder 21 is independent of the case 3, and a surface-approaching pressure imparting mechanism 4 such as an elastic body for approaching to and separating from the first processing member 10 provided with the second ring 20 can be provided between the case 3 and the second holder 21. In this case, as shown in FIG. 9(C), the second processing member 20 is not a ring, but is a member corresponding to the second holder 21, and the lower surface of the member can serve as the second processing surface 2. As shown in FIG. 10(A), in the apparatus shown in FIG. 9(C), the first processing member 10 is not a ring either, and in other embodiments similar to the apparatus shown in FIG. 9 (A) and FIG. 9(B), the site corresponding to the first holder 11 can serve as the first processing member 10, and its upper surface can serve as the first processing surface 1.

In the embodiments described above, at least the first fluid is supplied from the first processing member 10 and the second processing member 20, that is, from the central part of the first ring 10 and the second ring 20, and after processing (mixing (reaction)) of the other fluids, the processed fluid is discharged to the outside in the radial direction.

Figure 10B:
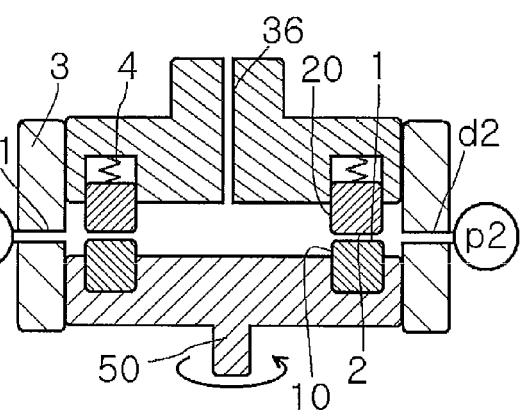

Alternatively, as shown in FIG. 10(B), the first fluid can be supplied in the direction from the outside to the inside of the first ring 10 and second ring 20. In this case, the outside of the first holder 11 and the second holder 21 is sealed with the case 3, the first introduction part d1 is arranged directly in the case 3, and the opening of the introduction part is arranged in a site inside the case and corresponding to the abutting position of the rings 10 and 20, as shown in the figure. In the apparatus in FIG. 1(A), a discharge part 36 is arranged in the position in which the first introduction part d1 is arranged, that is, in the central position of the ring 1 of the first holder 11. The opening of the second introduction part d2 is arranged in the opposite side of the opening of the case behind the central shaft of rotation of the holder. However, the opening of the second introduction part d may be, similar to the opening of the first introduction part d1, arranged in a site inside the case and corresponding to the abutting position of the rings 10 and 20. As described above, the embodiment is not limited to the one where the opening of the second introduction part d is formed to the opposite side of the opening of the first introduction part d1.

In this case, the outside of the diameter of both the rings 10 and 20 is on the upstream side, and the inside of both the rings 10 and 20 is on the downstream side.

As such, as shown in FIG. 16(E), when the processed fluid moves from outside to inside, the first processing surface 1 of the first processing member 10 may also be provided with groove-like depressions 13 . . . 13 extending in the direction from outside to inside of the first processing member 10. When the groove-like depressions 13 . . . 13 are formed, the balance ratio K described above is preferably set as 100% or more of unbalance type. As a result, dynamical pressure is generated in the groove-like depressions 13 . . . 13 upon rotating, the first and second processing surfaces 1 and 2 can rotate in a surely non-contact state, so that the risk of abrasion and the like due to contact can be eliminated. In the embodiment shown in FIG. 16(E), the separating force due to the pressure of the processed fluid is generated in an inner end 13a of the depressions 13.

Figure 10C:
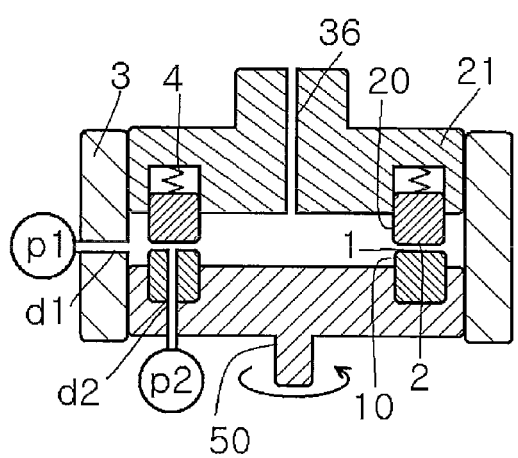
Figure 10D:
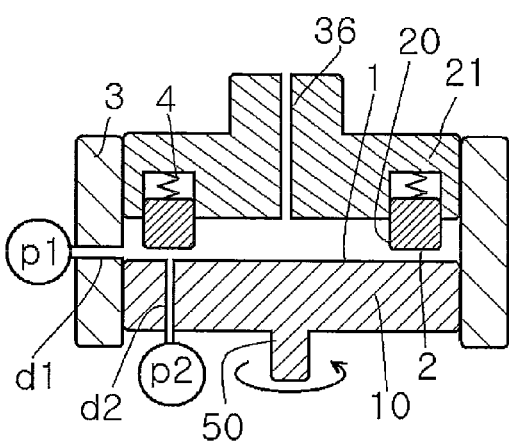

As shown in FIG. 10(C), in the apparatus shown in FIG. 10(B), the second introduction part d2, which is arranged in the side of the case 3, can be arranged in the first ring 11 in space of the mentioned position, and its opening can be arranged in the first processing surface 1. In this case, as shown in FIG. 10(D), the first processing member 10 is not formed as a ring. Similarly in the apparatuses shown in FIG. 9(A), FIG. 9(B) and FIG. 10(A), in other embodiments, the site corresponding to the first holder 11 is the first processing member 10, its upper surface being the first processing surface 1, the second introduction part d2 being arranged in the first processing member 10, and its opening may be arranged in the first processing surface 1.

Figure 11A:
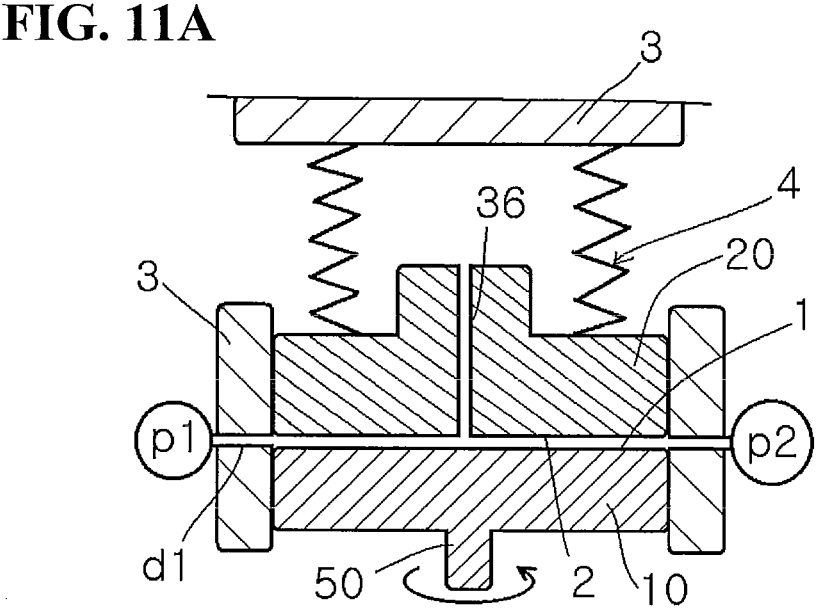
FIG. 11(A) and FIG. 11(B) each show a schematic vertical sectional view showing the concept of still another embodiment of the apparatus shown in FIG. 1.

As shown in FIG. 11(A), in the apparatus shown in FIG. 10(D), the second processing member 20 is not formed as a ring, and in other embodiments, the member corresponding to the second holder 21 serves as the second processing member 20, and its lower surface serves as the second processing surface 2. Then, the second processing member 20 is a member independent of the case 3, and the same surface-approaching pressure imparting mechanism 4 as one in the apparatuses shown in FIG. 9(B), FIG. 9(C) and FIG. 10(A) can be arranged between the case 3 and the second processing member 20.

Figure 11B:
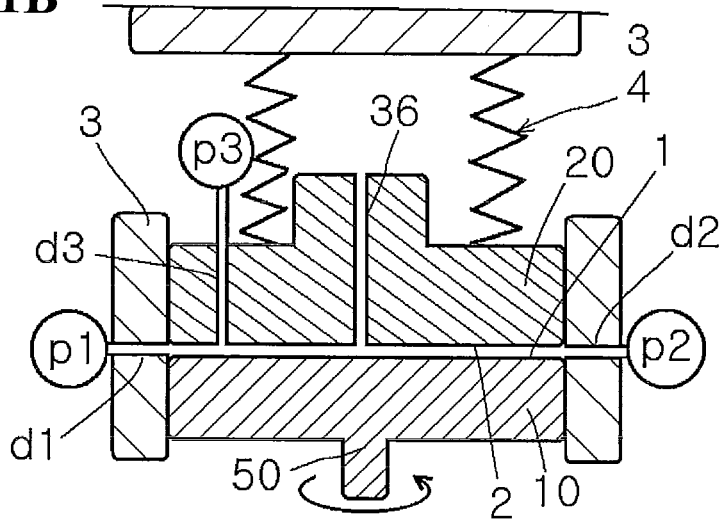
Figure 11C:
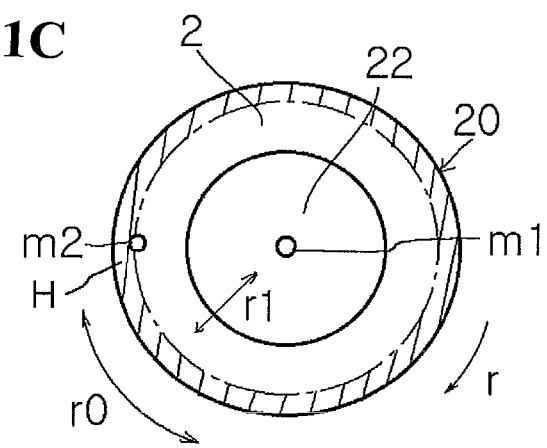
FIG. 11(C) is a schematic bottom view showing an important part of the apparatus shown in FIG. 1(A).

As shown in FIG. 11(B), the second introduction part d2 in the apparatus shown in FIG. 11(A) serves as the third introduction part d3, and separately the second introduction part d2 can be arranged. In this case, the opening of the second introduction part d2 is arranged downstream from the opening of the third introduction part d3 in the second processing surface 2.

In the apparatuses shown in FIG. 4 and the apparatuses shown in FIG. 5(A), FIG. 7(A), FIG. 7(B), FIG. 7(D), FIG. 8(B) and FIG. 8(C), other processed fluids flow into the first processed fluid before reaching the processing surfaces 1 and 2, and these apparatuses are not suitable for the fluid which is rapidly crystallized or separated. However, these apparatuses can be used for the fluid having a low reaction speed.

The fluid processing apparatus suitable for carrying out the method according to the present invention is summarized as follows.

As described above, the fluid processing apparatus comprises a fluid pressure imparting mechanism that imparts predetermined pressure to a processed fluid, at least two processing members, that is, a first processing member 10 arranged in a sealed fluid flow path through which a processed fluid at the predetermined pressure flows and a second processing member 20 capable of approaching to and separating from the first processing member 10, at least two processing surfaces of a first processing surface 1 and a second processing surface 2 arranged in a position in which they are faced with each other in the processing members 10 and 20, and a rotation drive mechanism that relatively rotates the first processing member 10 and the second processing member 20, wherein at least two processed fluids are mixed (and reacted when the mixing is accompanied by reaction) between the processing surfaces 1 and 2. Of the first processing member 10 and the second processing member 20, at least the second processing member 20 has a pressure-receiving surface, at least a part of the pressure-receiving surface is comprised of the second processing surface 2, and the pressure-receiving surface receives pressure applied by the fluid pressure imparting mechanism to at least one of the fluids to generate a force to move in the direction of separating the second processing surface 2 from the first processing surface 1. In this apparatus, the processed fluid that has received said pressure passes through the space between the first processing surface 1 and the second processing surface 2 capable of approaching to and separating from each other, thereby generating a desired mixing (reaction) between the processed fluids with the processed fluids being passed between the processing surfaces 1 and 2 and forming a fluid film of predetermined thickness.

In this fluid processing apparatus, at least one of the first processing surface 1 and the second processing surface 2 is preferably provided with a buffer mechanism for regulation of micro-vibration and alignment.

In this processing apparatus, one of or both the first processing surface 1 and the second processing surface 2 is preferably provided with a displacement regulating mechanism capable of regulating the displacement in the axial direction caused by abrasion or the like thereby maintaining the thickness of a fluid film between the processing surfaces 1 and 2.

In this fluid processing apparatus, a pressure device such as a compressor for applying predetermined feeding pressure to a fluid can be used as the fluid pressure imparting mechanism.

As the pressure device, a device capable of regulating an increase and decrease in feeding pressure is used. This is because the pressure device should be able to keep established pressure constant and should be able to regulate an increase and decrease in feeding pressure as a parameter to regulate the distance between the processing surfaces.

The fluid processing apparatus can be provided with a separation preventing part for defining the maximum distance between the first processing surface 1 and the second processing surface 2 and preventing the processing surfaces 1 and 2 from separating from each other by the maximum distance or more.

The fluid processing apparatus can be provided with an approach preventing part for defining the minimum distance between the first processing surface 1 and the second processing surface 2 and preventing the processing surfaces 1 and 2 from approaching to each other by the minimum distance or less.

The fluid processing apparatus can be one wherein both the first processing surface 1 and the second processing surface 2 are rotated in opposite directions.

The fluid processing apparatus can be provided with a temperature-regulating jacket for regulating the temperature of either or both of the first processing surface 1 and the second processing surface 2.

The fluid processing apparatus is preferably one wherein at least a part of either or both of the first processing surface 1 and the second processing surface 2 is mirror-polished.

The fluid processing apparatus can be one wherein one of or both the first processing surface 1 and the second processing surface 2 is provided with depressions.

The fluid processing apparatus preferably includes, as a means for feeding one processed fluid to be mixed (reacted) with another processed fluid, a separate introduction path independent of a path for another processed fluid, at least one of the first processing surface and the second processing surface is provided with an opening leading to the separate introduction path, and another processed fluid sent through the separate introduction path is introduced into the processed fluid.

The fluid processing apparatus for carrying out the present invention comprises a fluid pressure imparting mechanism that imparts predetermined pressure to a fluid, at least two processing surfaces of a first processing surface 1 and a second processing surface 2 capable of approaching to and separating from each other which are connected to a sealed fluid flow path through which the processed fluid at the predetermined pressure is passed, a surface-approaching pressure imparting mechanism that imparts surface-approaching pressure to the space between the processing surfaces 1 and 2, and a rotation drive mechanism that relatively rotates the first processing surface 1 and the second processing surface 2, whereby at least two processed fluids are mixed (reacted) between the processing surfaces 1 and 2, at least one processed fluid pressurized with the fluid pressure imparting mechanism is passed through the space between the first processing surface 1 and the second processing surface 2 rotating to each other and supplied with surface-approaching pressure, and another processed fluid is passed, so that the processed fluid pressurized with the fluid pressure imparting mechanism, while being passed between the processing surfaces and forming a fluid film of predetermined thickness, is mixed with another processed fluid, whereby a desired mixing (reaction) is caused between the processed fluids.

The surface-approaching pressure imparting mechanism can constitute a buffer mechanism of regulating micro-vibration and alignment and a displacement regulation mechanism in the apparatus described above.

The fluid processing apparatus for carrying out the present invention comprises a first introduction part that introduces, into the apparatus, at least one of two processed fluids to be mixed (reacted), a fluid pressure imparting mechanism p that is connected to the first introduction part and imparts pressure to the processed fluid, a second introduction part that introduces at least the other fluid of the two processed fluids to be mixed (reacted), at least two processing members, that is, a first processing member 10 arranged in a sealed fluid flow path through which the other processed fluid is passed and a second processing member 20 capable of relatively approaching to and separating from the first processing member 10, at least two processing surfaces, that is, a first processing surface 1 and a second processing surface 2 arranged so as to be opposite to each other in the processing members 10 and 20, a holder 21 that accepts the second processing member 20 so as to expose the second processing surface 2, a rotation drive mechanism that relatively rotates the first processing member 10 and the second processing member 20, and a surface-approaching pressure imparting mechanism 4 that presses the second processing member 20 against the first processing surface 1 such that the second processing surface 2 is contacted against or made close to the first processing surface 1, wherein the processed fluids are mixed (reacted) between the processing surfaces 1 and 2, the holder 21 is provided with an opening of the first introduction part and is not movable so as to influence the space between the processing surfaces 1 and 2, at least one of the first processing member 10 and the second introduction part 20 is provided with an opening of the second introduction part, the second processing member 20 is circular, the second processing surface 2 slides along the holder 21 and approaches to and separates from the first processing surface 1, the second processing member 20 includes a pressure-receiving surface, the pressure-receiving surface receives pressure applied from the fluid pressure imparting mechanism p to the processed fluid to generate a force to move in the direction of separating the second processing surface 2 from the first processing surface 1, at least a part of the pressure-receiving surface is comprised of the second processing surface 2, one of the processed fluids to which pressure was applied is passed through the space between the first processing surface 1 and the second processing surface 2 rotating to each other and capable of approaching to and separating from each other, and the other processed fluid is supplied to the space between the processing surfaces 1 and 2, whereby both the processed fluids form a fluid film of predetermined thickness and pass through the space between both the processing surfaces 1 and 2, the passing processed fluid are mixed thereby promoting a desired mixing (reaction) between the processed fluids, and the minimum distance for generating the fluid film of predetermined thickness is kept between the processing surfaces 1 and 2 by the balance between the surface-approaching pressure by the surface-approaching pressure imparting mechanism 4 and the force of separating the processing surfaces 1 and 2 from each other by the fluid pressure imparted by the fluid pressure imparting mechanism p.

In this processing apparatus, the second introduction part can be, similarly being connected to the first introduction part, arranged to be connected to a separate fluid pressure imparting mechanism and to be pressurized. The processed fluid introduced from the second introduction part is not pressurized by the separate fluid pressure imparting mechanism, but is sucked and supplied into the space between the processing surfaces 1 and 2 by negative pressure generated in the second introduction part by the fluid pressure of the processed fluid introduced into the first introduction part. Alternatively, the other processed fluid flows downward by its weight in the second introduction part and can be supplied into the space between the processing surfaces 1 and 2.

As described above, the apparatus is not limited to the one wherein the opening of the first introduction part as an inlet for feeding the other processed fluid into the apparatus is arranged in the second holder, and the opening of the first introduction part may be arranged in the first holder. The opening of the first introduction part may be formed with at least one of the processing surfaces. However, when the processed fluid to be previously introduced into the space between the processing surfaces 1 and 2 should, depending on the reaction, be supplied from the first introduction part, the opening of the second introduction part as an inlet for feeding the other processed fluid into the apparatus should be arranged downstream from the opening of the first introduction part in any of the processing surfaces.

As the fluid processing apparatus for carrying out the present invention, the following apparatus can be used.

This processing apparatus comprises a plurality of introduction parts that separately introduce two or more processed fluids to be mixed (reacted), a fluid pressure imparting mechanism p that imparts pressure to at least one of the two or more processed fluids, at least two processing members, that is, a first processing member 10 arranged in a sealed fluid flow path through which the processed fluid is passed and a second processing member 20 capable of approaching to and separating from the first processing member 10, at least two processing surfaces 1 and 2, that is, a first processing surface 1 and a second processing surface 2 arranged in a position in which they are faced with each other in the processing members 10 and 20, and a rotation drive mechanism that relatively rotates the first processing member 10 and the second processing member 20, wherein the processed fluids are mixed (reacted) between the processing surfaces 1 and 2, at least the second processing member 20 of the first processing member 10 and the second processing member 20 includes a pressure-receiving surface, at least a part of the pressure-receiving surface is comprised of the second processing surface 2, the pressure-receiving surface receives pressure applied by the fluid pressure imparting mechanism to the processed fluid to generate a force to move in the direction of separating the second processing surface 2 from the first processing surface 1, the second processing member 20 includes an approach regulating surface 24 that is directed to the opposite side of the second processing surface 2, the approach regulating surface 24 receives predetermined pressure applied to the processed fluid to generate a force to move in the direction of approaching the second processing surface 2 to the first processing surface 1, a force to move in the direction of separating the second processing surface 2 from the first processing surface 1 as a resultant force of total pressure received from the processed fluid is determined by the area ratio of the projected area of the approach regulating surface 24 in the approaching and separating direction to the projected area of the pressure-receiving surface in the approaching and separating direction, the processed fluid to which pressure was applied is passed through the space between the first processing surface 1 and the second processing surface 2 that rotate relative to each other and capable of approaching to and separating from each other, the other processed fluid to be mixed (reacted) with the processed fluid is mixed in the space between the processing surfaces, and the mixed processed fluid forms a fluid film of predetermined thickness and simultaneously passes through the space between the processing surfaces 1 and 2, thereby giving a desired product while passing through the space between the processing surfaces.

The fluid processing method according to the present invention is summarized as follows. The fluid processing method comprises applying predetermined pressure to a first fluid, connecting at least two processing surfaces, that is, a first processing surface 1 and a second processing surface 2, which are capable of approaching to and separating from each other, to a sealed fluid flow path through which the processed fluid that has received the predetermined pressure is passed, applying a surface-approaching pressure of approaching the first processing surface 1 and the second processing surface 2 each other, rotating the first processing surface 1 and the second processing surface 2 relative to each other, and introducing the processed fluid into the space between the processing surfaces 1 and 2, wherein the second processed fluid to be mixed (reacted) with the processed fluid is introduced through a separate flow path into the space between the processing surfaces 1 and 2 thereby mixing (reacting) both the processed fluids, the predetermined pressure applied to at least the first processed fluid functions as a separating force for separating the processing surfaces 1 and 2 from each other, and the separating force and the surface-approaching pressure are balanced via the processed fluid between the processing surfaces 1 and 2, whereby the distance between the processing surfaces 1 and 2 is kept in a predetermined minute space, the processed fluid is passed as a fluid film of predetermined thickness through the space between the processing surfaces 1 and 2, and when both the processed fluids are uniformly mixed (reacted) with each other while passing and accompanied by separation, a desired reaction product is crystallized or separated.

Figure 25:
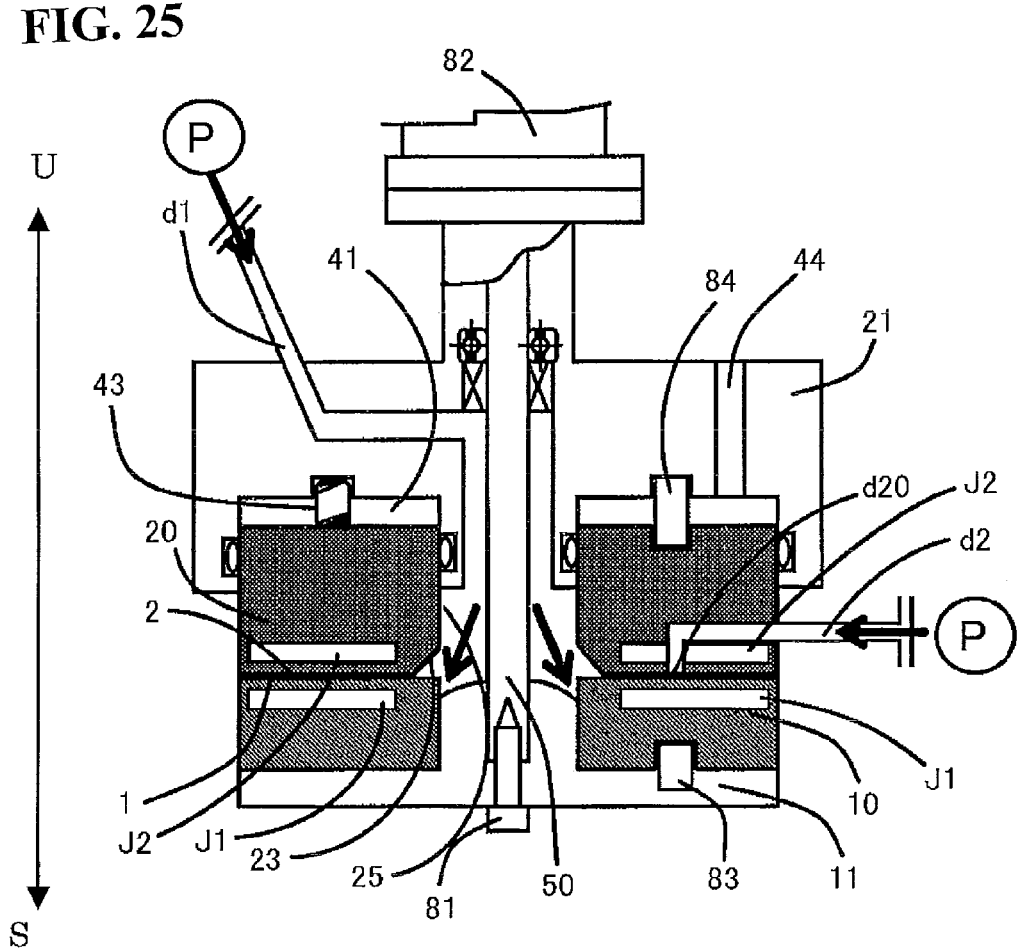
FIG. 25 is a schematic vertical sectional view showing outline of the apparatus of the present invention.
Figure 26A:
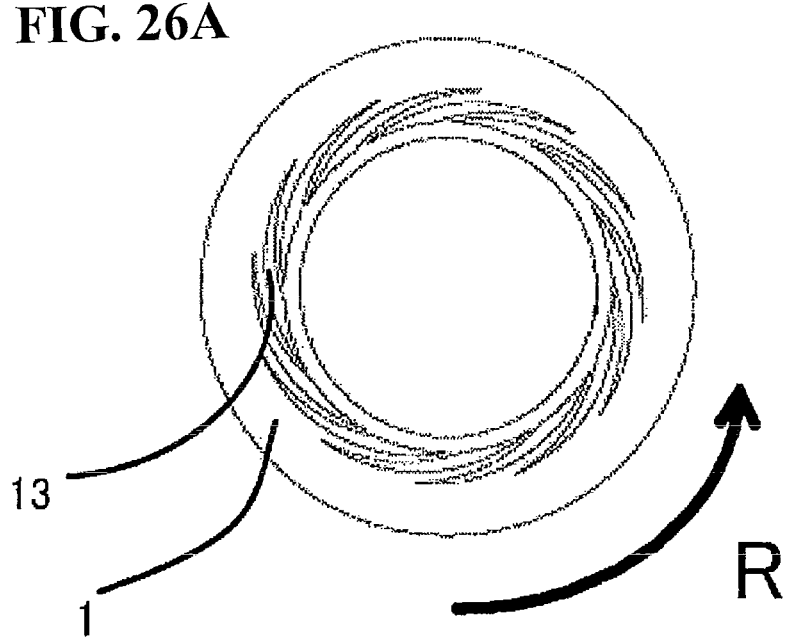
FIG. 26(A) is a schematic plane view of the first processing surface in the apparatus shown in FIG. 25.
Figure 26B:
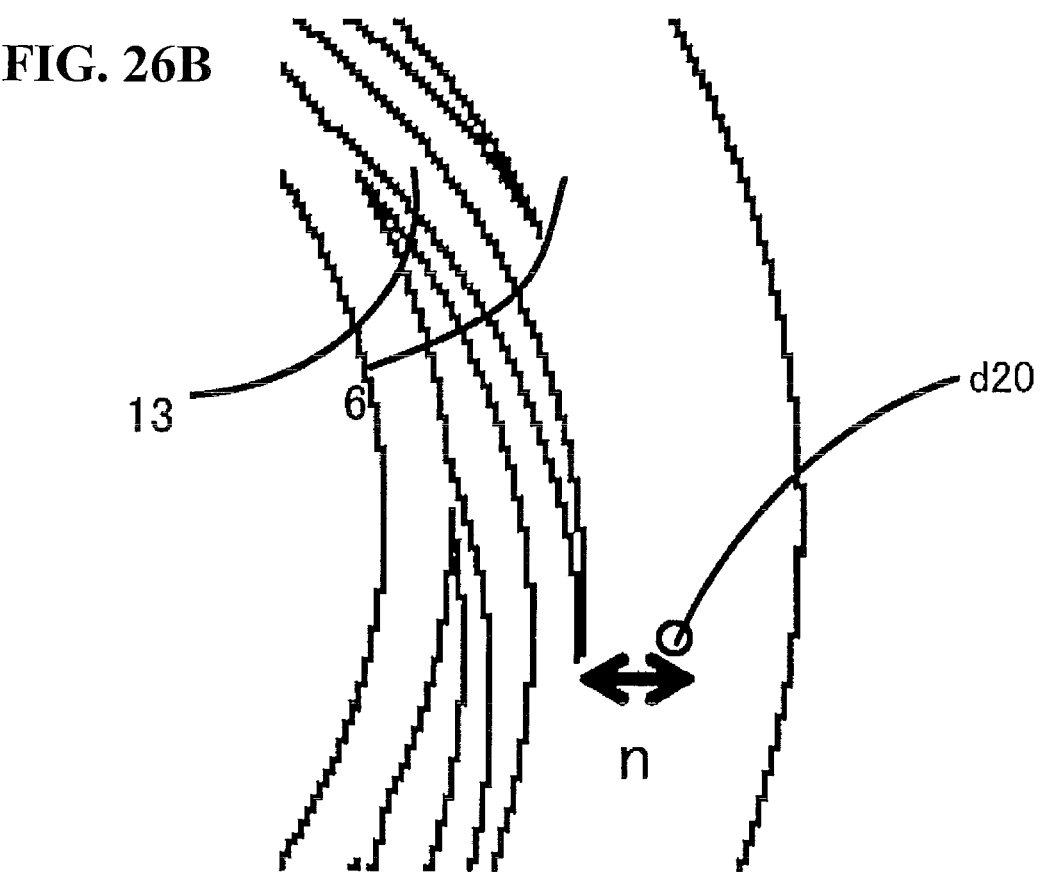
FIG. 26(B) is an enlarged view showing an important part of the first processing surface in the apparatus shown in FIG. 25.
Figure 27A:
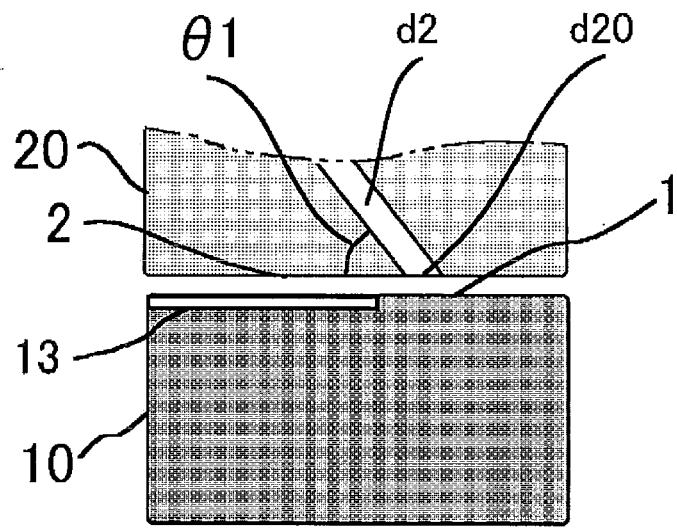
FIG. 27(A) is a sectional view of the second introduction path.
Figure 27B:
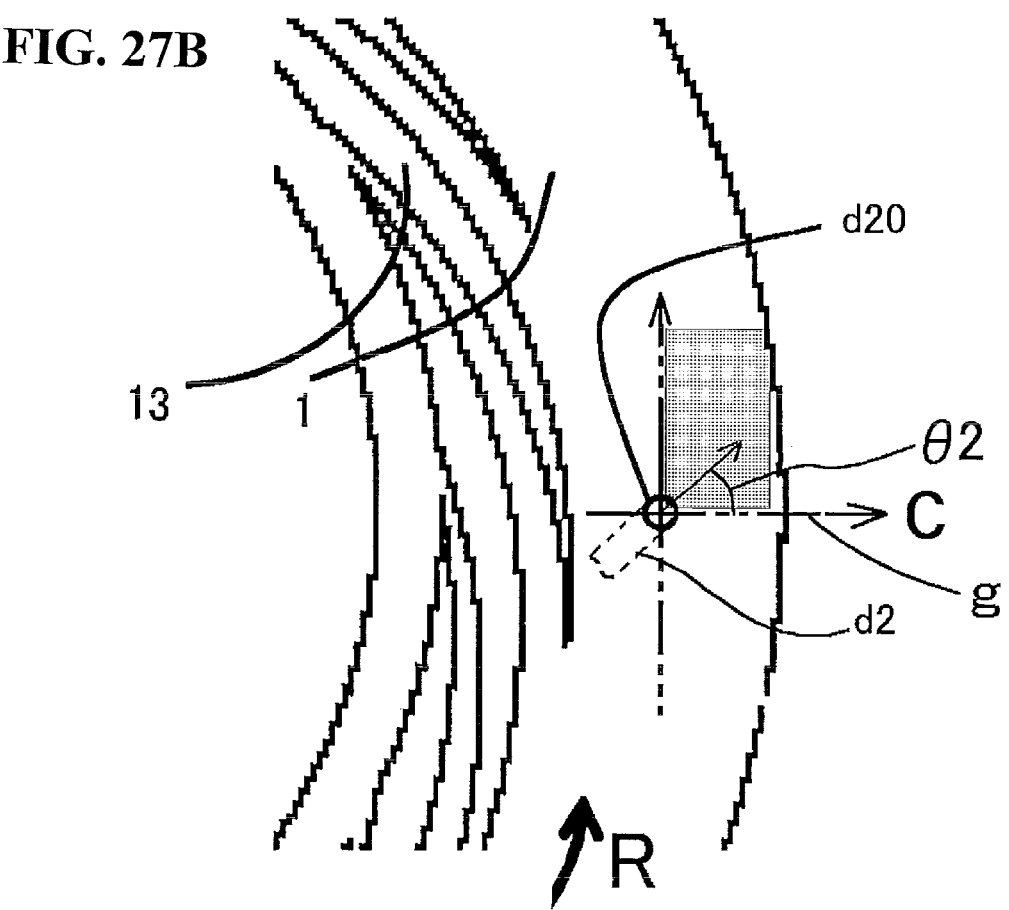
FIG. 27(B) is an enlarged view showing an important part of the processing surface for explaining the second introduction path.

Hereinafter, other embodiments of the present invention are described in detail. FIG. 25 is a schematic sectional view of a fluid processing apparatus wherein processed materials are processed between processing surfaces, at least one of which rotates relative to the other, and which are capable of approaching to and separating from each other. FIG. 26(A) is a schematic plane view of the first processing surface in the apparatus shown in FIG. 25, and FIG. 26(B) is an enlarged view of an important part of the processing surface in the apparatus shown in FIG. 25. In FIG. 27(A) is a sectional view of the second introduction path, and FIG. 27(B) is an enlarged view of an important part for explaining the second introduction path.

In FIG. 25, arrows U and S show upward and downward directions respectively. In FIG. 26(A) and FIG. 27(B), arrow R shows the direction of rotation. In FIG. 27(B), arrow C shows the direction of centrifugal force (radial direction).

This apparatus uses at least two fluids, at least one of which contains at least one kind of the processed material, and the fluids join together in the space between the processing surfaces arranged to be opposite so as to be able to approach to and separate from each other, at least one of which rotates relative to the other, thereby forming a thin film fluid, and the materials to be processed are processed in the thin film fluid. The "process" includes not only a form in which a processed material is reacted, but also a form in which only mixing or dispersion is conducted without accompanying reaction.

As shown in FIG. 25, this apparatus includes a first holder 11, a second holder 21 arranged over the first holder 11, a fluid pressure imparting mechanism P and a surface-approaching pressure imparting mechanism. The surface-approaching pressure imparting mechanism is comprised of a spring 43 and an air introduction part 44.

The first holder 11 is provided with a first processing member 10 and a rotary shaft 50. The first processing member 10 is a circular member called a maintaining ring and provided with a mirror-polished first processing surface 1. The rotary shaft 50 is fixed to the center of the first holder 11 with a fixing device 81 such as a bolt and is connected at its rear end to a rotation drive device 82 (rotation drive mechanism) such as a motor, and the drive power of the rotation drive device 82 is transmitted to the first holder 1 thereby rotating the first holder 11. The first processing member 10 is integrated with the first holder 11 and rotated.

A receiving part capable of receiving the first processing member 10 is arranged on the upper part of the first holder 11, wherein the first processing member 10 has been fixed to the first holder 11 by insertion to the receiving part. The first processing member 10 has been fixed with a rotation preventing pin 83 so as not to be rotated relative to the first holder 11. However, a method such as fitting by burning may be used for fixing in place of the rotation-preventing pin 83 in order to prevent rotation.

The first processing surface 1 is exposed from the first holder 11 and faced with the second holder 21. The material for the first processing surface includes ceramics, sintered metal, abrasion-resistant steel, other hardened metals, and rigid materials subjected to lining, coating or plating.

The second holder 21 is provided with a second processing member 20, a first introduction part d1 for introducing a fluid from the inside of the processing member, a spring 43 as a surface-approaching pressure imparting mechanism, and an air introduction part 44.

The second processing member 20 is a circular member called a compression ring and includes a second processing surface 2 subjected to mirror polishing and a pressure-receiving surface 23 (referred to hereinafter as separation regulating surface 23) which is located inside the second processing surface 2 and adjacent to the second processing surface 2. As shown in the figure, the separation regulating surface 23 is an inclined surface. The method of the mirror polishing to which the second processing surface 2 was subjected is the same as that to the first processing surface 1. The material for the second processing member 20 may be the same as one for the first processing member 10. The separation regulating surface 23 is adjacent to the inner periphery 25 of the circular second processing member 20.

A ring-accepting part 41 is formed in the bottom (lower part) of the second holder 21, and the second processing member 20 together with an O-ring is accepted in the ring-accepting part 41. The second processing member 20 is accepted with a rotation preventive 84 so as not to be rotated relative to the second holder 21. The second processing surface 2 is exposed from the second holder 21. In this state, the second processing surface 2 is faced with the first processing surface 1 of the first processing member 10.

The ring-accepting part 41 arranged in the second holder 21 is a depression for mainly accepting that side of the second ring 20 which is opposite to the processing surface 2 and is a groove formed in a circular form when viewed in a plane.

The ring-accepting part 41 is formed in a larger size than the second ring 20 and accepts the second ring 20 with sufficient clearance between itself and the second ring 20.

By this clearance, the second processing member 20 is accepted in the ring-accepting part 41 such that it can be displaced not only in the axial direction of the accepting part 41 but also in a direction perpendicular to the axial direction. The second processing member 20 is accepted in the ring-accepting part 41 such that the central line (axial direction) of the second processing member 20 can be displaced so as not to be parallel to the axial direction of the ring-accepting part 41.

The spring 43 is arranged as a processing member-biasing part in at least the ring-accepting part 41 of the second holder 21. The spring 43 biases the second processing member 20 toward the first processing member 10. As another bias method, air pressure such as one in the air introduction part 44 or another pressurization means for applying fluid pressure may be used to bias the second processing member 20 held by the second holder 21 in the direction of approaching the second processing member 20 to the first processing member 10.

The surface-approaching pressure imparting mechanism such as the spring 43 or the air introduction part 44 biases each position (each position in the processing surface) in the circumferential direction of the second processing member 20 evenly toward the first processing member 10.

The first introduction part d1 is arranged on the center of the second holder 21, and the fluid which is pressure-fed from the first introduction part d1 to the outer periphery of the processing member is first introduced into the space surrounded with the second processing member 20 held by the second holder 21, the first processing member 10, and the first holder 11 that holds the first processing member 10. Then, the feeding pressure (supply pressure) of the fluid by the fluid pressure imparting mechanism P is applied to the pressure-receiving surface 23 arranged in the second processing member 20, in the direction of separating the second processing member 20 from the first processing member 10 against the bias of the biasing part.

Figure 29A:
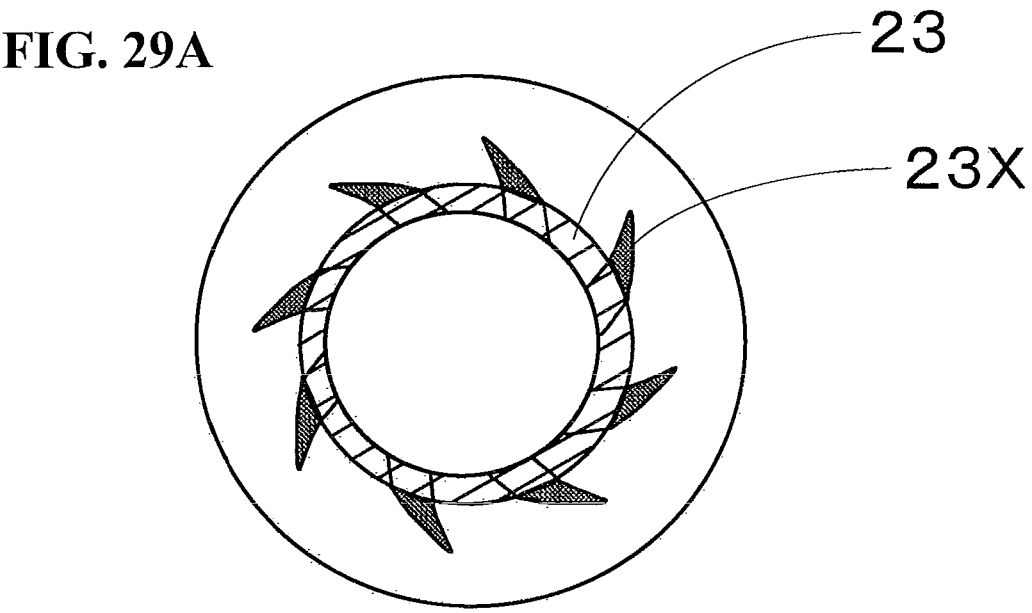
FIG. 29(A) is a bottom view of the second processing member.
Figure 29B:
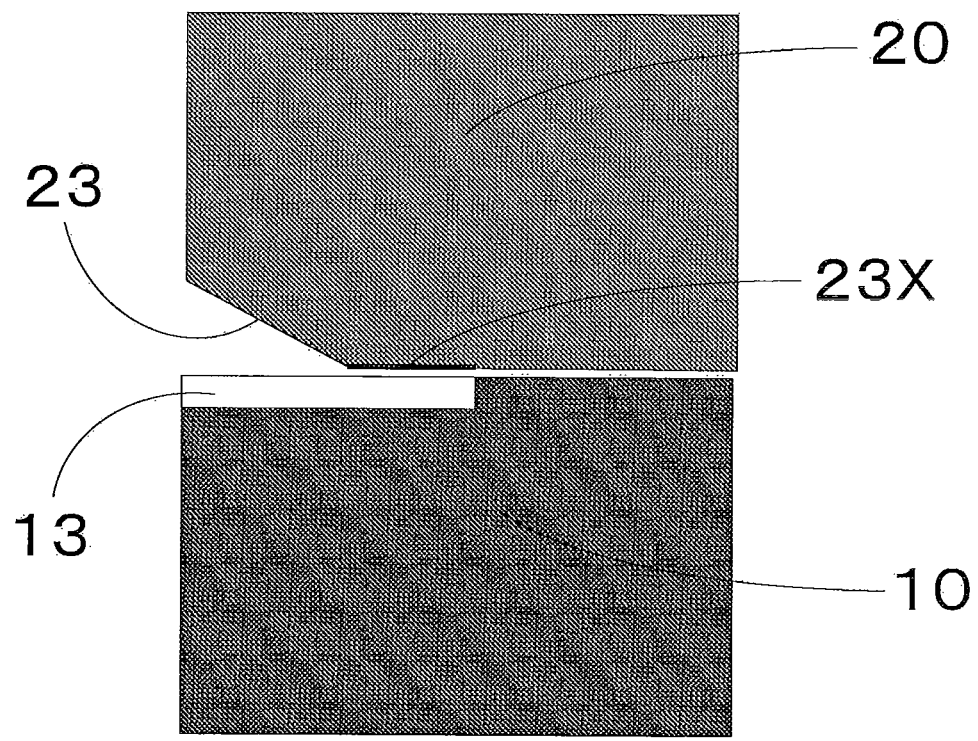
FIG. 29(B) is an enlarged sectional view showing an important part thereof.

For simplifying the description of other components, only the pressure-receiving surface 23 is described, as shown in FIG. 29(A) and FIG. 29(B), properly speaking, together with the pressure-receiving surface 23, a part 23X not provided with the pressure-receiving surface 23, out of the projected area in the axial direction relative to the second processing member 20 in a grooved depression 13 described later, serves as a pressure-receiving surface and receives the feeding pressure (supply pressure) of the fluid by the fluid pressure imparting mechanism P.

The apparatus may not be provided with the pressure-receiving surface 23. In this case, as shown in FIG. 26(A), the effect (micro-pump effect) of introduction of the processed fluid into the space between the processing surfaces formed by rotation of the first processing surface 1 provided with the grooved depression 13 formed to function the surface-approaching pressure imparting mechanism may be used. The micro-pump effect is an effect by which the fluid in the depression 13 advances with speed toward the end in the circumferential direction by rotation of the first processing surface 1 and then the fluid sent to the end of the depression 13 further receives pressure in the direction of the inner periphery of the depression 13 thereby finally receiving pressure in the direction of separating the processing surface and simultaneously introducing the fluid into the space between the processing surfaces. Even if the first processing surface 1 is not rotated, the pressure applied to the fluid in the depression 13 arranged in the first processing surface 1 finally acts on the second processing surface 2 to be separated as a pressure-receiving surface.

For the depression 13 arranged on the processing surface, its total area in the horizontal direction relative to the processing surface, and the depth, number, and shape of depressions, can be established depending on the physical properties of a fluid containing materials to be processed and reaction products.

The pressure-receiving surface 23 and the depression 13 may be arranged in the same apparatus.

The depression 13 is a depression having a depth of 1 μm to 50 μm, preferably 3 μm to 20 μm, which is arranged on the processing surface, the total area thereof in the horizontal direction is 5% to 50%, preferably 15% to 25%, based on the whole of the processing surface, the number of depressions is 3 to 50, preferably 8 to 24, and the depression extends in a curved or spiral form on the processing surface or bends at a right angle, having depth changing continuously, so that fluids with high to low viscosity, even containing solids, can be introduced into the space between the processing surfaces stably by the micro-pump effect. The depressions arranged on the processing surface may be connected to one another or separated from one another in the side of introduction, that is, inside the processing surface.

As described above, the pressure-receiving surface 23 is inclined. This inclined surface (pressure-receiving surface 23) is formed such that the distance in the axial direction between the upstream end in the direction of flow of the processed fluid and the processing surface of the processing member provided with the depression 13 is longer than the distance between the downstream end and the aforesaid processing surface. The downstream end of this inclined surface in the direction of flow of the processed fluid is arranged preferably on the projected area in the axial direction of the depression 13.

Figure 28A:
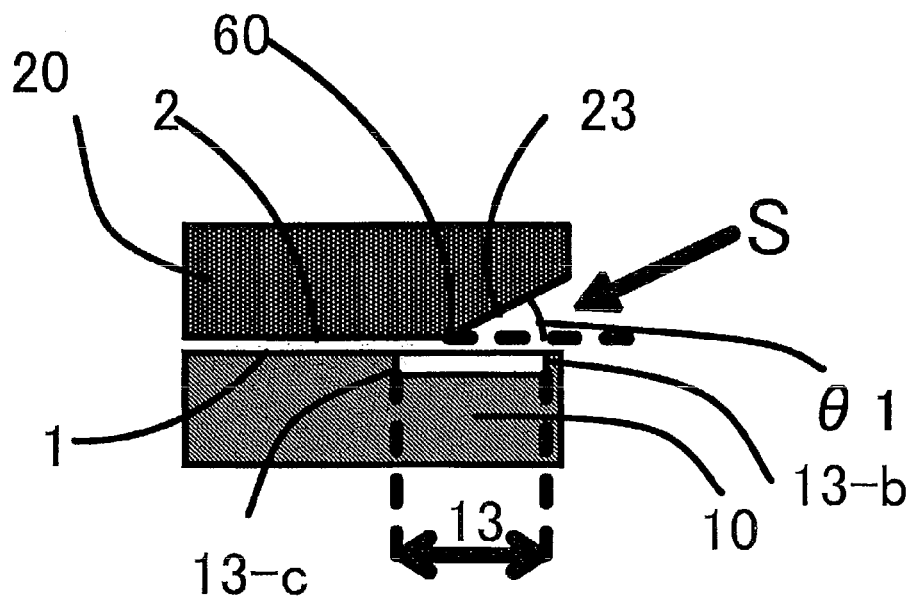
FIG. 28(A) and FIG. 28(B) are each an enlarged sectional view of an important part for explaining an inclined surface arranged in the processing member.
Figure 28B:
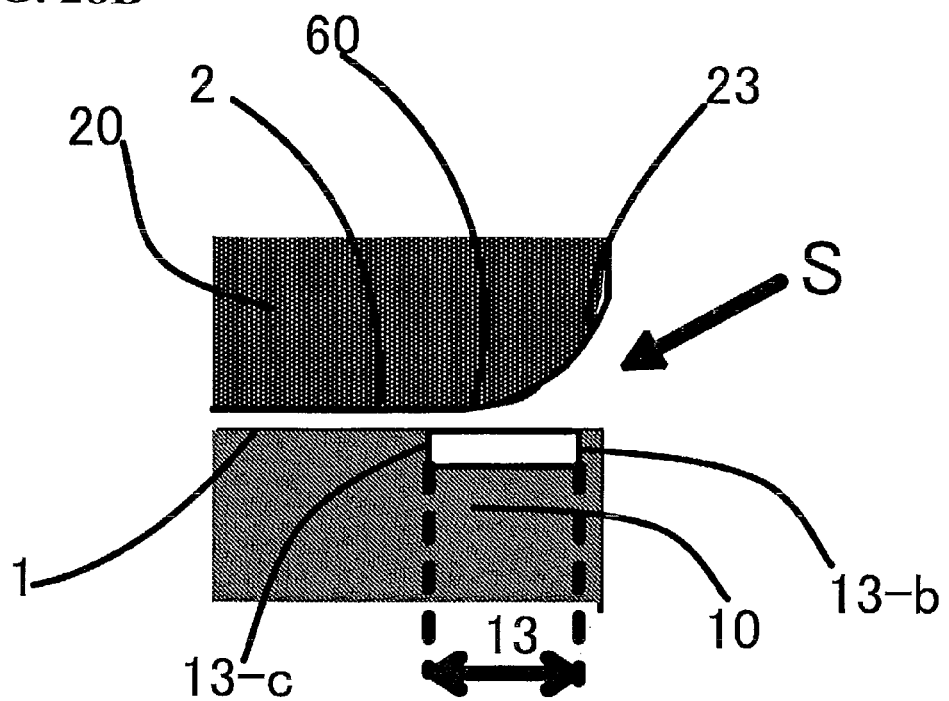

Specifically, as shown in FIG. 28(A), a downstream end 60 of the inclined surface (pressure-receiving surface 23) is arranged on the projected area in the axial direction of the depression 13. The angle θ1 of the inclined surface to the second processing surface 2 is preferably in the range of 0.1° to 85°, more preferably in the range of 10° to 55°, still more preferably in the range of 15° to 45°. The angle θ1 can vary depending on properties of the processed product before processing. The downstream end 60 of the inclined surface is arranged in the region extending from the position apart downstream by 0.01 mm from an upstream end 13-*b* to the position apart upstream by 0.5 mm from a downstream end 13-*c* in the depression 13 arranged in the first processing surface 1. The downstream end 60 of the inclined surface is arranged more preferably in the region extending from the position apart downstream by 0.05 mm from the upstream end 13-*b* to the position apart upstream by 1.0 mm from the downstream end 13-*c*. Like the angle of the inclined surface, the position of the downstream end 60 can vary depending on properties of a material to be processed. As shown in FIG. 28(B), the inclined surface (pressure-receiving surface 23) can be a curved surface. The material to be processed can thereby be introduced more uniformly.

The depressions 13 may be connected to one another or separated from one another as described above. When the depressions 13 are separated, the upstream end at the innermost peripheral side of the first processing surface 1 is 13-*b*, and the upstream end at the outermost peripheral side of the first processing surface 1 is 13-*c*.

In the foregoing description, the depression 13 was formed on the first processing surface 1 and the pressure-receiving surface 23 was formed on the second processing surface 2. On the contrary, the depression 13 may be formed on the second processing surface 2, and the pressure-receiving surface 23 may be formed on the first processing surface 1.

Alternatively, the depression 13 is formed both on the first processing surface 1 and the second processing surface 2, and the depression 13 and the pressure-receiving surface 23 are alternately arranged in the circumferential direction of each of the respective processing surfaces 1 and 2, whereby the depression 13 formed on the first processing surface 1 and the pressure-receiving surface 23 formed on the second processing surface 2 are faced with each other and simultaneously the pressure-receiving surface 23 formed on the first processing surface 1 and the depression 13 formed on the second processing surface 2 are faced with each other.

A groove different from the depression 13 can be formed on the processing surface. Specifically, as shown in FIG. 16(F) and FIG. 16(G), a radially extending novel depression 14 instead of the depression 13 can be formed outward in the radial direction (FIG. 16(F)) or inward in the radial direction (FIG. 16(G)). This is advantageous for prolongation of retention time between the processing surfaces or for processing a highly viscous fluid.

The groove different from the depression 13 is not particularly limited with respect to the shape, area, number of depressions, and depth. The groove can be formed depending on the object.

The second introduction part d2 independent of the fluid flow path introduced into the processing surface and provided with the opening d20 leading to the space between the processing surfaces is formed on the second processing member 20.

Specifically, as shown in FIG. 27(A), the direction of introduction of the second introduction part d2 from the opening d20 of the second processing surface 2 is inclined at a predetermined elevation angle ($\theta1$) relative to the second processing surface 2. The elevation angle ($\theta1$) is arranged at more than 0° and less than 90°, and when the reaction speed is high, the angle ($\theta1$) is preferably arranged at 1° to 45°.

As shown in FIG. 27(B), the direction of introduction of the second processing surface 2 from the opening d20 has directionality in a plane along the second processing surface 2. The direction of introduction of the second fluid is in the direction in which a component on the processing surface is made apart in the radial direction and in the direction in which the component is forwarded in the rotation direction of the fluid between the rotating processing surfaces. In other words, a predetermined angle ($\theta2$) exists facing the rotation direction R from a reference line g in the outward direction and in the radial direction passing through the opening d20.

The angle ($\theta2$) is also arranged at more than 0° and less than 90° at which the fluid is discharged from the opening d20 in the shaded region in FIG. 27(B). When the reaction speed is high, the angle ($\theta2$) may be small, and when the reaction speed is low, the angle ($\theta2$) is preferably arranged larger. This angle can vary depending on various conditions such as the type of fluid, the reaction speed, viscosity, and the rotation speed of the processing surface.

The bore diameter of the opening d20 is preferably 0.2 µm to 3000 µm, more preferably 10 µm to 1000 µm. When the diameter of the opening d20 does not substantially influence the flow of a fluid, the diameter of the second introduction part d2 may be established in this range. Depending on whether the fluid is intended to be transferred straight or dispersed, the shape of the opening d20 is preferably changed and can be changed depending on various conditions such as the type of fluid, reaction speed, viscosity, and rotation speed of the processing surface.

The opening d20 in the separate flow path may be arranged at a position nearer to the outer diameter than a position where the direction of flow upon introduction by the micro-pump effect from the depression arranged in the first processing surface 1 is converted into the direction of flow of a spiral laminar flow formed between the processing surfaces. That is, in FIG. 26(B), the distance n from the outermost side in the radial direction of the processing surface of the depression 13 arranged in the first processing surface 1 to the outside in the radial direction is preferably 0.5 mm or more. When a plurality of openings are arranged for the same fluid, the openings are arranged preferably concentrically. When a plurality of openings are arranged for different fluids, the openings are arranged preferably concentrically in positions different in radius. This is effective for the reactions such as cases (1) A+B→C and (2) C+D→E should occur in due order, but other case, i.e., A+B+C→F should not occur, or for circumventing a problem that an intended reaction does not occur due to insufficient contact among the processed materials.

The processing members are dipped in a fluid, and a fluid obtained by mixing (reaction) between the processing surfaces can be directly introduced into a liquid outside the processing members or into a gas other than air.

Further, ultrasonic energy can be applied to the processed material just after being discharged from the space between the processing surfaces or from the processing surface.

Then, the case where temperature regulating mechanisms J1 and J2 are arranged in at least one of the first processing member 10 and the second processing member 20 for generating a temperature difference between the first processing surface 1 and the second processing surface 2 is described.

The temperature regulating mechanism is not particularly limited. A cooling part is arranged in the processing members 10 and 20 when cooling is intended. Specifically, a piping for passing ice water and various cooling media or a cooling element such as a Peltier device capable of electric or chemical cooling is attached to the processing members 10 and 20.

When heating is intended, a heating part is arranged in the processing members 10 and 20. Specifically, steam as a temperature regulating medium, a piping for passing various hot media, and a heating element such as an electric heater capable of electric or chemical heating is attached to the processing members 10 and 20.

An accepting part for a new temperature regulating medium capable of directly contacting with the processing members may be arranged in the ring-accepting part. The temperature of the processing surfaces can be regulated by heat conduction of the processing members. Alternatively, a cooling or heating element may be embedded in the processing members 10 and 20 and electrified, or a path for passing a cooling medium may be embedded, and a temperature regulating medium (cooling medium) is passed through the path, whereby the temperature of the processing surfaces can be regulated from the inside. By way of example, the temperature regulating mechanisms J1 and J2 which are pipes (jackets) arranged inside the processing members 10 and 20 are shown in FIG. 25.

By utilizing the temperature regulating mechanisms J1 and J2, the temperature of one of the processing surfaces is made higher than that of the other, to generate a temperature difference between the processing surfaces. For example, the first processing member 10 is heated to 60° C. by any of the methods, and the second processing member 20 is set at 15° C. by any of the methods. In this case, the temperature of the fluid introduced between the processing surfaces is changed from 60° C. to 15° C. in the direction from the first processing surface 1 to the second processing surface 2. That is, the fluid between the processing surfaces has a temperature gradient. The fluid between the processing surfaces initiates convection due to the temperature gradient, and a flow in a direction perpendicular to the processing surface is generated. The flow in a direction perpendicular to the processing surface refers to a flow in which components flowing in a direction perpendicular to at least the processing surface are contained in flowing components.

Even when the first processing surface 1 or the second processing surface 2 rotates, the flow in a direction perpendicular to the processing surface is continued, and thus the flow in a direction perpendicular to the processing surface can be added to a spiral laminar flow between the processing surfaces caused by rotation of the processing surfaces. The temperature difference between the processing surfaces is 1° C. to 400° C., preferably 5° C. to 100° C.

The rotary shaft 50 in this apparatus is not limited to a vertically arranged shaft. For example, the rotary shaft may be arranged at a slant. This is because the influence of gravity can be substantially eliminated by a thin fluid film formed between the processing surfaces 1 and 2 during processing. As shown in FIG. 25, the first introduction part d1 coincides with the shaft center of the second ring 20 in the second holder 21 and extends vertically. However, the first introduction part d1 is not limited to the one coinciding with the shaft center of the second ring 20, and as far as it can supply the first processing fluid to the space surrounded with the rings 10 and 20, the part d1 may be arranged at a position outside the shaft center in the central part 22 of the second holder 21 and may extend obliquely as well as vertically. Regardless of the angle at which the part d1 is arranged, a flow perpendicular to the processing surface can be generated by the temperature gradient between the processing surfaces.

When the temperature gradient of the fluid between the processing surfaces is low, heat conduction merely occurs in the fluid, but when the temperature gradient exceeds a certain border value, a phenomenon called Benard convection is generated in the fluid. This phenomenon is governed by Rayleigh number Ra, a dimensionless number, defined by the following equation:

$$Ra = L^3 \cdot g \cdot \beta \cdot \Delta T / (\alpha \cdot \nu)$$

wherein L is the distance between processing surfaces; g is gravitational acceleration; β is coefficient of volumetric thermal expansion of fluid; ν is dynamic viscosity of fluid; α is heat diffusivity of fluid; and ΔT is temperature difference between processing surfaces. The critical Rayleigh number at which Benard convection is initiated to occur, although varying depending on the properties of a boundary phase between the processing surface and the processed fluid, is regarded as about 1700. At a value higher than this value, Benard convection occurs. Under the condition where the Rayleigh number Ra is a large value of about $10^{10}$ or more, the fluid becomes a turbulent flow. That is, the temperature difference ΔT between the processing surfaces or the distance L between the processing surfaces in this apparatus are regulated such that the Rayleigh number Ra becomes 1700 or more, whereby a flow perpendicular to the processing surface can be generated between the processing surfaces, and the reaction procedures described above can be carried out.

However, the Benard convection hardly occurs when the distance between the processing surfaces is about 1 μm to 10 μm. Strictly, when the Rayleigh number is applied to a fluid between the processing surfaces having a distance of 10 μm or less therebetween to examine the conditions under which Benard convection is generated, the temperature difference should be several thousands of degrees or more in the case of water, which is practically difficult. Benard convection is one related to density difference in temperature gradient of a fluid, that is, to gravity. When the distance between the processing surfaces is 10 μm or less, there is high possibility of minute gravity field, and in such a place, buoyancy convection is suppressed. That is, it is the case where the distance between the processing surfaces is 10 μm or more that Benard convection actually occurs.

When the distance between the processing surfaces is about 1 μm to 10 μm, convection is generated not due to density difference but due to surface tension difference of a fluid resulting from temperature gradient. Such convection is Marangoni convection. This phenomenon is governed by Marangoni number Ma, a dimensionless number, defined by the following equation:

$$Ma = \sigma \cdot \Delta T \cdot L / (\rho \cdot \nu \cdot \alpha)$$

wherein L is the distance between processing surfaces; ν is dynamic viscosity of fluid; α is heat diffusivity of fluid; ΔT is temperature difference between processing surfaces; ρ is density of fluid; and σ is temperature coefficient of surface tension (temperature gradient of surface tension). The critical Marangoni number at which Marangoni convection is initiated to occur is about 80, and under the conditions where the Marangoni number is higher than this value, Marangoni convection occurs. That is, the temperature difference ΔT between the processing surfaces or the distance L between the processing surfaces in this apparatus is regulated such that the Marangoni number Ma becomes 80 or more, whereby a flow perpendicular to the processing surface can be generated between the processing surfaces even if the distance therebetween is as small as 10 μm or less, and the mixing (reaction) procedures described above can be carried out.

For calculation of Rayleigh number, the following equations were used.

$$Ra = \frac{L^3 \cdot \beta \cdot g}{\nu \cdot \alpha} \Delta T \qquad \text{[Equation 1]}$$

$$\Delta T = (T_1 - T_0)$$

$$\alpha = \frac{k}{\rho \cdot C_p}$$

L is the distance (m) between processing surfaces; β is coefficient of volumetric thermal expansion (1/K); g is gravitational acceleration (m/s$^2$); ν is dynamic viscosity (m$^2$/s); α is heat diffusivity (m$^2$/s); ΔT is temperature difference (K) between processing surfaces; ρ is density (kg/m$^3$); Cp is isobaric specific heat (J/kg·K); k is heat conductivity (W/m·K); $T_1$ is temperature (K) at high temperature side in processing surface; and $T_0$ is temperature (K) at low temperature side in processing surface.

When the Rayleigh number at which Benard convection is initiated to occur is the critical Rayleigh number $Ra_C$, the temperature difference $\Delta T_{C1}$ is determined as follows:

$$\Delta T_{C1} = \frac{Ra_C \cdot \nu \cdot \alpha}{L^3 \cdot \beta \cdot g} \qquad \text{[Equation 2]}$$

For calculation of Marangoni number, the following equations were used.

$$Ma = \frac{\sigma_t \cdot L}{\rho \cdot \nu \cdot \alpha} \Delta T \qquad \text{[Equation 3]}$$

$$\Delta T = (T_1 - T_0)$$

$$\alpha = \frac{k}{\rho \cdot C_p}$$

L is the distance (m) between processing surfaces; ν is dynamic viscosity (m$^2$/s); α is heat diffusivity (m$^2$/s); ΔT is temperature difference (K) between processing surfaces; ρ is density (kg/m$^3$); Cp is isobaric specific heat (J/kg·K); k is heat conductivity (W/m·K); $\sigma_t$ is surface tension temperature coefficient (N/m·k); $T_1$ is temperature (K) at high temperature side in processing surface; and $T_0$ is temperature (K) at low temperature side in processing surface.

When the Marangoni number at which Marangoni convection is initiated to occur is the critical Marangoni number $Ma_C$, the temperature difference $\Delta T_{C2}$ is determined as follows:

$$\Delta T_{C2} = \frac{Ma_C \cdot \rho \cdot v \cdot \alpha}{\sigma_t \cdot L} \qquad [\text{Equation 4}]$$

The materials for the processing surfaces arranged to be opposite to each other so as to be able to approach to and separate from each other, at least one of which rotates relative to the other, are not particularly limited, and the processing surfaces 1 and 2 can be prepared from ceramics, sintered metals, abrasion-resistant steels, other metals subjected to hardening treatment, or rigid materials subjected to lining, coating or plating. In the present invention, the distance between the processing surfaces 1 and 2 arranged to be opposite to each other so as to be able to approach to and separate from each other, at least one of which rotates relative to the other, is 0.1 μm to 100 μm, particularly preferably 1 μm to 10 μm.

Hereinafter, the present invention will be specifically described in more detail with reference to some chemical reactions as examples, but the invention is not limited to these examples. These chemical reactions are merely some examples of all the organic reactions using an organic compound as a starting material. Further, the words "first fluid, first introduction part d1" and "second fluid, second introduction part d2" are not intended to limit the order of introduction, and the first fluid may be introduced into the second introduction part d2 and the second fluid may be introduced into the first introduction part d1.

According to the present invention, an organic reaction is performed by forced uniform mixing between the processing surfaces 1 and 2 arranged to be opposite to each other so as to be able to approach to and separate from each other, at least one of which rotates relative to the other, in the apparatus shown in FIG. 1(A).

(1: Friedel-Crafts Acylation Reaction)

A Friedel-Crafts acylation reaction is generally represented by the following chemical reaction formula.

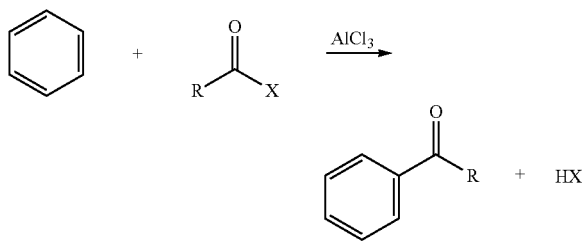

In the formula above, X is a halogen element, particularly preferably Cl or Br.

As shown in the above chemical reaction formula, the Friedel-Crafts acylation reaction, to which the present invention is applied, is an electrophilic substitution reaction which introduces an acyl group onto an aromatic ring.

In the case of the Friedel-Crafts acylation reaction, a fluid containing at least one acylating agent and at least one strong acid is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The preferred acylating agents used in the Friedel-Crafts acylation reaction are acid halides using a substance selected from the group consisting of aliphatic and aromatic carboxylic acids, aliphatic and aromatic halocarboxylic acids, aliphatic and aromatic sulfonic acids, and mixed acid anhydrides and symmetric acid anhydrides thereof, ketenes, esters, lactones, and amides. Further, the Friedel-Crafts acylation reaction can be performed also by using an acid anhydride selected from the group consisting of mixed acid anhydrides and phenyl butyric anhydride.

The strong acid used in the Friedel-Crafts acylation reaction is not particularly limited, but is preferably a catalytically active acid, particularly preferably an acid selected from the group consisting of chloroacetic acid, trifluoroacetic anhydride, trifluoromethanesulfonic anhydride and dihalogenated phosphoric acid, sulfuric acid, sulfonic acids such as alkylsulfonic acids (e.g., methanesulfonic acid) or arylsulfonic acids, iron(III) halides, tin tetrachloride, aluminum halides, alkylaluminum halides, boron trihalides, $BeCl_2$, $CdCl_2$, $ZnCl_2$, $GaCl_3$, $SbCl_3$, $BiCl_3$, $TiCl_4$, $ZrCl_4$, $VCl_4$, $SbCl_5$, alkyl-metal compounds, metal alkoxides, complex compounds (e.g., $Me_2TiCl_2$, $Pd(PPh_3)_4$, $RuCl_2(PPh_3)_2$), and Lewis acids.

Then, a fluid containing at least one organic compound is introduced as a second fluid directly through another flow path, that is, the second introduction part d2 into the first fluid film formed between the processing surfaces 1 and 2.

The organic compound used in the Friedel-Crafts acylation reaction is not particularly limited as long as it has an aromatic ring, and the Friedel-Crafts acylation reaction can be performed using a compound selected from the group consisting of olefins, aromatic compounds (e.g., anisole), heteroaromatic compounds, and metallocenes.

The organic compound, the acylating agent, and the strong acid used in the Friedel-Crafts acylation reaction are preferably in the form of a liquid or solution. A solvent which can be used for such a purpose is not particularly limited, and examples thereof include water such as ion-exchange water, purified water, tap water, and ultrapure water and organic solvents. However, the solvent is preferably selected from the group consisting of chlorinated hydrocarbons, paraffins, ethers, acid amides, nitriles, carbon disulfide, nitroaliphatic compounds, and nitroaromatic compounds.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the Friedel-Crafts acylation reaction can be performed.

It is to be noted that a fluid containing all the organic compound, the acylating agent, and the strong acid to such an extent that the reaction performed in the space between the processing surfaces is not affected may be used as a first fluid or a second fluid.

(2: Friedel-Crafts Alkylation Reaction)

A Friedel-Crafts alkylation reaction is generally represented by the following chemical reaction formula.

[Chemical 2]

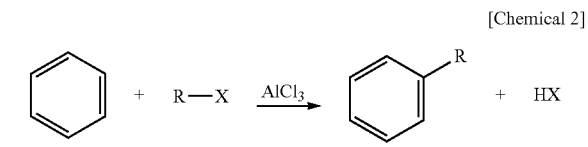

In the formula above, X is a halogen element, particularly preferably Cl or Br.

As shown in the above chemical reaction formula, the Friedel-Crafts alkylation reaction, to which the present invention is applied, is an electrophilic substitution reaction which introduces an alkyl group onto an aromatic ring.

In the case of the Friedel-Crafts alkylation reaction, a fluid containing at least one catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The catalyst used in the Friedel-Crafts alkylation reaction is not particularly limited, but is preferably a Lewis acid (if necessary, dissolved in an ionic liquid), a protic acid, an ionic liquid, an organic metal catalyst and/or a mixture of two or more of them, particularly preferably chloroacetic acid, trifluoroacetic anhydride, trifluoromethanesulfonic anhydride, dihalogenated phosphoric acid, sulfuric acid, hydrogen chloride, phosphoric acid, a sulfonic acid (very particularly preferably, an alkylsulfonic acid such as methanesulfonic acid or an allylsulfonic acid), an iron trihalide, tin tetrachloride, an aluminum halide, an alkylaluminum halide, a boron trihalide, an ionic liquid being in an eutectic liquid state at room temperature such as N-butyl-N-methylimidazolium tetrachloroaluminate, N-ethyl-N-methylimidazolium tetrachloroaluminate, N-ethyl-N-methylimidazolium tetrafluoroborate, or an N-alkylated pyridinium imidazolium salt, particularly a tetrafluoroborate and/or hexafluorophosphate thereof, halogenated antimony, $BeCl_2$, $CdCl_2$, $ZnCl_2$, $GaCl_3$, $BiCl_3$, $TiCl_4$, $ZrCl_4$, $VCl_4$, an alkyl-metal compound, a metal alkoxide, $TiCl_2(CH_3)_2$, $Pd(PPh_3)_4$, $RuCl_2(PPh_3)_2$, or a mixture of two or more of these catalysts.

Then, a fluid containing at least one alkylating reagent and at least one organic compound is introduced as a second fluid directly through another flow path, that is, the second introduction part d2 into the first fluid film formed between the processing surfaces 1 and 2.

The preferred alkylating reagents used in the Friedel-Crafts alkylation reaction are olefins (particularly preferably, ethene, propene, dodecene, or a linear olefin having a chain length of 20 to 30 carbon atoms), alkyl halides (particularly preferably, methyl chloride, methyl iodide, ethyl chloride, isopropyl chloride, tert-butyl chloride, benzyl chloride, or cyclohexyl chloride), alcohols, ethers, inorganic and organic acid esters, epoxides, aldehydes, ketones, thiols, dialkyl sulfates, alkyl p-tolylsulfonates, trifluoromethanesulfonic acid or esters thereof, aliphatic diazo compounds and/or trialkyloxonium tetrafluoroborates.

The organic compound used in the Friedel-Crafts alkylation reaction is not particularly limited as long as it has an aromatic ring, but is preferably an aromatic or heteroaromatic compound. These aromatic or heteroaromatic compounds include monocyclic and polycyclic compounds as well as compounds having a monocyclic and/or polycyclic, homo- or hetero-aromatic basic structure or partial structure, for example, in the form of substituents. The aromatic compounds used are particularly preferably benzene, naphthalene, azulene, anthracene, phenanthrene, pyrene, fluorene, quinones such as o-benzoquinone and p-benzoquinone, naphthoquinone, fluorenone, anthrone, phenanthrone, anthraquinone, and/or derivatives thereof, particularly alkyl derivatives thereof.

The preferred heteroaromatic compounds used in the Friedel-Crafts alkylation reaction are oxygen-containing heteroaromatic compounds and/or derivatives thereof. Particularly preferred are, for example, furans such as benzo-fused furan and dibenzofuran, dibenzodioxane, pyrylium cations, and benzopyranone.

The heteroaromatic compounds used are likewise preferably nitrogen-containing aromatic compounds and/or derivatives thereof. Particularly preferred are, for example, pyrrole, pyrazole, imidazole, triazole, tetrazole, pyridine, pyrazine, pyrimidine, pyridinium salts, triazine, tetrazine, pyridine N-oxide, benzo-fused pyrroles such as indole, carbazole, benzimidazole, or benzotriazole, phenazine, quinoline, isoquinoline, cinnoline, quinazoline, phenanthroline, bipyridyl and higher homologues thereof, acridine, acridone, and/or pyrene.

Further, the heteroaromatic compounds used are preferably sulfur-containing heteroaromatic compounds and/or derivatives thereof. Particularly preferred are, for example, thiophene, benzo-fused thiophenes, particularly benzothiophene or dibenzothiophene, acenaphthylene, thiazole, isothiazole, biphenylene, purine, benzothiadiazole, oxazole, and/or isoxazole.

Organic compounds which can be used other than the above-mentioned heteroaromatic compounds are likewise preferably organic metal compounds whose organic moieties can be alkylated by Friedel-Crafts alkylation, particularly preferably metallocenes of metals belonging to Group 4 to Subgroup 8 in the periodic table, very particularly preferably metallocenes of metals belonging to Group 4 to Subgroup 8 in the periodic table and having at least one cyclopentadienyl ligand.

The catalyst, the alkylating reagent, and the organic compound used in the Friedel-Crafts alkylation reaction are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated hydrocarbons (particularly preferably, dichloromethane, chloroform, 1,2-dichloroethane, or 1,1,2,2-tetrachloroethane), paraffins, hexane, ligroin, ethers (particularly preferably, diethyl ether), acid amides (particularly preferably, N,N-dimethylformamide), nitriles (particularly preferably, acetonitrile), carbon disulfide, nitroaliphatic compounds (particularly preferably, nitromethane), nitroaromatic compounds (particularly preferably, nitrobenzene), or mixtures of two or more of them.

In addition to the above-mentioned solvents, ionic liquids being in a eutectic liquid state at room temperature are preferably used. Particularly preferred ionic liquids used are N-butyl-N-methylimidazolium tetrachloroaluminate, N-ethyl-N-methylimidazolium tetrachloroaluminate, N-ethyl-N-methylimidazolium tetrafluoroborate, or N-alkylated pyridinium imidazolium, particularly a tetrafluoroborate and/or hexafluorophosphate thereof, or a mixture of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the Friedel-Crafts alkylation reaction can be performed.

It is to be noted that a fluid containing all the catalyst, the alkylating reagent, and the organic compound to such an extent that the reaction performed in the space between the processing surfaces is not affected may be used as a first fluid or a second fluid.

(3: Nitration Reaction)

A nitration reaction is generally represented by the following chemical reaction formula.

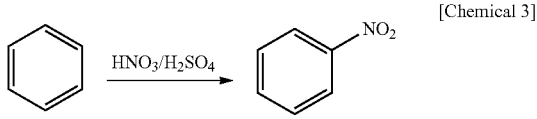 [SMILES: c1ccccc1 ; O=[N+]([O-])c1ccccc1]

[Chemical 3]

As shown in the above chemical reaction formula, the nitration reaction, to which the present invention is applied, includes an electrophilic substitution reaction which introduces a nitro group by the action of nitric acid. Preferably, nitric acid is allowed to act under acid conditions in the presence of sulfuric acid. Sulfuric acid is an acid stronger than nitric acid, and therefore nitric acid is protonated and dehydrated by sulfuric acid to form nitronium ion ($NO_2^+$), thereby improving reactivity.

In the case of the nitration reaction, a fluid containing at least one nitrating reagent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The preferred nitrating reagents used in the nitration reaction are dilute nitric acid, 100% nitric acid, nitrates, such as potassium nitrate, dissolved in 100% sulfuric acid, mixtures of nitric acid and sulfuric acid (nitrating acid), general nitric acid esters, mixtures of inorganic and organic anhydrides and nitric acid, and dinitrogen pentaoxide.

Then, a fluid containing at least one organic compound is introduced as a second fluid directly through another flow path, that is, the second introduction part d2 into the first fluid film formed between the processing surfaces 1 and 2.

The organic compound used in the nitration reaction is not particularly limited, but is preferably toluene, 1,2,3,4-tetrahydroisoquinoline, N-methoxycarbonyl-1,2,3,4-tetrahydroisoquinoline, or a benzofuran derivative. Further, suitable organic compounds are all monocyclic and polycyclic, homoaromatic or heteroaromatic compounds and compounds having a monocyclic or polycyclic, homoaromatic or heteroaromatic basic structure or partial structure, for example, in the form of substituents. Suitable aromatic compounds are particularly benzene and derivatives thereof, naphthalene and derivatives thereof, azulene and derivatives thereof, anthracene and derivatives thereof, phenanthrene and derivatives thereof, pyrene and derivatives thereof; fluorene and derivatives thereof, quinones such as ortho- and para-benzoquinone and derivatives thereof, all known naphthoquinones and derivatives thereof, fluorenone, anthrone, phenanthrone, and all known anthraquinones and derivatives thereof. Heteroaromatic compounds which can be used are, for example, oxygen-containing heteroaromatic systems (furans), such as benzo-fused furan and derivatives thereof, and derivatives thereof, dibenzofuran and derivatives thereof, dibenzodioxane and derivatives thereof, pyrylium cations and derivatives thereof, benzopyranone and derivatives thereof, nitrogen-containing heteroaromatic systems and derivatives thereof such as pyrrole, pyrazole, imidazole, triazole, tetrazole, pyridine, pyrazine, pyrimidine, pyridinium salts, triazine, tetrazine, pyridine-N-oxide and derivatives thereof, benzo-fused pyrroles (indole, carbazole, benzimidazole, and benzotriazole) and derivatives thereof, phenazine and derivatives thereof, quinoline and isoquinoline, quinoline, quinazoline, and quinoxaline, phenanthroline and derivatives thereof, bipyridyls and higher homologues thereof, acridine, acridone and derivatives thereof, and pyrene and derivatives thereof, and suitable sulfur-containing heteroaromatic systems and derivatives thereof such as thiophene and derivatives thereof, benzo-fused thiophenes (benzothiophene and dibenzothiophene) and derivatives thereof. Further, acenaphthylene, thiazole, isothiazole, biphenylene, purine, benzothiadiazole, oxazole, and isooxazole can also be used.

The nitrating reagent and the organic compound used in the nitration reaction are preferably in the form of a liquid or solution. A solvent which can be used for such a purpose is not particularly limited, and examples thereof include water such as ion-exchange water, purified water, tap water, and ultrapure water and organic solvents. The solvents which can be used are, for example, dilute and concentrated acids such as sulfuric acid, nitric acid, acetic acid, and trifluoroacetic acid; acid anhydrides such as acetic anhydride and trifluoroacetic anhydride; mixtures of acids and salts such as a mixture of concentrated sulfuric acid and $KNO_3$ and mixtures of any other combinations; halogenated hydrocarbons such as chloroform, carbon tetrachloride, dichloromethane, and tetrachloroethane; esters such as ethyl acetate; ethers such as tetrahydrofuran, diethyl ether, and t-butyl methyl ether; mixtures of two or more of the above-mentioned solvents of all types; and ionic solvents such as 1-ethyl-3-methylimidazolium tetrachloroaluminate, n-butylpyridinium tetrachloroaluminate, and 1-ethyl-3-methylimidazolium tetrahydroborate.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the nitration reaction can be performed.

It is to be noted that a fluid containing all the nitrating reagent and the organic compound to such an extent that the reaction performed in the space between the processing surfaces is not affected may be used as a first fluid or a second fluid.

(4: Bromination Reaction)

In the case of a bromination reaction, a fluid containing at least one brominating reagent and, if necessary, at least one catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The preferred brominating reagents used in the bromination reaction are elemental bromine, dibromoisocyanuric acid, N-bromosuccinimide, hypobromous acid, organic hypobromite, particularly preferably trifluoro hypobromite, N-bromoacetamide, N-bromophthalimide, pyridinium perbromide, and/or dioxane dibromide.

The catalyst used if necessary in the bromination reaction is not particularly limited, but is preferably elemental iodine or an inorganic acid (particularly preferably sulfuric acid or nitric acid and/or a Lewis acid), particularly preferably an aluminum halide, an iron halide, a zinc halide, or an antimony halide. It is to be noted that when a catalyst is used, the catalyst is contained in at least one of a first fluid and a second fluid. However, the catalyst is preferably contained in a fluid in which the catalyst is inactive.

Then, a fluid containing at least one organic compound is introduced as a second fluid directly through another flow path, that is, the second introduction part d2 into the first fluid film formed between the processing surfaces 1 and 2.

The organic compound used in the bromination reaction is not particularly limited, but is preferably an aromatic or heteroaromatic compound. These aromatic or heteroaromatic compounds include monocyclic or polycyclic compounds as well as compounds having a monocyclic and/or polycyclic, homoaromatic or heteroaromatic basic compound or partial structure, for example, in the form of substituents. The organic compounds used in the bromination reaction also include organic metal compounds whose organic moieties are susceptible to bromination. The organic compounds used are likewise preferably aldehydes or ketones having at least one hydrogen atom in the α-position relative to a carbonyl group or unsaturated aliphatic compounds. The aromatic compounds used are preferably alkylated aromatic compounds, very preferably toluene, xylene or mesitylene, benzene, naphthalene, azulene, anthracene, phenanthrene, pyrene, fluorene, quinones such as ortho- or para-benzoquinone and naphthoquinone, fluorenone, anthrone, phenanthrone, anthraquinone, and/or derivatives thereof. The heteroaromatic compounds used are particularly preferably oxygen-containing heteroaromatic compounds and/or derivatives thereof, very particularly preferably furans such as benzo-fused furan, dibenzofuran, and dibenzodioxane, pyrylium cations, or benzopyranone. The heteroaromatic compounds used are likewise preferably nitrogen-containing heteroaromatic compounds and/or derivatives thereof such as pyrrole, pyrazole, imidazole, triazole, tetrazole, pyridine, pyrazine, pyrimidine, pyridinium salts, triazine, tetrazine, or pyridine N-oxide, benzo-fused pyrroles such as indole, carbazole, benzimidazole, benzotriazole, phenazine, quinoline, isoquinoline, cinnoline, quinazoline, phenanthroline, bipyridyl and higher homologue, acridine, acridone, and/or pyrene. Further, the heteroaromatic compounds used are particularly preferably sulfur-containing heterocompounds and/or derivatives thereof such as thiophene, benzo-fused thiophenes, particularly benzothiophene or dibenzothiophene, acenaphthylene, thiazole, isothiazole, biphenylene, purine, benzothiadiazole, oxazole, and/or isoxazole.

The brominating reagent, the catalyst, and the organic compound used in the bromination reaction are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated hydrocarbons (particularly preferably dichloromethane, chloroform, tetrachloromethane or tetrachloroethane), esters (particularly preferably ethyl acetate), ethers (particularly preferably tetrahydrofuran, diethyl ether, or tert-butyl methyl ether), carboxylic acids (particularly preferably acetic acid), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the bromination reaction can be performed.

It is to be noted that a fluid containing all the brominating reagent and the organic compound or all the brominating reagent, the catalyst, and the organic compound to such an extent that the reaction performed in the space between the processing surfaces is not affected may be used as a first fluid or a second fluid.

(5: Baeyer-Villiger Oxidation Reaction)

In the case of a Baeyer-Villiger oxidation reaction, a fluid containing at least one oxidant is introduced as a first fluid through the first introduction part d1, which is one flow path, into a space between the processing surfaces 1 and 2 arranged to be opposite to each other so as to be able to approach to and separate from each other, at least one of which rotates relative to the other, to form a first fluid film between the processing surfaces.

The oxidant used in the Baeyer-Villiger oxidation reaction is not particularly limited, but is preferably used either in pure form or in the form of a mixture, and is more preferably used in pure form. In a case where the oxidant is used in the form of a mixture, it is preferred that the oxidant is mixed with an inorganic or organic peroxide, hydrogen peroxide, an adduct of hydrogen peroxide and urea, a transition metal peroxo complex, a mixture of a peroxo compound with an organic acid and/or an inorganic acid and/or a Lewis acid, an organic peracid, an inorganic peracid, or dioxirane, or a mixture of two or more of these oxidants is used. The inorganic peroxide used is particularly preferably ammonium peroxide, an alkali metal peroxide, ammonium persulfate, an alkali metal persulfate, ammonium perborate, an alkali metal perborate, ammonium percarbonate, an alkali metal percarbonate, an alkaline-earth metal peroxide, zinc peroxide, or a mixture of two or more of these oxidants. The alkali metal peroxide used is preferably sodium peroxide. The organic peroxide used is particularly preferably tert-butyl hydroperoxide, cumene hydroperoxide, menthyl hydroperoxide, 1-methylcyclohexane hydroperoxide, or a mixture of two or more of these compounds. The transition metal peroxo complex used is particularly preferably a peroxo complex of a transition metal, namely iron, manganese, vanadium, or molybudenum or a mixture of two or more of these peroxo complexes. Here, the peroxo complex may contain two or more same or different transition metals. The peroxo compound with an inorganic acid is particularly preferably potassium peroxodisulfate with sulfuric acid, the peroxo compound with a Lewis acid is particularly preferably hydrogen peroxide with boron trifluoride. The organic peroxide used is particularly preferably perbenzoic acid, m-chloroperbenzoic acid, magnesium monoperphthalic acid, peracetic acid, peroxytrifluoroacetic acid, or a mixture of two or more of these peracids.

Then, a fluid containing at least one organic carbonyl compound is introduced as a second fluid directly through another flow path, that is, the second introduction part d2 into the first fluid film formed between the processing surfaces 1 and 2.

The organic carbonyl compound used in the Baeyer-Villiger oxidation reaction is not particularly limited, but is preferably an aliphatic, cycloaliphatic, aromatic, or heteroaromatic ketone. In the Baeyer-Villiger oxidation reaction, to which the present invention is applied, a mixture of various organic carbonyl compounds can be used, but only one carbonyl compound is preferably used in each case. The organic carbonyl compound used is particularly preferably acetone, cyclohexanone, cyclopentanone, or butanone.

The oxidant and the organic carbonyl compound used in the Baeyer-Villiger oxidation reaction are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated hydrocarbons (particularly preferably dichloromethane, chloroform, 1,2- dichloroethane, or 1,1,2,2-tetrachloroethane), paraffins, hexane, ligroin, ethers (particularly preferably diethyl ether), acid amides (particularly preferably N,N-dimethylformamide), nitriles (particularly preferably acetonitrile), carbon disulfide, nitroaliphatic compounds (particularly preferably nitromethane), nitroaromatic compounds (particularly preferably nitrobenzene), mixtures of two or more of these solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the Baeyer-Villiger oxidation reaction can be performed.

It is to be noted that a fluid containing all the oxidant and the organic carbonyl compound to such an extent that the reaction performed in the space between the processing surfaces is not affected may be used as a first fluid or a second fluid.

(6: Metathesis Reaction)

In the case of a metathesis reaction, a fluid containing at least one metathesis catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The metathesis catalyst used in the metathesis reaction is not particularly limited, but all metathesis catalysts suitable for metathesis reactions or mixtures of at least two of these catalysts can be used. Preferably, only one metathesis catalyst is used in the method according to the present invention. More specifically, at least one metathesis catalyst selected from carbene or carbyne complexes or mixtures of two or more of these complexes is used. In a particularly preferred aspect, the carbene complex used is at least one selected from bis(tricyclohexylphosphine)benzylideneruthenium dichloride ($Cl_2(Cy_3P)_2Ru=CHPh$, "Grubbs" catalyst), a variant or derivative of the "Grubbs" catalyst, 2,6-diisopropylphenylimidoneophylidenemolybdenum bis(hexafluoro-tert-butoxide) ($(2,6-iPr_2C_6H_3N=Mo\{OC(CF_3)_2Me\}_2=CHCMe_2Ph$, "Schrock" catalyst), a variant or derivative of the "Schrock" catalyst, or a mixture of two or more of the above-mentioned complexes.

Then, a fluid containing at least one unsaturated organic compound is introduced as a second fluid directly through another flow path, that is, the second introduction part d2 into the first fluid film formed between the processing surfaces 1 and 2.

The unsaturated organic compound used in the metathesis reaction is not particularly limited, but is preferably selected from aliphatic, aromatic, or heteroaromatic alkenes. Aliphatic alkenes which can be used are all aliphatic alkenes which are known to those skilled in the art and which are suitable as substrates for metathesis reactions. This also includes linear and branched alkenes. Aromatic alkenes which can be used are all aromatic alkenes which are known to those skilled in the art and which are suitable as substrates for metathesis reactions. This includes compounds and/or derivatives having a monocyclic and/or polycyclic homoaromatic basic structure or a corresponding moiety, for example, in the form of substituents. Heteroaromatic alkenes which can be used are all heteroaromatic alkenes which are known to those skilled in the art, and which are suitable as substrates for metathesis reactions, and which contain at least one heteroatom. This includes heteroaromatic compounds and/or derivatives thereof having at least one monocyclic and/or polycyclic heteroaromatic basic structure or a corresponding moiety, for example, in the form of substituents. The heteroaromatic basic structures or moieties particularly preferably contain at least one oxygen, nitrogen, or sulfur atom.

The metathesis catalyst and the unsaturated organic compound used in the metathesis reaction are preferably in the form of a liquid or solution. A solvent which can be used for such a purpose is not particularly limited, and examples thereof include water such as ion-exchange water, purified water, tap water, and ultrapure water and organic solvents. However, the preferred solvents are water, halogenated solvents (particularly preferably dichloromethane, chloroform, 1,2-dichloroethane or 1,1,2,2-tetrachloroethane), linear, branched, or cyclic paraffins (particularly preferably pentane, hexane, heptane, octane, cyclopentane, cycloheptane, or cyclooctane) or linear, branched, or cyclic ethers (particularly preferably diethyl ether, methyl tert-butyl ether, tetrahydrofuran, or dioxane), aromatic solvents (particularly preferably toluene, xylene, ligroin, or phenyl ether), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the metathesis reaction can be performed.

It is to be noted that a fluid containing all the metathesis catalyst and the unsaturated organic compound to such an extent that the reaction performed in the space between the processing surfaces is not affected may be used as a first fluid or a second fluid.

(7: Reduction Reaction)

In the case of a reduction reaction of an organic compound with the use of a hydride and/or a derivative thereof, a fluid containing at least one hydride and/or derivative thereof is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The hydride and/or derivative thereof used in the reduction reaction is not particularly limited, but is preferably at least one selected from boron hydrides, aluminum hydrides, tin hydrides, and silicon hydrides, derivatives thereof, and mixtures of two or more of them. Preferably, in each case, only one hydride or derivative thereof is used as a reducing agent in the method according to the present invention. A derivative of a hydride is a compound structurally analogous to the hydride, in which at least one hydrogen atom has been replaced by a radical other than a hydrogen atom, but at least one hydrogen atom is still present. The boron hydrides or derivatives thereof used are preferably lithium borohydride, sodium borohydride, potassium borohydride, rubidium borohydride, cesium borohydride, zinc borohydride, calcium borohydride, copper borohydride, tetraalkylammonium borohydride, trialkylphosphonium borohydride, or triarylphosphonium borohydride, or alkyl, aryl, alkoxy, aryloxy, acyloxy, cyano, or heteroaryl derivatives of the borohydrides, or mixtures of two or more of the above-mentioned compounds. The borohydrides or derivatives thereof used are likewise preferably boranes, particularly diborane, or alkyl, aryl, alkoxy, aryloxy, acyloxy, or heteroaryl derivatives of the boranes, complexes of the boranes or of the above-mentioned derivatives with amines, phosphines, ethers or sulfides as ligands (in each case, the ligands may be the same or different), or mixtures of two or more of the above-mentioned compounds. The aluminum hydrides or derivatives thereof used are preferably alane ($AlH_3$), complex aluminum hydrides, particularly lithium aluminum hydride, sodium aluminum hydride, potassium aluminum hydride, or alkyl, aryl, alkoxy, aryloxy, or acyloxy derivatives of alane or of the aluminum hydrides, for example, sodium bis(2-methoxyethoxy)aluminum hydride or diisobutylaluminum hydride. The aluminum hydrides or derivatives thereof used are likewise preferably complexes of alane, of the aluminum hydrides, or of the above-mentioned derivatives with amines, phosphines, ethers, or sulfides as ligands (in each case, the ligands may be the same or different), or mixtures of two or more of the above-mentioned compounds. Preferred silicon hydrides or derivatives thereof include silanes, particularly monosilane, and alkyl, aryl, alkoxy, aryloxy, acyloxy, cyano, or heteroaryl derivatives of the silanes, or mixtures of two or more of the above-mentioned compounds. Examples of preferred tin hydrides or derivatives thereof include stannanes, particularly monostannane, and alkyl, aryl, alkoxy, aryloxy, acyloxy, cyano, or heteroaryl derivatives of the stannanes, and mixtures of two or more of the above-mentioned compounds. Alkenes and alkynes can be inserted into the B—H bonds of boranes. As a result of hydrolysis or peroxohydrolysis of organoboranes formed in these hydroboration reactions, hydrocarbons or alcohols can be obtained. Therefore, it must be taken into account that, where appropriate, these hydroborations can likewise occur in the case of unsaturated compounds that should be reduced according to the present invention when boranes and/or derivatives of the boranes are used as reducing agents. Suitable substituents of the hydride derivatives are all alkyl, aryl, alkoxy, aryloxy, acyloxy, or heteroaryl substituents which are known to those skilled in the art and which can be used in reductions of aliphatic, aromatic, or heterocyclic compounds.

Then, a fluid containing at least one organic compound is introduced as a second fluid directly through another flow path, that is, the second introduction part d2 into the first fluid film formed between the processing surfaces 1 and 2.

The organic compound used in the reduction reaction is not particularly limited, but preferred aliphatic, aromatic, or heterocyclic organic compounds are aliphatic, aromatic, or heterocyclic carbonyl compounds, such as aldehydes and ketones, carboxylic acids, carboxylic acid halides, carboxylic acid esters, corresponding thio or seleno analogues of the above-mentioned compounds, nitriles, halides, or azides. The aliphatic carbonyl compounds, carboxylic acids, carboxylic acid halides, carboxylic acid esters, corresponding thio or seleno analogues of the above-mentioned compounds, nitriles, halides, or azides which can be used are all aliphatic compounds from the above-mentioned groups of substance which are known to those skilled in the art and which are suitable as substrates for reductions using hydrides and/or derivatives thereof. Linear, branched, saturated and unsaturated compounds are also included herein. The aromatic carbonyl compounds, carboxylic acids, carboxylic acid halides, carboxylic acid esters, corresponding thio or seleno analogues of the above-mentioned compounds, nitriles, halides, or azides which can be used are all aromatic compounds from the above-mentioned groups of substance which are known to those skilled in the art and which are suitable as substrates for reductions using hydrides and/or derivatives thereof. This also includes compounds and/or derivatives having a monocyclic and/or polycyclic homoaromatic basic structure or a corresponding moiety, for example, in the form of substituents. The heterocyclic carbonyl compounds, carboxylic acids, carboxylic acid halides, carboxylic acid esters, corresponding thio or seleno analogues of the above-mentioned compounds, nitriles, halides, or azides which can be used are all heterocyclic compounds from the above-mentioned groups of substance which are known to those skilled in the art, which are suitable as substrates for reductions using hydrides and/or derivatives thereof, and which contain at least one heteroatom. The heterocyclic compounds also include heterocyclic compounds and/or derivatives thereof having at least one monocyclic and/or polycyclic heterocyclic basic structure or a corresponding moiety, for example, in the form of substituents. Here, the term "heterocyclic" also includes saturated, unsaturated, and heteroaromatic compounds. The heterocyclic basic structures or moieties particularly preferably contain at least one oxygen, nitrogen, or sulfur atom.

The hydride and/or derivative thereof and the organic compound used in the reduction reaction are preferably in the form of a liquid or solution. A solvent which can be used for such a purpose is not particularly limited, and examples thereof include water such as ion-exchange water, purified water, tap water, and ultrapure water and organic solvents. The preferred solvents are aromatic solvents (particularly preferably toluene, xylene, ligroin, or phenyl ether), linear, branched, or cyclic hydrocarbon compounds (particularly preferably pentane, hexane, heptane, octane, cyclopentane, cyclohexane, cycloheptane, or cyclooctane), or linear, branched, or cyclic ethers (particularly preferably diethyl ether, methyl tert-butyl ether, tetrahydrofuran, or dioxane), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the reduction reaction of the organic compound with the use of the hydride and/or derivative thereof can be performed.

It is to be noted that a fluid containing all the hydride and/or derivative thereof and the organic compound to such an extent that the reaction performed in the space between the processing surfaces is not affected may be used as a first fluid or a second fluid.

(8: Dehydration Reaction)

In the case of a dehydration reaction of an organic compound, a fluid containing at least one dehydrating agent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The dehydrating agent used in the dehydration reaction of an organic compound is not particularly limited, but is at least one selected from acids, acid anhydrides, acid halides, carbodiimides or cyanoformates, or mixtures of two or more of these dehydrating agents. The acids used are preferably p-toluenesulfonic acid, methanesulfonic acid, trifluoroacetic acid, sulfuric acid, hydrochloric acid, perchloric acid, or a mixture of two or more of these acids. The preferred acid anhydrides are acetic anhydride, trifluoroacetic anhydride, trifluoromethanesulfonic anhydride, or a mixture of two or more of them. Chlorosulfonic acid, chlorosulfonyl isocyanate, acetyl chloride, trichloroacetyl chloride, p-toluenesulfonyl chloride, methanesulfonyl chloride, phosgene, diphosgene, triphosgene, phosphorus oxychloride, phosphorus trichloride, phosphorus tribromide, hexachlorocyclophosphatriazine, thionyl chloride, and mixtures of two or more of them are preferred acid halides. Further, ethyl cyanoformate is a preferred cyanoformate. Examples of preferred carbodiimides include dicyclohexylcarbodiimide, carbonyldiimidazole, and a mixture of them.

Then, a fluid containing at least one organic compound is introduced as a second fluid directly through another flow path, that is, the second introduction part d2 into the first fluid film formed between the processing surfaces 1 and 2.

The organic compound used in the dehydration reaction of an organic compound is not particularly limited, but is preferably selected from aliphatic, aromatic, or heteroaromatic alcohols, amides, or aldoximes. Here, in the present application, the term "dehydration reaction" means that an unsaturated organic compound is generated by dehydration or, in a case where the compound is already unsaturated, the unsaturated character of the compound is increased by dehydration. This includes, for example, dehydration of alcohols to generate alkenes and dehydration of amides or aldoximes to generate nitriles. The aliphatic alcohols, amides, or aldoximes which can be used are all aliphatic compounds from the above-mentioned groups of substance which are known to those skilled in the art and which are suitable as substrates for dehydrations in which unsaturated compounds are generated. This also includes linear, branched, saturated, or unsaturated compounds. The aromatic alcohols, amides or aldoximes which can be used are all aromatic compounds from the above-mentioned groups of substance which are known to those skilled in the art and which are suitable as substrates for dehydrations in which unsaturated compounds are generated. Thus, this includes compounds and/or derivatives having a monocyclic and/or polycyclic homoaromatic basic structure or a corresponding moiety, for example, in the form of substituents. The heteroaromatic alcohols, amides, or aldoximes which can be used are all heteroaromatic compounds from the above-mentioned groups of substance which are known to those skilled in the art, and which are suitable as substrates for dehydrations in which unsaturated compounds are generated, and which contain at least one heteroatom. The heteroaromatic compounds include heteroaromatic compounds and/or derivatives thereof having at least one monocyclic and/or polycyclic heteroaromatic basic structure or a corresponding moiety, for example, in the form of substituents. The heteroaromatic basic structures or moieties preferably contain at least one oxygen, nitrogen, or sulfur atom.

The dehydrating agent and the organic compound used in the dehydration reaction of an organic compound are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cycloheptane, or cyclooctane), or linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, N-methylpyrrolidone), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the dehydration reaction of an organic compound can be performed.

It is to be noted that a fluid containing all the dehydrating agent and the organic compound to such an extent that the reaction performed in the space between the processing surfaces is not affected may be used as a first fluid or a second fluid.

(9: Beckmann Rearrangement)

Beckmann rearrangement is generally represented by the following chemical reaction formula.

[Chemical 4]

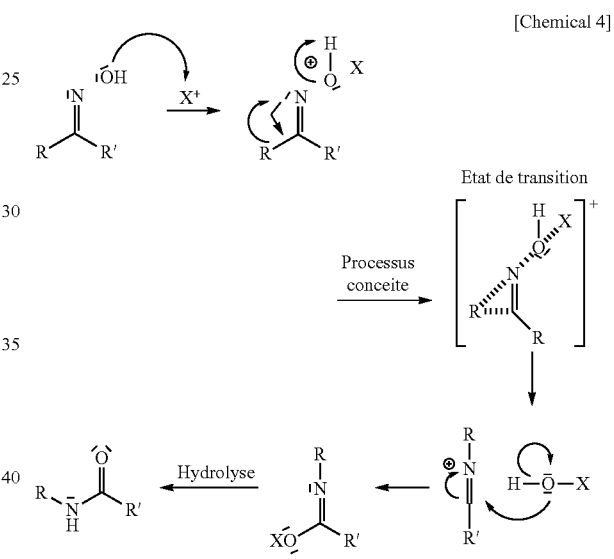

As shown in the above chemical reaction formula, Beckmann rearrangement is a rearrangement reaction to obtain an N-substituted amide from a ketoxime.

In the case of the Beckmann rearrangement, a fluid containing at least one rearrangement reagent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The rearrangement reagent used in the Beckmann rearrangement is preferably at least one selected from acids, acid anhydrides, acid halides, carbodiimides, cyanformates, Lewis acids, or mixtures of two or more of these rearrangement reagents. The acids used are preferably p-toluenesulfonic acid, methanesulfonic acid, trifluoroacetic acid, sulfuric acid, hydrochloric acid, perchloric acid, or a mixture of two or more of these acids. The preferred acid anhydrides are acetic anhydride, trifluoroacetic anhydride, trifluoromethanesulfonic anhydride, or mixtures of two or more of them. Chlorosulfonic acid, chlorosulfonyl isocyanate, acetyl chloride, trichloroacetyl chloride, p-toluenesulfonyl chloride, methanesulfonyl chloride, phosgene, diphosgene, triphosgene, phosphorus oxychloride, phosphorus trichloride, phosphorus tribromide, hexachlorocyclophosphatriazine, thionyl chloride, or mixtures of two or more of them are preferred acid halides. Further, ethyl cyanoformate is a preferred cyanoformate. Dicyclohexylcarbodiimide and/or carbonyldiimidazole are/is a preferred carbodiimide. The preferred Lewis acids include aluminum compounds, preferably aluminum trichloride, methylaluminum dichloride, dimethylaluminum chloride, diisobutylaluminum hydride, titanium compounds, preferably $TiCl_4$, tin compounds, preferably $SnCl_4$, zinc compounds, preferably $ZnCl_2$, boron compounds, preferably $BCl_3$, or mixtures of at least two of the above-mentioned compounds.

Then, a fluid containing at least one organic oxime is introduced as a second fluid directly through another flow path, that is, the second introduction part d2 into the first fluid film formed between the processing surfaces 1 and 2.

The organic oxime used in the Beckmann rearrangement is not particularly limited, but is selected from aliphatic, aromatic, or heterocyclic aromatic ketoximes. The aliphatic ketoximes which can be used are all aliphatic ketoximes suitable as substrates for Beckmann rearrangements. Linear, branched, cyclic, saturated, and unsaturated compounds are also included herein. The aromatic ketoximes which can be used are all aromatic ketoximes suitable as substrates for Beckmann rearrangements. Therefore, heteroaromatic ketoximes, which can be used as a monocyclic and/or polycyclic homoaromatic basic structure, are all heteroaromatic ketoximes which are suitable as substrates for Beckmann rearrangements and which contain at least one heteroatom. Further, the heteroaromatic ketoximes include heteroaromatic compounds and/or derivatives thereof having at least one monocyclic and/or polycyclic heteroaromatic basic structure or a corresponding moiety, for example, in the form of substituents. The heteroaromatic basic structures or moieties particularly preferably contain at least one oxygen, nitrogen, and/or sulfur atom.

The rearrangement reagent and the organic oxime used in the Beckmann rearrangement are preferably in the form of a liquid or solution. A solvent which can be used for such a purpose is not particularly limited, and examples thereof include water such as ion-exchange water, purified water, tap water, ultrapure water and organic solvents. The solvents which can be used are, for example, halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cycloheptane, or cyclooctane), or linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, pyridine or N-methylpyrrolidone), or mixtures of two or more of these solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the Beckmann rearrangement can be performed.

It is to be noted that a fluid containing all the rearrangement reagent and the organic oxime to such an extent that the reaction performed in the space between the processing surfaces is not affected may be used as a first fluid or a second fluid.

(10: Oximation)

In the case of oximation of an organic carbonyl compound and/or a CH-acid compound, a fluid containing at least one oximation reagent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The oximation reagent used in the oximation reaction is not particularly limited, but is at least one selected from hydroxylamine, hydroxylamine O-ethers, salts of nitrous acid, organic nitrites, or mixtures of at least two of these oximation reagents. Examples of the preferred organic nitrites include tert-butyl nitrite, n-pentyl nitrite, isopentyl nitrite, isopropyl nitrite, or mixtures of at least two of these nitrites.

Then, a fluid containing at least one organic carbonyl compound and/or at least one CH-acid compound is introduced as a second fluid directly through another flow path, that is, the second introduction part d2 into the first fluid film formed between the processing surfaces 1 and 2.

The organic carbonyl compound or the CH-acid compound used in the oximation of an organic carbonyl compound and/or a CH-acid compound is not particularly limited, but is preferably selected from aliphatic, aromatic, or heteroaromatic aldehydes, ketones, or CH-acid compounds. The aliphatic aldehydes, ketones, or CH-acid compounds used can be any aliphatic compounds from the above-mentioned groups of substance which are suitable as substrates for oximation reactions. This also includes linear, branched, cyclic, saturated, and unsaturated compounds. The aromatic aldehydes, ketones, or CH-acid compounds used can be any aromatic compounds from the above-mentioned groups of substance which are suitable as substrates for oximation reactions. Thus, this includes compounds and/or derivatives having a monocyclic and/or polycyclic homoaromatic basic structure or a corresponding moiety, for example, in the form of substituents. The heteroaromatic aldehydes, ketones, or CH-acid compounds used can be any heteroaromatic compounds from the above-mentioned groups of substance which are suitable as substrates for oximation reactions and which contain at least one heteroatom. The heteroaromatic compounds include heteroaromatic compounds and/or derivatives thereof having at least one monocyclic and/or polycyclic heteroaromatic basic structure or a corresponding moiety, for example, in the form of substituents. The heteroaromatic basic structures or moieties preferably contain at least one oxygen, nitrogen and/or sulfur atom.

The oximation reagent and the organic carbonyl compound and/or the CH-acid compound used in the oximation of an organic carbonyl compound and/or a CH-acid compound are preferably in the form of a liquid or solution. A solvent which can be used for such a purpose is not particularly limited, and examples thereof include water such as ion-exchange water, purified water, tap water, ultrapure water and organic solvents. The preferred solvents are water, ethers (particularly preferably, diethyl ether, methyl tert-butyl ether, tetrahydrofuran, or dioxane), aromatic solvents (particularly preferably, toluene, xylene), ligroin or phenyl ether, halogenated solvents (particularly preferably, dichloromethane, chloroform, 1,2-dichloroethane, or 1,1,2,2-tetrachloroethane), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the oximation of an organic carbonyl compound and/or a CH-acid compound can be performed.

It is to be noted that a fluid containing all the oximation reagent and the organic carbonyl compound and/or the CH-acid compound to such an extent that the reaction performed in the space between the processing surfaces is not affected may be used as a first fluid or a second fluid.

(11: 1,3-Dopolar Cycloaddition)

In the case of 1,3-dipolar cycloaddition of an organic compound, a fluid containing at least one dipolarophile is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The dipolarophile used in the 1,3-cycloaddition of an organic compound is not particularly limited, and dipolarophiles which can be used are all dipolarophiles suitable for 1,3-dipolar cycloadditions or mixtures of at least two dipolarophiles. The dipolarophile used is at least one selected from olefins, acetylenes, aldehydes, ketones, imines, nitriles, furans, thiophenes, or mixtures of two or more of these dipolarophiles. All dipolarophilic functional groups which directly react in 1,3-dipolar cycloadditions are present in the above-mentioned various 1,3-dipolar organic compounds. These compounds react in intramolecular cycloadditions when this is sterically possible. Here, only one 1,3-dipolar functional group or a combination of at least two 1,3-dipolar functional groups and only one dipolarophilic group or a combination of at least two dipolarophilic groups, which are in each case the same or different, can be present in the organic compound. Preferably, only one 1,3-dipolar functional group and only one dipolarophilic functional group are present.

Then, a fluid containing at least one organic compound is introduced as a second fluid directly through another flow path, that is, the second introduction part d2 into the first fluid film formed between the processing surfaces 1 and 2.

The organic compound is not particularly limited, but is preferably selected from aliphatic, aromatic, or heterocyclic aromatic nitrile ylides, nitrile imines, nitrile oxides, diazoalkanes, azides, azomethine ylides, azomethine imines, nitrones, carbonyl ylides, carbonyl imines, or carbonyl oxides. The aliphatic nitrile ylides, nitrile imines, nitrile oxides, diazoalkanes, azides, azomethine ylides, azomethine imines, nitrones, carbonyl ylides, carbonyl imines, or carbonyl oxides which can be used are all aliphatic compounds from the above-mentioned groups of substance which are known to those skilled in the art and which are suitable as substrates for 1,3-dipolar cycloadditions. Further, linear, branched, cyclic, saturated, and unsaturated compounds are also included. The aromatic nitrile ylides, nitrile imines, nitrile oxides, diazoalkanes, azides, azomethine ylides, azomethine imines, nitrones, carbonyl ylides, carbonyl imines, or carbonyl oxides which can be used are all aromatic compounds from the above-mentioned groups of substance which are suitable as substrates for 1,3-dipolar cycloadditions. Thus, compounds and/or derivatives having a monocyclic and/or polycyclic homoaromatic basic structure or a corresponding moiety, for example, in the form of substituents are included. Heteroaromatic nitrile ylides, nitrile imines, nitrile oxides, diazoalkanes, azides, azomethine ylides, azomethine imines, nitrones, carbonyl ylides, carbonyl imines, or carbonyl oxides which can be used are all heteroaromatic compounds from the above-mentioned groups of substance which are suitable as substrates for 1,3-dipolar cycloadditions and which contain at least one heteroatom. The heteroaromatic compounds include heteroaromatic compounds and/or derivatives thereof having at least one monocyclic and/or polycyclic heteroaromatic basic structure or a corresponding moiety, for example, in the form of substituents. The heteroaromatic basic structures or moieties particularly preferably contain at least one oxygen, nitrogen, and/or sulfur atom.

The dipolarophile and the organic compound used in the 1,3-dipolar cycloaddition of an organic compound are preferably in the form of a liquid or solution. A solvent which can be used for such a purpose is not particularly limited, and examples thereof include water such as ion-exchange water, purified water, tap water, and ultrapure water and organic solvents. The preferred solvents are water, ethers (particularly preferably, diethyl ether, methyl tert-butyl ether, tetrahydrofuran, or dioxane), aromatic solvents (particularly preferably, toluene, xylene, ligroin, or phenyl ether), halogenated solvents (particularly preferably, dichloromethane, chloroform, 1,2-dichloroethane, or 1,1,2,2-tetrachloroethane), or mixtures of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the 1,3-dipolar cycloaddition of an organic compound can be performed.

It is to be noted that a fluid containing all the dipolarophile and the organic compound to such an extent that the reaction performed in the space between the processing surfaces is not affected may be used as a first fluid or a second fluid.

(12: Oxidation of Tertiary Amine and/or Nitrogen-Containing Aromatic Heterocyclic Compound to Amine Oxide)

In the case of oxidation of a tertiary amine and/or a nitrogen-containing aromatic heterocyclic compound to an amine oxide, a fluid containing at least one oxidant is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The oxidant used in the oxidation of a tertiary amine and/or a nitrogen-containing aromatic heterocyclic compound to an amine oxide is not particularly limited, and all oxidants suitable for oxidation of tertiary amines and/or nitrogen-containing aromatic heterocyclic compounds to amine oxides or mixtures of at least two of these oxidants can be used as oxidants in the method according to the present invention. The oxidant is preferably at least one selected from inorganic and organic peroxides, hydrogen peroxide, mixtures of peroxo compounds with organic acids and/or inorganic acids and/or Lewis acids, organic peracids, inorganic peracids, dioxiranes, or mixtures of at least two of these oxidants. The inorganic peroxides used are preferably ammonium peroxide, alkali metal peroxides, preferably sodium peroxide, ammonium persulfate, alkali metal persulfates, ammonium perborate, alkali metal perborates, ammonium percarbonate, alkali metal percarbonates, alkaline-earth metal peroxides, zinc peroxide, or a mixture of at least two of these peroxides. The organic peroxides used are preferably tert-butyl hydroperoxide, cumene hydroperoxide, menthyl hydroperoxide, 1-methylcyclohexane hydroperoxide, or a mixture of at least two of these peroxides. Potassium peroxodisulfate with sulfuric acid is used as the peroxo compound with an inorganic acid, and hydrogen peroxide with boron trifluoride is used as the peroxo compound with a Lewis acid. The preferred organic peracids are peroxybenzoic acid, m-chloroperoxybenzoic acid, p-nitroperoxybenzoic acid, magnesium monoperoxyphthalic acid, peroxyacetic acid, peroxymaleic acid, or peroxytrifluoroacetic acid. A mixture of at least two of these peracids can also be used.

Then, a fluid containing at least one tertiary amine and/or at least one nitrogen-containing aromatic heterocyclic compound is introduced as a second fluid directly through another flow path, that is, the second introduction part d2 into the first fluid film formed between the processing surfaces 1 and 2.

The tertiary amine and/or nitrogen-containing aromatic heterocyclic compound are/is not particularly limited, but the tertiary amine is preferably an aliphatic, cycloaliphatic, aromatic, or heteroaromatic tertiary amine. The aliphatic, cycloaliphatic, aromatic, or heteroaromatic groups bonded to the nitrogen atom may be the same or different. All nitrogen-containing aromatic heterocyclic compounds known to those skilled in the art as substrates for oxidation to amine oxides can be used as nitrogen-containing aromatic heterocyclic compounds in the method according to the present invention. The nitrogen-containing heterocyclic compounds used have a ring size preferably of 5 to 7 atoms, particularly preferably of 5 or 6 atoms. The nitrogen-containing aromatic heterocyclic compound used is particularly preferably pyridine and/or pyrimidine and/or pyrazine. The nitrogen-containing aromatic heterocyclic compounds also include aromatic compounds and/or derivatives thereof having at least one monocyclic and/or polycyclic nitrogen-containing aromatic basic structure or a corresponding partial structure, for example, in the form of substituents. These nitrogen-containing aromatic basic structures or partical structures can also contain other heteroatoms, preferably oxygen and/or sulfur.

The oxidant and the tertiary amine and/or nitrogen-containing aromatic heterocyclic compound used in the oxidation of a tertiary amine and/or a nitrogen-containing aromatic heterocyclic compound to an amine oxide are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cycloheptane, or cyclooctane), linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, pyridine or N-methylpyrrolidone), or mixtures of two or more of these solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the oxidation of a tertiary amine and/or nitrogen-containing aromatic heterocyclic compound to an amine oxide can be performed.

It is to be noted that a fluid containing all the oxidant and the tertiary amine and/or N-containing aromatic heterocyclic compound to such an extent that the reaction performed in the space between the processing surfaces is not affected may be used as a first fluid or a second fluid.

(13: Epoxidation)

In the case of epoxidation of an olefin, a fluid containing at least one oxidant is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The oxidant used in the epoxidation of an olefin is not particularly limited, and oxidants or mixtures of at least two oxidants can be used as oxidants in the method according to the present invention. The oxidant is preferably at least one compound selected from inorganic and organic peroxides, hydrogen peroxide, chromyl compounds, chromium oxides, alkali metal hypochlorites, alkaline-earth metal hypochlorites, N-bromosuccinimide, transition metal peroxo complexes, mixtures of peroxo compounds with organic acids and/or inorganic acids and/or Lewis acids, organic peracids, inorganic peracids, and dioxiranes, or a mixture of at least two of these oxidants. The inorganic peroxides used are preferably ammonium peroxide, alkali metal peroxides (particularly preferably, sodium peroxide), ammonium persulfate, alkali metal persulfates, ammonium perborate, alkali metal perborates, ammonium percarbonate, alkali metal percarbonates, alkaline-earth metal peroxides, zinc peroxide, or a mixture of at least two of these compounds. The transition metal peroxo complexes used are preferably peroxo complexes of iron, manganese, vanadium, or molybdenum or a mixture of at least two of these peroxo complexes. The peroxo complex may also contain two or more same or different metals, preferably selected from iron, manganese, vanadium, and molybdenum. Preferably, potassium peroxodisulfate with sulfuric acid is used as the peroxo compound with an inorganic acid, and hydrogen peroxide with boron trifluoride is used as the peroxo compound with a Lewis acid. The organic peracids used are preferably peroxybenzoic acid, m-chloroperoxybenzoic acid, p-nitroperoxybenzoic acid, magnesium monoperoxyphthalic acid, peroxyacetic acid, peroxymaleic acid, peroxytrifluoroacetic acid, peroxyphthalic acid, peroxylauric acid, or a mixture of at least two of these peracids. The preferred dioxiranes are dimethyldioxirane, methyl(trifluoromethyl)dioxirane, and a mixture of these dioxiranes. The organic peroxides used are preferably tert-butyl hydroperoxide, cumene hydroperoxide, menthyl hydroperoxide, 1-methylcyclohexane hydroperoxide, or a mixture of at least two of these organic peroxides.

Then, a fluid containing at least one olefin is introduced as a second fluid directly through another flow path, that is, the second introduction part d2 into the first fluid film formed between the processing surfaces 1 and 2.

The olefin is not particularly limited, but is preferably an aliphatic, aromatic, or heterocyclic aromatic olefin, particularly preferably 1-phenylcyclohexene, cyclohexene, or styrene. Any aliphatic olefins which are suitable as substitutes for epoxidations can be used as aliphatic olefins. These include linear, branched, and cyclic olefins. Any aromatic olefins which are suitable as substitutes for epoxidations can be used as aromatic olefins. In the present invention, these include compounds and/or derivatives having a monocyclic and/or polycyclic homoaromatic parent structure or a corresponding partial structure, for example, in the form of substituents. Any heterocyclic aromatic olefins which are suitable expoxidation substrates and which contain at least one heteroatom can be used as heterocyclic olefins. In the present invention, the heterocyclic aromatic olefins include heterocyclic aromatic compounds and/or derivatives thereof having at least one monocyclic and/or polycyclic heterocyclic aromatic parent structure or a corresponding partial structure, for example, in the form of substituents. The heterocyclic aromatic parent structures or partial structures particularly preferably contain at least one oxygen, nitrogen, and/or sulfur atom.

The oxidant and the olefin used in the epoxidation of an olefin are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cycloheptane, or cyclooctane), linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, pyridine or N-methylpyrrolidone), or mixtures of at least two of the above-mentioned solvents.

The olefin can also be oxidized with an optically-active oxidant or in the presence of an optically-active compound to obtain an optically-active epoxide. In this case, the olefin is preferably oxidized with tert-butyl hydroperoxide in the presence of a chiral reagent, preferably titanium tetraisopropoxide, diethyl (R,R)-tartrate and/or diethyl (S,S)-tartrate to obtain an optically-active epoxide. It is also preferred that the olefin is oxidized with optically-active (R,R)-trans-1,2-bis[(2-hydroxy-3,5-ditert-butylbenzylidene)amino]cyclohexanemanganese dichloride or (S,S)-trans-1,2-bis[(2-hydroxy-3,5-ditert-butylbenzylidene)amino]cyclohexanemanganese dichloride (Jacobsen's catalyst) and dimethyl dioxirane and/or sodium hypochlorite.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the epoxidation of an olefin can be performed.

It is to be noted that a fluid containing all the oxidant and the olefin to such an extent that the reaction performed in the space between the processing surfaces is not affected may be used as a first fluid or a second fluid.

(14: Formylation)

In the case of formylation of an organic compound, a fluid containing at least one formylation agent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The formylation agent used in the formylation of an organic compound is not particularly limited, and formylation agents which can be used in the method according to the present invention are formulation agents which are known to those skilled in the art and which are suitable for formylations and mixtures of at least two of these formylation agents. Preferably, only one formylation agent is used. The formylation agents also include formylation agents formed in situ, i.e., formylation agents formed just before or during the formylation reaction. The formylation agent used is preferably an N,N-disubstituted formamide, an N-alkylformanilide, an N,N-disubstituted amide, or a mixture of at least two of these compounds in the presence of an inorganic acid chloride, an inorganic ester, an acid anhydride, an adduct of triphenylphosphine and bromine, cyanuric chloride, hexachlorocyclotriphosphazane, or a mixture of at least two of these compounds. As the N,N-disubstituted formamide, an N-aryl-N-alkylformamide (particularly preferably, N-phenyl-N-methyl formamide), an N,N-dialkylformamide (particularly preferably, N,N-dimethylformamide), a vinyl N,N-dialkylformamide, or a mixture of at least two of these compounds is preferably used. As the N-alkylformanilide, N-methylformanilide is preferably used. As the N,N-disubstituted amide, an N,N-dialkylacetamide (particularly preferably, N,N-dimethylacetamide), an N,N-dialkylpropionamide (particularly preferably, N,N-dimethylpropionamide), an N,N-dialkylbenzamide (particularly preferably, N,N-dimethylbenzamide), or a mixture of at least two of these compounds is preferably used. As the inorganic acid chloride, phosphorus oxychloride, thionyl chloride, phosgene, a phosgene substitute, particularly diphosgene or triphosgene, pyrophosphoryl chloride, oxalyl chloride, sulfuryl chloride, benzoyl bromide, or a mixture of at least two of these compounds is preferably used. As the acid anhydride, trifluoromethansulfonic anhydride is preferably used. As the inorganic ester, a dialkyl sulfate is preferably used, and dimethyl sulfate is particularly preferably used. The molar ratio of the N,N-disubstituted formamide and/or the N-alkylformanilide and/or the N,N-disubstituted amide to the inorganic acid chloride and/or the inorganic ester and/or the acid anhydride is preferably equimolar. Further, the acid chloride and/or the inorganic ester and/or the acid anhydride are/is preferably present in a 2-fold to 10-fold molar excess, particularly preferably in 3-fold to 5-fold molar excess, based on the N,N-disubstituted formamide and/or the N-alkylformanilide and/or the N,N-disubstituted amide. In a further preferred aspect of the method according to the present invention, the formylation agent used is zinc(II) cyanide in the presence of a protic acid, preferably hydrochloric acid.

Then, a fluid containing at least one organic compound is directly introduced as a second fluid through the second introduction part d2, which is a separate flow path, into the first fluid film formed between the processing surfaces 1 and 2.

The organic compound is not particularly limited, and all organic compounds can be used for formylations in the method according to the present invention. The organic compounds are preferably selected from olefins, alkynes, aromatic compounds, heteroaromatic compounds, transition metal complexes, CH-acid compounds, enamides, and mixtures of at least two of these compounds. The olefins which can be used are all olefins which are suitable as substrates for formylations. These include linear, branched, and cyclic olefins. The use of unsubstituted or substituted ethylene as olefin is preferred. The alkynes which can be used are all alkynes which are suitable as substrates for formylations. These include linear, branched, and cyclic alkynes. The use of substituted acetylene as alkynes is preferred. The aromatic compounds which can be used are all aromatic compounds which are suitable as substrates for formylations. These include compounds and/or derivatives having a monocyclic and/or polycyclic homoaromatic framework or a corresponding substructure, for example, in the form of substituents. The aromatic compounds may be substituted or unsubstituted, and azulene, indole, phenol, an aromatic amine, or a mixture of at least two of these compounds is preferred. The heteroaromatic compounds which can be used are all heteroaromatic compounds which are suitable as substrates for formylations and which contain at least one heteroatom. The heteroaromatic compounds include heteroaromatic compounds and/or derivatives thereof having a monocyclic and/or polycyclic heteroaromatic framework or a corresponding substructure, for example, in the form of substituents. These heteroaromatic frameworks or substructures preferably contain at least one oxygen, nitrogen, and/or sulfur atom. The heteroaromatic compounds may be substituted or unsubstituted, and the use of furan, thiophene, pyrrole, benzofuran, benzothiophene, pyrazole, imidazole, thiazole, oxazole, pyrimidine, porphyrin, hydantoin, thiohydantoin, imidazolone, pyrazolone, or a mixture of at least two of these compounds is particularly preferred. The transition metal complexes which can be used are all transition metal complexes which are suitable as substrates for formylations. Particularly, as the transition metal complexes, metallocene compounds, preferably ferrocene, carbonyl compounds of transition metals, preferably carbonyl compounds of iron, chromium, or manganese, and mixtures of at least two of these compounds are preferred. The CH-acid compounds which can be used are all CH-acid compounds which are suitable as substrates for formylations and which contain at least one acid proton in the α position relative to a carbonyl group. The preferred CH-acid compounds are enols, enol ethers, β-keto compounds, particularly preferably pyrazole-3,5-dione, or mixtures of at least two of these compounds. The enamides which can be used are all enamides which are suitable as substrates for formylations. As the enamide, vinylformamide is preferably used, and 3-dimethylaminopropenal is particularly preferably used.

The formylation agent and the organic compound used in the formylation of an organic compound are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cyclohexane, cycloheptane, or cyclooctane), linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing solvents (particularly preferably, N,N-dimethylformamide or N-methylpyrrolidone), or mixtures of at least two of the above-mentioned solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the formylation of an organic compound can be performed.

It is to be noted that a fluid containing all the formylation agent and the organic compound to such an extent that the reaction performed in the space between the processing surfaces is not affected may be used as a first fluid or a second fluid.

(15: Indole)

In the case of obtaining an indole compound, a fluid containing at least one catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The catalyst used in the case of obtaining an indole compound is not particularly limited, and all catalysts which are suitable for producing indoles or mixtures of at least two of these catalysts can be used. Preferably, only one catalyst is used. In a further preferred aspect of the method according to the present invention, the catalyst used is an inorganic acid, an organic acid, a Lewis acid, or a mixture of at least two of these catalysts. The inorganic acid used can preferably be sulfuric acid, hydrochloric acid, perchloric acid, (poly)phosphoric acid, trifluoroacetic acid, nitric acid, or a mixture of at least two of these inorganic acids. The organic acid used can preferably be chlorosulfonic acid, p-toluenesulfonic acid, methanesulfonic acid, trifluoromethanesulfonic acid, or a mixture of at least two of these organic acids. The Lewis acid used can preferably be a boron/halogen compound, particularly preferably $BF_3$, a metal halide, particularly preferably $ZnC_{12}$, $SnCl_4$, $AlCl_3$, $FeCl_3$, $TiCl_4$, or $MgCl_2$, very particularly preferably, $ZnCl_2$, or a mixture of at least two of these Lewis acids. In a further preferred aspect of the method according to the present invention, one or more catalysts are used in an amount between 0.1 and 110 mol %, particularly preferably between 1 and 100 mol %, very particularly preferably between 10 and 50 mol %, with respect to the amount of one or more arylhydrazones used.

Then, a fluid containing at least one arylhydrazone is introduced as a second fluid directly through another flow path, that is, the second introduction part d2 into the first fluid film formed between the processing surfaces 1 and 2.

The arylhydrazone used in the case of obtaining an indole compound is not particularly limited, and all arylhydrozones which are known as substrates for producing indoles can be used. In a preferred aspect of the method according to the present invention, at least one arylhydrazone of an organic keton or of an organic aldehyde, particularly preferably an arylhydrazone of an aliphatic, aromatic, or heteroaromatic ketone or of an aliphatic, aromatic, or heteroaromatic aldehyde is used. The suitable arylhydrazones of aliphatic ketones or of aliphatic aldehydes are all arylhydrazone of aliphatic ketones or of aliphatic aldehydes which are suitable as substrates for producing indoles. This includes arylhydrazones of linear, branched, and cyclic, saturated and unsaturated ketones and/or arylhydrazones of linear, branched, and cyclic, saturated and unsaturated aldehydes. The suitable arylhydrazones of aromatic ketones or of aromatic aldehydes are all arylhydrazones of aromatic ketones or of aromatic aldehydes which are suitable as substrates for producing indoles. This includes arylhydrazones of aromatic aldehydes and ketones which have a monocyclic and/or polycyclic homoaromatic basic structure or a corresponding moiety, for example, in the form of substituents. The suitable arylhydrazones of heteroaromatic ketones or of heteroaromatic aldehydes are all arylhydrazones of heteroaromatic ketones or of heteroaromatic aldehydes which are suitable as substrates for producing indoles and which contain at least one heteroatom. The arylhydrazones of heteroaromatic ketones or of heteroaromatic aldehydes include arylhydrazones of heteroaromatic ketones or of heteroaromatic aldehydes which have at least one monocyclic and/or polycyclic heteroaromatic basic structure or a corresponding moiety, for example, in the form of substituents. These heteroaromatic basic structures or moieties preferably contain at least one oxygen, nitrogen, and/or sulfur atom. The arylhydrazones of aliphatic, aromatic, or heteroaromatic ketones and aldehydes can be produced by conventional methods known per se to those skilled in the art. The arylhydrazones are preferably produced by condensation of the corresponding arylhydrazines with the corresponding aliphatic, aromatic, or heteroaromatic ketones or aldehydes. In a further preferred aspect of the method according to the present invention, the arylhydrazone used is a phenylhydrazone, particularly preferably a phenylhydrazone of an aliphatic, aromatic, or heteroaromatic ketone or aldehyde. In a further preferred aspect of the method according to the present invention, the arylhydrazone of an aliphatic, aromatic, or heteroaromatic ketone and/or of an aliphatic, aromatic, or heteroaromatic aldehyde is formed in situ in at least one microreactor, and is preferably formed from the corresponding arylhydrazine and the corresponding aliphatic, aromatic, or heteroaromatic ketone and/or the corresponding aliphatic, aromatic, or heteroaromatic aldehyde. In-situ formation means that the arylhydrazone is formed just before conversion to the corresponding indole. The arylhydrazone can likewise preferably be formed preferably from the corresponding arylhydrazine and the corresponding aliphatic, aromatic, or heteroaromatic ketone and/or the corresponding aliphatic, aromatic, or heteroaromatic aldehyde in at least one microreactor and isolated before conversion to the corresponding indole.

The catalyst and the arylhydrazone used in the case of obtaining an indole compound are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cyclohexane, cycloheptane, or cyclooctane), or linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, pyridine or N-methylpyrrolidone), or mixtures of at least two of the above-mentioned solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, an indole compound can be obtained.

It is to be noted that a fluid containing all the catalyst and the arylhydrazone to such an extent that the reaction performed in the space between the processing surfaces is not affected may be used as a first fluid or a second fluid.

(16: Alkylidene Group Rearrangement)

In the case of transferring an alkylidene group to an organic compound, a fluid containing at least one alkylidene group transfer reagent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The alkylidene group transfer reagent used in the case of transferring an alkylidene group to an organic compound is not particularly limited, and all alkylidene group transfer reagents suitable for alkylidene group transfer reactions or mixtures of at least two of these reagents can be used. Preferably, only one alkylidene group transfer reagent is used. The alkylidene group transfer reagents also include alkylidene group transfer reagents formed in situ, i.e., alkylidene group transfer reagents formed just before or during the alkylidene group transfer reaction. In another preferred aspect of the present invention, the alkylidene group transfer reagents used are reagents for transferring, as alkylidene groups, a methylene group ($=CH_2$), an ethylidene group ($=CH-CH_3$), or an isopropylidene group ($=C(CH_3)_2$), preferably a methylene group ($=CH_2$). In another preferred aspect of the present invention, the alkylidene group transfer reagents used are [(cyclopentadienyl)$_2$-Ti($CH_2$)—(Cl)—Al—($CH_3$)$_2$] ("Tebbe reagent"), biscyclopentadienyltitanadialkyl compounds, alkyl compounds of transition metals, alkylidene compounds of transition metals, or mixtures of at least two of these compounds. The biscyclopentadienyltitanadialkyl compound used can preferably be dimethyltitanocene. The alkylidene compound of a transition metal, which can be formed optionally or in situ, can preferably be at least one compound represented by the following general formula (I): $CR_2=MLn$, wherein n is an integer of 1 to 9, preferably 1 to 6, particularly preferably 1 or 2 and depends on one or more ligands represented by L and a transition metal represented by M, the groups R are the same or different and each are an organic group, preferably an optionally-substituted alkyl or aryl group, M represents a transition metal, preferably titanium, zirconium, or hafnium, particularly preferably titanium, the groups L are the same or different and each are an organic or inorganic ligand, preferably a cyclopentadienyl group or a pentamethylcyclopentadienyl group. In a case where the alkylidene group transfer reagent is formed in situ, it is formed preferably by a mixture of a compound represented by the general formula: $R_1—CH_2—X$, wherein $R_1$ is an organic group or a halogen group and X is an halogen group, zinc, and titanium tetrachloride, particularly preferably by a mixture of methylene bromide, zinc, and titanium tetrachloride.

Then, a fluid containing at least one organic compound is introduced as a second fluid directly through another flow path, that is, the second introduction part d2 into the first fluid film formed between the processing surfaces 1 and 2.

The organic compound used in the case of transferring an alkylidene group to an organic compound is not particularly limited, and all organic compounds known as substrates for alkylidene group transfer reactions can be used. The organic compound is preferably selected from the group consisting of ketones, lactones, carboxylic acid esters, carboxylic acid amides, or mixtures of at least two of these compounds. The ketones which can be used are all ketones suitable as substrates for alkylidene group transfer reactions. This also includes aliphatic, vinylogenic, aromatic, and heteroaromatic ketones. The lactones which can be used are all lactones suitable as substrates for alkylidene group transfer reactions. This also includes aliphatic, vinylogenic, aromatic, and heteroaromatic lactones. The carboxylic acid esters which can be used are all carboxylic acid esters which are suitable as substrates for alkylidene group transfer reactions and which are known to those skilled in the art. This also includes aliphatic, vinylogenic, aromatic, and heteroaromatic carboxylic acid esters. The carboxylic acid amides which can be used are all carboxylic acid amides which are suitable as substrates for alkylidene group transfer reactions and which are known to those skilled in the art. This also includes aliphatic, vinylogenic, aromatic, and heteroaromatic carboxylic acid amides. The aliphatic ketones, lactones, carboxylic acid esters and carboxylic acid amides are also interpreted as saturated, unsaturated, and branched ketones, lactones, carboxylic acid esters, and carboxylic acid amides and cyclic ketones, carboxylic acid esters, and carboxylic acid amides, which may be optionally substituted. The vinylogenic ketones, lactones, carboxylic acid esters, and carboxylic acid amides are interpreted as ketones, lactones, carboxylic acid esters, and carboxylic acid amides having a double bond in the α position relative to a carbonyl group. The aromatic ketones, lactones, carboxylic acid esters, and carboxylic acid amides also include ketones, lactones, carboxylic acid esters, and carboxylic acid amides and/or derivatives thereof having a monocyclic and/or polycyclic homoaromatic basic structure or a corresponding moiety, for example, in the form of substituents. The heteroaromatic ketones, lactones, carboxylic acid esters, and carboxylic acid amides also include ketones, lactones, carboxylic acid esters, and carboxylic acid amides and/or derivatives thereof having at least one monocyclic and/or polycyclic heteroaromatic basic structure or a corresponding moiety, for example, in the form of substituents. These heteroaromatic basic structures or moieties particularly preferably contain at least one oxygen and/or nitrogen and/or sulfur atom.

The alkylidene group transfer reagent and the organic compound used in the case of transferring alkylidene groups to organic compounds are preferably in the form of a liquid or solution. A solvent which can be used for such a purpose is not particularly limited, and examples thereof include water such as ion-exchange water, purified water, tap water, and ultrapure water and organic solvents. The preferred solvents are halogenated solvents (particularly preferably, dichloromethane, chloroform, 1,2-dichloroethane, or 1,1,2,2-tetrachloroethane), linear, branched, or cyclic hydrocarbon compounds (particularly preferably, pentane, hexane, heptane, octane, cyclopentane, cyclohexane, cycloheptane, or cyclooctane), or linear, branched, or cyclic ethers (particularly preferably, diethyl ether, methyl tert-butyl ether, tetrahydrofuran, or dioxane), aromatic solvents (particularly preferably, toluene, xylene, ligroin, or phenyl ether), N-containing heterocyclic solvents (particularly preferably, pyridine or N-methylpyrrolidone), or mixtures of at least two of the above-mentioned solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the transferring of an alkylidene group to an organic compound can be performed.

It is to be noted that a fluid containing all the alkylidene group transfer reagent and the organic compound to such an extent that the reaction performed in the space between the processing surfaces is not affected may be used as a first fluid or a second fluid.

(17: Coupling Reaction)

Coupling reactions are generally represented by the following chemical reaction formulas.

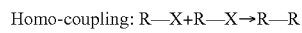

Homo-coupling: R—X+R—X→R—R

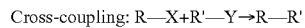

Cross-coupling: R—X+R'—Y→R—R'

It is to be noted that a reaction where two units having the same structure are bonded together is referred to as a homo coupling, and a reaction where two units having different structures are bonded together is referred to as a cross coupling (hetero coupling).

In the present invention, the term "coupling reaction" refers to such a reaction as described above where two chemical substances are selectively bonded together.

In the case of, for example, the coupling reaction, a fluid containing at least one organic compound containing at least one elimination group and at least one catalyst is introduced as a first fluid through one flow path, that is, the first introduction part d1 into a space between the processing surfaces 1 and 2 arranged to be opposite to each other so as to approach to and separate from each other, at least one of which rotates relative to the other, to form a first fluid film between the processing surfaces.

The organic compounds containing at least one elimination group used in the coupling reaction are all organic compounds containing at least one elimination group which are known to those skilled in the art as substrates for coupling reactions. The organic compounds containing at least one elimination group used in the method according to the present invention can preferably be aryl halides (particularly preferably aryl bromides or aryl iodides, very particularly preferably aryl iodides), heteroaryl halides (particularly preferably heteroaryl bromides or heteroaryl iodides, very particularly preferably heteroaryl iodides), vinyl halides (particularly preferably vinyl bromides or vinyl iodides, very particularly preferably vinyl iodides), and mixtures of at least two of the above-mentioned compounds. The compounds containing at least one elimination group used in the method according to the present invention can likewise preferably be organic fluoroalkylsulfonates (preferably aryl fluoroalkylsulfonates, heteroaryl fluoroalkylsulfonates, or vinyl fluoroalkylsulfonates), or organic perfluoroalkylsulfonates (preferably aryl perfluoroalkylsulfonates, heteroaryl perfluoroalkylsulfonates, or vinyl perfluoroalkylsulfonates), or mixtures of at least two of the above-mentioned compounds. The perfluoroalkylsulfonates used in the method according to the present invention can particularly preferably be aryl trifluoromethanesulfonates, heteroaryl trifluoromethanesulfonates, vinyl trifluoromethanesulfonates, or mixtures of at least two of the above-mentioned compounds. In another particularly preferred aspect of the method according to the present invention, the perfluoroalkylsulfonates used can be aryl nonafluorobutanesulfonates, heteroaryl nonafluorobutanesulfonates, vinyl nonafluorobutanesulfonates, or mixtures of at least two of the above-mentioned compounds. The aryl halides, aryl fluoroalkylsulfonates, and aryl perfluoroalkylsulfonates include aromatic organic compounds, in which a halogen, fluoroalkylsulfonate, or perfluoroalkylsulfonate group is bonded to the aromatic ring of the aryl group not directly but via, for example, an alkylene group in, for example, benzyl halides, benzyl trifluoromethanesulfonates, or benzyl nonafluorobutanesulfonates. The heteroaryl halides, heteroaryl fluoroalkylsulfonates, and heteroaryl perfluoroalkylsulfonates include aromatic organic compounds, in which a halogen, fluoroalkylsulfonate, or perfluoroalkylsulfonate group is bonded to the aromatic ring of the heteroaryl group not directly but via, for example, an alkylene group. These heteroaryl groups preferably contain, as a heteroatom, at least one oxygen and/or nitrogen and/or sulfur atom.

The catalyst used in the coupling reaction is not particularly limited, and all catalysts suitable for coupling reactions of organic compounds and mixtures of at least two of these catalysts can be used. Preferably, only one catalyst is used in each case. The catalysts also include catalysts formed in situ, that is, catalysts formed just before or during the coupling reaction. In another preferred aspect of the present invention, the catalyst used is at least one compound containing palladium in oxidation state 0. The compound containing palladium in oxidation state 0 can preferably be tris(dibenzylideneaceton)bispalladium. The catalyst used in the method according to the present invention is likewise preferably at least one compound containing palladium in oxidation state (+II) in the presence of at least one base, preferably in the presence of at least one inorganic salt, and preferably in the presence of at least one ligand. The palladium compound containing palladium in oxidation state (II) used in the method according to the present invention can preferably be palladium chloride (II), palladium acetate (II), bis(triphenylphosphine)palladium (II) dichloride, or a mixture of at least two of these compounds. The bases which can be used in the method according to the present invention are all bases which are known to those skilled in the art and which are suitable for coupling reactions of organic compounds. The bases used can preferably be organic amines, particularly preferably triethylamine, diethylamine, or tri-n-butylamine, nitrogen-containing, optionally aromatic, heterocyclic compounds, particularly preferably pyridine or N-methylpyrrolidone, or mixtures of at least two of the above-mentioned compounds. The inorganic salts which can be used in the method according to the present invention are all inorganic salts which are known to those skilled in the art and which are suitable for coupling reactions of organic compounds. The inorganic salt used is preferably copper iodide (I).

Then, a fluid containing at least one organic compound containing at least one vinylic or acetylenic hydrogen atom is introduced as a second fluid directly through another flow path, that is, the second introduction part d2 into the first fluid film formed between the processing surfaces 1 and 2.

The organic compound containing at least one vinylic or acetylenic hydrogen atom used in the coupling reaction is not particularly limited, and all organic compounds which are suitable as substrates for coupling reactions and which contain at least one vinylic or acetylenic hydrogen atom can be used. In the method according to the present invention, at least one non-branched, branched, cyclic, aromatic, or heteroaromatic alkene or alkyne is preferred, and at least one non-branched, branched, cyclic, aromatic, or heteroaromatic alkene is particularly preferred. The aromatic compounds containing at least one vinylic or acetylenic hydrogen atom also include organic compounds and/or derivatives thereof which have a monocyclic and/or polycyclic homoaromatic basic structure or a corresponding partial structure, for example, in the form of substituents and which have a vinylic or acetylenic hydrogen atom. Heteroaromatic compounds containing at least one vinylic or acetylenic hydrogen atom also include organic compounds and/or derivatives thereof which have a monocyclic and/or polycyclic heteroaromatic basic structure or a corresponding partial structure, for example, in the form of substituents and which have at least one vinylic or acetylenic hydrogen atom. These heteroaromatic basic structures or partial structures particularly preferably contain at least one oxygen and/or nitrogen and/or sulfur atom.

The organic compound containing at least one vinylic or acetylenic hydrogen atom, the organic compound containing at least one elimination group, and the catalyst used in the coupling reaction are preferably in the form of a liquid or solution. A solvent which can be used for such a purpose is not particularly limited, and examples thereof include water such as ion-exchange water, purified water, tap water, and ultra-pure water and organic solvents. The preferred solvents are halogenated solvents (particularly preferably dichloromethane, chloroform, 1,2-dichloroethane, or 1,1,2,2-tetrachloroethane), linear, branched, or cyclic hydrocarbon compounds (particularly preferably pentane, hexane, heptane, octane, cyclopentane, cyclohexane, cycloheptane, or cyclooctane), or linear, branched, or cyclic ethers (particularly preferably diethyl ether, methyl tert-butyl ether, tetrahydrofuran, or dioxane), aromatic solvents (particularly preferably toluene, xylene, ligroin, or phenyl ether), N-containing heterocyclic solvents (particularly preferably pyridine or N-methylpyrrolidone), or mixtures of at least two of the above-mentioned solvents.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More preferably, the coupling reaction can be performed. At least one organic compound containing at least one elimination group may be reacted with at least one organic compound containing at least one vinylic or acetylenic hydrogen atom, or the organic compound used may simultaneously contain both at least one elimination group and at least one vinylic or acetylenic hydrogen atom. Thus, coupling reactions, to which the present invention is applied, include both intermolecular coupling reactions and intramolecular coupling reactions.

It is to be noted that a fluid containing all the organic compound containing at least one vinylic or acetylenic hydrogen atom, the organic compound containing at least one elimination group, and the catalyst to such an extent that the reaction performed in the space between the processing surfaces is not affected may be used as a first liquid or a second liquid.

(18: Acetoacetylation Reaction)

In the case of, for example, an acetoacetylation reaction, a fluid containing at least one organic compound selected from alcohols, amines, and thiols and, if necessary, at least one catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The alcohols, amines, and thiols used in the acetoacetylation reaction are all active hydrogen-containing compounds represented by the chemical formulas ROH, NHRR', and RSH.

The catalyst used if necessary in the acetoacetylation reaction is not particularly limited, and examples thereof include amines, particularly tertiary amines, or ammonium salts thereof. For example, sterically-hindered tertiary amines are suitable as the catalysts. Suitable examples of the catalyst are dimethylstearylamine, tributyl methyl ammonium chlorides, NH₄ acetate, and 1,4-diazobicyclo[2,2,2]-octane (=DABCO).

Then, a fluid containing at least one diketene is introduced as a second fluid directly through another flow path, that is, the second introduction part d2 into the first fluid film formed between the processing surfaces 1 and 2.

At least one diketene used in the acetoacetylation reaction is represented by the following formula.

[Chemical 5]

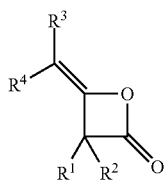

When the diketene and/or the active hydrogen-containing compound are/is in the form of a liquid or gas at reaction temperature in the acetoacetylation reaction, they may be supplied in substance or in the form of a solution. When they are solid at reaction temperature, they are appropriately supplied as a first fluid and a second fluid in the form of a suspension or solution. Suitable diluents and solvents are known to those skilled in the art, and are therefore not illustrated in detail. In a preferred embodiment, the diketene or/and the active hydrogen-containing compound are supplied in the form of an aqueous solution or aqueous suspension.

In the formula for the acetoacetylation reaction, X is NR', O, or S; R and R' are each independently H, linear, branched, or cyclic alkyl or alkenyl having 1 to 18 carbon atoms, aryl, or heteroaryl, in which one or more hydrogens in the alkyl, alkenyl, aryl, and heteroaryl groups may be substituted by an inert substituent; $R^1$, $R^2$, $R^3$, and $R^4$ are each independently H, linear, branched, or cyclic alkyl or alkenyl having 1 to 18 carbon atoms, aryl, or heteraryl, in which one or more hydrogens in the alkyl, alkenyl, aryl, and heteroaryl groups may be substituted by an inert substituent, or $R^1$ and $R^2$ and/or $R^3$ and $R^4$ are bonded together to form methylene units of a cycloalkane ring —CH₂—(CH₂)$_k$—CH₂— (wherein k=0, 1, 2, 3, or 4). The alkenyl is an aliphatic carbon group having at least one C═C double bond. A plurality of double bonds may be present and may be conjugated. The inert substituent is a substituent which is substantially unreactive under the reaction conditions used for the reaction between the diketene and the active hydrogen-containing compound. Typical examples of the inert substituent are alkyls, aralkyls, alkoxys, halogens, particularly F, Cl, and Br, —CN, and —NO₂, where alkyl and alkoxy groups are preferably 1 to 6 carbon atoms and aralkyl is preferably C6-C10-aryl-C1-C6-alkyl, for example, including benzyl. Further, the inert substituent may be a group which is reactive per se, for example —OH or —NH, but is protected by a protecting group. The aryl is understood to be a group containing at least one aromatic ring. Examples of such an aryl are phenyl, sulfophenyl, naphthyl, and another polycyclic aromatic, for example, pyrene, which may be substituted by inert substituents. The heteroaryl contains at least one, optionally a plurality of heteroatoms, for example, N, O, S, or/and P, in the aromatic ring structure. Examples of the heteroaryl are pyridyl, pyrimidyl, thiazolyl, quinolinyl, and indolyl. Further, $R^1$, $R^2$, $R^3$, and $R^4$ are each independently H or liner or branched alkyl having 1 to 18 carbon atoms, generally 1 to 12 carbon atoms, for example, 1 to 6 carbon atoms. Such alkyls are optionally substituted by inert substituents. Further, R may be aryl or heteroaryl, and R' may be H, aryl, or heteroaryl. Preferably, R is selected from any one of the groups represented by the following formulas (I), (II), and (III), and R' is selected from H or any one of the groups represented by the following formulas (I), (II), and (III).

[Chemical 6]

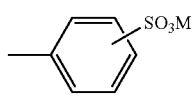

(I)

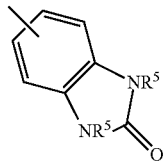

(II)

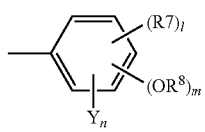

(III)

In the formulas above, M is hydrogen or an alkali metal, particularly Na or K; Y is halogen, particularly Cl, $R^5$ and $R^6$ are each independently hydrogen or linear or branched alkyl having 1 to 6 carbon atoms, particularly methyl or/and ethyl, R7 and $R^8$ are each independently linear, branched, or cyclic alkyl or alkenyl having 1 to 18 carbon atoms, in which one or more hydrogens may be substituted by an inert substituent, l, m, and n are each an integer of 0 to 5, and l+m+n≤5.

In the specific case of the acetoacetylation reaction, the corresponding amines, that is, compounds of the formula HNRR' (wherein R is a compound of any one of the formulas (I), (II), and (III), R' is H or a compound of any one of the formulas (I), (II), and (III), and R' is more preferably H) are used.

In a specific case, R is a compound of the formula (II), $R^5$ and $R^6$ are each H, and R' is H. That is, the compound containing active hydrogen is 5-aminobenzimidazolone-2.

In the further case of the acetoacetylation reaction, the compound containing active hydrogen is an aliphatic alcohol. That is, X is O, and R is a linear or branched alkyl which is optionally substituted by an inert substituent. In general, aliphatic alcohols having 1 to 12 carbon atoms, particularly 1 to 6 carbon atoms are used. Particularly, the compound containing active hydrogen may be methanol, ethanol, (iso)propanol, or tertiary butanol.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the acetoacetylation reaction can be performed.

More specifically, β-ketocarboxylic acid derivatives of the following formula or salts thereof can be obtained. Particularly preferred products are methyl 3-oxobutanoate, ethyl 3-oxobutanoate, isopropyl 3-oxobutanoate, isobutyl 3-oxobutanoate, tert-butyl 3-oxobutanoate, 4-acetoacetylaminobenzensulfonic acid, 5-acetoacetylamino-2-benzimidazolone, acetoacetylaminobenzene, 4-acetoacetamino-1,3-dimethylbenzene, 2-acetoacetylmethoxybenzene, 2-chloroacetoacetaminobenzene, 3-acetoacetamino-4-methoxytoluene-sulfonic acid, or salts thereof. R, $R^1$, $R^2$, $R^3$, $R^4$, and X are the same as those mentioned above.

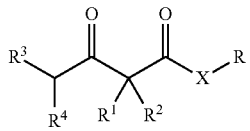

[Chemical 7]

(19: Reaction Between Succinic Acid Diester and Nitril)

In the case of a reaction between a succinic acid diester and a nitrile, a fluid containing at least one nitrile represented by $R_1$—CN which is in a dissolved form in the presence of a strong base, or nitrile represented by $R_2$—CN which is in a dissolved form in the presence of a strong base, or mixture of these nitriles is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

In the formula for the reaction between the succinic acid diester and nitrile, $R_1$ and $R_2$ are the same or different, respectively representing isocyclic or heterocyclic aromatic group that was unsubstituted or substituted. The isocyclic aromatic groups $R_1$ and $R_2$ are preferably monocyclic, dicyclic, tricyclic or tetracyclic group, particularly monocyclic or tetracyclic: for example, phenyl, biphenyl and naphthyl. The heterocyclic aromatic groups $R_1$ and $R_2$ are preferably monocyclic, dicyclic or tricyclic, and can further have one or more condensed benzene rings. The cyano group may be present not only on a heterocyclic ring but also on an isocyclic ring. Examples of the heterocyclic group include pyridyl, pyrimidyl, pyrazinyl, triazinyl, furyl, pyrrolyl, thiophenyl, quinolyl, coumarinyl, benzofuranyl, benzimidazolyl, benzoxazolyl, dibenzofuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalamidyl, chromonyl, naphtholactamyl, quinolonyl, orthosulfobenzimidyl, maleimidyl, naphthalidinyl, benzimidazolonyl, benzoxazolonyl, benzothiazolonyl, benzothiazothionyl, quinazolonyl, quinoxalonyl, phthalazonyl, dioxopyrimidinyl, pyridonyl, isoquinolonyl, isoquinolinyl, isothiazolyl, benzoisoxazolyl, benzoisothiazolyl, indazolonyl, acridonyl, quinazolinedionyl, quinoxalindionyl, benzoxazindionyl, benzoxadinolyl and naphthalimidyl. The aforementioned isocyclic and heterocyclic aromatic groups may have the following usual substituents: for example, (1) halogen atoms such as chlorine, bromine and fluorine atoms. And, (2) branched or non-branched alkyl groups having the number of carbon atom with 1 to 18, preferably with 1 to 12, more preferably with 1 to 8, even more preferably with 1 to 4. These alkyl groups may be substituted with one or more, for example, with one, two, three, four or five substituents selected from the group comprising F, OH, CN, —$OCOR_{16}$, $OR_{17}$, $COOR_{16}$, $CONR_{17}R_{18}$ and $R_{16}$—O—$CONHR_{16}$, wherein $R_{16}$ is an alkyl, for example, an aryl such as naphthyl, benzyl, halobenzyl, phenyl, halophenyl, alkoxyphenyl or alkylphenyl, or a heterocyclic group; $R_{17}$ and $R_{18}$ may be the same or different, respectively representing hydrogen or alkyl, the alkyl being cyano, a hydroxyl group or $C_5$ to $C_6$-cycloalkyl, aryl or heteroaryl, particularly may be substituted with phenyl or halogen-, alkyl- or alkoxy-substituted phenyl; or $R_{17}$ and $R_{18}$ are combined with a nitrogen atom to form a 5- or 6-membered heterocycle such as morpholine, piperidine or phthalimide. Other possible substituents on the alkyl group include a mono- or dialkylated amino group, an aryl group such as a naphthyl, phenyl, halophenyl, alkylphenyl or alkoxyphenyl, and a heterocyclic group such as 2-thienyl, 2-benzoxazolyl, 2-benzothiazolyl, 2-benzimidazolyl, 6-benzimidazolonyl, 2-, 3- or 4-pyridyl and 2-, 4- or 6-quinolyl. The alkyl has the meaning mentioned at the beginning of (2). Examples of the unsubstituted and substituted alkyl group include methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl and benzyl. And, (3) alkoxy group: —$OR_{19}$. The $R_{19}$ is a hydrogen, the above-defined alkyl or aryl, $C_5$ to $C_6$-cycloalkyl, aralkyl or heterocyclic group. The $R_{19}$ group is preferably methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienyl or pyranylmethyl. (4) —$SR_{19}$ group. The $R_{19}$ is as defined in (3). Specific examples of $R_{19}$ include methyl, ethyl, n-propyl, isopropyl, phenyl, o-, m- or p-chlorophenyl, o-, m- or p-methylphenyl, α- or β-naphthyl, cyclohexyl, benzyl, thienyl or pyranylmethyl. (5) Cyano group. (6) Group of formula: —$NR_{17}R_{18}$. The $R_{17}$ and $R_{18}$ are as defined in (2). Examples include amino, methylamino, dimethylamino, ethylamino, diethylamino, isopropylamino, β-hydroxyethylamino, β-hydroxypropylamino, N,N-bis(β-hydroxyethyl)amino, N,N-bis(β-cyanoethyl)amino, cyclohexylamino, phenylamino, N-methylphenylamino, benzylamino, dibenzylamino, piperidyl and morpholyl. (7) Group of formula: —$COOR_{16}$. The $R_{16}$ is as defined in (2). Examples include methyl, ethyl, tert-butyl, phenyl, o-, m- or p-chlorophenyl, o-, m- or p-methylphenyl and α- or β-naphthyl. (8) Group of formula: —$COR_{19}$. The $R_{19}$ is as defined in (3). Examples include methyl, ethyl, tert-butyl, phenyl, o-, m- or p-chlorophenyl, o-, m- or p-methylphenyl and α- or β-naphthyl. (9) Group of formula: —$NR_{20}COR_{16}$. The $R_{16}$ is as defined in (2), and the $R_{20}$ is a hydrogen, alkyl, aryl (for example, naphthyl or particularly unsubstituted or halogen-, alkyl- or —O-alkyl-substituted phenyl), $C_5$ to $C_6$-cycloalkyl, aralkyl or —$COR_{16}$, and two $COR_{16}$ may be combined with a nitrogen atom to form a heterocyclic ring. The alkyl $R_{20}$ can have carbon atoms, the preferable number of which is described in (2). Examples include acetylamino, propionylamino, butyrylamino, benzoylamino, p-chlorobenzoylamino, p-methylbenzoylamino, N-methylacetylamino, N-methylbenzoylamino, N-succinic acid imide and N-phthalimide. (10) Group of formula: —$NR_{19}COOR_{16}$. The $R_{19}$ and $R_{16}$ are as defined in (2) or (3). Examples include —$NHCOOCH_3$, $NHCOOC_2H_5$ and $NHCOOC_6H_5$. (11) Group of formula: —$NR_{19}CONR_{17}R_{18}$. The $R_{10}$, $R_{17}$ and $R_{18}$ are defined in (3) or (2). Examples include ureido, N-methylureido, N-phenylureido and N,N'-2',4'-dimethylphenylureido. (12) Group of formula: —$NHSO_2R_{16}$. The $R_{16}$ is as defined in (2). Examples include methanesulfonylamino, phenylsulfonylamino, p-tolylsulfonylamino and β-naphthylsulfonylamino. (13) Group of formula: —$SO_2R_{16}$ or —$SOR_{16}$. The $R_{16}$ is as defined in (2). Examples include methylsulfonyl, ethylsulfonyl, phenylsulfonyl, 2-naphthylsulfonyl and phenylsulfoxydyl. (14) Group of formula: —$SO_2OR_{16}$. The $R_{16}$ is as defined in (2). Examples of $R_{16}$ include methyl, ethyl, phenyl, o-, m- or p-chlorophenyl, o-, m- or p-methylphenyl and α- or β-naphthyl. (15) Group of formula: —$CONR_{17}R_{18}$. The $R_{17}$ and $R_{18}$ are as defined in (2). Examples include carbamoyl, N-methylcarbamoyl, N-ethylcarbamoyl, N-phenylcarbamoyl, N,N-dimethylcarbamoyl, N-methyl-N-phenylcarbamoyl, N-α-naphthylcarbamoyl and N-piperidylcarbamoyl. (16) Group of formula: —$SO_2NR_{17}R_{18}$. The $R_{17}$ and $R_{18}$ are as defined in (2). Examples include sulfamoyl, N-methylsulfamoyl, N-ethylsulfamoyl, N-phenylsulfamoyl, N-methyl-N-phenylsulfamoyl and N-morpholylsulfamoyl. (17) Group of formula: —N=N—$R_{21}$. The $R_{21}$ is a coupling element group, or an unsubstituted, halogen-, alkyl- or —O-alkyl-substituted phenyl group. The alkyl $R_{21}$ can have carbon atoms, the preferably number of which is described in (2). Examples of R21 include acetoacetoarylide, pyrazolyl, pyridonyl, o- or p-hydroxyphenyl, o-hydroxynaphthyl, p-aminophenyl and p-N,N-dimethylaminophenyl groups. (18) Group of formula: —$OCOR_{16}$. The $R_{16}$ is as defined in (2). Examples of $R_{16}$ include methyl, ethyl, phenyl, and o-, m- or p-chlorophenyl. (19) Group of formula: —$OCONHR_{16}$. The $R_{16}$ is as defined in (2). Examples of $R_{16}$ include methyl, ethyl, phenyl, and o-, m- or p-chlorophenyl. In preferable embodiments in the reaction between the succinic acid diester and nitrile, R1 and R2 independently represent phenyl; phenyl substituted with one or two chlorine atoms, one or two methyl groups, methoxy, trifluoromethyl, cyano, methoxycarbonyl, tert-butyl, dimethylamino or cyanophenyl; naphthyl; biphenyl; pyridyl; pyridyl substituted with amyloxy; furyl or thienyl. In particular, preferable $R_1$ and $R_2$ respectively represents phenyl, 3- or 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-methylphenyl, 4-tert-butylphenyl, 4-dimethylaminophenyl, 4-(p-cyanophenyl)phenyl, 1- or 2-naphthyl, 4-biphenylyl, 2-pyridyl, 6-amyloxy-3-pyridyl, 2-furyl or 2-thienyl.

Particularly, a nitrile of the following formula is preferable.

[Chemical 8]

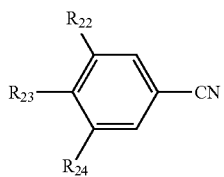

In the formula above, $R_{22}$, $R_{23}$ and $R_{24}$ independently represent a hydrogen, fluorine, chlorine, bromine, carbamoyl, cyano, trifluoromethyl, $C_2$ to $C_{13}$-alkylcarbamoyl, $C_1$ to $C_{12}$-alkyl, $C_1$ to $C_{12}$-alkoxy, $C_1$ to $C_{12}$-alkylmercapto, $C_2$ to $C_{13}$-alkoxycarbonyl, $C_2$ to $C_{13}$-alkanoylamino, $C_1$ to $C_{12}$-monoalkylamino, $C_2$ to $C_{24}$-dialkylamino, unsubstituted or halogen-, $C_1$ to $C_{12}$-alkyl- or $C_1$ to $C_{12}$-alkoxy-substituted phenyl, phenylmercapto, phenoxycarbonyl, phenylcarbamoyl or benzoylamino, and the alkyl or phenyl group is unsubstituted or substituted with a halogen, $C_1$ to $C_{12}$-alkyl or $C_1$ to $C_{12}$-alkoxy, and at least one of $R_{22}$, $R_{23}$ and $R_{24}$ is a hydrogen.

More specifically, the nitrile is represented by the following formula.

[Chemical 9]

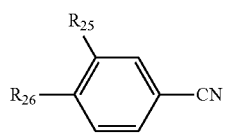

In the formula above, one of $R_{25}$ and $R_{26}$ is a hydrogen, chlorine, bromine, $C_1$ to $C_4$-alkyl, cyano, $C_1$ to $C_4$-alkoxy, unsubstituted or chlorine-, methyl- or $C_1$ to $C_4$-alkoxy-substituted phenyl, carbamoyl, $C_2$ to $C_5$-alkylcarbamoyl, or unsubstituted or chlorine-, methyl- or $C_1$ to $C_4$-alkoxy-substituted phenylcarbamoyl, and the other is a hydrogen.

The strong base used in the reaction between the succinic acid diester and nitrite is not particularly limited. Preferable examples of such bases include alkali metal amides such as lithium amide, sodium amide and potassium amide; alkali metal hydrides such as lithium hydride, sodium hydride and potassium hydride; and alkali earths or alkali metal alkoxides derived from particularly C1 to C10 primary, secondary or tertiary aliphatic alcohols, such as lithium methoxide, sodium methoxide, potassium methoxide, lithium ethoxide, sodium ethoxide, potassium ethoxide, lithium n-propoxide, sodium n-propoxide, potassium n-propoxide, lithium isopropoxide, sodium isopropoxide, potassium isopropoxide, lithium n-butoxide, sodium n-butoxide, potassium n-butoxide, lithium sec-butoxide, sodium sec-butoxide, potassium sec-butoxide, lithium tert-butoxide, sodium tert-butoxide, potassium tert-butoxide, lithium 2-methyl-2-butoxide, sodium 2-methyl-2-butoxide, potassium 2-methyl-2-butoxide, lithium 2-methyl-2-pentoxide, sodium 2-methyl-2-pentoxide, potassium 2-methyl-2-pentoxide, lithium 3-methyl-3-pentoxide, sodium 3-methyl-3-pentoxide, potassium 3-methyl-3-pentoxide, lithium 3-ethyl-3-pentoxide, sodium 3-ethyl-3-pentoxide, and potassium 3-ethyl-3-pentoxide. A mixture of the above bases can also be used. The strong base used in the reaction between the succinic acid diester and nitrile is preferably an alkali metal alkoxy wherein the alkyl metal is specifically sodium or potassium, and the alkoxide is derived from a secondary or tertiary alcohol. Accordingly, particularly preferable examples of the strong base include sodium isopropoxide, potassium isopropoxide, sodium sec-butoxide, potassium sec-butoxide, sodium tert-butoxide, potassium tert-butoxide, sodium tert-amyloxide and potassium tert-amyloxide.

The strong base can be used in the following fluid containing a succinic acid diester.

Then, a fluid containing at least one kind of succinic acid diester is introduced as a second fluid directly through another flow path, that is, the second introduction part d2 into the first fluid film formed between the processing surfaces 1 and 2.

The succinic acid diester used in the reaction between the succinic acid diester and nitrile is not particularly limited. Examples of the succinic acid diester include dialkyl, diaryl or monoalkyl monoaryl esters, among which the dialkyl succinates or diaryl succinates can be asymmetric. However, symmetric succinic acid diesters, particularly symmetric dialkyl succinates are preferably used. When diaryl succinates or monoaryl monoalkyl succinates are present, the aryl is specifically unsubstituted phenyl or phenyl substituted with a halogen such as chlorine or $C_1$ to $C_6$-alkyl such as methyl, ethyl, isopropyl or tert-butyl, or $C_1$ to $C_6$ alkoxy such as methoxy or ethoxy. In the case of dialkyl succinates or monoalkyl monoaryl succinates, the alkyl can be non-branched or branched, preferably branched, and have the number of carbon atom preferably with 1 to 18, particularly with 1 to 12, more preferably with 1 to 8, even more preferably with 1 to 5. The branched alkyl is preferably sec- or tert-alkyl such as isopropyl, sec-butyl, tert-butyl, tert-amyl or cyclohexyl. Examples of the succinic acid diester include dimethyl succinate, diethyl succinate, dipropyl succinate, dibutyl succinate, dipentyl succinate, dihexyl succinate, diphenyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1-dimethylpentyl]succinate, di-[1-methyl-1-ethylbutyl]succinate, di-[1,1-diethylpropyl]succinate, diphenyl succinate, di-[4-methylphenyl]succinate, di-[2-methylphenyl]succinate, di-[4-chlorophenyl]succinate, monoethyl monophenyl succinate, and dicyclohexyl succinate. Diisopropyl succinate is particularly preferable.

The strong base used in the reaction between the succinic acid diester and the nitrile, the nitrile represented by $R_1$—CN or the nitrile represented by $R_2$—CN, or a mixture of these nitriles, and the succinic diester are preferably in the form of a liquid or solution, and the solvent that can be used therein includes, but is not limited to, water such as ion-exchange water, purified water, tap water and ultrapure water and an organic solvent. Preferable examples of the organic solvent include C1 to C10 primary, secondary or tertiary alcohols such as methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, and 2,4,4-trimethyl-2-pentanol; glycols such as ethylene glycol or diethylene glycol; ethers such as tetrahydrofuran and dioxane; glycol ethers such as ethylene glycol methyl ether, ethylene glycol ethyl ether, diethylene glycol monomethyl ether and diethylene glycol monoethyl ether; polar aprotic solvents such as acetonitrile, benzonitrile, dimethylformamide, N,N-dimethylacetamide, nitrobenzene, and N-methylpyrrolidone; aliphatic or aromatic hydrocarbons such as benzene and alkyl-, alkoxy- or halogen-substituted benzene such as toluene, xylene, anisole or chlorobenzene; and aromatic heterocycles such as pyridine, picoline and quinoline. When reactant nitrites or reactant succinic acid diesters of formula (VI) or (VII) are liquid in the temperature range where they are reacted, they can be used as the solvent. The solvent used may be a mixture. The reaction between the succinic acid diester and nitrile is conducted in an alcohol as a solvent, particularly in a secondary or tertiary alcohol. The tertiary alcohol is preferably tert-butanol alcohol and tert-amyl alcohol. In this relation, to be noted are mixtures of these preferable solvents and aromatic hydrocarbons such as toluene and xylene or halogen-substituted benzene such as chlorobenzene.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the succinic acid diester and nitrite can be reacted.

Alternatively, a mixture in which a strong base and a nitrile represented by $R_1$—CN, a nitrite represented by $R_2$—CN, or a fluid containing these nitriles, and succinic acid diester are mixed to such an extent that the reaction between the processing surfaces is not affected may be used as a first or second fluid.

Specifically, a diketopyrrolopyrrole pigment can be synthesized. In this case, the reaction between the succinic acid diester and nitrile can be carried out in the presence of a pigment dispersant, preferably dispersants based on diketopyrrolopyrrole and quinacridone. Such dispersants include, for example, compounds of the following formula.

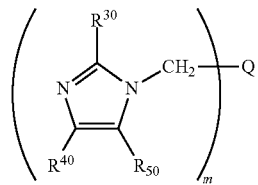

[Chemical 10]

In the formula above, R30, R40 and R50 are independent or different, and respectively each represent a hydrogen, chlorine, bromine, fluorine, nitro, C1 to C6 alkyl, C1 to C6 alkoxy, benzoylamino, an isocyclic or heterocyclic aromatic group, particularly a hydrogen or methyl, and Q is quinacridone group or diketopyrrolopyrrole group, preferably a quinacridone group which may be substituted with one, two, three or four substituents selected from F, Cl, Br, C1 to C4-alkyl, C1 to C4-alkoxy, carboxamide which may be substituted with a C1 to C6-alkyl group, and phenoxy, or a diketopyrrolopyrrole group which may be substituted as described above, and m is 0.1 to 4.

The dispersant also includes compounds of the following formula. In the formula, R30, R40, R50, m and Q are as defined above.

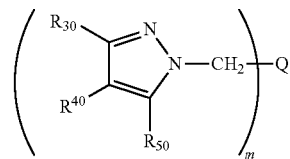

[Chemical 11]

The dispersant also includes the following compounds. In the formula, R30, R40, R50, m and Q are as defined above. R60 has the meaning of R30, R40 or R50, and R30 to R60 each preferably represent a hydrogen, methyl group or chlorine.

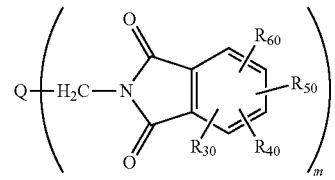

[Chemical 12]

The dispersant also includes compounds of the following compound.

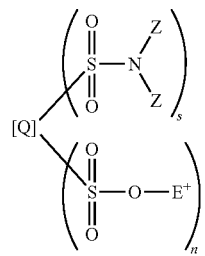

[Chemical 13]

In the formula above, Q is as defined above; s and n independently represent 0 to 4, but both of them are not set to zero; $E^+$ is $H^+$ or $M^{f+}/f$ (f: 1, 2 or 3) corresponding to a metal cation $M^{f+}$ from the major groups I to V or the transition group I or II or IV to VIII in the periodic table of chemical elements, such as $Li^{1+}$, $Na^{1+}$, $K^{1+}$, $Mg^{2+}$, $Ca^{2+}$, $Sr^{2+}$, $Ba^{2+}$, $Mn^{2+}$, $Cu^{2+}$, $Ni^{2+}$, $Co^{2+}$, $Zn^{2+}$, $Fe^{2+}$, $Al^{3+}Cr^{3+}$ or $Fe^{3+}$; ammonium ion N+R9R10R11R12; R9, R10, R11 and R12 independently represent a hydrogen atom, C1 to C30-alkyl, C2 to C30-alkenyl, C5 to C30-cycloalkyl, phenyl, (C1 to C8)-alkyl-phenyl, (C1 to C4)-alkylene-phenyl (for example, benzyl) or a (poly)alkyleneoxy group of formula —[CH(R80)-CH(R80)-O]k-H (k is 1 to 30, two R80 independently represent a hydrogen, C1 to C4-alkyl, or a combination thereof when k is greater than 1); R9, R10, R11 and/or R12 which are alkyl, alkenyl, cycloalkyl, phenyl or alkylphenyl may be substituted with amino, hydroxyl group and/or carboxyl; R9 and R10 may be combined with a quaternary nitrogen atom to form a 5- to 7-membered saturated ring system further having another heteroatom selected from the group comprising O, S and N as desired, such as pyrrolidone, imidazolizine, hexamethyleneimine, piperidine, piperazine or morpholine; R9, R10 and R11 may be combined with a quaternary nitrogen atom to form a 5- to 7-membered aromatic ring system which further has another heteroatom selected from the group comprising O, S and N as desired and which may be condensed with another ring if necessary, such as pyrrole, imidazole, pyridine, picoline, pyrazine, quinoline or isoquinoline; or E+ defines an ammonium ion of the following formula.

[Chemical 14]

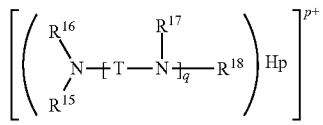

In the formula above, R15, R16, R17 and R18 independently represent a hydrogen or a (poly)alkyleneoxy group of formula —[CH(R80)-CH(R80)O]k-H; k is 1 to 30, and two R80 independently represent a hydrogen, C1 to C4-alkyl, or a combination thereof when k is greater than 1); q is 1 to 10, preferably 1, 2, 3, 4 or 5; p is 1 to 5 provided that p is equal to or smaller than (q+1); T is a branched or non-branched C2 to C6-alkylene group; or T can be a combination of branched or non-branched C2 to C6-alkylene groups when q is greater than 1; two Z groups are the same or different and Z has the definition of Z1 or Z4; and Z1 is a group represented by —[X—Y]$_q$R$^{91}$.

In the formula by —[X—Y]$_q$R$^{91}$, X is a C2 to C6-alkylene group, a C5 to C7-cycloalkylene group or a combination thereof; these groups may be substituted with one to four groups selected from C1 to C4-alkyl groups, hydroxyl groups, (C1 to C4)-hydroxyalkyl groups and/or 1 to 2 groups selected from other C5 to C7-cycloalkyl groups; or X may be a combination having the above meaning when q is greater than 1.

Y is —O—, a group of the following formula, or —NR90 group; or Y can be a combination having the above meaning when q is greater than 1; q is 1 to 10, preferably 1, 2, 3, 4 or 5; R90 and R91 independently represent a hydrogen atom, a branched or non-branched (C1 to C20)-alkyl group that was substituted or unsubstituted fluorinated or perfluorinated, a substituted or unsubstituted C5 to C7-cycloalkyl group, or a substituted or unsubstituted fluorinated or perfluorinated (C2 to C20)-alkenyl group; their substituents can be a hydroxyl group, phenyl, cyano, chlorine, bromine, amino, C2 to C4-acyl or C1 to C4-alkoxy, and the number of substituents is preferably 1 to 4; or R90 and R91 are combined with a nitrogen atom to form a saturated, unsaturated or aromatic 5- to 7-membered heterocyclic ring, and the ring may have one or two other nitrogen, oxygen or sulfur atoms, or may be substituted with one, two or three substituents selected from the group comprising OH, phenyl, CN, Cl, Br, C1 to C4-alkyl, C1 to C4-alkoxy, C2 to C4-acyl and carbamoyl, or may have a saturated, unsaturated or aromatic carbocyclic or heterocyclic rings in which one or two benzo-elements were condensed; Z4 is a hydrogen, a hydroxyl group, amino, phenyl, (C1 to C4)-alkylene-phenyl, C5 to C7-cycloalkyl or C1 to C20-alkyl; the phenyl ring, (C1 to C4)-alkylene-phenyl group and alkyl group may be substituted with one or more, for example, one, two, three or four substituents from the group comprising Cl, Br, CN, NH2, OH, C6H5, mono-, di- or tri-C1 to C4-alkoxy-substituted C6H5, carbamoyl, C2 to C4-acyl and C1 to C4-alkoxy (for example, methoxy or ethoxy); the phenyl ring and (C1 to C4)-alkylene-phenyl group may be substituted with NR90R91 (R90 and R91 are as defined above); or the alkyl group is perfluorinated or fluorinated.

[Chemical 15]

The dispersant also includes compounds of the following formula.

[Chemical 16]

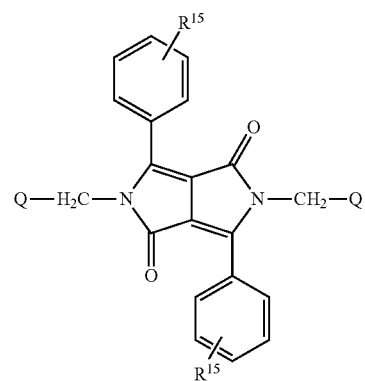

In the formula above, R15 is a hydrogen, chlorine, bromine, fluorine, C1 to C6-alkyl, C1 to C6-alkoxy, phenyl, di-(C1 to C6-alkyl)amino, C1 to C6-alkylthio, phenylthio or phenoxy; preferably R15 is bound at position 4 to a phenyl group; Q is as defined above; the compound of the formula (IX) has 0 to 6 $SO_3$-$E^+$ groups; and E is as defined above.

The dispersant also includes compounds of the following formula. In the formula, R30, R40, m and Q are as defined above.

[Chemical 17]

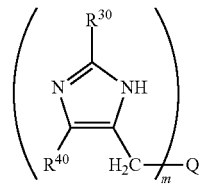

The method of the present invention can be carried out preferably using a saccharine-containing pigment dispersant based on quinacridone and diketopyrrolopyrrole.

In the case of the reaction between the succinic acid diester and nitrile, it is also possible to use auxiliary substance selected from the group comprising a surfactant, a filler, a standardization agent, a resin, an antifoaming agent, an anti-dust agent, a spreading agent, a light-shielding coloring agent, a preservative, a drying retardant, a rheology regulating additive, and a combination thereof. The useful surfactant includes anionic, cationic and nonionic substances or mixtures thereof. The useful anionic substances include, for example, fatty acid taurides, fatty acid N-methyl taurides, fatty acid isethionates, alkyl phenyl sulfonates, alkyl naphthalene sulfonates, alkyl phenol polyglycol ether sulfates, aliphatic alcohol polyglycol ether sulfates, fatty acid amide polyglycol ether sulfates, alkyl sulfosuccinamates, alkenyl succinic acid monoesters, aliphatic alcohol polyglycol ether sulfosuccinates, alkane sulfonates, fatty acid glutamates, alkyl sulfosuccinates, fatty acid sarcosides; fatty acids such as palmitic acid, stearic acid and oleic acid; resin acids such as aliphatic resins, naphthenates and abietic acid, alkali soluble resins such as rosin-modified maleic acid resin, and soaps such as alkali metal salts of condensation products based on cyanuric chloride, taurine, N,N'-diethylaminopropylamine, and p-phenylenediamine. Resin soap that is an alkali metal salt of resin acid is particularly preferable. The useful cationic substances include, for example, quaternary ammonium salts, aliphatic amine alkoxylates, alkoxylated polyamines, aliphatic aminopolyglycol ethers, aliphatic amines, di- and polyamines derived from aliphatic amines or aliphatic alcohols, alkoxylates derived from the di- and polyamines, imidazolines derived from fatty acids, and salts of these cationic substances. The useful nonionic substances include, for example, amine oxides, aliphatic alcohol polyglycol ethers, fatty acid polyglycol esters, betaines such as aliphatic amide N-propyl betaine, phosphonates of aliphatic alcohols or aliphatic alcohol polyglycol ethers, aliphatic acid amide ethoxylates, aliphatic alcohol-alkylene oxide adducts, and alkyl phenol polyglycol ethers.

Both the dispersant and the auxiliary substance, or either the dispersant or the auxiliary substance, may be present in either the first or second fluid or in a new third fluid different from the first and second fluids.

The salt obtained by the reaction of the succinic acid diester and nitrile can also be hydrolyzed. When the hydrolysis is carried out, a fluid containing a substance formed by the reaction of the nitrile with the succinic acid ester, and a fluid containing at least one kind of a hydrolyzing agent are allowed to join together between the processing surfaces. In this case, a fluid containing a substance formed by the reaction of the nitrile with the succinic acid ester is used again as a first fluid, and a fluid containing at least one kind of hydrolyzing agent is used as a second fluid, and the first fluid and the second fluid are allowed to join in the processing surfaces. In another embodiment, the reaction of the succinic acid diester with nitrile is conducted upstream from the processing surfaces, and the reaction between a fluid containing the resulting reaction product and the hydrolyzing agent may be conducted downstream from the processing surfaces. A fluid in which the hydrolyzing agent is mixed with a fluid containing the succinic acid diester or nitrile to such an extent that the reaction between the processing surfaces is not affected can also be used.

The hydrolyzing agent used in the salt obtained in the reaction between the succinic acid diester and nitrile is not particularly limited, and preferable examples include water, alcohols and acids, or alcohols or acids, as well as mixtures thereof, and appropriately selected solvents other than those described above. The useful alcohols include, for example, methanol, ethanol, isopropanol, isobutanol, tert-butanol and tert-amyl alcohol. The acids include, for example, an inorganic acid such as hydrochloric acid, phosphoric acid, preferably sulfuric acid, or aliphatic or aromatic carboxylic acids or sulfonic acids such as formic acid, acetic acid, propionic acid, butyric acid, hexanoic acid, oxalic acid, benzoic acid, phenylacetic acid, benzenesulfonic acid or p-toluenesulfonic acid, preferably acetic acid and formic acid or an acid mixture.

(20: Alkoxide)

In the case of a reaction between an alkali metal and an alcohol, a fluid containing at least one alcohol is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The alcohol used in the case of the reaction between an alkali metal and an alcohol is not particularly limited, and preferred alcohols are s-butanol, t-butanol, t-amyl alcohol, 3,7-dimethyl-1,6-octadien-3-ol (linalool), 3,7,11-trimethyl-3,6,10-dodecatrien-3-ol, 3,7,11,15-tetramethyl-1-hexadecen-3-ol, and tetrahyrolinalool. A relatively long-chain alcohol, e.g., stearyl alcohol or a polyhydric alcohol is more preferably used.

Then, a fluid containing at least one alkali metal is introduced as a second fluid directly through another flow path, that is, the second introduction part d2 into the first fluid film formed between the processing surfaces 1 and 2.

The alkali metal is not particularly limited, and preferred alkali metals are lithium, sodium, potassium, or lithium, sodium or potassium alloy, particularly preferably sodium or potassium, very particularly preferably sodium.

The alcohol and the alkali metal used in the case of the reaction between an alkali metal and an alcohol are preferably in the form of a liquid or solution. A solvent which can be used for such a purpose is not particularly limited.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the alkali metal and the alcohol can be reacted.

It is to be noted that a fluid containing a strong alcohol and an alkali metal to such an extent that the reaction performed in the space between the processing surfaces is not affected may be used as a first fluid or a second fluid.

(21: Aldol Reaction)

In the case of an aldol reaction, a fluid containing at least one catalyst is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The catalyst used in the aldol reaction is not particularly limited, and examples thereof include heterogeneous basic anion exchangers, metal oxides of Mo, W, Ca, Mg, and Al, and basic zeolites. As described above, the catalyst may be contained in a fluid or may be adhered to at least one of the processing surfaces 1 and 2 by, for example, vapor deposition. Alternatively, the catalyst may be deposited between the processing surfaces.

Then, a fluid containing at least one aldehyde and/or at least one ketone is introduced as a second fluid directly through another flow path, that is, the second introduction part d2 into the first fluid film formed between the processing surfaces 1 and 2.

Preferred aldehydes and/or ketones used in the aldol reaction are an aldehyde $R_1CHO$ ($R_1$=C1 to C12-alkyl, C5 to C12-cycloalkyl, aryl, C14-aralkyl) or a second aldehyde $R_2CHO$($R_2$=H, C1 to C12-alkyl, C5 to C12-cycloalkyl, aryl, C14-aralkyl), or a ketone $R_1R_2CO$($R_1,R_2$=C1 to C12-alkyl, C5 to C12-cycloalkyl, aryl, $C_{1-4}$-aralkyl), or another ketone $R_3R_4CO$ ($R_3,R_4$=C1 to C12-alkyl, C5 to C12-cycloalkyl, aryl, C14-aralkyl). All the aldehydes and ketones mentioned above can be each independently unsubstituted or substituted by the same or different substituents.

The catalyst and the aldehyde and/or ketone used in the case of the aldol reaction are preferably in a liquid or solution. A solvent which can be used for such a purpose is not particularly limited.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the aldol reaction can be performed.

It is to be noted that a fluid containing all the catalyst and the aldehyde and/or ketone to such an extent that the reaction performed in the space between the processing surfaces is not affected may be used as a first fluid or a second fluid.

(22: Boration Reaction)

In the case of a boration reaction, a fluid containing at least one boron compound is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The boron compound used in the boration reaction if necessary is not particularly limited, but is a compound represented by the formula $BX_3$.

In the formula above, the groups X are the same or different from one another and are selected from the group consisting of fluorine, chlorine, bromine, iodine, $C_1$ to $C_5$-alkoxy, N,N-di($C_1$ to $C_5$-alkyl)amino, and ($C_1$ to $C_5$-alkyl)thio.

Then, a fluid containing at least one lithium aromatic and/or at least one lithiated aliphatic compound or at least one magnesium aromatic and/or at least magnesium aliphatic compound is introduced as a second fluid directly through another flow path, that is, the second introduction part d2 into the first fluid film formed between the processing surfaces 1 and 2.

The lithium aromatic and lithiated aliphatic compound used in the boration reaction is a compound represented by the formula nR-Li.

In the formula above, n is 1, 2, or 3, R is a linear or branched $C_1$ to $C_6$-alkyl, $C_1$ to $C_6$-alkyl substituted by a group selected from the group consisting of $R_1O$, $R_1R_1'N$, phenyl, substituted phenyl, fluorine, and $R_1S$ (wherein $R_1$, $R_1'$ are linear or branched $C_1$ to $C_6$-alkyl), phenyl, phenyl substituted by a group selected from the group consisting of $C_1$ to $C_6$-alkyl, $C_1$ to $C_6$-alkoxy, $C_1$ to $C_5$-thioether, silyl, fluorine, chlorine, dialkylamino, diarylamino, and alkylarylamino, six-membered heteroaryl containing 1 or 2 nitrogen atoms, 5-membered heteroaryl containing 1 or 2 heteroatoms selected from the group consisting of N, O, and S, or substituted or unsubstituted bicyclic or tricyclic aromatic.

The magnesium aromatic and/or magnesium aliphatic compound used in the boration reaction is a Grignard compound represented by the formula nR-Met.

In the formula above, n and R are the same as those defined in the formula representing the lithium aromatic and lithiated aliphatic compound, Met is MgY, wherein Y is fluorine, chlorine, bromine, or iodine.

The boron compound and the lithium aromatic and/or lithiated aliphatic compound or the magnesium aromatic and/or magnesium aliphatic compound used in the case of the boration reaction are preferably in the form of a liquid or solution. A solvent used for such a purpose is not particularly limited, and examples thereof include water such as ion-exchange water, purified water, tap water, and ultrapure water and organic solvents. For example, the solvents are aliphatic and aromatic ethers and hydrocarbons, and amines having no hydrogen on the nitrogen, preferably triethylamine, diethyl ether, tetrahydrofuran, toluene, toluene/THF mixtures, anisole, and diisopropyl ether, particularly preferably toluene, THF, or diisopropyl ether.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More preferably, the boration reaction can be performed. Even more specifically, an alkylated or arylated boron compound can be synthesized.

It is to be noted that a fluid containing all the boron compound and the lithium aromatic and/or lithiated aliphatic compound or the magnesium aromatic and/or magnesium aliphatic compound to such an extent that the reaction performed in the space between the processing surfaces is not affected may be used as a first fluid or a second fluid.

(23: Oxidation Reaction)

In the case of an oxidation reaction, a fluid containing at least one organic compound having an unsaturated bond is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first film fluid between the processing surfaces.

The organic compound having an unsaturated bond used in the oxidation reaction is not particularly limited as long as it has one or more unsaturated bonds such as C—C double bond in its molecule, and may contain, in addition to the unsaturated bond, a functional group inactive against ozone. Examples of such an organic compound include unsaturated aliphatic hydrocarbons having 5 to 20 carbon atoms such as 1-hexene, 1-heptene, 2-heptene, 1-octene, 2-octene, isooctene, cyclohexene, cyclooctene, 1,5-cyclooctadiene, carene, limonene, and pinene, unsaturated alcohols having 5 to 20 carbon atoms such as terpineol and geraniol, and unsaturated aliphatic carboxylic acids such as chrysanthemic acid, citronellic acid, linoleic acid, linolenic acid, and maleic acid and ester derivatives thereof.

Then, a fluid containing ozone is introduced as a second fluid directly through another flow path, that is, the second introduction part d2 into the first fluid film formed between the processing surfaces 1 and 2.

As the ozone used in the oxidation reaction, an ozone-containing gas with a controlled ozone concentration generated by an ozone generator is usually supplied at a controlled flow rate. For example, when supplied, the ozone-containing gas may be mixed with a gas, such as nitrogen, inactive against the reaction.

The organic compound having an unsaturated bond used in the case of the oxidation reaction is preferably in the form of a liquid or solution. A solvent which can be used for such a purpose is not particularly limited as long as it can dissolve the organic compound to supply the organic compound in the form of a solution into the space between the processing surfaces. Such a solvent is not particularly limited as long as it can dissolve the organic compound and is inactive against the reaction. Examples thereof include alcohol-based solvents such as methanol, ethanol, and isopropanol, aromatic hydrocarbon-based solvents such as toluene, xylene, chlorobenzene, and dichlorobenzene, saturated aliphatic hydrocarbon-based solvents such as n-hexane, cyclohexane, n-heptane, and petroleum ether, halogenated hydrocarbon-based solvents such as dichloromethane, 1,2-dichloroethane, chloroform, carbon tetrachloride, chlorobenzene, and dichlorobenzene, and water. These solvents can be used singly or in combination of two or more of them.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the oxidation reaction can be performed.

It is to be noted that a fluid containing all the organic compound having an unsaturated bond and the ozone to such an extent that the reaction performed in the space between the processing surfaces is not affected may be used as a first fluid or a second fluid.

After the completion of the reaction between the organic compound having an unsaturated bond and the ozone performed in the space of the processing surfaces, an oxygen-containing compound is extracted by subjecting a reaction solution usually obtained by the reaction to decomposition treatment. Examples of the decomposition treatment include reductive decomposition treatment and oxidative decomposition treatment. Such decomposition treatment may be performed in the space between the processing surfaces or may be performed after the reaction solution is taken out of the space between the processing surfaces.

The reductive decomposition treatment is performed by, for example, bringing the reaction solution into contact with a reducing agent. Examples of the reducing agent include sulfide compounds such as dimethyl sulfide, diethyl sulfide, diphenyl sulfide, and β-thiodiglycol, phosphine compounds such as triphenylphosphine, tri-o-tolylphosphine, tri-n-butylphosphine, and tricyclohexylphosphine, alkali-metal sulfites such as sodium sulfite and potassium sulfite, and alkali-metal iodides such as sodium iodide and potassium iodide, thiourea, and glyoxylic acid. As the oxygen-containing compound, an aldehyde or a ketone is obtained. Alternatively, the reaction solution may be subjected to reduction treatment using a metal such as zinc, or may be reacted with hydrogen in the presence of a metal catalyst such as palladium carbon, platinum oxide, or Raney nickel. Also in this case, an aldehyde or a ketone is obtained. As the reducing agent, a metal hydride such as lithium aluminum hydride or sodium boron hydride can also be used. In this case, an alcohol is obtained as the oxygen-containing compound.

The oxidative decomposition treatment is usually performed by bringing the reaction solution into contact with an oxidant. Examples of the oxidant include alkaline hydrogen peroxide, formic acid-hydrogen peroxide, and chromic acid-sulfuric acid. As the oxygen-containing compound, a carboxylic acid, a carboxylic acid ester, or a ketone is obtained.

(24: Dimerization Reaction)

In the case of a dimerization reaction, a fluid containing at least one acid is introduced as a first fluid through one flow path, that is, the first introduction part d1 into a space between the processing surfaces 1 and 2 arranged to be opposite to each other so as to approach to and separate from each other, at least one of which rotates relative to the other, to form a first fluid film between the processing surfaces.

The acid used in the dimerization reaction is not particularly limited, but is preferably a Lewis acid. Preferred examples of the Lewis acid include $TiCl_4$, $SnCl_4$, and various complexes (e.g., ether complexes, alcohol complexes, phenol complexes, and water complexes) of $BF_3$. Among them, $BF_3$-$Et_2O$ and $SnCl_4$ are preferred.

Then, a fluid containing a vinyl compound or a vinylidene compound is introduced as a second fluid directly through another flow path, that is, the second introduction part d2 into the first fluid film formed between the processing surfaces 1 and 2.

The vinyl compound or vinylidene compound used in the dimerization reaction is not particularly limited, and examples of the vinyl compound (raw oil) include those having a cyclohexane ring, those having a benzene ring, and α-olefins, such as vinylcyclohexene, styrene, 1-hexene, 1-heptene, 1-octene, 1-nonene, 1-decene, and 1-dodecene. Here, chain α-olefins are mentioned as the α-olefins, but the α-olefins are not limited thereto and may have substituents in their side chain. On the other hand, suitable examples of the vinylidene compound (raw oil) include those having a benzene ring such as α-methylstyrene and compounds represented by the following general formula.

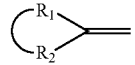

[Chemical 18]

Specific examples of the compounds represented by the above general formula include methylene cyclic compounds which may have substituents. Examples of the methylene cyclic compounds include methylenecyclopropane, methylenecyclobutane, methylenecyclopentane, methylenecyclohexane, methylenecycloheptane, methylenecyclooctane, methylenecyclononane, methylenecyclodecane, methylenebicyclo[3.1.0]hexane, methylenebicyclo[2.2.1]heptane, methylenebicyclo[3.1.1]heptane, and methylenebicyclo[2.2.2]octane. These methylene cyclic compounds may have substituents. Examples of the substituents include chain alkyl groups (each having about 1 to 6 carbon atoms) such as a methyl group, an ethyl group, a propyl group, a butyl group, a pentyl group, and a hexyl group, cyclic alkyl groups (each having about 1 to 6 carbon atoms) such as a cyclopropyl group, a cyclobutyl group, a cyclopentyl group, and a cyclohexyl group, and phenyl groups which may have these substituents, and heterocycles which may have these substituents. Examples of the heterocycles include an oxirane ring, an oxetane ring, a pyran ring, a furan ring, a thiirane ring, a thiophene ring, a pyrrole ring, a pyrazole ring, and an oxazoline ring. A preferred methylene cyclic compound is methylenebicyclo[2.2.1]heptane.

The acid and the vinyl compound or vinylidene compound used in the case of the oxidation reaction are preferably in the form of a liquid or solution. A solvent which can be used for such a purpose is not particularly limited as long as it can dissolve the vinyl compound or vinylidene compound or a catalyst, and examples thereof include water such as ion-exchange water, purified water, tap water, and ultrapure water and organic solvents. Further, the solvent used is not particularly limited as long as it can be used for handling the vinyl compound or vinylidene compound or a catalyst in the reaction or for controlling the progress of the reaction. Specific examples of such a solvent include saturated hydrocarbons such as various pentanes, various hexanes, various octanes, various nonanes, and various decanes, alicyclic hydrocarbons such as cyclopentane, cyclohexane, methylcyclohexane, and decalin, ether compounds such as diethyl ether and tetrahydrofuran, halogen-containing compounds such as methylene chloride, dichloroethane, and hydrofluorocarbon, and nitro compounds such as nitromethane and nitrobenzene. Among them, halogen-containing compounds and nitromethane are preferred.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the dimerization reaction can be performed.

It is to be noted that a fluid containing all the acid and the vinyl compound or vinylidene compound to such an extent that the reaction performed in the space between the processing surfaces is not affected may be used as a first fluid or a second fluid.

(25: Cationic Polymerization)

In the case of a cationic polymerization reaction, a fluid containing at least one cation is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The cation used in the cationic polymerization reaction is not particularly limited, but is preferably one generated by electrolytic oxidation of a cation precursor due to its excellent stability. As the cation precursors, compounds having a trimethylsilyl group such as compounds represented by the following formulas (IV) to (VII) are preferably used. In the formulas, Me is a methyl group and Bu is an n-butyl group.

[Chemical 19]

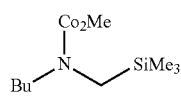
(IV)

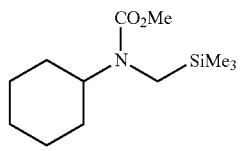
(V)

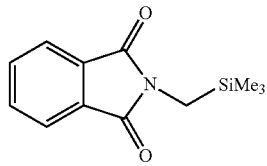
(VI)

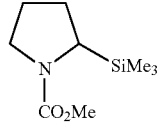
(VII)

By electrolytically oxidizing each of the cation precursors, a cation pool can be generated. In the cationic polymerization, such a cation pool is preferably used. For example, by electrolytically oxidizing the compounds represented by the formulas (IV) and (VII), a cation pool of a cation represented by the following formula (VIII) and a cation pool of a cation represented by the following formula (IX) can be generated, respectively.

[Chemical 20]

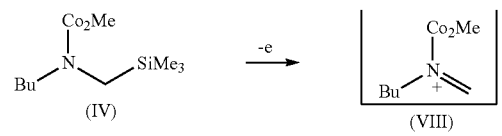

[Chemical 21]

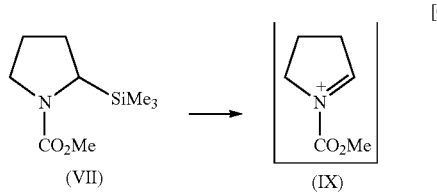

As a method for generating a cation pool by electrolytically oxidizing a cation precursor, for example, the following method can be used. It is to be noted that this method is one which has been actually experimented by the present inventors.

A two chamber-type electrolytic device was prepared, which had a carbon felt attached to an anode chamber, a platinum plate attached to a cathode chamber, and a glass filter as a separator. Eight milliliters of a methylene chloride solution of 0.3 M tetrabutylammonium tetrafluoroborate ($Bu_4NBF_4$) and compound (4) (90.0 mg, 0.414 mmol) were added to the anode chamber and 8.0 mL of a methylene chloride solution of 0.3 M $Bu_4NBF_4$ and trifluoromethanesulfonic acid (144.6 mg, 0.964 mmol) were added to the cathode chamber. Then, both the chambers were stirred using magnetic stirrers to perform constant-current electrolysis (5.0 mA) at −78° C. By the passage of 2.5 F/mol of electricity, a cation pool of the cation represented by the formula (6) was generated in the anode chamber.

Other examples of a cation pool include those of cations represented by the following formulas (X) to (XII), wherein Me is a methyl group.

[Chemical 22]

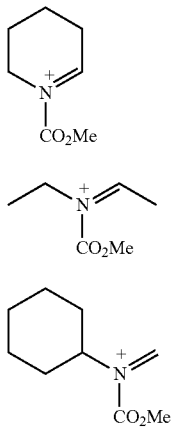

Then, a fluid containing at least one cation polymerizable monomer is introduced as a second fluid directly through another flow path, that is, the second introduction part d2 into the first fluid film formed between the processing surfaces 1 and 2.

The cation polymerizable monomer used in the cationic polymerization reaction is not particularly limited as long as it is a monomer that can polymerize by cationic polymerization, but is preferably a vinyl derivative having an electron-releasing substituent due to its high cationic polymerizability. Typical examples of such a vinyl derivative having an electron-releasing substituent include derivatives whose ethylene skeleton is substituted by an alkyl group or an aryl group, such as isobutylene, styrene, and α-methylstyrene, and derivatives such as vinyl ethers, vinylsulfides, and N-vinylcarbazole having substituents on the heteroatom. Among them, as monomers having particularly high cationic polymerizability, isobutyl vinyl ether, n-butyl vinyl ether, methylvinylsulfide, N-vinylcarbazole, and α-methylstyrene can be mentioned.

The cationic polymerizable monomer and the cation used in the case of the cationic polymerization reaction are preferably in the form of a liquid or solution. A solvent which can be used for such a purpose is not particularly limited.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the cationic polymerization reaction can be performed.

It is to be noted that a fluid containing all the cationic polymerizable monomer and the cation to such an extent that the reaction performed in the space between the processing surfaces is not affected may be used as a first fluid or a second fluid.

(26: Halogen-Metal Exchange Reaction, Metal-Electrophilic Group Exchange Reaction)

In the case of a halogen-metal exchange reaction, a fluid containing at least one metalation reagent is introduced as a first fluid through one flow path, that is, the first introduction part d1 into a space between the processing surfaces 1 and 2 arranged to be opposite to each other so as to be able to approach to and separate from each other, at least one of which rotates relative to the other, to form a first fluid film between the processing surfaces.

The metalation reagent used in the halogen-metal exchange reaction is not particularly limited, and examples thereof include a Grignard reagent, a lithium magnesium ate complex, a lithium copper ate complex, and an organic lithium reagent. Examples of the Grignard reagent include aryl chlorides, aryl bromides, and aryl iodides. As the organic lithium reagent, a conventionally-known organic lithium compound can be used. Examples of such an organic lithium compound include: alkyllithiums such as methyllithium, ethyllithium, propyllithium, butyllithium, pentyllithium, hexyllithium, methoxymethyllithium, and ethoxymethyllithitum; alkenyllithiums such as vinyllithium, allyllithium, propenyllithium, and butenyllithium; alkynyllithiums such as ethynyllithium, butynyllithium, pentyllithium, and hexynyllithium; and aralkyllithiums such as benzyllithium and phenylethyllithium. Among them, alkyllithiums, alkenyllithiums, and alkynyllithiums are preferred. Among them, methyllithium, ethyllithium, propyllithium, n-butyllithium, sec-butyllithium, iso-butyllithium, tert-butyllithium, n-hexyllithium, n-octyllithium, n-decyllithium, vinyllithium, allyllithium, methoxymethyllithium, benzyllithium, phenyllithium, 2-thienyllithium, and tri(n-butyl)mangesiumlithium are preferred, and n-butyllithium is more preferred.

Then, a fluid containing at least one halogen compound is introduced as a second fluid directly through another flow path, that is, the second introduction part d2, into the first fluid film formed between the processing surfaces 1 and 2.

The halogen compound used in the halogen-metal exchange reaction is not particularly limited, and examples thereof include chlorine compounds, bromine compounds, and iodine compounds. Among them, bromine compounds and iodine compounds are preferred due to their high reactivity.

[Chemical 23]

More specifically, in the halogen compound represented by the above general formula (wherein X is a halogen element), a ring denoted by A is specifically a monocyclic or polycyclic 6- to 10-membered aromatic ring such as benzene, naphthalene, anthracene, and phenanthrene; a monocyclic or polycyclic 3- to 10-membered saturated ring such as cyclopropane, cyclobutane, cycloheptane, cyclohexane, and cyclooctane; a monocyclic or polycyclic 3- to 10-membered partially-saturated ring such as cyclopentene, cyclohexene, cyclooctene, and indan; or a 5- to 10-membered monocyclic or polycyclic hetero ring containing 1 to 4 atoms selected from nitrogen, oxygen, and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene. Preferred are a phenyl group and the hetero rings, more preferred are the hetero rings, even more preferred are the 5- or 6-membered hetero rings, and particularly preferred are pyridine, pyridazine, pyrimidine, pyrazine, furan, oxazole, thiophene, and thiazole.

Further, the ring denoted by A may further have a substituent. The number of and the kinds of substituents are not particularly limited. Specific examples of the substituent include linear, branched, or cyclic alkyl groups having 1 to 20 carbon atoms (including alkyls substituted by cycloalkyl) such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopropyl, cyclobutyl, cyclopentyl, cyclohexyl, cycloheptyl, cyclooctyl, cyclononyl, and cyclodecyl; linear, branched, or cyclic alkenyl groups having 2 to 20 carbon atoms such as vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, hexadienyl, and dodecatrienyl; linear, branched, or cyclic alkynyl groups having 2 to 20 carbon atoms such as ethynyl, butynyl, pentynyl, hexynyl, heptynyl, octynyl, nonynyl, cyclooctynyl, cyclononynyl, and cyclodecynyl; 5- to 10-membered monocyclic or bicyclic aryl groups such as phenyl, naphthyl, and anthranyl; alkoxy groups having 1 to 20 carbon atoms such as methoxy, ethoxy, propoxy, butoxy, pentyloxy, hexyloxy, heptyloxy, octyloxy, nonyloxy, decyloxy, dodecyloxy, hexadecyloxy, and octadecyloxy; aryloxy groups such as phenoxy and naphthyloxy; alkylthio groups having 1 to 20 carbon atoms such as methylthio, ethylthio, propylthio, butylthio, pentylthio, hexylthio, heptylthio, octylthio, nonylthio, decylthio, dodecylthio, hexadecylthio, and octadecylthio; arylthio groups such as phenylthio and naphthylthio; substituted carbonyl groups such as acyls having 2 to 20 carbon atoms including acetyl, propanoyl, butanoyl, pentanoyl, hexanoyl, and heptanoyl, benzoyl, and naphthoyl; substituted oxycarbonyl groups such as methoxycarbonyl, ethoxycarbonyl, tert-butoxycarbonyl, n-decyloxycarbonyl, and phenoxycarbonyl; substituted carbonyloxy groups such as acyloxys having 2 to 20 carbon atoms including acetyloxy, propanoyloxy, butanoyloxy, pentanoyloxy, hexanoyloxy, and heptanoyloxy, benzoyloxy, and naphthoyloxy; substituted sulfonyl groups such as methylsulfonyl, ethylsulfonyl, propylsulfonyl, butylsulfonyl, pentylsulfonyl, hexylsulfonyl, heptylsulfonyl, octylsulfonyl, phenylsulfonyl, and naphtylsulfonyl; carbamoyl groups substituted by one or two groups selected from alkyls, alkenyls, and aryls, such as N-methylcarbamoyl and N,N-diphenylcarbamoyl; sulfamoyl groups substituted by one or two groups selected from alkyls, alkenyls, and aryls, such as N-phenylsulfamoyl and N,N-diethylcarbamoyl; substituted carbonylamino groups such as acylaminos having 2 to 20 carbon atoms including acetylamino, tert-butylcarbonylamino, and n-hexylcarbonylamino, benzoylamino, and naphthoylamino; ureido groups substituted by one or two groups selected from alkyls, alkenyls, and aryls, such as N-methylureido and N,N-diethylureido; substituted sulfonylamino groups such as sulfonylaminos having 1 to 20 carbon atoms including methylsulfonylamino, tert-butylsulfonylamino, and n-octylsulfonylamino, phenylsulfonylamino, and naphthylsulfonylamino; monosubstituted or disubstituted amino groups such as methylamino, phenylamino, tert-butoxycarbonylamino, pivaloylamino, benzylamino, phthaloylamino, N,N-dimethylamino group, N,N-diethylamino group, N,N-diphenylamino group, and N-methyl-N-phenylamino group; nitro group; cyano group; substituted silyl groups such as trimethylsilyl and triethylsilyl; halogen atoms such as fluorine, bromine, chlorine, and iodine; and 5- to 10-membered monocyclic or polycyclic heterocyclic residues containing 1 to 4 atoms selected from nitrogen, oxygen, and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene. Preferred are alkyl groups having 2 to 16 carbon atoms, alkenyl groups having 2 to 16 carbon atoms, alkynyl groups having 2 to 16 carbon atoms, aryl groups, alkoxy groups having 2 to 16 carbon atoms, aryloxy groups, alkylthio groups having 2 to 16 carbon atoms, arylthio groups, substituted carbonyl groups having 2 to 17 carbon atoms, substituted oxycarbonyl groups having 2 to 17 carbon atoms, substituted carbonyloxy groups having 2 to 17 carbon atoms, substituted sulfonyl groups having 1 to 16 carbon atoms, monosubstituted or disubstituted carbamoyl groups having 2 to 17 carbon atoms, monosubstituted or disubstituted sulfamoyl groups having 1 to 16 carbon atoms, substituted carbonylamino groups having 2 to 17 carbon atoms; monosubstituted or disubstituted ureido groups having 2 to 17 carbon atoms; substituted sulfonylamino groups having 1 to 16 carbon atoms; monosubstituted or disubstituted amino groups having 1 to 16 carbon atoms; nitro groups, cyano groups, substituted silyl groups having 1 to 16 carbon atoms, halogen atoms, and the heterocyclic residues. More preferred are alkyl groups having 2 to 8 carbon atoms, alkenyl groups having 2 to 8 carbon atoms, alkynyl groups having 2 to 8 carbon atoms, aryl groups, alkoxy groups having 2 to 8 carbon atoms, aryloxy groups, alkylthio groups having 2 to 8 carbon atoms, arylthio groups, substituted carbonyl groups having 2 to 9 carbon atoms, substituted oxycarbonyl groups having 2 to 9 carbon atoms, substituted carbonyloxy groups having 2 to 9 carbon atoms, substituted sulfonyl groups having 1 to 8 carbon atoms; monosubstituted or disubstituted carbamoyl groups having 2 to 9 carbon atoms, monosubstituted or disubstituted sulfamoyl groups having 1 to 8 carbon atoms, substituted carbonylamino groups having 2 to 9 carbon atoms, monosubstituted or disubstituted ureido groups having 2 to 9 carbon atoms, substituted sulfonylamino groups having 1 to 8 carbon atoms, monosubstituted or disubstituted amino groups having 1 to 8 carbon atoms, nitro groups, cyano groups, substituted silyl groups having 1 to 8 carbon atoms, halogen atoms, and the heterocyclic residues. Particularly preferred are alkyl groups having 2 to 8 carbon atoms, alkenyl groups having 2 to 8 carbon atoms, alkynyl groups having 2 to 8 carbon atoms, aryl groups, alkoxy groups having 2 to 8 carbon atoms, aryloxy groups, alkylthio groups having 2 to 8 carbon atoms, arylthio groups, substituted carbonyl groups having 5 to 9 carbon atoms, substituted oxycarbonyl groups having 5 to 9 carbon atoms, substituted carbonyloxy groups having 5 to 9 carbon atoms, substituted sulfonyl groups having 4 to 8 carbon atoms, monosubstituted or disubstituted carbamoyl groups having 5 to 9 carbon atoms, monosubstituted or disubstituted sulfamoyl groups having 4 to 8 carbon atoms, substituted carbonylamino groups having 5 to 9 carbon atoms; monosubstituted or disubstituted ureido groups having 5 to 9 carbon atoms, substituted sulfonylamino groups having 4 to 8 carbon atoms, monosubstituted or disubstituted amino groups having 4 to 8 carbon atoms, nitro groups, cyano groups, substituted silyl groups having 1 to 8 carbon atoms, halogen atoms, and the heterocyclic residues.

It is to be noted that a hydrocarbon having one carbon atom, such as a methyl group, a methoxy group, or a methylthio group, directly bonded to an aryl group is likely to undergo deprotonation reaction by a strong base such as butyl lithium, and therefore there is a fear that a by-product is generated. Further, a methoxy group is likely to cause radical reaction, and therefore there is a fear that a by-product such as bisaryl is generated by generation of a carbon radical. For this reason, when the ring denoted by A is an aromatic ring and the aromatic ring has a substituent such as an alkyl, alkoxy, or alkylthio group, the substituent preferably has 2 or more carbon atoms. Further, when the ring denoted by A has a carbonyl group as a substituent, the ring A is preferably substituted by a group, such as a tert-butyl group, which has 4 or more carbon atoms and which is bulky and highly sterically hindered because the occurrence of a side reaction can be prevented during the reaction with the lithium reagent. These substituents may be further substituted by other substituents, and such other substituents are not particularly limited as long as they have no effect on the reaction. Examples of such other substituents include lower alkyl groups such as methyl, ethyl, propyl, and butyl, aryl groups such as phenyl and naphthyl, and halogen atoms such as chlorine and fluorine.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the halogen-metal exchange reaction can be performed.

It is to be noted that a fluid containing all the metalation reagent and the halogen compound to such an extent that the reaction performed in the space between the processing surfaces is not affected may be used as a first fluid or a second fluid.

Further, if necessary, a compound such as one represented by the general formula (XIII) obtained by the halogen-metal exchange reaction may be reacted with an electrophilic compound in the space between the processing surfaces subsequently to the halogen-metal exchange reaction to obtain a compound such as one represented by the general formula (XIV). It is to be noted that Li in the following formula (XIII) may be a metal such as Mg. In the following formula (XIV), Y is an electrophilic group.

[Chemical 24]

(XIII)

(XIV)

The electrophilic compound is not particularly limited as long as it is a compound containing a functional group having electron acceptability, but is preferably a compound that reacts with an electron-dense functional group or an unshared electron pair. These electrophilic compounds include all electrophilic compounds used in halogen-metal exchange reactions using well-known organolithium reagents. Specific examples of such compounds include: halogen molecules such as chlorine, bromine, and iodine; inorganic materials such as solid sulfur, sulfur dioxide, and oxygen; carbon dioxide; nitriles such as acetonitrile, propionitrile, and benzonitrile; imines such as benzophenone imine and acetophenone imine; silicon halides such as chlorotrimethylsilane and chlorotriethylsilane; tin compounds such as dibutyltin dichloride and diphenyltin dibromide; aldehydes such as paraformaldehyde, acetoaldehyde, propionaldehyde, butylaldehyde, acrylaldehyde, benzaldehyde, and nicotinealdehyde; ketones such as acetone, 2-butanone, benzophenone, acetophenone, DMF, and tert-butyl-4-oxo-1-piperidinecarboxylate; esters such as ethyl chloroformate, phenyl chloroformate, methyl formate, ethyl formate, ethyl acetate, butyl acetate, octyl acetate, phenyl acetate, methyl benzoate, ethyl benzoate, and phenyl benzoate; acid anhydrides such as acetic anhydride, phthalic anhydride, succinic anhydride, and maleic anhydride; acyl halides such as acetyl chloride, benzoyl chloride, and 2-pyridinecarbonyl chloride; oxiranes such as oxirane and 2-methyl-oxirane; aziridines such as 6-azabicyclo[3,1,0]hexane and 7-azabicyclo[4,1,0]heptane; α,β-unsaturated ketones such as 3-oxo-1,3-diphenyl-1-propene and 2-methyl-3-oxo-3-diphenyl-1-propene; alkyl halides such as methyl iodide, ethyl iodide, butyl iodide, methyl bromide, ethyl bromide, hexyl bromide, octyl bromide, 1,2-diiodoethane, 1,2-dibromoethane, 1,6-diiodohexane, 1,8-dibromooctane, and 1,2-dibromocyclopentene; acid imides such as N-bromosuccinic imide, N-iodosuccinic imide, N-chlorosuccinic imide, and N-bromophthalic imide; disulfides such as dimethyldisulfide and diphenyldisulfide; phosphines such as chlorodiphenylphosphine and chlorodimethylphosphine; and phosphine oxides such as chlorodiphenylphosphine oxide and chlorodimethylphosphine oxide. Among them, chlorotrimethylsilane, benzaldehyde, and DMF are preferred.

The metalation reagent and the halogen compound used in the case of the halogen-metal exchange reaction and the electrophilic reaction are preferably in the form of a liquid or solution. A solvent which can be used for such a purpose is not particularly limited as long as, when the halogen compound, metalation reagent, and electrophilic compound used are not in a liquid form, it can dissolve them and is inactive in the reaction, and examples thereof include water such as ion-exchange water, purified water, tap water, and ultrapure water and organic solvents. Specific examples of the organic solvents include aromatic hydrocarbon compounds such as benzene, toluene, xylene, methylene, durene, ethyl benzene, diethyl benzene, isopropyl benzene, diisopropyl benzene, diphenyl methane, chlorobenzene, 1,2-dichlorobenzene, and 1,2,4-trichlorobenzene; polar solvents such as pyridine, acetonitrile, DMF, N,N-dimethylacetoamide, N-methylpyrrolidone, and 1,3-dimethyl-2-imidazolidinone; acetic acid esters such as methyl acetate, ethyl acetate, and butyl acetate; alkanes such as n-pentane, n-hexane, n-heptane, cyclohexane, decane, and paraffins and perfluoroalkanes; ethers such as dimethyl ether, diethyl ether, diisopropyl ether, dibutyl ether, dimethoxyethane, petroleum ether, tetrahydrofuran (abbreviated as THF), dioxane, trioxane, and diglyme; ureas such as N,N-dimethylimidazolidinone; tertiary amines such as trimethylamine, triethylamine, tributylamine, and N,N,N',N'-tetramethylethylenediamine; and halogenated alkanes such as methylene chloride and dichloroethane, all of which can be used irrespective of whether they are polar or nonpolar. Preferred are THF, diethyl ether, diisopropyl ether, dibutyl ether, dimethoxyethane, toluene, xylene, and 1,3-dimethyl-2-imidazolidinone, and more preferred are THF, dibutyl ether, dimethoxyethane, and toluene. These solvents can be used singly or in combination of two or more of them. When these solvents are used in combination of two or more of them, the mixing ratio can be appropriately determined.

By using the halogen-metal exchange reaction and the electrophilic reaction, the following compounds can be typically obtained.
[Chemical 25]
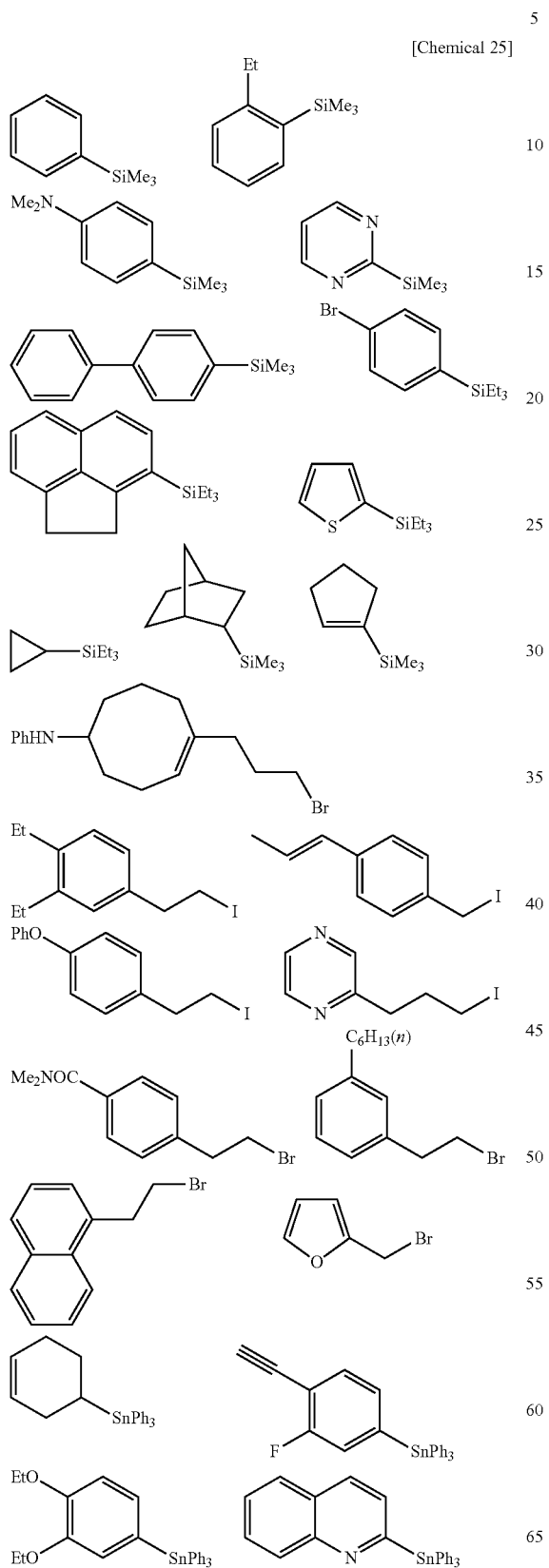
[Chemical 26]
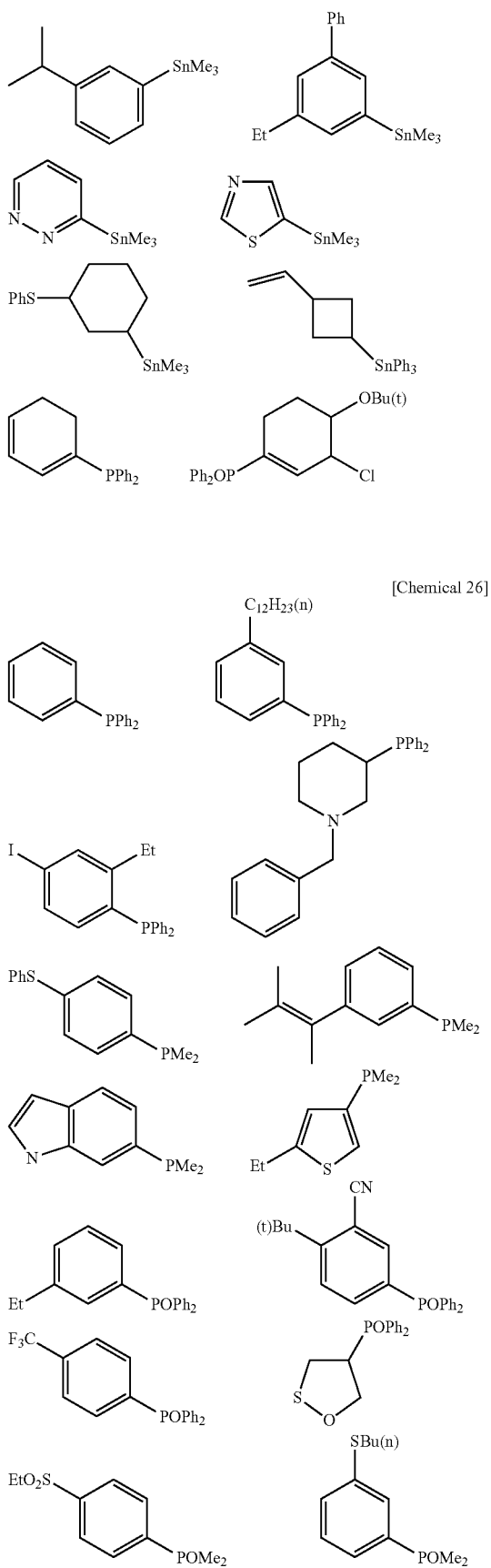

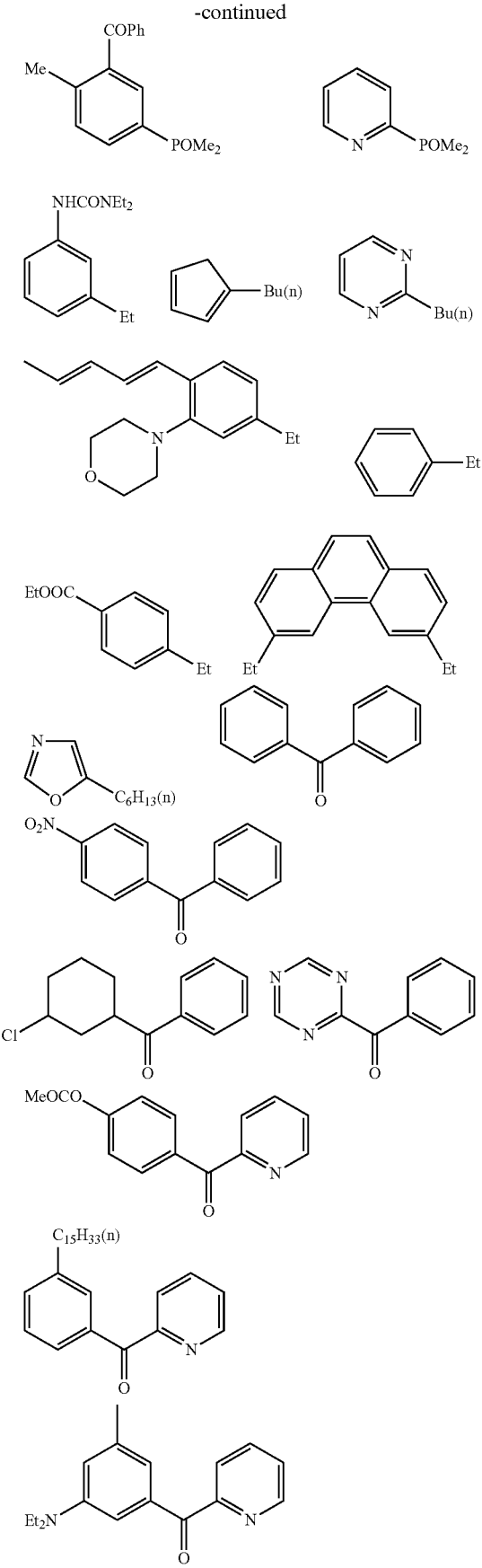
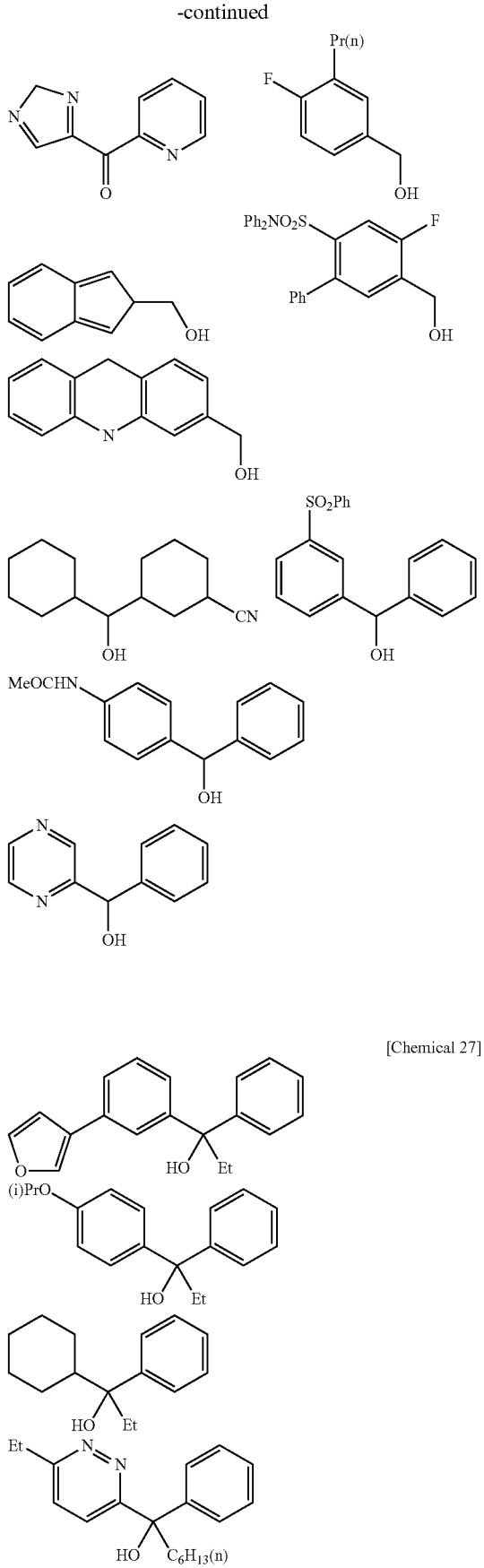

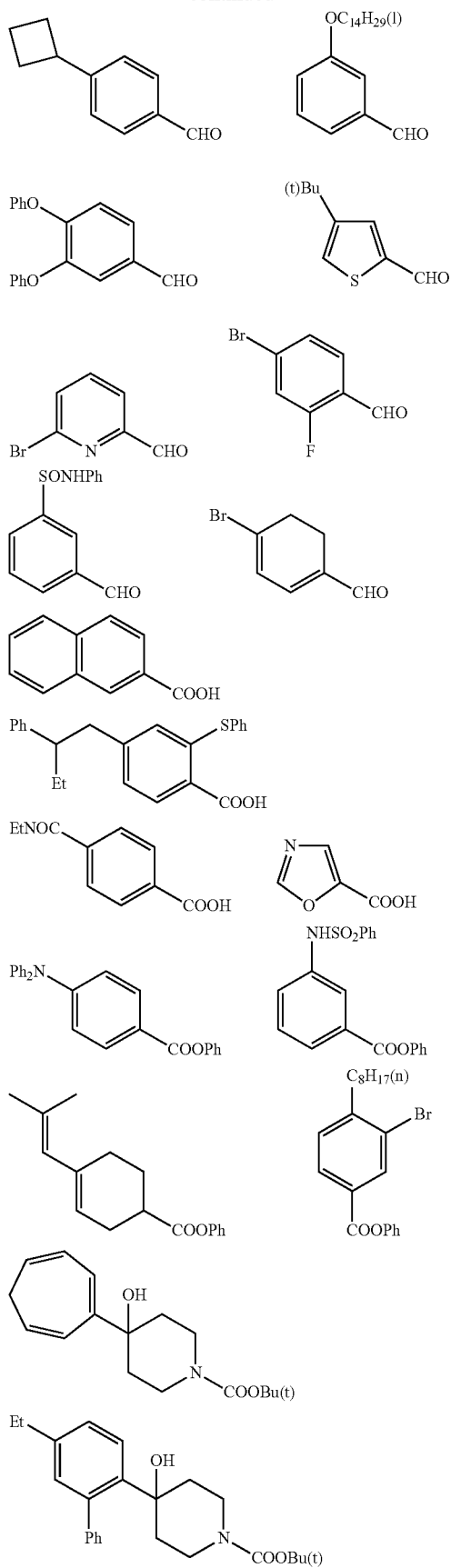
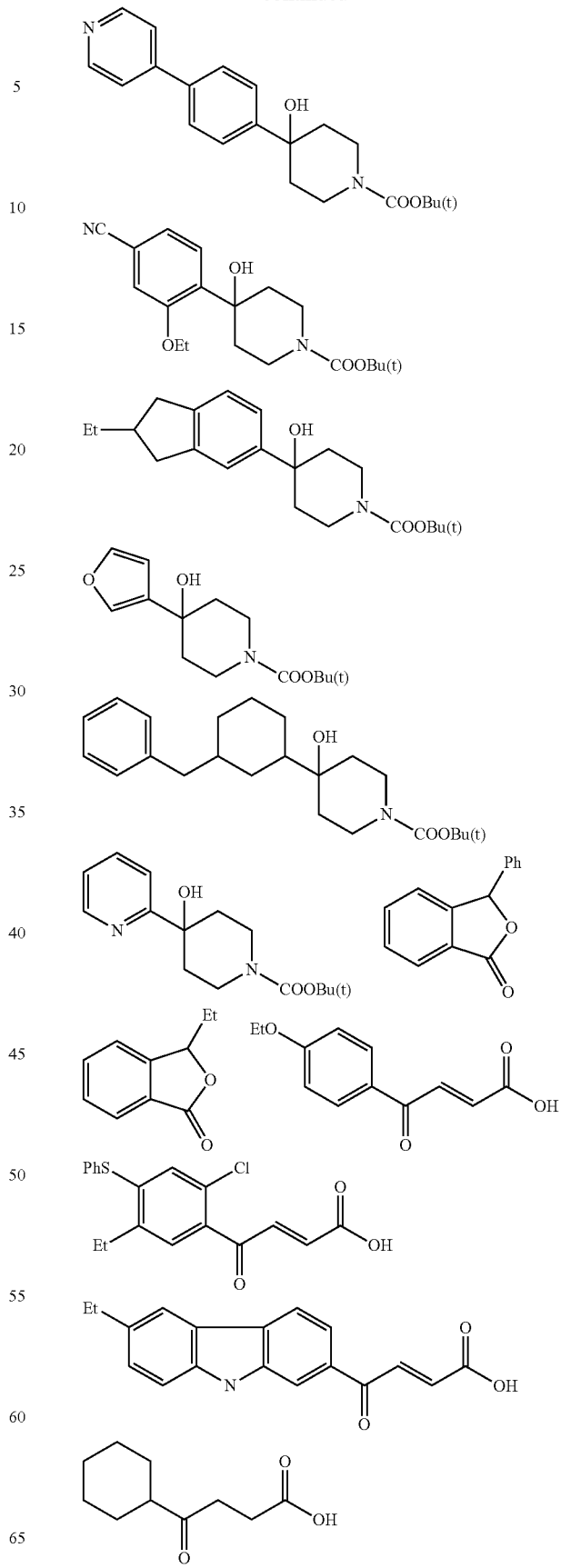

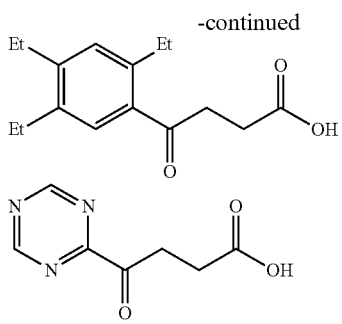

(27: Reduction Reaction for Aldehyde Synthesis)

In the case of a reduction reaction between an alkyl ester and a metal hydride-based reducing agent, a fluid containing at least one metal hydride-based reducing agent is introduced as a first fluid through one flow path, that is, the first introduction path d1 into a space between the processing surfaces 1 and 2 arranged to be opposite to each other so as to be able to approach to and separate from each other, at least one of which rotates relative to the other, to form a first fluid film between the processing surfaces.

The metal hydride-based reducing agent used in the reduction reaction is not particularly limited, but is preferably an aluminum-based one. Examples of the aluminum-based one include lithium aluminum hydride, sodium aluminum hydride, potassium aluminum hydride, or alkyl (e.g., isobutyl), aryl, alkoxy, aryloxy, or acyloxy derivatives of aluminum hydrides, or complexes of aluminum hydrides or of the above-mentioned derivatives with amines, phosphines, ethers, or sulfides as ligands. These reducing agents may be used singly or in combination of two or more of them. Among them, diisobutylaluminum hydride is a particularly preferred example.

Then, a fluid containing at least one alkyl ester is introduced as a second fluid directly through another flow path, that is, the second introduction part d2 into the first fluid film formed between the processing surfaces 1 and 2.

The alkyl ester used in the reduction reaction (herein, the term "ester" refers to a carboxylic acid ester) is not particularly limited, and examples thereof include alkyl esters represented by the formula: $R^1$—$CO_2$—$R^2$ (wherein $R^1$ represents an alkyl group which may be substituted, an aralkyl group which may be substituted, a cycloalkyl group which may be substituted, or a heterocyclic group which may be substituted and which is obtained by replacing one or more ring-forming carbon atoms in the alkyl group or in the cycloalkyl group with heteroatoms at positions other than the α position, or an aryl group which may be substituted and which may have one or more heteroatoms as aromatic ring-forming atoms at positions other than the position at which the carbonyl group of the ester is bonded, and $R^2$ represents an alkyl group). Preferred examples of the heteroatom include nitrogen and oxygen. The alkyl group as an example of $R^1$ is preferably a C1 to C20 alkyl group, more preferably a C1 to C10 alkyl group, even more preferably a C1 to C8 alkyl group, particularly preferably a C1 to C4 alkyl group. Specific examples of the alkyl group include methyl, ethyl, propyl, isopropyl, butyl, sec-butyl, tert-butyl, pentyl, hexyl, heptyl, octyl, nonyl, decyl, pentadecyl, and eicosanyl groups. Examples of the aralkyl group include those formed from a 6- to 10-membered ring aryl group which may contain a heteroatom (e.g., phenyl, naphtyl, pyridyl, indolyl, quinolyl, isoquinolyl) and a C1 to C4 alkyl group. Particularly preferred specific examples of the aralkyl group include a benzyl group, a phenylethyl group, and a pyridylmethyl group. Examples of the cycloalkyl group include C5 to C7 cycloalkyl groups. Preferred specific examples of the cycloalkyl group include cyclopentyl, cyclohexyl, and cycloheptyl groups. Examples of the heterocyclic group include piperidyl, tetrahydrofuranyl, tetrahydropyranyl, and dioxanyl groups. Examples of the aryl group include 6- to 10-membered ring aryl groups which may contain a heteroatom. Specific examples of the aryl group include phenyl, naphthyl, pyridyl, indolyl, quinolyl, and isoquinolyl groups. Each of the above-mentioned groups may be substituted, and examples of substituents include benzyl, phenyl, C1 to C6 alkyl, amino, alkoxycarbonylamino (e.g., Boc amino), and alkylcarbonylamino groups. Particularly preferred specific examples of $R^1$ include pentyl, cyclohexyl, benzyl, N-benzylpiperidyl, pyridyl, 1-Boc amino-2-phenylethyl groups. However, the specific examples of $R^1$ are not limited to the above-mentioned examples. This is because the processing device used in the present invention is intended to enhance mixing efficiency, and therefore the present invention can be applied to the reduction reaction as long as $R^1$ does not interfere with the reduction of the alkyl ester by the metal hydride-based reducing agent. Examples of $R^2$ include C1 to C20 alkyl groups. Among them, C1 to C10 alkyl groups are preferred, C1 to C6 alkyl groups are more preferred, and C1 to C4 alkyl groups are particularly preferred. Specific examples of such alkyl groups include methyl, ethyl, propyl, isopropyl, butyl, sec-butyl, tert-butyl, pentyl, hexyl, heptyl, octyl, nonyl, decyl, pentadecyl, and eicosanyl groups.

The metal hydride-based reducing agent and the alkyl ester used in the case of the reduction reaction are preferably in the form of a liquid or solution. A solvent which can be used for such a purpose is not particularly limited as long as it can dissolve the alkyl ester and the metal hydride-based reducing agent, and examples thereof include water such as ion-exchange water, purified water, tap water, and ultrapure water and organic solvents. Further, the solvent used is not particularly limited as long as it can be used for handling the alkyl ester and the metal hydride-based reducing agent in the reaction or for controlling the progress of the reaction.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. More specifically, the reduction reaction can be performed. Even more specifically, an aldehyde can be obtained by reducing the alkyl ester.

It is to be noted that a fluid containing all the metal hydride-based reducing agent and the alkyl ester to such an extent that the reaction performed in the space between the processing surfaces is not affected may be used as a first fluid or a second fluid.

It is to be noted that, contrary to the above, in the cases of the above-described various reactions, the second fluid may be introduced through the first introduction part d1 and the first fluid may be introduced through the second introduction part d2 as long as the reactions can be performed in the space between the processing surfaces 1 and 2. That is, the expression "first" or "second" for each fluid has a meaning for merely discriminating an $n^{th}$ fluid among a plurality of fluids present, and third or more fluids can also be present.

Further, both of the first and second fluids may contain the same organic compound and reactant, or a plurality of fluids each containing a different one of all the substances involved in the reaction may be used.

The production rate of an organic compound produced, or, when fine particles are obtained by separation, the particle size or monodispersity of the fine particles, or the type of crystal can be controlled by changing the rotating speed of the processing surfaces 1 and 2 or the distance between the processing surfaces 1 and 2 and the flow rate or temperature of the thin film fluid or the concentration of a raw material.

In addition, the space between the processing surfaces may be heated (warmed), or may be irradiated with ultraviolet ray (UV). Particularly, when a difference in temperature is set between the first processing surface 1 and the second processing surface 2, there is an advantage that the reaction can be promoted, since convection can be generated in a thin film fluid.

More specifically, for heating (warming), at least one of the processing member 10 and the processing member 20 can be provided, for example, with a heater or a jacket for circulating a heating medium to heat (warm) the thin film fluid. For irradiation with ultraviolet ray (UV), at least one of the processing member 10 and the processing member 20 can be provided, for example, with an element such as UV lamp to irradiate the thin film fluid with ultraviolet ray (UV) from the corresponding processing surface. For supplying with ultrasonic energy, at least one of the processing member 10 and the processing member 20 can be provided, for example, with an ultrasonic wave oscillator.

The neutralization reaction is conducted in a container capable of securing a depressurized or vacuum state, and a secondary side at which the fluid after processing is discharged can be depressurized or vacuumized to remove a gas generated during the reaction, to remove a gas discharged from the processing member, or to remove the solvent of the fluid. This makes it possible to, even when the removal of the solvent is performed at almost the same time as the organic reaction, discharge a fluid, which contains an organic compound obtained by the organic reaction performed in the space between the processing surfaces, as a mist from the processing surfaces, thereby increasing the surface area of the fluid. This is advantageous in that the removal of solvent can be performed very efficiently.

As has been described above, according to the invention of the present application, it is possible to provide a production method of an organic compound capable of controlling reaction selectivity at a higher level as compared to a conventional reaction method and of achieving a high yield of a product. Further, depending on a necessary amount of production, the present invention can grow in size by using general scale-up concept. Further, it is also possible to provide a reaction method and a production method of an organic compound which are capable of securing reaction uniformity irrespective of whether the viscosity of a fluid is low or high because the reaction is performed in a forced thin film fluid and therefore the viscosity of a fluid has a low impact on reaction uniformity, and of achieving a high productivity, and of achieving scale-up production while minimizing risks specific to organic reactions because the reaction is performed in a thin film fluid. The production method according to the present invention is capable of achieving low contamination levels during the production process and is also capable of, when crystals are separated, controlling the crystallinity of the crystals with high accuracy.

Further, as described above, the processing apparatus may also have the third introduction part d3 in addition to the first introduction part d1 and the second introduction part d2. In this case, for example, an organic compound, a solution containing a reactant, and another organic compound different from the organic compound or a dispersant can be separately introduced into the processing apparatus through these three different introduction parts. This makes it possible to individually control the concentration or pressure of each of the solutions, that is, to control a reaction of producing an organic compound with higher accuracy. When the processing apparatus is provided with four or more introduction parts, the foregoing applies and fluids to be introduced into the processing apparatus can be subdivided in this manner.

EXAMPLES

Hereinafter, the present invention is described in detail with reference to Examples, but the present invention is not limited to only Examples.

It is to be noted that in the following examples, the term "from the center" means "through the first introduction part d1" of the processing apparatus shown in FIG. 1(A), the term "first fluid" refers to the above-described first fluid to be processed, the term "second fluid" refers to the above-described second fluid to be processed introduced through the "second introduction part d2" of the processing apparatus shown in FIG. 1(A). Further, in a case where a third fluid is used, the term "third fluid" refers to the above-described third fluid to be processed introduced through the "third introduction part d3" of the processing apparatus shown in FIG. 1(B).

Example 1

Friedel-Crafts Acylation Reaction

A mixture obtained by mixing butyric acid and trifluoroacetic anhydride in the ratio of 1:1.44 was sent as a first fluid from the center at a ratio of supply pressure/back pressure of 0.02 MPa/0.01 Mpa, a rotation speed of 500 rpm, and a sending temperature of 45° C., and pure benzo[b]furanone was introduced as a second fluid into a space between the processing surfaces at 10 mL/min. The first fluid and the second fluid were mixed in a thin film fluid, and then a solution obtained after processing was discharged from the space between the processing surfaces at 20 mL/min. As a result of HPLC analysis, it was confirmed that 2-butyrylbenzofuranone was obtained in a yield of 76%. It is to be noted that in this Example, a seal-less processing apparatus using magnetic coupling was used.

Comparative Example 1

Friedel-Crafts Acylation Reaction (Batch Method)

A mixture obtained by mixing butyric acid and trifluoroacetic anhydride in a ratio of 1:1.44 was placed in a 200-mL container purged with nitrogen. Then, pure benzo[b]furanone was added dropwise into the container under stirring at 20000 rpm by CLEARMIX (manufactured by M Technique Co., Ltd.). As a result of HPLC analysis, it was confirmed that 2-butyrylbenzofuranone was obtained in a yield of 32%.

Example 2

Friedel-Crafts Alkylation Reaction

Ninety-six percent concentrated sulfuric acid was sent as a first fluid from the center at a ratio of supply pressure/back pressure of 0.08 MPa/0.05 MPa, a rotation speed of 1000 rpm, and a sending temperature of 25° C., and a solution obtained by mixing benzene and cyclohexene in a volume ratio (benzene/cyclohexene) of 4/5 was introduced as a second fluid into a space between the processing surfaces at 17 mL/min. The first fluid and the second fluid were mixed in a thin film fluid, and then a solution obtained after processing was discharged from the space between the processing surfaces at 32 mL/min. After extraction and solvent removal, it was confirmed by combined GC/MS analysis that the area percentage of cyclohexylbenzene in the chromatogram was 64%.

Comparative Example 2

Friedel-Crafts Alkylation Reaction (Batch Method)

Ninety-six percent concentrated sulfuric acid was placed in a 200-mL container purged with nitrogen. Then, a solution obtained by mixing benzene and cyclohexene in a volume ratio (benzene/cyclohexene) of 4/5 was added dropwise into the container under stirring at 20000 rpm by CLEARMIX (manufactured by M Technique Co., Ltd) while the temperature of the liquid in the container was maintained at 25° C. After extraction and solvent removal, it was confirmed by combined GC/MS analysis that the area percentage of cyclohexylbenzene in the chromatogram was 18%.

Example 3

Nitration Reaction

One hundred percent nitric acid was sent as a first fluid from the center at a ratio of supply pressure/back pressure of 0.05 MPa/0.03 MPa, a rotation speed of 1000 rpm, and a sending temperature of 10° C., and a mixed solution of toluene and acetic anhydride (1:1) was introduced as a second fluid into a space between the processing surfaces at 10 mL/min. The first fluid and the second fluid were mixed in a thin film fluid, and then a solution obtained after processing was discharged from the space between the processing surfaces at 20 mL/min. After extraction and solvent removal, it was confirmed by combined GC/MS analysis that the area percentage of O-nitrotoluene in the chromatogram was 82%. It is to be noted that in this Example, a seal-less processing apparatus using magnetic coupling was used.

Comparative Example 3

Nitration Reaction (Batch Method)

One hundred percent nitric acid was placed in a 200-mL container purged with nitrogen. Then, a mixed solution of toluene and acetic anhydride (1:1) was added dropwise into the container under stirring at 20000 rpm by CLEARMIX (manufactured by M Technique Co., Ltd) while the temperature of the liquid in the container was maintained at 10° C. After extraction and solvent removal, it was confirmed by combined GC/MS analysis that the area percentage of O-nitrotoluene in the chromatogram was 38%.

Example 4

Bromination Reaction

A 5.5 mol/L bromine/tetrachloromethane solution was sent as a first fluid from the center at a ratio of supply pressure/back pressure of 0.10 MPa/0.03 MPa, a rotation speed of 500 rpm, and a sending temperature of 15° C., and a 5.0 mol/L mesitylene/tetrachloromethane solution was introduced as a second fluid into a space between the processing surfaces at 15 mL/min. The first fluid and the second fluid were mixed in a thin film fluid, and then a solution obtained after processing was discharged from the space between the processing surfaces at 33 mL/min. As a result of GC/MS analysis, it was confirmed that the area percentage of 1-bromomesitylene in the chromatogram was 93%.

Comparative Example 4

Bromination Reaction (Batch Method)

A 5.5 mol/L bromine/tetrachloromethane solution was placed in a 200-mL container purged with nitrogen. Then, a 5.0 mol/L mesitylene/tetrachloromethane solution was added dropwise into the container under stirring at 20000 rpm by CLEARMIX (manufactured by M Technique Co., Ltd.) while the temperature of the liquid in the container was maintained at 15° C. As a result of GC/MS analysis, it was confirmed that the area percentage of 1-bromomesitylene in the chromatogram was 44%.

Example 5

Bayer-Villiger Oxidation Reaction

A 0.625 mol/L m-chloroperbenzoic acid/0.25 mol/L trifluoroacetic acid/dichloromethane solution was sent as a first fluid from the center at a ratio of supply pressure/back pressure of 0.13 MPa/0.04 MPa, a rotation speed of 2000 rpm, and a sending temperature of 30° C., and a 0.25 mol/L cyclohexanone/dichloromethane solution was introduced as a second fluid into a space between the processing surfaces at 23 mL/min. The first fluid and the second fluid were mixed in a thin film fluid, and then a solution obtained after processing was discharged from the space between the processing surfaces at 43 mL/min. As a result of GC/MS analysis, it was confirmed that the yield of caprolactone was 100%.

Comparative Example 5

Bayer-Villiger Oxidation Reaction (Batch Method)

A 0.625 mol/L m-chloroperbenzoic acid/0.25 mol/L trifluoroacetic acid/dichloromethane solution was placed in a 200-mL container purged with nitrogen. Then, a 0.25 mol/L cyclohexanone/dichloromethane solution was added dropwise into the container under stirring at 20000 rpm by CLEARMIX (manufactured by M Technique Co., Ltd.) while the temperature of the liquid in the container was maintained at 30° C. As a result of GC/MS analysis, it was confirmed that the yield of caprolactone was 54%.

Example 6

Metathesis Reaction

A 0.01 mol/L bis(tricyclohexylphosphine)benzylidene ruthenium dichloride ("Grubbs" catalyst)/dichloromethane solution was sent as a first fluid from the center at a ratio of supply pressure/back pressure of 0.05 MPa/0.01 MPa, a rotation speed of 500 rpm, and a sending temperature of 25° C., and a 0.2 mol/L 1,7-octadiene/dichloromethane solution was introduced as a second fluid into a space between the processing surfaces at 10 mL/min. The first fluid and the second fluid were mixed in a thin film fluid, and then a solution obtained after processing was discharged from the space between the processing surfaces at 21 mL/min. As a result of GC/MS analysis, it was confirmed that 1,7-octadiene was completely converted and the production rate of cyclohexene was 90% or higher.

Comparative Example 6

Metathesis Reaction (Batch Method)

A 0.01 mol/L bis(tricyclohexylphosphine)benzylidene ruthenium dichloride ("Grubbs" catalyst) was placed in a 200-mL container purged with nitrogen. Then, a 0.2 mol/L 1,7-octadiene/dichloromethane solution was added dropwise into the container under stirring at 20000 rpm by CLEARMIX (manufactured by M Technique Co., Ltd.) while the temperature of the liquid in the container was maintained at 25° C. As a result of GC/MS analysis, the production rate of cyclohexene was 34% or less.

Example 7

Reduction Reaction

A 20% diisobutyl aluminum hydride (DIBAL-H)/hexane solution was sent as a first fluid from the center at a ratio of supply pressure/back pressure of 0.11 MPa/0.06 MPa, a rotation speed of 1000 rpm, and a sending temperature of 25° C., and a 5.0 mol/L methyl 3-(3-methyl-3H-imidazole-4-yl) acrylate/toluene solution was introduced as a second fluid into a space between the processing surfaces at 8 mL/min. The first fluid and the second fluid were mixed in a thin film fluid, and then a solution obtained after processing was discharged from the space between the processing surfaces at 23 mL/min. After extraction and solvent removal, it was confirmed by GC/MS analysis that the production rate of 3-(3-methyl-3H-imidazole-4-yl)prop-2-en-1-ol was 90% or higher.

Comparative Example 7

Reduction Reaction (Batch Method)

A 20% diisobutyl aluminum hydride (DIBAL-H)/hexane solution was placed in a 200-mL container purged with nitrogen. Then, a 5.0 mol/L methyl 3-(3-methyl-3H-imidazole-4-yl)acrylate/toluene solution was added dropwise into the container under stirring at 20000 rpm by CLEARMIX (manufactured by M Technique Co., Ltd.) while the temperature of the liquid in the container was maintained at 25° C. After extraction and solvent removal, it was confirmed by GC/MS analysis that the production rate of 3-(3-methyl-3H-imidazole-4-yl)prop-2-en-1-ol was 22% or less.

Example 8

Dehydration Reaction

A 1.5 mol/L methanesulfonyl chloride/N-methylpyrrolidone solution was sent as a first fluid from the center at a ratio of supply pressure/back pressure of 0.10 MPa/0.03 MPa, a rotation speed of 1000 rpm, and a sending temperature of 25° C., and a 1.0 mol/L benzaldoxime/N-methylpyrrolidone solution was introduced as a second fluid into a space between the processing surfaces at 20 mL/min. The first fluid and the second fluid were mixed in a thin film fluid, and then a solution obtained after processing was discharged from the space between the processing surfaces at 44 mL/min. As a result of HPLC analysis, substantially complete conversion of benzaldoxime to benzonitrile was observed.

Comparative Example 8

Dehydration Reaction (Batch Method)

A 21.5 mol/L methanesulfonyl chloride/N-methylpyrrolidone solution was placed in a 200-mL container purged with nitrogen. Then, a 1.0 mol/L benzaldoxime/N-methylpyrrolidone solution was added dropwise into the container under stirring at 20000 rpm by CLEARMIX (manufactured by M Technique Co., Ltd.) while the temperature of the liquid in the container was maintained at 25° C. As a result of HPLC analysis, unsatisfactory conversion of benzaldoxime to benzonitrile was observed.

Example 9

Beckmann Rearrangement

A 0.15 mol/L methanesulfonyl chloride/pyridine solution was sent as a first fluid from the center at a ratio of supply pressure/back pressure of 0.15 MPa/0.07 MPa, a rotation speed of 500 rpm, and a sending temperature of 25° C., and a 0.1 mol/L acetophenone oxime/pyridine solution was introduced as a second fluid into a space between the processing surfaces at 30 mL/min. The first fluid and the second fluid were mixed in a thin film fluid, and then a solution obtained after processing was discharged from the space between the processing surfaces at 58 mL/min. As a result of HPLC analysis, substantially complete conversion to acetanilide was observed.

Comparative Example 9

Beckmann Rearrangement (Batch Method)

A 0.15 mol/L methanesulfonyl chloride/pyridine solution was placed in a 200-mL container purged with nitrogen. Then, a 0.1 mol/L acetophenone oxime/pyridine solution was added dropwise into the container under stirring at 20000 rpm by CLEARMIX (manufactured by M Technique Co., Ltd.) while the temperature of the liquid in the container was maintained at 25° C. As a result of HPLC analysis, unsatisfactory conversion to acetanilide was observed.

Example 10

Oximation

A 0.16 mol/L hydroxylamine hydrochloride/1 N sodium hydroxide solution was sent as a first fluid from the center at a ratio of supply pressure/back pressure of 0.15 MPa/0.07 MPa, a rotation speed of 500 rpm, and a sending temperature of 15° C., and a 0.12 mol/L 5-bromo-2-allyloxybenzaldehyde/dioxane solution was introduced as a second fluid into a space between the processing surfaces at 15 mL/min. The first fluid and the second fluid were mixed in a thin film fluid, and then a solution obtained after processing was discharged from the space between the processing surfaces at 30 mL/min. As a result of HPLC analysis, substantially complete conversion to 5-bromo-2-allyloxybenzaldoxime was observed.

Comparative Example 10

Oximation (Batch Method)

A 0.16 mol/L hydroxylamine hydrochloride/1 N sodium hydroxide solution was placed in a 200-mL container purged with nitrogen. Then, a 0.12 mol/L 5-bromo-2-allyloxybenzaldehyde/dioxane solution was added dropwise into the container under stirring at 20000 rpm by CLEARMIX (manufactured by M Technique Co., Ltd.) while the temperature of the liquid in the container was maintained at 15° C. As a result of HPLC analysis, unsatisfactory conversion to 5-bromo-2-allyloxybenzaldoxime was observed.

Example 11

1,3-Dipolar Cycloaddition

An about 10% aqueous sodium hypochlorite solution was sent as a first fluid from the center at a ratio of supply pressure/back pressure of 0.10 MPa/0.07 MPa, a rotation speed of 500 rpm, and a sending temperature of 15° C., and a 0.2 mol/L 5-bromo-2-allyloxybenzaldoxime/dichloromethane solution was introduced as a second fluid into a space between the processing surfaces at 15 mL/min. The first fluid and the second fluid were mixed in a thin film fluid, and then a solution obtained after processing was discharged from the space between the processing surfaces at 30 mL/min. After cleaning all the reaction flow paths and reaction routes, a 0.1 mol/L cyclopentadiene/dichloromethane solution was again sent as a new first fluid from the center at a ratio of supply pressure/back pressure of 0.10 MPa/0.07 MPa, a rotation speed of 500 rpm, and a sending temperature of 15° C., and the previously-obtained discharged solution (a mixture of the first fluid and the second fluid) was introduced as a new second fluid into the space between the processing surfaces at 13 mL/min. As a result of HPLC analysis, substantially complete conversion to 8-bromo-3α,4-dihydro-3H-[1]-benzopyrano[4,3-c]-2-isooxazole was observed.

Comparative Example 11

1,3-Dipolar Cycloaddition (Batch Method)

An about 10% aqueous sodium hypochlorite solution was placed in a 200-mL container purged with nitrogen. Then, a 0.2 mol/L 5-bromo-2-allyloxybenzaldoxime/dichloromethane solution and a 0.1 mol/L cyclopentadiene/dichloromethane solution were added dropwise into the container under stirring at 20000 rpm by CLEARMIX (manufactured by M Technique Co., Ltd.) while the temperature of the liquid in the container was maintained at 15° C. As a result of HPLC analysis, unsatisfactory conversion to 8-bromo-3α,4-dihydro-3H-[1]-benzopyrano[4,3-c]-2-isooxazole was observed.

Example 12

Oxidation of Tertiary Amine and/or Nitrogen-Containing Aromatic Heterocyclic Compound to Amine Oxide A 0.0058 mol/L m-chloroperbenzoic acid/saturated aqueous sodium hydrogen carbonate mixed solution was sent as a first fluid from the center at a ratio of supply pressure/back pressure of 0.05 MPa/0.02 MPa, a rotation speed of 1000 rpm, and a sending temperature of 5° C., and a 0.008 mol/L 1-[3-(4-amidinophenyl)-2-oxo-5-oxazolidinylmethyl]piperazine-4-acetic acid/saturated sodium hydrogen carbonate solution was introduced as a second fluid into a space between the processing surfaces at 10 mL/min. The first fluid and the second fluid were mixed in a thin film fluid, and then a solution obtained after processing was discharged from the space between the processing surfaces at 19 mL/min. As a result of HPLC analysis, the production rate of 1-[3-4-amidinophenyl)-2-oxo-5-oxazolidinylmethyl]-4-oxopiperazine-4-acetic acid was 60%.

Comparative Example 12

Oxidation of Tertiary Amine and/or Nitrogen-Containing Aromatic Heterocyclic Compound to Amine Oxide (Batch Method)

A 0.0058 mol/L m-chloroperbenzoic acid/saturated aqueous sodium hydrogen carbonate mixed solution was placed in a 200-mL container purged with nitrogen. Then, a 0.008 mol/L 1-[3-(4-amidinophenyl)-2-oxo-5-oxazolidinylmethyl]piperazine-4-acetic acid/saturated sodium hydrogen carbonate solution was added dropwise into the container under stirring at 20000 rpm by CLEARMIX (manufactured by M Technique Co., Ltd.) while the temperature of the liquid in the container was maintained at 5° C. As a result of HPLC analysis, the production rate of 1-[3-4-amidinophenyl)-2-oxo-5-oxazolidinylmethyl]-4-oxopiperazine-4-acetic acid was 12%.

Example 13

Epoxidation

A 0.25 mol/L m-chloroperbenzoic acid/dichloromethane solution was sent as a first fluid from the center at a ratio of supply pressure/back pressure of 0.10 MPa/0.03 MPa, a rotation speed of 500 rpm, and a sending temperature of 25° C., and a 0.2 mol/L 1-phenylcyclohexene/dichloromethane solution was introduced as a second fluid into a space between the processing surfaces at 30 mL/min. The first fluid and the second fluid were mixed in a thin film fluid, and then a solution obtained after processing was discharged from the space between the processing surfaces at 72 mL/min. As a result of HPLC analysis, the production rate of 1,2-epoxy-1-phenylcyclohexane as a product of epoxidation was 70% or higher.

Comparative Example 13

Epoxidation (Batch Method)

A 0.25 mol/L m-chloroperbenzoic acid/dichloromethane solution was placed in a 200-mL container purged with nitrogen. Then, a 0.2 mol/L 1-phenylcyclohexene/dichloromethane solution was added dropwise into the container under stirring at 20000 rpm by CLEARMIX (manufactured by M Technique Co., Ltd.) while the temperature of the liquid in the container was maintained at 25° C. As a result of HPLC analysis, the production rate of 1,2-epoxy-1-phenylcyclohexane as a product of epoxidation was 24% or less.

Example 14

Formylation

A 0.25 mol/L indole/N,N-dimethylformamide solution was sent as a first fluid from the center at a ratio of supply pressure/back pressure of 0.07 MPa/0.02 MPa, a rotation speed of 500 rpm, and a sending temperature of 25° C., and a 0.425 mol/L phosphorus oxychloride/N,N-dimethylformamide solution was introduced as a second fluid into a space between the processing surfaces at 10 mL/min. The first fluid and the second fluid were mixed in a thin film fluid, and then a solution obtained after processing was discharged from the space between the processing surfaces at 24 mL/min. As a result of HPLC analysis, the production rate of indole-3-carboxaldehyde was 70% or higher.

Comparative Example 14

Formylation (Batch Method)

A 0.25 mol/L indole/N,N-dimethylformamide solution was placed in a 200-mL container purged with nitrogen. Then, a 0.425 mol/L phosphorus oxychloride/N,N-dimethylformamide solution was added dropwise into the container under stirring at 20000 rpm by CLEARMIX (manufactured by M Technique Co., Ltd.) while the temperature of the liquid in the container was maintained at 25° C. As a result of HPLC analysis, the production rate of indole-3-carboxaldehyde was 19% or less.

Example 15

Indole Reaction

A 0.25 mol/L 1,3-cyclohexanedione/50% sulfuric acid solution was sent as a first fluid from the center at a ratio of supply pressure/back pressure of 0.07 MPa/0.02 MPa, a rotation speed of 500 rpm, and a sending temperature of 25° C., and a 0.25 mol/L phenylhydrazine/50% sulfuric acid solution was introduced as a second fluid into a space between the processing surfaces at 18 mL/min. The first fluid and the second fluid were mixed in a thin film fluid, and then a solution obtained after processing was discharged from the space between the processing surfaces at 29 mL/min. As a result of HPLC analysis, the production rate of 1,2,3,4-tetrahydrocarbazol-4-one was 80% or higher.

Comparative Example 15

Indole Reaction (Batch Method)

A 0.25 mol/L 1,3-cyclohexanedione/50% sulfuric acid solution was placed in a 200-mL container purged with nitrogen. Then, a 0.25 mol/L phenylhydrazine/50% sulfuric acid solution was added dropwise into the container under stirring at 20000 rpm by CLEARMIX (manufactured by M Technique Co., Ltd.) while the temperature of the liquid in the container was maintained at 25° C. As a result of HPLC analysis, the production rate of 1,2,3,4-tetrahydrocarbazol-4-one was 24% or less.

Example 16

Alkylidene Group Rearrangement

A 5 mol/L benzophenone/tetrahydrofuran solution was sent as a first fluid from the center at a ratio of supply pressure/back pressure of 0.07 MPa/0.02 MPa, a rotation speed of 500 rpm, and a sending temperature of 0° C., and a 0.5 M [(cyclopentadienyl)$_2$Ti(CH$_2$)(Cl)Al(CH$_3$)$_2$] ("Tebbe catalyst")/toluene solution was introduced as a second fluid into a space between the processing surfaces at 18 mL/min. The first fluid and the second fluid were mixed in a thin film fluid, and then a solution obtained after processing was discharged from the space between the processing surfaces at 29 mL/min. As a result of HPLC analysis, it was confirmed that the benzophenone was completely converted to 1,1-diphenylethylene.

Comparative Example 16

Alkylidene Group Rearrangement (Batch Method)

A 0.5 mol/L benzophenone/tetrahydrofuran solution was placed in a 200-mL container purged with nitrogen. Then, a 0.5 M [(cyclopentadienyl)$_2$Ti(CH$_2$)(Cl)Al(CH$_3$)$_2$] ("Tebbe catalyst")/toluene solution was added dropwise into the container under stirring at 20000 rpm by CLEARMIX (manufactured by M Technique Co., Ltd.) while the temperature of the liquid in the container was maintained at 0° C. As a result of HPLC analysis, unsatisfactory conversion of the benzophenone to 1,1-diphenylethylene was confirmed.

Example 17

Coupling

A 0.13 mol/L phenyl iodide, 0.01 mol/L triphenylphosphine, 0.0025 mol/L palladium(II) acetate/N-methylpyrrolidone solution was sent as a first fluid from the center at a ratio of supply pressure/back pressure of 0.15 MPa/0.10 MPa, a rotation speed of 1000 rpm, and a sending temperature of 75° C., and a 0.16 mol/L styrene/0.16 mol/L tri-n-butylamine/N-methylpyrrolidone solution was introduced as a second fluid into a space between the processing surfaces at 10 mL/min. The first fluid and the second fluid were mixed in a thin film fluid, and then a solution obtained after processing was discharged into the space between the processing surfaces at 24 mL/min. As a result of HPLC analysis, the production rate of trans-stilbene was 90% or higher.

Comparative Example 17

Coupling (Batch Method)

A 0.13 mol/L phenyl iodide, 0.01 mol/L triphenylphosphine, 0.0025 mol/L palladium(II) acetate/N-methylpyrrolidone solution was placed in a 200-mL container purged with nitrogen. Then, a 0.16 mol/L styrene/0.16 mol/L tri-n-butylamine/N-methylpyrrolidone solution was added dropwise into the container under stirring at 20000 rpm by CLEARMIX (manufactured by M Technique Co., Ltd.) while the temperature of the liquid in the container was maintained at 75° C. As a result of HPLC analysis, the production rate of trans-stilbene was 54% or less.

Example 18

Acetoacetylation Reaction

Diketene was sent as a first fluid from the center at a ratio of supply pressure/back pressure of 0.15 MPa/0.10 MPa, a rotation speed of 1000 rpm, and a sending temperature of 45° C., and a 1 mmol/L 1,4-diazabicyclo[2,2,2]octane/isopropanol solution was introduced as a second fluid into a space between the processing surfaces at 10 mL/min. The first fluid and the second fluid were mixed in a thin film fluid, and then a solution obtained after processing was discharged from the space between the processing surfaces at 24 mL/min. As a result of GC/MS analysis, the production rate of isopropyl 3-oxobutanoate was 98% or higher.

Comparative Example 18

Acetoacetylation Reaction (Batch Method)

Diketene was placed in a 200-mL container purged with nitrogen. Then, a 1,4-diazabicyclo[2,2,2]octane/isopropanol solution was added dropwise into the container under stirring at 20000 rpm by CLEARMIX (manufactured by M Technique Co., Ltd.) while the temperature of the liquid in the container was maintained at 45° C. As a result of GC/MS analysis, the production rate of isopropyl 3-oxobutanoate was 56% or less.

Example 19

Diketopyrolopyrrole a) Amyl Oxide Solution (Raw Material A)
124 g of sodium was introduced into 1365 g of anhydrous tert-amyl alcohol at 100° C. to obtain a mixture. The mixture was intensively stirred under reflux until the sodium was completely reacted, and was then cooled to 100° C. An amyl oxide solution was obtained.
b) Raw Material B
300 g of p-chlorobenzonitrile and 328.6 g of diisopropyl succinate were introduced into 800 g of anhydrous tert-amyl alcohol and dissolved therein at 90° C.
c) Synthesis of Pigment
The raw material B was sent as a first fluid from the center at a ratio of supply pressure/back pressure of 0.05 MPa/0.01 MPa, a rotation speed of 1000 rpm, and a sending temperature of 90° C., and the raw material A was introduced as a second fluid into a space between the processing surfaces at 30 mL/min. The first fluid and the second fluid were mixed in a thin film fluid, and a solution obtained after processing was discharged from the space between the processing surfaces at 54 mL/min. The discharged solution was introduced into water at 80° C. to hydrolyze a pigment salt to obtain a pigment suspension. The pigment suspension was filtered by suction, washed with methanol, and then neutralized by washing with water. An aqueous C.I. Pigment Red was obtained.

Comparative Example 19

Diketopyrolopyrrole (Batch Method)

The raw material B was placed in a 200-mL container purged with nitrogen. Then, the raw material A was added dropwise into the container under stirring at 20000 rpm by CLEARMIX (manufactured by M Technique Co., Ltd.) while the temperature of the liquid in the container was maintained at 90° C. A discharged solution was introduced into water at 80° C. to hydrolyze a pigment salt to obtain a pigment suspension. The pigment suspension was filtered by suction, washed with methanol, and then neutralized by washing with water. However, an aqueous C.I. Pigment Red was not completely obtained.

Example 20

Alkoxide

Tert-amyl alcohol was sent as a first fluid from the center at a ratio of supply pressure/back pressure of 0.40 MPa/0.25 MPa, a rotation speed of 1000 rpm, and a sending temperature of 120° C., and sodium was introduced as a second fluid at 103° C. into a space between the processing surfaces at 10 mL/min. The first fluid and the second fluid were mixed in a thin film fluid, and then a solution obtained after processing was discharged from the space between the processing surfaces at 19 mL/min. As a result, a solution of sodium t-amyl oxide and t-amyl alcohol was obtained.

Example 21

Boration

A THF solution of trimethyl borate (0.5 mol) was sent as a first fluid from the center at a ratio of supply pressure/back pressure of 0.15 MPa/0.04 MPa, a rotation speed of 500 rpm, and a sending temperature of 0° C., and a THF solution of phenylmagnesium chloride (0.5 mol) was introduced as a second fluid into a space between the processing surfaces at 34 mL/min. The first fluid and the second fluid were mixed in a thin film fluid, and then a solution obtained after processing was discharged from the space between the processing surfaces at 71 mL/min. As a result of HPLC analysis, the production rate of phenylboronic acid was 96% or higher.

Comparative Example 20

Boration (Batch Method)

A THF solution of trimethyl borate (0.5 mol) was placed in a 200-mL container purged with nitrogen. Then, a THF solution of phenylmagnesium chloride (0.5 mol) was added dropwise into the container under stirring at 20000 rpm by CLEARMIX (manufactured by M Technique Co., Ltd.) while the temperature of the liquid in the container was maintained at 0° C. As a result of HPLC analysis, the production rate of phenylboronic acid was 44% or less.

Example 22

Ozone

A 10% methanol solution of methyl trans-3,3-dimethyl-2-(2-methyl-1-propenyl)cyclopropane carboxylate was sent as a first fluid from the center at a ratio of supply pressure/back pressure of 0.52 MPa/0.31 MPa, a rotation speed of 1000 rpm, and a sending temperature of 0° C., and an ozone gas (ozone concentration: 65 g/m$^3$, oxygen concentration: 90 wt % or higher) was introduced as a second fluid into a space between the processing surfaces at 130 mL/min. The first fluid and the second fluid were mixed in a thin film fluid, and then a solution obtained after processing was discharged from the space between the processing surfaces. As a result of GC analysis, the conversion rate of the methyl trans-3,3-dimethyl-2-(2-methyl-1-propenyl)cyclopropane carboxylate was 98.7%, and the total yield of oxygen-containing compounds was 97.4% (methyl 3,3-dimethyl-2-formylcyclopropane carboxylate: 2.3%, methyl 3,3-dimethyl-2-(dimethoxymethyl)cyclopropane carboxylate: 95.1%).

Example 23

Dimerization

A halogenated solution (hydrofluorocarbon (HFC)) of $BF_3$-$Et_2O$ was sent as a first fluid from the center at a ratio of supply pressure/back pressure of 0.07 MPa/0.01 MPa, a rotation speed of 1000 rpm, and a sending temperature of 18° C., and methylenebicyclo[2.2.1]heptane was introduced as a second fluid into a space between the processing surfaces at 30 mL/min. The first fluid and the second fluid were mixed in a thin film fluid, and then a solution obtained after processing was discharged from the space between the processing surfaces at 54 mL/min. As a result of GC-FID analysis, the production rate of a target dimer was 87% or higher, and the ratio of the unreacted raw material was 1% or less.

Comparative Example 21

Dimerization (Batch Method)

A halogenated solution (hydrofluorocarbon (HFC)) of $BF_3$-$Et_2O$ was placed in a 200-mL container purged with nitrogen. Then, methylenebicyclo[2.2.1]heptane was added dropwise into the container under stirring at 20000 rpm by CLEARMIX (manufactured by M Technique Co., Ltd.) while the temperature of the liquid in the container was maintained at 18° C. As a result of GC-FID analysis, the production rate of a target dimer was 42% or less, and the ratio of the unreacted raw material was 17%.

Example 24

Cationic Polymerization

A cation pool (XXII) generated from a 0.05 mol/L dichloromethane solution of a compound (XX) was sent as a first fluid from the center at a ratio of supply pressure/back pressure of 0.07 MPa/0.01 MPa, a rotation speed of 1000 rpm, and a sending temperature of −78° C., and a 1.25 mol/L dichloromethane solution of n-butyl vinyl ether was introduced as a second fluid into a space between the processing surfaces at 50 mL/min. The first fluid and the second fluid were mixed in a thin film fluid, and then a solution obtained after processing was discharged from the space between the processing surfaces at 108 mL/min. The discharged solution was directly collected into a solution obtained by diluting a 25 mass % aqueous ammonia solution 20-fold with methanol to terminate the reaction. Solvent removal, extraction, drying, and removal of $Bu_4NBF_4$ derived from the cation pool were performed, and then the thus obtained solution was dried and solidified to obtain a polymer. The number-average molecular weight (Mn) and molecular weight distribution (Mw/Mn) of the polymer were determined by gel permeation chromatography (GPC). As a result, Mn was 5400, and Mw/Mn was 1.15.

[Chemical 28]

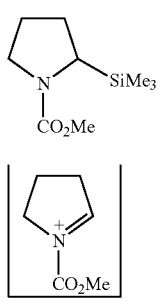

Comparative Example 22

Cationic Polymerization (Batch Method)

A cation pool (XXII) generated from a 0.05 mol/L dichloromethane solution of a compound (XX) was placed in a 200-mL container purged with nitrogen. Then, a 1.25 mol/L dichloromethane solution of n-butyl vinyl ether was added dropwise into the container under stirring at 20000 rpm by CLEARMIX (manufactured by M Technique Co., Ltd.) while the temperature of the liquid in the container was maintained at −78° C. The reaction was terminated using a solution obtained by diluting a 25 mass % aqueous ammonia solution 20-fold with methanol. Solvent removal, extraction, drying, and removal of $Bu_4NBF_4$ derived from the cation pool were performed, and the thus obtained solution was dried and solidified to obtain a polymer. The number-average molecular weight (Mn) and molecular weight distribution (Mw/Mn) of the polymer were determined by gel permeation chromatography (GPC). As a result, Mn was 3820, and Mw/Mn was 3.56.

Example 25

Halogen-Metal Exchange Reaction

A 1.58 mol/L n-butyl lithium/n-hexane solution was sent as a first fluid from the center at a ratio of supply pressure/back pressure of 0.15 MPa/0.04 MPa, a rotation speed of 2000 rpm, and a sending temperature of 25° C., and a 0.316 mol/L 2,6-dibromopyridine/THF solution was introduced as a second fluid into a space between the processing surfaces at 20 mL/min. Further, a 3.16 mol/L DMF/THF solution was introduced as a third fluid into the space between the processing surfaces at 20 mL/min. The first, second, and third fluids were mixed in a thin film fluid, and then, a solution obtained after processing was discharged from the space between the processing surfaces at 153 mL/min. As a result of HPLC analysis, the final reaction rate was 93%.

Comparative Example 23

Halogen-Metal Exchange Reaction (Batch Method)

A 1.58 mol/L n-butyl lithium/n-hexane solution was placed in a 200-mL container purged with nitrogen. Then, a 0.316 mol/L 2,6-dibromopyridine/THF solution and a 3.16 mol/L DMF/THF solution were added dropwise into the container under stirring at 20000 rpm by CLEARMIX (manufactured by M Technique Co., Ltd.) while the temperature of the liquid in the container was maintained at 25° C. As a result of HPLC analysis, the final reaction rate was 33%.

Example 26

Reduction Reaction for Aldehyde Synthesis

A 1 mol/L toluene solution of diisobutylaluminum hydride was sent as a first fluid from the center at a ratio of supply pressure/back pressure of 0.10 MPa/0.08 MPa, a rotation speed of 2000 rpm, and a sending temperature of −30° C., and a 0.92 mol/L ethyl N-benzyl isonipecotate/toluene solution was introduced as a second fluid into a space between the processing surfaces at 15 mL/min. The first fluid and the second fluid were mixed in a thin film fluid, and then a solution obtained after processing was discharged from the space between the processing surfaces at 30 mL/min. The discharged solution was collected into methanol. The thus obtained slurry solution was filtered under a reduced pressure to obtain a filtrate, and the filtrate was analyzed by gas chromatography. As a result, the reaction rate was 89%, and the ratio of N-benzylisonipecotinyl aldehyde (2) as a target substance contained in a reaction product was 97%, and the ratio of N-benzyl-4-pyperidyl methanol (3) as a side-product was only 3%.

Comparative Example 24

Production of N-Benzylisonipecotinyl Aldehyde (−30° C.: Batch Method)

A 1.0 mol/L diisobutylaluminum hydride/toluene solution was placed in a 200-mL container purged with nitrogen, and was cooled to −30° C. Then, 20 mL of a 0.92 mol/L toluene solution of ethyl N-benzylisonipecotate was added dropwise into the container under stirring at 20000 rpm by CLEARMIX (manufactured by M Technique Co., Ltd.) while the temperature of the liquid in the container was maintained at −30° C. After the completion of the dropwise addition, the liquid in the container was stirred at −30° C. for 1 hour, and methanol was added. The thus obtained slurry of insoluble matter was removed by filtration under reduced pressure to obtain a filtrate, and the filtrate was analyzed by gas chromatography. As a result, the reaction rate was 84%. However, the ratio of N-benzylisonipecotinyl aldehyde as a target substance contained in a reaction product was only 42%, whereas the ratio of N-benzyl-4-piperidyl methanol as a side-product was 58%.

In each of Examples according to the present invention, the amount of energy required to obtain a reaction product was one-tenth or less of that in Comparative Example in spite of the fact that the production rate was higher than that in Comparative Example. From the result, it has been found that the production methods used in Examples are excellent in energy efficiency.

The invention claimed is:

1. A method for producing an organic compound, the method comprising the steps of:
    providing at least two fluids to be processed, the at least two fluids including a fluid containing at least one kind of organic compound;
    providing at least two processing members of a first processing member and a second processing member, the second processing member being capable of relatively approaching to and separating from the first processing member, and a rotation drive mechanism for rotating the first processing member and the second processing member relative to each other,
    wherein the at least two processing members are provided with at least two processing surfaces of a first processing surface and a second processing surface disposed in a position they are faced with each other, and each of the processing surfaces constitutes a part of a flow path through which at least one fluid of the two fluids to be processed is passed; and
    passing the at least two fluids to be processed between the first and second processing surfaces being capable of approaching and separating from each other and rotating relative to each other, and joining the at least two fluids together in a thin film fluid formed between the two processing surfaces arranged to be opposite to each other so as to able to approach to and separate from each other, at least one of which rotating relative to the other, whereby the organic reaction is performed in the thin film fluid, reacting in the thin film fluid a component contained in one kind of the fluid with a component contained in one kind of the other fluid,
    wherein the method further comprises the steps of:
    providing supply pressure to the fluid to be processed to generate a force to move in the direction of separating at least two processing surfaces, the force thereby generated being balanced with a force to move in the direction of approaching at least two processing surfaces, thereby keeping a minute space in the distance between the first and second processing surfaces, and
    passing the at least one fluid of the two fluids to be processed in a minute space kept between the two processing surfaces, thereby forming the thin film fluid of the at least one fluid of the two fluids to be processed;
    providing an another introduction path independent of the flow path provided to pass the at least one fluid of the two fluids, wherein at least one opening leading to the introduction path is arranged in at least either the first processing surface or the second processing surface;
    introducing the other one fluid of the two fluids between the two processing surfaces through the introduction path; and
    mixing the at least one fluid of the two fluids and the other one fluid of the two fluids one in the thin film fluid.

2. The method for producing an organic compound according to claim 1, wherein:
    a fluid pressure imparting mechanism for imparting predetermined pressure to a fluid to be processed is provided,
    of the first and second processing members, at least the second processing member is provided with a pressure-receiving surface,
    at least a part of the pressure-receiving surface is comprised of the second processing surface,
    the pressure-receiving surface receives a pressure that imparts to the fluid to be processed by the fluid pressure imparting mechanism thereby generating a force to move in the direction of separating the second processing surface from the first processing surface, and
    the fluid to be processed under the imparted pressure is passed between the first and second processing surfaces, whereby the fluid to be processed forms a thin film fluid.

3. The method for producing an organic compound according to claim 1, wherein:
    a grooved depression causing the micro-pump effect by a relative rotation of the first and second processing surfaces is formed in at least any one of the processing surfaces of the first and second members,
    the grooved depression introduces one kind of the fluid to the space between the first and second processing surfaces,
    the opening is arranged in the downstream side of the grooved depression, and
    one kind of the other fluid is introduced to the space between both the processing surfaces from the opening.

4. The method for producing an organic compound according to claim 1, wherein:
    in at least any one of the first and second processing surfaces a grooved depression extending from its upstream to downstream is formed,
    the grooved depression introduces one kind of the fluid to the space between the first and second surfaces,
    the opening is arranged in the downstream side of the grooved depression, and
    one kind of the other fluid is introduced to the space between both the processing surfaces from the opening.

5. A method for producing an organic compound according to claim 3, wherein:
the opening is arranged in the downstream side of the position at which the direction of the flow of one kind of the fluid introduced from the grooved depression to the space between both the processing surfaces is converted into the direction of a spiral flow formed between both the processing surfaces.

6. The method for producing an organic compound according to claim 3, wherein:
the opening is arranged in a distance of 0.5 mm or more from the most downstream end of the grooved depression in the downstream side.

7. The method for producing an organic compound according to claim 1, wherein:
the thin film fluid is a laminar flow thin film fluid and the reaction is performed under the condition of the laminar flow in the thin film fluid.

8. The method for producing an organic compound according to claim 1, wherein:
the method is carried out by at least any one of heating (warming) at least either one of the processing surfaces, irradiating a ultraviolet (UV) beam between both the processing surfaces, and applying a ultrasonic energy between both the processing surfaces.

9. The method for producing an organic compound according to claim 1, wherein:
the reaction is performed in a vessel capable of securing a reduced pressure or a vacuum state, and
a secondary side to which at least a fluid after the treatment is discharged from the space between the first and second processing surfaces is made to a reduced pressure or a vacuum state, whereby a gas generated during the reaction and a gas contained in the fluid to be processed are deaired, or a solvent in the fluid is removed.

10. The method for producing an organic compound according to claim 1, wherein:
combination of one kind of the fluid, one kind of the other fluid, and the reaction is at least one selected from the group consisting of the following first to twenty-seventh combinations:
a first combination comprising:
a fluid containing at least one organic compound,
a fluid containing at least one reacting agent, and
the reaction in which an organic reaction is performed between the organic compound and the reacting agent,
a second combination comprising:
a fluid containing one or two selected from three members composed of an acylating agent, a strong acid, and an organic compound,
a fluid containing at least one not selected in the above three members thereby resulting in containing all the three members in the fluid to be processed, and
the reaction in which a Friedel-Craft acylation reaction is performed,
a third combination comprising:
a fluid containing at least one nitration reagent,
a fluid containing at least one organic compound, and
the reaction in which a nitration reaction is performed,
a fourth combination comprising:
a fluid containing at least one brominating reagent,
a fluid containing at least one organic compound, and
the reaction in which a bromination reaction is performed,
a fifth combination comprising:
a fluid containing at least one oxidant,
a fluid containing at least one organic carbonyl compound, and
the reaction in which a Baeyer-Villiger oxidation reaction is performed,
a sixth combination comprising:
a fluid containing at least one metathesis catalyst,
a fluid containing at least one unsaturated organic compound, and
the reaction in which a metathesis reaction is performed,
a seventh combination comprising:
a fluid containing at least one hydride and/or its derivative,
a fluid containing at least one organic compound, and
the reaction in which a reduction reaction is performed,
a eighth combination comprising:
a fluid containing at least one dehydrating agent,
a fluid containing at least one organic compound, and
the reaction in which a dehydration reaction is performed,
a ninth combination comprising:
a fluid containing at least one transfer reagent,
a fluid containing at least one organic oxime, and
the reaction in which a Beckmann rearrangement of the organic oxime is performed,
a tenth combination comprising:
a fluid containing at least one oximation reagent,
a fluid containing at least one organic carbonyl compound and/or CH-acid compound, and
the reaction in which an oximation reaction of the organic carbonyl compound and/or CH-acid compound is performed,
an eleventh combination comprising:
a fluid containing at least one dipolarophile,
a fluid containing at least one organic compound, and
the reaction in which a 1,3-dipolar cycloaddition of the organic compound is performed,
a twelfth combination comprising:
a fluid containing at least one oxidant,
a fluid containing at least one tertiary amine and/or at least one nitrogen-containing aromatic heterocyclic compound, and
the reaction in which the tertiary amine and/or the nitrogen-containing aromatic heterocyclic compound is oxidized to an amine oxide,
a thirteenth combination comprising:
a fluid containing at least one oxidant,
a fluid containing at least one olefin, and
the reaction in which the olefin is epoxidized,
a fourteenth combination comprising:
a fluid containing at least one formylating agent,
a fluid containing at least one organic compound, and
the reaction in which a formylation reaction is performed,
a fifteenth combination comprising:
a fluid containing at least one catalyst,
a fluid containing at least one aryl hydrazone, and
the reaction in which a reaction to obtain an indole compound is performed,
a sixteenth combination comprising:
a fluid containing at least one alkylidene group transfer reagent,
a fluid containing at least one organic compound, and
the reaction in which the alkylidene group is transferred to the organic compound,
a seventeenth combination comprising:
a fluid containing at least one or two selected from three members composed of a catalyst, an organic compound containing at least one vinyl hydrogen atom or acetylenic hydrogen atom, and an organic compound containing at least one eliminating group,
a fluid containing at least one not selected in the above three members thereby resulting in containing all the three members in the fluid to be processed, and
the reaction in which a coupling reaction is performed,
a eighteenth combination comprising:
a fluid containing at least one or two selected from three members composed of at least one organic compound selected from an alcohol, a thiol, and an amine, a catalyst, and diketene,
a fluid containing at least one not selected in the above three members thereby resulting in containing all the three members in the fluid to be processed, and
the reaction in which an acetoacetylation reaction is performed,
a nineteenth combination comprising:
a fluid containing at least one or two selected from three members composed of any nitrile represented by $R_1$—CN and $R_2$—CN (wherein $R_1$ and $R_2$ each are an unsubstituted or substituted isocyclic or heterocyclic aromatic group), a mixture of the nitriles, and a succinate diester,
a fluid containing at least one not selected in the above three members thereby resulting in containing all the three members in the fluid to be processed, and
the reaction in which the nitrile and the succinate diester are reacted or along with the reaction a salt generated by the reaction is hydrolyzed,
a twentieth combination comprising:
a fluid containing at least one alkaline metal,
a fluid containing at least one alcohol, and
the reaction in which the alkaline metal and the alcohol are reacted,
a twenty-first combination comprising:
a fluid containing at least one aldehydes and/or ketones,
a fluid containing at least one catalyst in liquid or quasi-liquid state, and
the reaction in which an aldol reaction is performed,
a twenty-second combination comprising:
a fluid containing at least one compound selected from a lithium aromatic and/or lithium aliphatic compound or a magnesium aromatic and/or magnesium aliphatic compound,
a fluid containing at least one boron compound, and
the reaction in which a boration reaction is performed,
a twenty-third combination comprising:
a fluid containing at least one organic compound containing a unsaturated bond,
a fluid containing at least one ozone, and
the reaction in which an oxidation reaction is performed,
a twenty-fourth combination comprising:
a fluid containing at least one acid,
a fluid containing at least one vinyl compound or vinylidene compound, and
the reaction in which a dimerization reaction is performed,
a twenty-fifth combination comprising:
a fluid containing at least one monomer capable of undergoing a cationic polymerization reaction,
a fluid containing at least one cation, and
the reaction in which a cationic polymerization reaction is performed,
a twenty-sixth combination comprising:
a fluid containing at least one metalation reagent (lithium, magnesium),
a fluid containing at least one halogen compound, and
the reaction in which a halogen-metal exchange reaction is performed, and
a twenty-seventh combination comprising:
a fluid containing at least one alkyl esters,
a fluid containing at least one metal hydride-based reducing agent, and
the reaction in which a reduction reaction is performed.

11. The method for producing an organic compound according to claim 3, wherein:
in at least any one of the first and second processing surfaces a grooved depression extending from its upstream to downstream is formed,
the grooved depression introduces one kind of the fluid to the space between the first and second surfaces,
the opening is arranged in the downstream side of the grooved depression, and
one kind of the other fluid is introduced to the space between both the processing surfaces from the opening.

* * * * *